US008592556B2

(12) United States Patent
Altermann et al.

(10) Patent No.: US 8,592,556 B2
(45) Date of Patent: Nov. 26, 2013

(54) PHAGE φMRU POLYNUCLEOTIDES AND POLYPEPTIDES AND USES THEREOF

(75) Inventors: Eric Heinz Altermann, Palmerston North (NZ); Graeme Trevor Attwood, Ashhurst (NZ); Sinead Christine Leahy, Palmerston North (NZ); William John Kelly, Ashhurst (NZ); Robert Starr Ronimus, Palmerston North (NZ); Dong Li, Palmerston North (NZ); Zhanhao Kong, Shanghai (CN); Linley Rose Schofield, Palmerston North (NZ); Debjit Dey, Palmerston North (NZ); Catherine Mary Tootill, Palmerston North (NZ); Carrie Sang, Palmerston North (NZ); Christina Diane Moon, Palmerston North (NZ); Petrus Hendricus Janssen, Palmerston North (NZ)

(73) Assignee: Pastoral Greenhouse Research Limited, Wellington (NZ)

( * ) Notice: Subject to any disclaimer, the term of this patent is extended or adjusted under 35 U.S.C. 154(b) by 452 days.

(21) Appl. No.: 12/678,936
(22) PCT Filed: Sep. 25, 2008
(86) PCT No.: PCT/NZ2008/000248
 § 371 (c)(1),
 (2), (4) Date: Mar. 24, 2010
(87) PCT Pub. No.: WO2009/041831
 PCT Pub. Date: Apr. 2, 2009

(65) Prior Publication Data
 US 2010/0209999 A1 Aug. 19, 2010

Related U.S. Application Data

(60) Provisional application No. 60/975,104, filed on Sep. 25, 2007, provisional application No. 60/989,840, filed on Nov. 22, 2007, provisional application No. 60/989,841, filed on Nov. 22, 2007.

(51) Int. Cl.
 *C07K 1/00* (2006.01)
(52) U.S. Cl.
 USPC ............. 530/350; 424/185.1; 424/191.1; 424/192.1; 424/234.1; 424/93.4; 530/300; 530/355
(58) Field of Classification Search
 None
 See application file for complete search history.

(56) References Cited

U.S. PATENT DOCUMENTS 5,985,907 A * 11/1999 Wolin et al. ............. 514/408
2003/0219467 A1 11/2003 Miner et al.

FOREIGN PATENT DOCUMENTS

| WO | 9511041 | 4/1995 |
| WO | 9700086 | 1/1997 |
| WO | 03038109 | 5/2003 |
| WO | 2006102350 | 9/2006 |

OTHER PUBLICATIONS

NCBI DBEST Accession No. CB993593. May 1, 2003.
NCBI DBEST Accession No. CB991989. May 1, 2003.
Nagle DP, Jr. "Development of Genetic Systems in Methanogenic Archaebacteria". Developments in Industrial Microbiology Series (1989), 43-51, vol. 30.
International Preliminary Patentability Report corresponding to related PCT Application No. PCT/NZ2008/000248; Mailed Apr. 8, 2010, citations listed above.
Attwood G T et al: "Analysis of the Methanobrevibacter Ruminantium Draft Genome: Understanding Methanogen Biology to Inhibit Their Action in the Rumen", Australian Journal of Experimental Agriculture, CSIRO, Collingwod, AU, vol. 48, No. 1-2, Jan. 1, 2008, pp. 83-88.
Luo Yongneng et al: "Pseudomurein Endoisopeptidases PEIW and PEIP, Two Moderately Related Members of a Novel Family of Proteases Produced in Methanothermobacter Strains", FEMS Microbiology Letters, vol. 208, No. 1, Feb. 19, 2002, pp. 47-51.
Luo Yongneng et al: "The Genome of Archaeal Prophage PSIM100 Encodes the Lytic Enzyme Responsible for Autolysis of Methanothermobacter Wolfeii", Journal of Bacteriology, vol. 183, No. 19, Oct. 2001, pp. 5788-5792.
Baresi L et al: "Isolation of a Bacteriophage for a Methanogenic Bacterium", Abstracts of the General Meeting of the American Society for Microbiology, American Society for Microbiology, Washington, US, vol. 84, Mar. 9, 1984.
Sulakvelidze et al: "Bacteriophage Therapy", Antimicrobial Agents and Chemotherapy, American Society for Microbiology, Washington, DC, US, vol. 45, No. 3, Mar. 1, 2001, pp. 649-659.
Wright A D G et al: "Reducing Methane Emissions in Sheep by Immunization Against Rumen Methanogens", Vaccine, Elsevier Ltd, GB, vol. 22, No. 29-30, Sep. 28, 2004, pp. 3976-3985.
Newbold C J et al: "The Role of Ciliate Protozoa in the Lysis of Methanogenic Archaea in Rumen Fluid", Letters in Applied Microbiology, vol. 23, No. 6, 1996, pp. 421-425.
Fischetti Vincent A et al: "Reinventing Phage Therapy: Are the Parts Greater Than the Sum?", Nature Biotechnology, vol. 24, No. 12, Dec. 2006, pp. 1508-1511.
Leahy Sinead C et al: "The Genome Sequence of the Rumen Methanogen Methanobrevibacter Ruminantium Reveals New Possibilities for Controlling Ruminant Methane Emissions", PLOS One, vol. 5, No. 1, Jan. 2010, pp. E8926, 1-17.
UNIPROT Database. XP002624153; Accession No. D3DZZ6; Mar. 23, 2010.
European Search Report corresponding to related EP Application No. 08834643.2; Mailed Mar. 11, 2011, citations listed above.

* cited by examiner

*Primary Examiner* — Jennifer Graser
(74) *Attorney, Agent, or Firm* — Loeb & Loeb LLP

(57) ABSTRACT

The invention encompasses phage φmru including phage induction, phage particles, and the phage genome. Also encompassed are phage polypeptides, as well as polynucleotides which encode these polypeptides, expression vectors comprising these polynucleotides, and host cells comprising these vectors. The invention further encompasses compositions and methods for detecting, targeting, permeabilising, and inhibiting microbial cells, especially methanogen cells, using the disclosed phage, polypeptides, polynucleotides, expression vectors, or host cells.

14 Claims, 32 Drawing Sheets

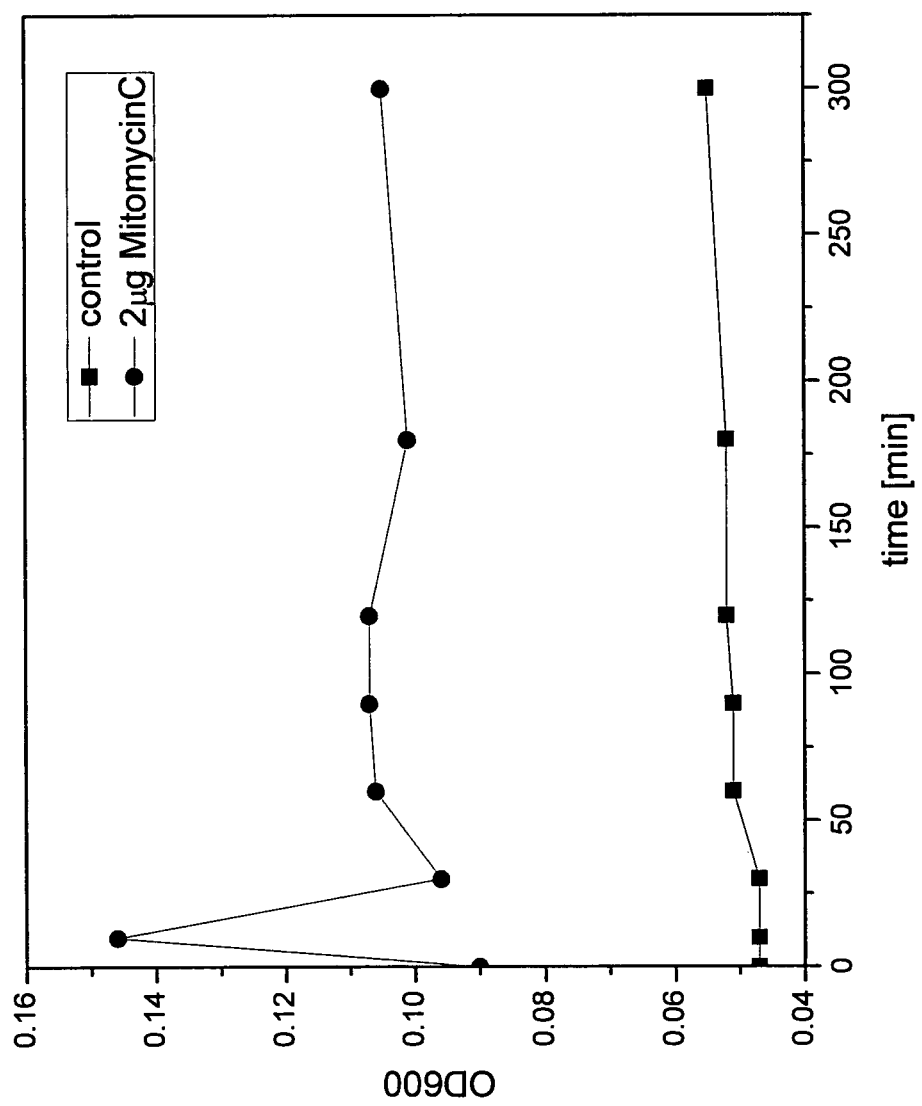

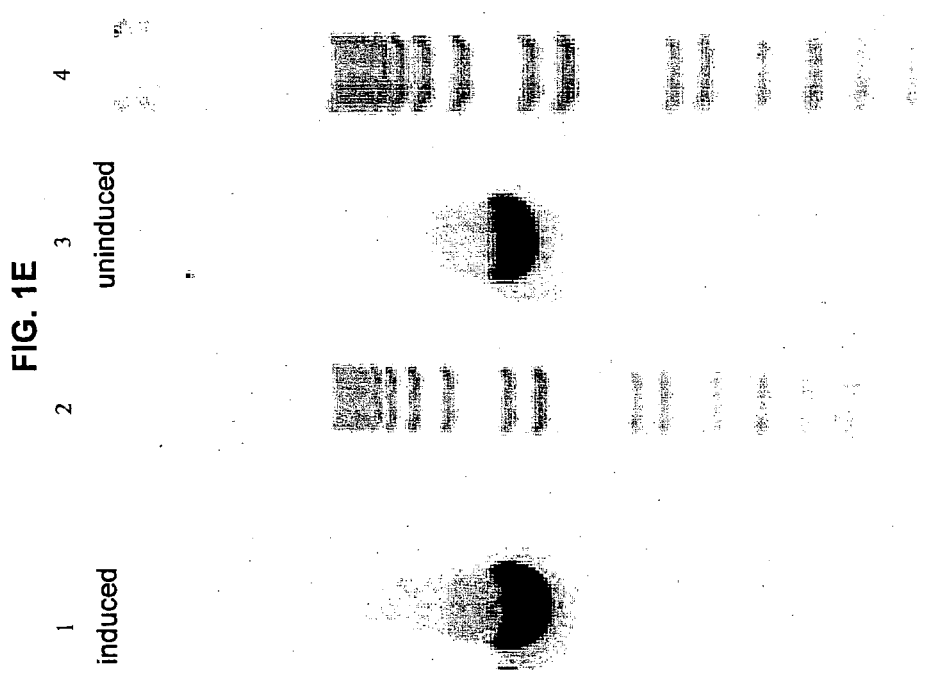

FIG. 2

Prophage φmru open reading frame annotation and comments

| ORF number | Annotation | Comment |
|---|---|---|
| 896 | potential abortive infection mechanism, CAAX amino terminal protease family | phage defense mechanism |
| 897+898 | transcriptional regulator | likely to act on ORF896, likely frameshift |
| 1451 | predicted phage related site-specific integrase | 1450 shows similarities to a DNA primase and 1452 reveals similarities to phage proteins and genome synteny suggests gene cluster, overall appearance of a mobile genetic element |
| 1572 | potential abortive infection mechanism, CAAX amino terminal protease family | phage defense mechanism |
| 1578 | potential abortive infection mechanism, CAAX amino terminal protease family | phage defense mechanism |
| 1579 | potential abortive infection mechanism, CAAX amino terminal protease family | phage defense mechanism |
| 1783 | phage structural protein | many genes in cluster 1776 to 1789 reveal similarities to phage proteins. 1989 is located at contig boundary, which could indicate a continuation of this phage remnant. |
| 1774+1775 | similar to GTPase subunit of restriction endonuclease | both genes resemble part of a (phage-specific) R/M system; the gene-cluster 1772 to 1775 predicted as involved in phage defence, based on gene synteny. |
| 1959 | potential abortive infection mechanism, CAAX amino terminal protease family | phage defence mechanism |

FIG. 3-1

Prophage φmru open reading frame annotation, predicted function, and comments

| GAMOLA ORF | Annotation | Predicted Function | Comment |
|---|---|---|---|
| Flanking genome region, genome integration locus | | | |
| 1980 | asn/thr-rich large prot. family | cell adhesion | by phage integration disrupted surface protein. N-terminus corresponds to ORF 2069 |
| | attL | core in bold | Tttttaattgattgaataattaattctgggtctgac (SEQ ID NO:143) |
| Integration Lytic/Lysogenic Switch | | | |
| 1981 | integrase | phage integrase | |
| 1983 | cons. hypo | | |
| 1984 | cons. hypo | DNA interaction | likely harbours a zinc binding domain and part of lytic-lysogenic switch |
| 1985 | cell division control protein | DNA interaction | likely part of lytic-lysogenic switch |
| DNA Replication | | | |
| 1988 | cons. hypo | DNA replication | DNA helicase or exonuclease, similarity |
| 1989 | cons. hypo | DNA replication | |
| 1990 | unknown | DNA replication | |
| 1991 | unknown | DNA replication | |
| 1992 | unknown | DNA replication | 1 TMH (Transmembrane helix) predicted, likely membrane protein |
| 1993 | exonuclease | DNA replication | similarity to exonucleases |
| 1995 | cons. hypo | DNA replication | |
| 1996 | cons. hypo | DNA replication | |
| 1998 | ATP-dependent DNA helicase | DNA replication | ATPase domain involved in replication control |
| 1999 | cons. hypo | DNA replication | |

FIG. 3-2

| GAMOLA ORF. | Annotation | Predicted Function | Comment |
|---|---|---|---|
| | terminator structure | resembles origin of replication | AAACCTTTATGGAAG TCGAGTAAGTATTGGTACGTATTATA AGTA TAAATACGTATCCTATACTTACTTTA TTAAAATTT (SEQ ID NO:144) |
| 2000 | cons. hypo | DNA replication | |
| 2001 | unknown | DNA replication | |
| 2002 | cons. hypo | DNA replication | |
| 2003 | unknown | DNA replication | |
| 2004 | unknown | DNA replication | |
| 2005 | phage associated protein | DNA replication | |
| 2006 | cons. hypo | ANTISENSE direction | adjacent terminator structure to 2007 |
| 2007 | cons. hypo | DNA replication | 2 TMHs predicted; likely to be a cytoplasmic membrane protein |
| 2008 | permease | DNA replication | 2 TMHs predicted; similarity to permease superfamily; 2007 and 2008 potentially a frameshift |
| 2010 | ParB-like partition protein | DNA replication | cleaves single stranded DNA and nicks supercoiled plasmid DNA at AT-rich regions |
| 2012 | cons. hypo | DNA replication | |
| 2013 | integral membrane protein | DNA replication | 5 TMHs predicted |
| DNA Packaging | | | |
| 2014 | cons. hypo | DNA packaging | terminase small subunit, in competition with 2015 |
| 2016 | terminase, large subunit | DNA packaging | |
| 2017 | cons. hypo | ANTISENSE direction | |
| 2018 | portal protein | DNA packaging | |
| Phage Capsid Module | | | |
| 2019 | minor head protein | structural module | head morphogenesis protein |
| 2021 | cons. hypo | structural module | |
| 2022 | phage associated protein | structural module | also similarities to ATPase |

FIG. 3-3

| GAMOLA ORF | Annotation | Predicted Function | Comment |
|---|---|---|---|
| 2023 | unknown | structural module | |
| 2024 | cons. hypo | structural module | |
| 2025 | cons. hypo | structural module | 1 TMH predicted |
| 2026 | unknown | structural module | |
| 2028 | cons. hypo | structural module | |
| 2029 | unknown | structural module | |
| 2031 | scaffold protein | structural module | similarity to scaffold protein domain |
| 2032 | cons. hypo | structural module | |
| 2033 | unknown | structural module | |
| 2034 | unknown | structural module | |
| 2035 | cons. hypo | structural module | |
| 2036 | unknown | structural module | |
| 2037 | unknown | structural module | |
| 2038 | phage head-tail adaptor | ANTISENSE direction | similarity to adaptor domain |
| 2039 | phage related protein | ANTISENSE direction | 1 TMH predicted |
| 2040 | phage capsid protein | structural module | similarity to structural protein |
| 2041 | major phage capsid protein | structural module | |
| 2042 | cons. hypo | structural module | 1 TMH predicted, potential signal sequence |
| 2043 | cons. hypo | structural module | |
| 2044 | phage related protein | structural module | |
| 2045 | cons. hypo | structural module | |
| 2046 | Cna_B collagen binding surface protein | structural module | predicted in phage docking |
| 2047 | cons. hypo | structural module | |
| 2049 | phage tail measurement protein | structural module | similarities, potential frameshift with ORF2051 |
| 2052 | phage tail protein | structural module | phage tail component |

FIG. 3-4

| GAMOLA ORF | Annotation | Predicted Function | Comment |
|---|---|---|---|
| 2053 | minor phage structural protein | structural module | |
| Lysis | | | |
| 2055 | phage related surface protein | Lysis | similarities to Intimins/potential role as holin based on synteny |
| 2058 | peptidase | | prediction as lysin based on location/synteny |
| Lysogenic conversion | | | |
| 2061 | dnd system-associated protein 3 | DNA sulfur modification system, dnd (degradation during electrophoresis) | |
| 2062 | dnd system-associated protein 1 | DNA sulfur modification system, dnd (degradation during electrophoresis) | |
| 2063 | dnd system-associated protein 2 | DNA sulfur modification system, dnd (degradation during electrophoresis) | |
| 2064 | type II restriction m6 adenine DNA methyltransferase | methyltransferase | |
| Phage integration site, genome integration locus | | | |
| | attR | | Cagaataaggataataattaattatatgttttattttt (SEQ ID NO:145), part of terminator structure |
| 2069 | asn/thr-rich large prot. family | cell adhesion | by phage integration disrupted surface protein. C-terminus corresponds to ORF 1980 |

FIG. 4A-1

| GAMOLA ORF | Nucleotide sequence / Description | SEQ ID NO: |
|---|---|---|
| | Flanking genome region, genome integration locus | |
| 1980 | gtgagaaatatgaagaataagagtttaatattaattctttattattactgattacaataataagcataggatctgttgttgcaacgga taatgaagaaattaataatgatataataataatattgataataatgaggatatcgctaatattgataatgtcgataact ccaatataacaatccaactgacataagaatagacaattcaaacctaaatagacaatagaaacagaactagattcaaatttaaataatct | 74 |
| | Integration lytic/lysogenic switch | |
| 1981 | atgaagacttttagacaacaacagctattggaagacccctgaattccagaactacctgttgcagagaccgaacctgacggagagcagcctgca gtcatacctcaatgccgccaccaacttcgtgaggttcacagggagccgttctacaagaccgtgcatgagctcagaagccagcagaacg ataggattgagaacaacatcatcataagttcaaccgaaccagtcaaggataaacatcatgcagtttgagttcata | 75 |
| 1983 | atgaatacattaaaaatagaatgttcaaaagatgattatatcataaagactgaaattcataaaatctgaaaatgagtgaaagttgaagt tcctgagaactggaactgcgactatgtgaatgctgtcgtcctgtggaagagaacatctgcgaagtgcttgaaaagggtgatgaaagaatgc ttttgattcctatgtgcggtgaactgcttcttgaaggagtgcaggaagatgaatacataagtacatttgccttcct | 76 |
| 1984 | atgggaatgaaaagttaagatcgaaagtaaagcaaaagtaaatatatgacaagaaacatctttctataattatatgacgattt atataatgaagatagattaattttattctccacatattttaacatatatatgataattattttaaaaagatataatccattatgttt taatgaactactctgaaatgaaattattgaagcaatgaaaaaattcagtcagaaggcattgatatt | 77 |
| 1985 | atgaaaacacaagatctaattaataataaatgatgaggaatctcctgtattcctcaacaggaagtctttgagatggactatgtgcc ggacatctacaaatacagggacgagcagctggcgaaaatggcgatgtactgcaattcaataccgacaacatagctccaagaacctgc aattgtgcggaggcaatgcgacaggaaagaccacaacattaaagcagttcttcaagatgttgaacgaggctttttcca | 78 |
| | DNA replication | |
| 1988 | atgtttttggaaaatgcgatggaaaagatacaatcagcatgtctcttcaagaaaagatgaatcttatattggaaactatgaaagcaa aggaagccccttcatatcctgtattcattgtaacatacctataaatgaagcagaagaatggtacaaaaatgaagaaataggagatcagg acttatataatttctatgatgataacttgattgaaactttggttgaaatttataaaaaaatcagaatat | 79 |
| 1989 | ttgataatttcttaaactaaaatttgacgtgtaatcatggaaattgacggagttcaatacacagaagcccaaat cagaagggctttagccattgaacgagacgtgcgctctcctaatttcgttgatatgttattgggaaagatcaaacctagcgaacttgcaa gcagagtttctgaaaaggtgatgcctaa | 80 |
| 1990 | atgtgctatgtgggaaacaccaggacattggtctatcacacagaggactgcttctgcaaccactgctgttgaacgagaacaagaccat tctagaggaaaagcctgtagacatgaaacctgcagcttctgcaaccacacagtttgacactgaatag | 81 |
| 1991 | tgtgttggatatggttgcagagatgttgcagagatgttgaaaacatcaggaaaggagaaggagatgatattccatctacctccttttcctgcattgt tttcctacaaggcaaaaagtattccgaatgctgctgcaaggctgaggcaaggatcaggcaaggtttgcacttgcacttgtaggcttca gaagagaggatgtcaaggtcatagaccaaggaccaacgaggagctgttcgtatga | 82 |

FIG. 4A-2

| GAMOLA ORF | Nucleotide sequence / Description | SEQ ID NO: |
|---|---|---|
| 1992 | atgagcatgcttgcagacttcgagcctgcaaggctccacaagaggacatgggctgaaaggcatgatgtgtcgaaatcctgctgtcatatg<br>ccttgccataagcattgcaatgctacttcttttcttgcgcttgcagagccgactgttgcaggagtgatttag | 83 |
| 1993 | atgactaaggaatttgaggacttcatgagaaggaacacagagacttgcttgttttcttgagatggacacagtggcatatctgaaatacct<br>tgagtccattatgacgaaaggagaatgcgcttacagattgttgaggcaatcgcacatctcttgacttctaccagataacct<br>tcagcaaaagactgaaaggaaattcctgaccagctttttgaaaaggacaagataacaaaggcttccttcacac | 84 |
| 1995 | atgatgagatagttactacaactaacgagaataatgtacctgtgacgttgactatgccatcgaggaatggaaggcataccagcagatt<br>gaccagagctattgacgaaacagattatcagacacacaggcaggaagtacaagaccaagagcgcttggcagaagtacgcacgtg<br>ccttcaacataaacacacagataatcgacaaggaaatcgtcaagaatgacaaggaatcgtcattgaggctgagtat | 85 |
| 1996 | atgattgagtgcataacaggaaggaggagacttcacggattggaggttcctcctcttccgacatcaagtacatagtttcagtgga<br>tgatgagggaaacctgttctgcgctgtcctgacttctattacagaagtccaggatgaaccctcacatctcaaacctgaatcctatt<br>gcaaacacatcagacaagtcttgaggaggacatagatgcaaatgctctag | 86 |
| 1998 | atggataatataaacaagaacaaaaacaagttagctaagtttgaagagttttttcagcactgtatacaaggacgaagtcatgaagtttt<br>ggaaaagtatcctgaggaaggacattggttgtgactatggaatttgaaatgtttgatcctgattgcagacttgcagacttgttgattgaaa<br>agcctgacgaagtaatcgcagcttcacagaaagcaatcaagaaacattgaccattgatgaaagatccaaagttgac | 87 |
| 1999 | atggctaacaagattagagttaatctcacggttgacctgaccctaatttgtgcaattagcaagacaagttaccttgcagaagcgaatt<br>ctttgagaatcagttgaagttgttcttaggattggatgtttgaagttggcagcttcgctgaactcttggtgtacaagaatgtcgagatggattaca<br>acgcactaagagagacaagttatgtcatgttcgcaaatcaagacagttgaattgaattcaataccgactggaaggaacttggaagag | 88 |
| 2000 | atgacaattggaagtttggacaatttggacaatcagatggaaagtcagatgaagatggagaaaacatgagaaccctgaagattcgactgttctgtttcttgaaat<br>gtacaaggcacttttgagatattggatgttgaagttggcagcttcgaacttcgtgatgtacaagaatgtcgagatggattaca<br>ccttgaagagatgccctcaagcagagacatgcctcaagcagagacagttaatcagaaggaaatcctttactgttcaataccgactggaaggaacttggaagag | 89 |
| 2001 | atgaatgtgaaaacagtcatgaaggtcatgaatgacctttataggattgtcaaaggagttgtcaaggagttgaatatgaatgaatatgagattgaatcaaaattcaat<br>ctacttctattccttccaaagtacatggaaggaagcattgttgattctgaaatattccgcaatctatgacctgcaccatattgaaag<br>gcatggataatgaatcatagtggacattctgaggttgaggcaatcctggtgatgagaagaaggattttgctatatgtg | 90 |
| 2002 | atgattagcgacgaatggaagagaatactatgtcaaggtcaacgaggaactggagcagttggaagtcaggttttttcagcaaggtcga<br>caggctcgtctttctgctcaatctcatcttccatcttccatcttccatttgaggagctgaaatcctgtgcgacaggatgcgacatac<br>tgacaacgatttggaaatgccaagttatcatcctaggaggaaagatgaattatag | 91 |
| 2003 | atgaattatatagggaatgggttgcaagcacagtttgcaagccagttcgagctcagttgcagggatgactgaggacggaaaggttttgcttcaagacaccatgcagcatagcta<br>cacatttcaaaggaggacatttgagataataaggagatgttccttaatttcgagtcctga | 92 |
| 2004 | atggatagaataaaggaattgaattgtatgcgaaacctgcaagcacagccatttgattccagacatcaacggagagatagcagtgaacat<br>ttgcaggataggttcagaggctgtcaacaaggacgaggacttacatattgcgtagactgacaccaaggaggaagctgtcatga | 93 |
| 2005 | atgttaagtaaaaaagaagccatacagatgacgctggacaatgacgctggacaatgagaagcactatcctgtt<br>aagtgcaagtactgcggaaagccgttcaccaagtctcaacaacaggcagatgtactgttca<br>gacagttgcagacgaatgcccttgagggaacagaagccaagataccaggctaaaaggagg | 94 |

FIG. 4A-3

| GAMOLA ORF | Nucleotide sequence / Description | SEQ ID NO: |
|---|---|---|
| | ctaaaaataaagcagaaagtgctgattgtgatgaatacaagaaatacggtttgggtagc tatggaacaagtgcgaacggacaagaaagacacaatttttcacatgagtacatggctatt caaaaggagatgaaaagaataggattgaagagataa | |
| 2006 | atgtatttgctaaattttgtcctaactgtggaaataagtagaagaaaatgataaattctgcattattgtggaaataaactaagagt tataattcctgaaaaaaaagtgaaaagaagtcaaatagtattaatgatgaaaaaactagcaaatatgttgaagtcattgatggctaa tgagatataaagtttttccatcaagtttacctgtgaaatatatatattattataagtgaattatgaacaacatctgatgaaata | 95 |
| 2007 | atgatttatgataaagcgacagttacaagcctcatagtgctatcctattgccattgatgagcatgttaggaatcggagaattgactca gaactacatattgcaatagtgagcgtatgagcgtatgataatgccctgtgttgtactacaacgagaagcacaacagcgatttgtgagcgaa ccaccaagtgcgactgcgagctttgctatggggagacgatgaagcacttatatga | 96 |
| 2008 | atgaagcacttatatgagataatccctacagagagacttgtttgattacagggttcctgaagacaacagtctcctcggcaatgataac cactgcgtagtgatattgttcaacagcataaccgagcacttacttcatgagtgggacgagataggaatcgttcttgaatcgttt ccatcaccatcgcctgcattacatagcgatgatagacaggaacgcaggaagaaggagagcttgacacg | 97 |
| 2010 | atgatagaaatcagcaccataaagatcagcgacataaagctgccgaatacaatccgaggataatgagccagctgaacacacaaagct cagaactccatggagacattcgagtgttgaccatcgagaacaaccacatcgaagaggccaccaaggtacg agtcttctgacaagtccatggagacacgagttcataaggagctccacctcaggcttgagatgtaggc | 98 |
| 2012 | atgacgtcgacaacctgctggatatgacaagtactgaggtcttattggaggaggtcacgacaagtgataccgtatg gcacaagaaccgcgaatcaaggactcaagtgtgccaggactacattcgtcaggacatcaaggcgctggagaaacgaggacgtca aggataccaagttcatccattcgtcaggcatgcagcagaccggctcacgattcagggattggattgacacggagaaggttctc gacagggttcccttcgacagcgtcgacagcgtgctccagaccatattgtatgcaagg | 99 |
| 2013 | atgattaatgaaggataagacctattgaattttgaattttcaatgacaagaagtcattttcgtcacattgttcgttgtgagcaatct gataagcaacctgttagccatcaagtttcaacttggattttgggattgacaaccgattgcgaaatctcctgttcccgttaggat acctatgcgacagcgtgattacagaagtctatgagagaggacagctcgaaggtcatattgcttgcttggctcttgca | 100 |
| DNA packaging | | |
| 2014 | atgcccgaaccttggaaaggcaaaggacgagaacgaaagcttgagccaataaaggcattcgatgtacttcaccgatcctgacaat ggacaagccacgaagcatgaggttctgtgcgagagacgaggctcggcagaaagatggtatattaggcaactccatgcctactcatccacat ggaactggtcgaaaggcagaggcatacgatgaacacataatattgaagaaacgttaaggaaagaagttttac | 101 |
| 2016 | gtgaaggacattgtcaatcattacgctaccttcaccgtacaaggtctgattgagtgcaggtctgtagtaagctaaaacaagttcaagct caatgagcctttatcgtgacagatgttgagtcgcaggtgctgcggttcaatcatgggatacggtgcaggtctcctattgtcgtgaccc ctatcaagaacgtcgctgaagccgaatccaaggtacgtcaggcaaagccaaggactgcgtgggaggaaccatcaag | 102 |
| 2017 | atgagtaagaaacaagaaatgatgagaattgaaaggttaaaacactatgaataatcccctattttaaaaatca tgatttaattaaaaaaaataaaaaaatgaaaaataactaatcaaatatttatgacgaaatataaagatatatattgaggaaaaatgaaaagcagataaaaa gaagagagaattttataagtattattattatgataattgcaaatatttttaaatacgacagcatatgttataaattaatatcaaagtaaat | 103 |

FIG. 4A-4

| GAMOLA ORF | Nucleotide sequence / Description | SEQ ID NO: |
|---|---|---|
| 2018 | aatttt | |
| | ttgagtaagaatgctaaagcagacgccttgttgtgaccactgaagacgatcctatgacattgtcgatgcagatgtcttgagagta tgcaataaagagcgaatctgacgagacaggaagcaagcagttgaagactgatgttggaatatgatgatacattgcttgagccgttgt atgacccattgcagttgtgtgagctattggagataaacacatatcatgagaactgtgtcgatgttgttgcaaggac | 104 |
| | Phage capsid module | |
| 2019 | atgatggcgctcaagtgtgcgtcattcaaagaggcagattcagaattcagagagaatacagaaggcgtttgatactcgaagagcagtg cagtaggagattgcggacttcttcagaaggcttgaggagaaatccacaagtcatgatgacactggagcaactggaattgggtcttt tccatctgaacaagttcagacatcatacaggacaggagtactatgacatcctgttcaagtactgc | 105 |
| 2021 | atgataattgaaattcctgaaatgacaggacagaagaaataattgccgaacgacagtttgtactgataacctactttgcaggaaaa tgacatgatgtcattgcctgacggaagtatgtctgccattcagaatgattcagcttttcactgaagagggcggtgaactgattggag agtgcattgaggaaaatcctactacaacctcgcttctacaatactgtctttgagcattggatgaaggaattgag | 106 |
| 2022 | atgttaagagtcgtagagagaacctattacaacaagaaatcaagacactagactgtcgaattagagaggcaggagtcaacacta ctcccttgctcgtcaaggacgtcagttgactatccactacgaatcctaccagaggtgagagaggaaggataaaagaggctaaggaaa aatacggtgaatcctactactatcactgagagacgttgagacctacttctattacttaggaagattctttagtgat | 107 |
| 2023 | atggacgcgataaacgttatcaaccaaaacaagtattagtagatgttttgtaccgtgggactgtaaacctgattgacatcgtcatcgg tgatcattggtctatgacaatccgacagtcagtgtagtcaagttgctacaccacagattggcttttgcaaccacagagattgatgagattg tattagaaacgaagaattgagttattaataacttacgagacgagagttctcaattttgttgaagtcccacat | 108 |
| 2024 | atgttttttgtcgatttgtgcgagaacgaacgaaatagcagcacagaacagcttctatcgcaatgagacgttgcagcagcaggatattgac caacagagcagttggagagatagtgagcactgttccttgaagtagacgtagaatcaccactaatctccgagattcctattat atagtgttgtcttatatgacaccattgagaggctgtcgatgacgaggctgcaaccttgaggaagtgttcatcatagaa | 109 |
| 2025 | gtggtgaattggttgaagctattgggagataacttctgatatctcctttagcattatttctctagtggagattgatattggt tgccatcgttctcaattcttatggttctcatcctcacctgaagaatgtaaggaaactgqtactgactatataagttacaggaaagttgata tttttttggagacatctcaaggagaccatagaggtttgaagattatgtcttagacaatttgaagagatgaaact | 110 |
| 2026 | atgacaatgaaagttactttgaagtgagaatgagaacagtgagaagtgaatgagaacgagagtacatgagcttacgattgcggtgattt tgatgacggaaacattgagattcgcgaaggatcgcgaagcatagtgatgaatgcaattgcttctgttttcattgcaagaatttgtct accatgagaacggagcaatacttgagataggtgagatgagtatctctttacctaagccaaatgagataaaagatttgaagatatac atgatagattgt | 111 |
| | gtgttggacgaattcgttgagaccctgttcgacacctgaagtgaatgagaacggagagtacacttaccgattgcggtgattt ctacatcgcaaagttgctccctgttcgcaacctgatatgtagtgatcaattgcttctgttctcattgcaagaattgtct accatgagaacggagcaatacttgagataggtgagatgagtactctttacctaagccaaatgagataaaagatttgagataac atgatagattgt | 112 |
| 2028 | atgtttttgaaggaatatttgaacaacgaggagaatgtaagacaacgtgattttactggagaagtccaatcagttacacaactg gttcgtagtcaacgctcaggacgagaggacaactgccaaccactcagtaagcagagaacagttagagagaactaagagaacctatgca | 113 |

FIG. 4A-5

| GAMOLA ORF | Nucleotide sequence / Description | SEQ ID NO: |
|---|---|---|
| | gagcagtgctcgcagacaatgacaaggcagagaggaacttctcccaacaagacctgttctctcttggtgcgatagac | |
| 2029 | ttgcagttggttgtagaaggtgagaatgtgagaattggaatgccttgcgataattgtgagatgttaagagagaacgaaccaatcaaggtgattga ctgaagtccaattctccattggaatggatttttktattcactttgagggaacggcttcaggatgttggctataatgggtga | 114 |
| 2031 | atggaactgatgactaggagaaggaggaaactcaaatcctccctttctattcccaagacggaaaaggagatgacgcgatagtggt gatgaagttcttcaaccctacggatttgggaacttggaacttgtattggaggcagagaaacaggagaatggtgattaccttttcttcggat atgttgaatcaccgataacacctgaattcaacgagtacggttacttctcattgtctgagttggagaaccttaagata | 115 |
| 2032 | atgttcgacagaagaaagaatttgtcaaaaagatgtatcatgtcggagacgttgtcgaactggttcatatggacgatgcacaggctcc acctagtggaaccagaggagagaaatactcttcgtagacgatattggtcaaatccatgtgagatgggagaacggctcaggtctggcactaa tatatgttgaggacaggttcaaagttgtagagagaagagaataa | 116 |
| 2033 | atgatttgttgtatcttttgatgacctgactgcaaggagaagtctacgattcagtcgattgagttttgtggtcaagtataaatt ctcatctcgtaaggaagcacagatttcgcattgaagtacggtcagaactgattgagaatga | 117 |
| 2034 | atgattgaacggaggaggattaggaatgaagtaagtacgatattttactatcttgatgaaatttcaaggaagttagatgacggtgaattatc cgatgagcaggttgattcctgttgcagatggagattcgtcgagagattcagtagaggaagcactatcacagacgagcaggcacaagatgtcatgaatg gagattattaa | 118 |
| 2035 | atgatgaaattaagtttgaaggaactcggtgaggaactgagatatactgtcagaaggtgattaaccttgatcaagtcgattatct gttgtacttggagacctgcattgcagacgaagcataacagagagacaggacagaagaaattatctgtagggacttctaa | 119 |
| 2036 | ttgtgagaacaggagagatttgattgttatttgagagtctaagtgcgaaaacattgacagaattgactacgtgagttgacgatgt cgcaatgaaatcgtcctgacagacgaaaaggtgtacgagaagaataaaagagtgctcaagtccaatgagattgactacgattgcaggg aagaccgtatttcgccaatctcataagatctcattaggataacttggtgtaa | 120 |
| 2037 | gtggtaaccgtgagagatgtcggattcaccattgaggaacggttcttccttactgctccttcaggaattggagtattccgaagtgggagga acagagagcgtcattgacagagccatcgcattgctgacacgagctcagaaccagagacttcgagttcaccgacgaagaacgggaac tcttggagatgctttttgtcattgtcagcgaccaatag | 121 |
| 2038 | atggctaaagaaaatgttatagattttataagattgagcgacaaaatgagcgacacacttggagttatttatatgtaactgaaagagggagg aaatatcattgctcatcttttggagaattggagcgagcagaaagtttaaaaagaggtttgccttgaatgatgatatctaacctattcacta aaaagagttctgattctaatgttcgtgcgaatctgtaaagaatattgatgatgaatctgttttgctgatgtcgct | 122 |
| 2039 | atggtagtcaaatgtcctaattgttttagtccacgtgtttcaaaatgtgaagatactaatattaaatggcaatgtgataaatgcaaatg caatttaaccatggtgcttttcgatattaatgctgaagaagtagaacaattaacaatagaaaaaaattgaaagagaacgagaaa gaactgaacaatttgaaagagctattaaagaagcaatttgaaagagagaagaactgaacaatttgaaaga | 123 |
| 2040 | ttgaccgagggtcagataaggcagattgcacatgagtatctgtcgacaagaacctgagttcttcgagaccag agaagttataggagttcctgtgagtcatatataacaaacagccctataagcctcaaggcttgacgaacagtcaatgagtatccaa aggaacctggatagcgcaccaaggatgaagaggagatgaaaaggcactcaatggagtacactgga | 124 |
| 2041 | atgggaaacgaagctacttttaaaccaattggtaaacgagcaggaaaaggcagtcttcaagtcctgagactgacatggagacaggaaa ggctgtattgaacgtcgagcagctaggttcttcctagaagaacgaacattagacaatacaattttaagagatcggactgactctcaagctga | 125 |

FIG. 4A-6

| GAMOLA ORF | Nucleotide sequence / Description | SEQ ID NO: |
|---|---|---|
| 2042 | tgaaatcattcaagaagcatctcaacaggtaggaataaacggaaggtcctcacaaacgatatgacgtgaacggcgagaccgaccct gagattcctgcggctgacgtcgactctgaagcttgacgttgacgtcaaagaagctcaaggca | 126 |
| 2043 | atgcggaggcgttgcctgaactctccagagcagctctatgattcgcatatcattgtcttctcattgcttctttataggattggttga ggcgatactgacttgtcattgtgattggaggacttgcaatatccgttcgcaagctcctagaaagcttatatgttttgaaggatg agttagtcttcctgaatgaactgtctgtgattgaagaagcatgaagaagaaaagtatgctgtcataaga | 127 |
| 2044 | atgacttgattggtacggaagatgtcatcgagttcacagagtcaagcctcagacattcagttcgagaaggagacacctccagcct ggaaacattgcttgagaagtggattctgcaggcagaagagactatataatctcctactgacttcaatgacttggaggagatac ctccagcagttgttaatgtctgcttagctcactgcaaacatgtcgcattgcacagcaaggcaaggaactcct | 128 |
| 2045 | ttggtgaaattgcagattgacgttgaggaactcaagccattggagccaagttgccaaaagttgccaaaaggacagttgtgttgactgc aaatgaattgcagagaaacctcaagaagttgagtcctgtgatcatggaagcttcaggcagctcttgggtaatcttccagacaggagaat tggaaaggactgtgaaaagcagtgcaaagtatgccattttcgtgaatgacgaacaggactgtacggtccttgggtcat | 129 |
| 2046 | atgagattcgtaaatactgcttcgcttgttcctcagactgtcaaggcatatcttgaaagggaaatctgcgaaggaggggttgcttgagga tgtagagacactcattccgtccgtgaacagcgacgttcctgttgaccacctgcgatatggataagtccagcacccactaccagatggt ctgcagtcagccaaatctctcaaacaagatagctcagttgtcaatgcgttgctatgtgcgtggaatacagcgatgacttggaagag gctgagatattggaataagcctagcagcaggttggctcaagcctgatgagaacttcaacaag | 130 |
| 2047 | atgggaattcgtgttgtaggaatgaagaagggcaaggtatgagttgcgggtcagcgccgactcccatcaggaagttcagcaaggc aaaggcttccttgaactccactccgaacacaaagtcaagcggctcaaggatgaagaagcacgtgcaggcgtgtacaagcctactg ccaacatcgaaggtgaagttgacttgaagtaggacattatctcaaggcttcctggacaattaccatttact | 131 |
| 2048 | atgttgtagttaagaaatccgatatttaaagggcgtaaaaaagattgaaaaagttgaagattgaggcttgacgagagacgagatgta cttgaaccgttgtcccaagccagatcaacgaggtcgacgagattgaggcaaaggctatgggaatcttgagaccaacgagaccgcac acaggggaagaaggcagaagccctaagagtgtggttgagagcaaaggaaagataaatctcgaattgcagcagaaggca | 132 |
| 2049 | ttgcctcaagcaatgtaatgaacatgtaagcagcagaggacatgcatcatctgtcgccaaaggttgaaaacagcttcaggaa attggaaacacacaataagcacaccctcaccacatctctttcaaacaccaagttcaatcaggaactcacttctttgaacagacttgg acaagtaaccaaaggctgaagcaggtaggcgtgaacgtcagtccagctcaaccagctttacaaatgctgaaagg | 133 |
| 2052 | atgcaagtgttacaaaatatccgagcaactgtttcacagaccactgaggaaagttcgtgtccttcagcaatctggcaaatcataaagaa caatgctgacggagcgcatgcgtgacgtgagcgtgttgttcttatcaaaagcaagaagcagtctccaaacagaccgtccacagtctcatgcaaag gcttcggattcagcctcacgaccttcctgaaggtgctgaacctactacaagtaacttatagcataggaaggaatgctgaagcgactacagc tcaaagaacaagactcacatatgcaactcggaggacctacaatc | 133 |
| 2053 | atgggcatagctattgtgttatggacaatgaggagaacttcctgacctgcaattcctgacccgatttatgcaccatcaatgagaccataga ggaattgggcttgaggactttgagttcaactacaagtttcaggactatgttgaggacaggatctttttcaggatagtaacaagatct ggattagcaattcccagagcttggaggactgccttatgataaacactcctgtgaggaacagcagcagcgtctatcaggag | 134 |
| | Lysis | |

FIG. 4A-7

| GAMOLA ORF | Nucleotide sequence / Description | SEQ ID NO: |
|---|---|---|
| 2055 | atggtcgagaagattacagtgagtcctcaggaagtcagaggatacgaggaaatgttgttgatgagaaggaattgaagattacgaagcta caggtgtgatgcgagagctcgagggtgatcaaggagttcaaggaagtattcagcgttctggttctgtcctgctctga gcattgccaatgttactgaggacactcgcagggcaggtgccgccacatctcgcctcatttgaggatgggaaggc | 135 |
| 2058 | atggttagattcagcagagacatgctccaggacggagcgaagagaatgttcaagttgctaagtggctaagaagggcgaaggttgcctaactactt gataatgtatgacatggacaggaataaggagtataagttggttccaaggaatatgcaggactgtatgagtccagaaacatattctgga ttaagaacggaaggggagcctaactatgttacactgttctgccttccgttgcaaggaatctcttgtgatggactaccagaacaccaattacacc tgttgcccaaccagttgtcccttgtccttgcctcacaaatgtctatacacttaagtcagaaagtgaatgcgctaaggctttggaactagcaa gggcagtgaacaagccctgcacag | 136 |
| | Lysogenic conversion | |
| 2061 | atgaaaaaacattgctttatttttaggggacagttttgccgatatatgcaatgaagcc atgttttgtgaaaaacattagtagaaggaaaactattggattcaattccgtgcagga aaggcttcagagataatactgtaaacatttgtaacctgaagtcaagatgcttaata agctctgtcagaagaaagattgaaatgcttgataaataaggtatcattctatgat atttataaaagattaaacatattcgtaaaattagaaataaggctgtccatggcatttaagtgatattgaagacaatgcaaatattct gcatgcctatctgatatcttctataaggagactgcttcagagagactccagaggattagaacactaatttcagcgaaggaattatacggccctatta tggacattgcctctaagctgaaacattgtaaactgataacctgttaaatgaacttgtctaaactaaaatattgaggactcttcaagcttgaagagctgtttatttcaagtcattgat gattatcttttgaaagtatgaaatagcttgacagtatcttcatattgacagatctattcaagaagatttttaaaggcattgaacagagccactagttttta taacttaagcgaattatctgattatgctttgcgtagtgttggagagagtttgatcctgaaaagaatcacacttgatttgcaaattaaaagaaaacctgaactc attcatctcattgctatccattatgatgctacagagagttgacagagaaaaactatttattttgaagaagcaatagacacttagcctcagtgttgaacc tttcaatgacaataatcttaacaattcgacagaaaaactatattatagagagcgaacatatttgaattcaatgaaaattcaaactacacatcatcaagtacat atgctaatgaagttagtttgtcacttcagtgattacactaaaccaaaaggaggatacaaaccctttttatgtgatgatgtgcatatctcaaggataaggactctcactttatca ctcttcccttattaatctatatttatgagatgctgacttcattgaactcaattactcttcgatataaggagacaatagtcctccgaattcctgaaagtgaggatggacaa agaaaatcatttcaactagagactatttcattgcctaattacctttcataataagacttgaacattaatgactgaaaagatttcataaaatac tatcaatgattcatgcgactattcattgcctaatttagatactttcatgaagagtattatgacatgcatgtttcataaggagtatctggttgatttagggagttgattttaggatactgaaaagatattgttatt atccgacattgcatcgtttcactgttttaattccttgaagtatgggagtatctggtgttatttaggagttgatttaacaattctgaaaagaaggt tttgatttcactcgttctaattaggtttgcagtattctatggaagagtatctatgaagaagagccttatcaagaataattcaaggataaggtttatttatttaaattattaa caccaatatcgtatgcctataataacagtctcataaggattacaaaatatctgttcactgaagttaaggacgctatttttattaaaccatctgttgataatt aatatctgtatgcctataataacaagtctcataaggattacaaatatctgttcactgaagttaaggacgctattttttattttaattgaaaggt tcctataagagaatactatgtgtattgacactttgattcatttaagtgtataaagttaaaattaaaaccatctgttgataatt | 137 |

FIG. 4A-8

| GAMOLA ORF | Nucleotide sequence / Description | SEQ ID NO: |
|---|---|---|
| | tgaaaaagtttattagatggtctcttttagaaataagatttaaaacagatataaaatttattttcagttgaatctaacaaaaga<br>aataccttaaatgttgattttcattattatcaattatcaatacataatgaaattatataatgttttaagcctaatcaatcagataagacgat<br>ttaataatttagatgaatttattattaattattagatgaagatacagatgatgattatatgtaattagtttagaaacttagaaga<br>atttatttgagtcaaatgattttgcactttgaatttaagagggttaa | |
| 2062 | atggattttcagaaaattatatatattattaaaacaatgacttgtgatgtaaataaa<br>aggaaataatacatcagattaatcaaaattctccattgttacctttaaaactaatact<br>cctaaaaagctaattttgaaaatgttttgatatatattggtgaattatccagaatc<br>ttattaaaactattgaaaaaattttaaattagtaatattgtttcaaattaatt<br>gataataatattgaaattgaaagatgaactaaggagtgaactaaggagtataacaaaattgctaaatgaa<br>tatttattcgatgaaaaaaatgatttaaaatctcaaatatctcatccgaattgtattatatatt<br>cctcttcaaataataaaagttctaatggaaacaggaagtagcattgttttttaagagat<br>attttttgtaagaataatcaaaatctttattaacttttttgaatcatatgattcaaatcac<br>attatcttaaatttaattttaaataactccctaattttacatcatcataaataactgaaact<br>atactgtaattcatttgaggaaattgcaaatttattttaatgaagatatcaattatgca<br>ttttatatctctctcaattaattctaaagcttaatgataataatgaattgaaaaattgtactatttattggactggga<br>atctgcaagtaaaatcgtaaatcattaaagtatatgtttaaacatcctaaccattatctaaaatgcagtcatag<br>atcaaatacactattagtacaaataatttattggaaaaagatattcagaatatttaataatttgacatcaattctaaaaat<br>aatttttacatttcttaaaaatgggttcagattataggtctgtaagaattccagataatttattaga<br>attaactgaaatttcttttgaaagttaaagcgtagaggttcgtatgttatgttataatattaatggtacgctttaaatcttgaag<br>atatagctaaaaatattgtaaagcgtagaggttcgtatgttatgttattaaatattaatagagatatgttgcttgtttaactgca<br>ttatgtgttaaagataagaaatattaagttaaatcaactatttaattgacaagaaagtgatagtgaagtgctcaatatgttaaaccagttttatgat<br>agaagtagtaattttttaactaaattaaatttaactactaaattaaatttgacaagaaagtgatagtgaagtgctcaatatgttaaaccagttttatgat | 138 |
| 2063 | atgttaaaccagtttttatgttgaagatgaccaaataatgtctttttatatgtctttttataatactaaattactatttgatgatactaagatttaagtggtgaaaatttttcat<br>tagttttgatgaagatgaccaaataatgtctttttatatagttcagaaaactaattttcttgttcctgaattcatat<br>atgtccatactatttcaggaaagaagaataataatacttattccataacattaatgagtcaaattgtcattctgaagttaacatt<br>aacgtagatttcttagttacttttaagaaatcaagttacttctcaagaggtgtttgaaggatactgcattagttatctgtaatga<br>agcaatagtagtattggaaaggtatgaaaagttacagaagaagaatgccattaaaatctatttcaaaaatttagagg<br>atgaaattaacgattctcaaattcttgaaactattctttactattccgataagcaaatcgctaagttcttgaatattcaagaagaagaattgtttcaa<br>acaacattatgggattatgaaactaaatcaaattcctcaaagatgttaaaaagtaaagatggtttgttagtgatgaagattaagagagttgaatctttaa<br>agatgaccaactaaatcaaattcctcaaagatgttaaaaagtaaagatgttaaaagatgattataatgaatatatttt<br>cacaatatggagataaaaagaacagcttaaaaatatgtttactgtctgagtttctattttaagtaagatgactggtataagca<br>gaatggaaaatggttaaaaatcaaggatgactttattaatcaacaaatcaaggatgactttattaatcaacaaatccttttaattacacaaatcttgaaaatctcacaga | 139 |

FIG. 4A-9

| GAMOLA ORF | Nucleotide sequence / Description | SEQ ID NO: |
|---|---|---|
| | aaatgctaaattattgggaaattcctaactcatttactaaactgaaaagaaacgaaatatcattgtttttaatcaaatcatt<br>ctcatgaagttagtttaagttcagtttgatcagattcttagtaattcttcaaaattcaaaaaaattcactattgcaaga<br>ggcaaatcattaatagtcaattttactctgattctagtgaaccaatttcaaaactataaaacataaaaatgaaaatatctc<br>tgaatttactttaatatttgttgtttgaattttgagcctgaaatttttaattctattaaatctcgttttagtgtcaatgtcaaatcta<br>aacagattattgtaacaaatgatgaggatagtttgatattgtttttggtactggttcaaaagaatagagaaatttaataagaaat<br>ggtgaaaagttatatcttttatgatgatgaatcttttaataatttctgaacaatctccctgcttggaatgatgaaaattaagtttaaatt<br>atataaagacaataattatgcccatttttatttttaatggagtaaaagctgttcaagatgtaaacagttctctatctcgtagaagaatttaaagaa<br>aagaagaaatatggaaaacttttatttttaatggagtaaaagctgttcaagatgtaaacagttctctatctcgtagaagaatttaaagaa<br>tttctaaaaatggaacgagaaactcattaaaacaggaaacatatttttatgctaaaagaatattgatggttcttcagaagacaatcttccaagtt<br>attcagtaacgagttagaaactgcttacatggacatattttaattattataagacttttgatgattctccagaagacaatcttccaagtt<br>tagtttatttaaatgatgattttaaaagagttatataagaaattttataactatcttcaataagaaactcagaaattgaagagaattct<br>atttttgtctgatttttaaatataaaaagaattttgcttaagttagtcgtattgaaactgataacaaataatgtattctccattatctcc<br>actaaatatcgcttatatttgttcaattagaagtttctaaacatgcgaaatgaggatttatccgtaaagaaagagctagttccaaata<br>acttaattccttatatttgttcagatgatgaacaacaaatgtatttatttctaatgttgttactgaaaaacttaatcaattgtcaaacattttaa<br>aaaagtgaagaagtatcaattgaacaactcctcaccaattaaaattaactaaaaaagttattcctgttgaaatcaatatttacaacgacgctgaaaagagt<br>ttactttattagtttaacactcctcgataaaacataaaacaaaaaagttattcctgttgaaatcaatatttacaacgacgctgaaaagagt<br>atttttattagatctagattgcctgataaaactaaaacaaaaaagttattcctgttgaaatcaatatttacaacgacgctgaaaagagt<br>tctttttgacaatttatttgattgtcagtctgaattcagtgcctactggaagaattgaattaaaaatcaataatcaatttgatcc<br>tatagatattatccaaatgattcaaaataatattgcaaatgacaatgacaatgacaaaactgaaactgaaaacggtttatctttattatcttca<br>tctataagtcaaatcaactacacattcagaatatagaacggttctgtgaaaaataacatactctttaaatatgtaatcctcttattaaaacagt<br>gttacatcaactactaacattcagaatatagaacggttctgtgaaaaataacatactctttaaatatgtaatcctcttattaaaacagt<br>gattaacttgaacgaacttgttgaagaattgtacgacaaatctcattggtaacattatgaacctacattgtatcgaatactttgacagt<br>tagaagaagacaatattgaagaattgtacgacaaatctcattggtaacattatgaacctacattgtatcgaatactttgacagt<br>tctgatagtaatttgatcattattcattacagcgatcaatatagttcctctagcaagtatgaagaattgtatgatgaatgtttaaagatgttta<br>acaatatgaggaaattataagagatttcctccaatctaaagttactgaagatgataggaaaaatcttaagattgcaggaaatcaatgaag<br>attcaattaatggtgaatggttacttgaccataaagtatttgttgactctaagttaataaaagaaatatcaagtttgaataatgcttcaagttcattggtgtaaaattcaatgaag<br>tattgcttatccattttgaccataaagtatttgttgactctaagttaataaaagaaatatcaagtttgaataatgcttcaagttcattggtgtaaattcaatgaag<br>agataaaataaaggaatttttgactctaagttaataaaagaaatatcaagtttgaataatgcttcattggtgtaaattcaatgaag<br>ataatagaatcgaagttatatctcttaaaactcaactacaaaattaatgtaactacatatttgggatgaaaaagtaaaagtaaatttctt<br>gataatacttataaactcttaaaactcaactacaaaattaatgtaactacatatttgggatgaaaaagtaaaagtaaatttctt<br>catccaaatattattgtccaatgaatatgtccaatgagcaaaaatttatatggttagaagagtacattggtaaggttcttgtttcattaaaaagaatct<br>cagaactattaatgatgaatatgatattttatatggttagaagagtacattggtaaggttcttgtttcattaaaaagaatct<br>catcacatctctatctatatgatgttgataagcaagtaattgagttaccagaagatttgcttattacgttagccactcctataag<br>agaaatccatgatgagattcagtcagatcagacaatacagatattcttgcagaaacattgttatcacatgtagatagtagagcaa | |

FIG. 4A-10

| GAMOLA ORF | Nucleotide sequence / Description | SEQ ID NO: |
|---|---|---|
|  | agaataatgatatatgcgattcaatgaggatatgtcaatagatgatgatttttgataatttaagtgaattgaggatagtttattgaa gaagaatcagaaattctgaagagcctgatgaagaattaactgatgcaacttcaagcagtgataatgaacttgagaatattgaga atctcctctaaaatttctaatgtcagagcattaattggaactgaaagggttataatcataaagtttattggaatttgacatcctt ctttagcacataggcatatgttaattcaaggaaaatctggacaaggtaaaacatattcattcaacgaatgttaaaagagttgtctatt caaggcattcctagcataattttgttgattatactgatggattcaagcctctcaattagaacactatcatgattgataaggacatatttattg aataagccaatattttgttgtaaagaaaatttccaataatctatcattaattctgtttatgggctagtattcaacagtccaatactttatat aagaagacaacagcactattgcgagccgattttaaatctatcattttgatttgaatatcctaaaagaagaaattctaaaagacgaatcaaatag caaacagtttagattgcttgataagtatgattatgagttattggataaaaatccgttcgcatccactgatttcgactgtcgtcttagataata tgcaaaacagtcttgaataaattaaactgagttacattcaattacctgcactttcaagatatacagacaattataactgaattcatccttggatttatgg aagacgtaaagttaactttacattatccaattgaagataatcctttcattgtgtttagtgaagctcataatctttgattttccaatgactctc aattacaaattaacaaatgtagtgaaggcaggaaaattggatggtctggtgtttgcaacacaatctgttaaagatctatgaaaattgatg atgtagtaaaattcttaagagaatgcagaagatcagaagatatattttccaatccaacgatgtttcaacaatagctaaagattttgtcaaaagacaat gaagataaaaaatatatgaaaaagagttatctcaattgacaaaaggatattgtattgttcaaggtctgcaatagatagattggcaa tttgtatcagccaaatcctgtaactgtaaaattgaggagataagtttttgatgaaaattaa | |
| 2064 | atgaaagtaaagacagaatagagaatactatttcaatgataaagaatggatgcttat atagacaaatatttgaagagtttactctgagttctgaacaagaagagcactgaatatt tggatagataaattaaataacgatcaattaacaagtgaaaaggaattatcataatttt tttgaaattattctttgaagattttactggttataaacgttctgatgttaaacatgaagag aatattggtgatgaaggccatcctgtagagtttgtattagaaaaagatggaaaagattat gtgattatagaactaaaggaacaacctacaaattatgctagtgctaaaaaagaaacctggacag caatcaccagtagagcaagctacaaatttagatttttaatccaacagcaagagataatttatatt acagtttcaaattatgatgaatttagatttgaaagatttggaaatctttaaaaatttttattagtattc tcattcaagtttaggcaattcgatgaagacataccctaaaaatttactaatgaacaaagtc agtaaatttcactttatcgatgaaagacataccaattttatccaattgtatagtgacactagattaatgatt attgaaagagaattagaaaatgaatttcttcagaagatattttcagagaagattgaagcaataaaattatct caaataataattaaatagattttattttcctttgtttgcagaagatttagcgcttatggag gaagagacaactgctgatagttaaatgtattattaacacccttaaagacataggaaaattaatcggaaat acaatgtggaataggtaatggatgattttcaaatcaaggaaataaacatagg gataaattgaagataggtcttttcttgaaattggaatttaaagaagatttttgaagac aaatatgaggatattgctaaactaattggagtttataaagatactcttaatccaatttc | 140 |

FIG. 4A-11

| GAMOLA ORF | Nucleotide sequence / Description | SEQ ID NO: |
|---|---|---|
| | attaatttattaataatttctacatatgactttgattcagaacttgatgtgtaaatatctta<br>ggacatattttgaaaacagtattagcgatattgaagagtaaaaatgataatcaagag<br>caaagaaaaaagatggagtgtattacactccagaatatattacagattatatttgtaga<br>aatacaattattccatatttaagtatttctggtaaagccagcacagttcatgaattatta<br>tacgaatatgaatcatctaattcattgatgttttagattcaaaattaactaacatcaaa<br>gttctagatcctgcctgtgtagtgggagcatgttaaataaatcagtagatatattattt<br>gaaattcatgaagcattacatgcaagtaaatatgctgagattcatctttagatagattt<br>tttgatagtttagaaaaacgaaaggaaatataagtaataatatttatggggttgatttg<br>aacgaggagtccgttgaaattactaacttcctaattatcctttattcctaaaattagcaactgtt<br>ggacttaaagaagggtttcaacttcctagttagataaacatattaaatgtgggattca<br>ttagtgatgatgagtggcgatttgatattattgtaggaaatcctccgtatgtggatatt<br>gaagttttgaaagtggcggatttgatattattgtaggaaatcctccgtatgtggatatt<br>aaagaaatgatgaaaaaacagcaaaatacatatttgataattatgaaacttcttttaac<br>aggataaattatattctacatttgtgaaaaaagttatattgctaaaaatgaaggg<br>attttttcatttatcatgcctaattccattttattctactactcctaaaatcaga<br>gaactaattcttaataatacatccatattatttaatcttgtaagaacttctgatgatgttttt<br>aaagatgctaaagtgaacctattatttaatctcaaaaagatatgatgaaggaaat<br>aagactaagatacttataaaaaagatgatgaaatattccaataataattattca<br>gaacattctttacacaagaaagatggttgaaaataatcaataataaagatattttttca<br>gatgattttactttgattttagtttagtttaactcctatgaaataatcaaggtatgagtgaggat<br>tattgtgattttagtttagttaactcctatgataaatataaggtatgagtgaggat<br>attattaaaaatagaaaaattccattacaagatataatgaaaatgggcgaaaagaataattataaaa<br>ttggatgggtccgatattacaagatataatgggaagaaaaatcttaaaaatcctagaatttta<br>tatgggactgttaggagcacctcggaagaaaaatcttaaaaatcctagaatttta<br>ataagacagatttatctatagctcctaaggaatctgaaaaaggattttgccgcttac<br>acagaagaagaattatataacgctcaaatgcttttaattagtattgaaagaaggcttt<br>gatgataaaaattattgaaatattttaggaataattaattctaaaatgatgacttgg<br>tattatgaagaaagattttatgataaaatataaaagaattttcaaaaattttgattgaa<br>aatgctaaaaatcttccagtcattattaattcaaattttttagatgagatatctaat<br>gtggattcaataatagagttaaataagagttttatagtgtaagaaatgcattcaaaca<br>tggcttaaaatagaatttgaaattgaaaaactctctaagaaagataaaaagtagtcattatgat<br>ttaaactttgaagaattcttaaagagataaaaagaaaaaagtagtcattagaccaaat<br>caaatacagacttgtccgaattatttaatgaagtttaggaaaaatagaatatctgcaa<br>agagagattaaagaagcagacgaaaaattaacctactgtctatgaattatatggttta | |

FIG. 4A-12

| GAMOLA ORF | Nucleotide sequence / Description | SEQ ID NO: |
|---|---|---|
|  | aatcatgaagaatagaaattatagaaaatagctttaatgattaa |  |
| 2065 | atggacgatgaaacattaatcctaattgaatacatcagaaacgcgccaacaagagaaatgtgcttaagtcatttgaaggagtggactt tataagaccaatccaaatttctaggaaaaacaggcattcaccaaacaatgtcagcaagaaattaaaggatcttcgcgaacatgaactgg tctatgtcataaatcctgagtcagtgttcctaaactttacaggcttactgaaaagggtaaaaatatgcttcaattcttgtag | 141 |
|  | Phage integration site, genome integration locus |  |
| 2069 | atgaataaaaattatcttatccctccttttagtattattagtagctatttctgtctctgcagttgcagcagcagatgcagatgtcac atataaacgatgctgcagatgtgtagacgatgttgcagacgatgttgcagacgatgtgatgctgatgcacaagacatccaaa ctaagcttgataatgctaaacctgagacacaattgaattagaaaacaagacatatgacgttgatacaacatttaat | 142 |

FIG. 4B-1

| GAMOLA ORF | Amino acid sequence / Description | SEQ ID NO: |
|---|---|---|
| | Flanking genome region, genome integration locus | |
| 1980 | vrnmknksllislllitiisigsvvatdneeinmdninnidnnedianidnvdvndsninnptdiridnsnlnreteldsninksn qiredeleqsnaknlksskisstitvdgsdenqmsnptiqsaidsanagdtiiitgksyvhchfivnkpltiiseigtsmspcpsntk gsgahgifyispeasgtvlkgfnltntygdydygilirgaenveiinctintvsdgdgirienatntkiadclikdsni | 1 |
| | Integration lytic/lysogenic switch | |
| 1981 | mktfrqqlledpefqnyllqrpnltesslqsylnaatnfvrftgepfyktvhelrsqqndrienniiirfnpnqsrininmqfefieylk grgctevsidsyvrymrtilstlgiilpkspklddtpqdwylltkddikyvldtanlqykavinfaavtglrvrdmrsltikdfmtate eyhgctevedfldsapdgmigfwelfpqktrkfrlpckvcntpessdlllfslnervkyfewknekdgtdlkitknd | 2 |
| 1983 | mntlkiecskddyiiktakansenelkvepenwncdyvnavlweedicevlekgdermllipmcgelllegvqedeyikyiclpvkyq dqmvliaki | 3 |
| 1984 | mgmkkvkieskaknnmtrneklfykylyddlynedrlilfstyfniydkfifkkdiihyvlmnyseneiieamkkideigsegidiktfi pkkycpkckkvmdsygkicpdcgtiliedekkigelqakdkayeeylekeyniylqnsyhnmigqsytikirtrkpkteteivripagt vtsrgkfnsisqhypsetytrqkvtrakykecrvlfdkekmilnidgtatklyydevceleypegevnelvtltlhn | 4 |
| 1985 | mktqdliniindeespvflnrevfemdyvpdiykyrdeqlakmamycnsipdniapknlqlcggnatgktttlkqffkmlneafpnivt vyincqlfntentvygkiynklygvkgsingksntmlfdkivarlkkenkiliigldffdsfksrdglnkmlynflriheaeegiqici ftvsnkgesesilllpsrqsstgfrysltstpwsrcttywttgapsvsila | 5 |
| | DNA replication | |
| 1988 | mflekcdgkdtismslqekmnliletmeskgspfiscihcnipineaeewykngeigdqdfinfyddvnlieesfgfeiykkseyptlh tqsinqiastypmnrtqnektplflrrerklyeitnifkshstneifismdsksklkheikydftlkelneifknyleedcsiyilndn rafvmtlghfqfefdvfgsakesyfvdveiddekydkifirssyyfnipvdeldglakilkqkriieegffeggqfly | 6 |
| 1989 | miiflklkfgrvimeklieidgvqyteaqirralaierdvrspnfvdmllgkikpselasrvsekgda | 7 |
| 1990 | mcyvgntrtlvyhtedcfcnhwlinenktileekpvdmkpcsfckpqfdte | 8 |
| 1991 | mldmvaemvenirkgegdgysiyppfscivflggkkyseccckaeardqkfalvnlvgfrredvkvidprtneelfv | 9 |
| 1992 | msmladfeparlhkrtwaerhdvreilaviclaisiamlllffalaeptvagvi | 10 |
| 1993 | mtkefedfmrrntgllvflrwdtvaylkyleshyderkyecayrlleaidnlfdfyqitfskktereipdqlfekdkinkgflshigka ckkqsdfygqrwkstrgirdayghysagnflfadiygclhrisddcyrilnfseyeieeka | 11 |
| 1995 | mneivtttnennvpvdvdyaieewkaygrltrelldetdyqthrgrkyktksawqkyarafnintqiidkeivkndkgivieaeytvra tlpngrfvesdgscdrresgkremsnhsikataktratnraiseligagdvsadeldpafdkvqhsktnhvieaevaeiiespydknag fetadkiepvdedpvcknwvkticktikaegkpclkgvligkartigtmtdeernrlieyiktlpkgevnldd | 12 |

FIG. 4B-2

| GAMOLA ORF | Amino acid sequence / Description | SEQ ID NO: |
|---|---|---|
| 1996 | mieciqeegdftdwevpsssdikyivsvddegnlfcscpdfyyrksrmnphisnpesyckhirqvleednrlqml | 13 |
| 1998 | mdninktktslakfeeffstvykdevmevlekypeertlvvdyenlemfdpdladlliekpdeviaasqkaiknidplmkdpkldikfknvsncidfvnadskyigklisfeakvmeakepkpildiavyecrgcmslreipqtinsslepslcpecggrsfrllqdeseflesqllivssddtskslkvlllrdecsfdlysmgqevritgilksfssnygyeyflecnlieilndsedseydeygnrnspeyr | 14 |
| 1999 | mankirvnltvdpnlwqlakdklpcsrseffenqlkmflgieddeseiikdiqtkeneinalrdklchvrkskqiklesnksmekamaslnrmhkkygkigenqirnlahvhkvdfddlkkecqdncmnifefaevpkhdsvm | 15 |
| 2000 | mtigsldnfgksdgenmpedfdcsvffemykalfeildvevgsfaelldvyknvemdytlkrhalkqeilywfntdwkeelgkekptekdkekwirqkigydsfvveqlevklkhirrmyetalkhsfeaik | 16 |
| 2001 | mnvktvmndliglskefegveyeiesknsiyfysfpkymkegivilkysaiydlhtilkgmdgiivdilevednpgdekkdllyvqievke | 17 |
| 2002 | misdeweeeyyvkvneeleqvevrffskvdrlvfaqsysssssfsfeeaeilcdricdiltndlgnakyylggkdel | 18 |
| 2003 | mnyrewvasqfelrmtedgrvcfktpcsyytfskedfeiiremflnfes | 19 |
| 2004 | mdrikelnvcgtckhshlipdingeiavnicrigseavnkdggltycvdwtprrkls | 20 |
| 2005 | mlskkeaiqmtldnekhypvkckycgkpftkshnrqmycsdscrrnalreqkaryqakrrlkikqkvlivdeykkyglgsygtsanghrknnfsheymaiqkemkriglkr | 21 |
| 2006 | mylakfcpncgnkveendkfciycgnklrviipekkvkrssnsindektskyvevidglmrykvfpsslpvkyiiykvnygttsdeiknilengnynykinihyflqnkklyfrspknpnmffkfhndrfneemrkdnkeiihissyarvhrpsltkifnfngektfilankhfeenirktrl | 22 |
| 2007 | miydkatvtslivaillplmsmlgigeltqnyilaivsgmialvvwyynekhnsdlvsgttkcdcelcyggddeali | 23 |
| 2008 | mkhlyeiipyrrtvwitgflkttvssamittgvviilfnsitehpyfmewdeigivlgivsitiaciyiamidrwkerrkeeldtiedyinrkaeeianmkvlrkleeleee | 24 |
| 2010 | mieistikitdikpaeynprimsqlehtklrnsmetfgvvdpiiinlknnhiigghqryevlldksmednefikelhlirlgdvgwafpesdleveddhekalnlalnniegewdlpklepiltdlkdvgfdieltgfsdieltelnlennlvfaeefepdeseedvdlediydepvkemlqcpacdhvdvvkrfkrvdsqgd | 25 |
| 2012 | mdvdnllgydkvlelrslleevtdk vipvwhknrgikdfkqmcqdynfvsisgwrnedvkddqfihfvrhahrngcrihgltrrkvldrvpfdsvdsssswlqtilyarlgdkqldskfaterrgdlavlsyikwmktqeeyykkwrhyhd | 26 |
| 2013 | minerirpylnfsfndkkvifvtlfvvsnlisnllaikvfnlgfwglttdcgnllfplgylmadvitevygertarrvillglfanilllvattltvympypsywtggqayaymfgftprivlagfiaylvggfvnarlmvlikkwtnskylfmrtigstlggelcdscicssiayygivpnsgillfilmgyvvkvtwevvmqpltyksiawarkdg | 27 |
| | DNA packaging | |
| 2014 | mpepwergrdengklepikafeyfteylmtmdkprsmrvlcerlgkkdgyirqlhaysstwnwveraeaydehlilkkrlrkekfydelv | 28 |

FIG. 4B-3

| GAMOLA ORF | Amino acid sequence / Description | SEQ ID NO: |
|---|---|---|
| 2016 | eselpnlrkrleyynknmndietdmttkptskahaydknskahsttlneillmigkpteiketsleadiesdnkidlenrvedditsdefmeseleymrkmieek | 29 |
| 2017 | mkdivnhygylspykptirsdskaknkfklnepyrgqmlsagaggsimgygagllivddpiknvaeaeskvrqaklkdwwggtiksrvgrrsnglppikiviaqrlhlkdlhgiiketeptipandafrilrnggsidpntwvdfnlpaicdseddilgrkigevlweeqrdyewlmaekrsmgsylfnsiyqgqpverdgeifkrewfqdevnhkltclidpkdipqlrywdfgasgdqgtsailtsy | 30 |
| 2017 | MSKKQEmmrierlkhyayqtglipifknhdlikkiengkitntdeikiyieenekqikrrefisiliydnckyfkydsicyklisвkvnnfeiksleelmneiesekkngfrknieekelikenenkgrlkeyvrivrreygldftsvkklklkidnnkirskeelneeiieekkktelrrivydsdlnwdlkweleskirhneittkeelikeirriefiniiydnnrdfkldyvtiqklvskigsneittkeelikem | 30 |
| 2018 | msknakadafvttedgsydivdadvleryaiksesdetgskqlktdgweyddtleplydplqicelleintyhencvdvvardsagigydivptgekekelnkpkltnflenepninellyqmnydrratgygalelirkdkssepvnlshissytlrrtsdgkrvkqrvgtktvwfviygknydkegnlcdvhsetgefhpynslskeeranellwtmeyttksyyglpkivgaipaiysdisrskyn | 31 |
| Phage capsid module | | |
| 2019 | mmalkvrhskrqiqnikreyrrrlileeqcsreiadffrrlerkihkvmdehweselglfhlnkvsdiiqdsrqeyydilfkyckdsymkgreaterrfnrklenismkadvnitrledlifkpdptirynlnnkvfqasahtmdrvdnrimenitqsyddglgideakdrltveynglksweaqriarteinsaqndgafdvygelgveyhqwtaqdervretpqadhrelhgkivkvgnsfsnglqypgdrt | 32 |
| 2021 | mieipgndrteeinlpngqfvlitylqendmmslpdgkyvcpfrmiqlfteeggeligecieenphyntrfyntvfehldegieyr | 33 |
| 2022 | mlrvvertyyqqeeiktldcrireagvntyslarqgavdyptyesynevreerikeakekygesyyyhwrdvetyfyylgrffsdleeiekylertvtykphreelkeamerldkrfeevinefwysleeyeditedvleqlkegdctvhceflikefkfvnvicriikqneinhkef | 34 |
| 2023 | mdainvinqnkilvdvlyrgtvnlidividgdalvydnptvvvkcyttdlafatteideivleneefellityedgefsillkshnlgelgyiewvi | 35 |
| 2024 | mvfvdlceneiadmvesfyrngdgssriltnravgeivehycsfevdgrittnlrdfllysvvlydtigeavddgvnleevfiiedrncytgksqviligg | 36 |
| 2025 | mvnwlkaigdnfsvdyllalfssgdlilvaivlnsygvispenvrelvidyisyrkvdifwrhlrrprmsfedyvldnfeemetgeltreqvvefvsrqerkgltfcneifiavplkkgskddiveilwneyfvedykenwleqhenlgwndwkkliikkeivenggddfqifrnhlidcvlmey | 37 |
| 2026 | mtmkvtfedengertvefgddvdfvliesdddgnieiregdweldgdsdddweeyddwdeeef | 38 |
| | mdefvetlfdtywkvnengeymsltdcgdfyiakvapcvrnwsiviecncfcffhckefvyhengalleigmeisslylsqmeikdlkiymidc | 39 |
| 2028 | mflegifeqdgenvreqviywrksnqvhnwfvvnaqdgedncqphsvsreqleelrdlcravladndkaeellptrpgffgaidydewyyydlqytvekidevlkddrylyfeycsww | 40 |
| 2029 | mqlvvegenmecpcdncemlirenepikvidwksnspfgngixihfwrrerlqdvgyng | 41 |

FIG. 4B-4

| GAMOLA ORF | Amino acid sequence / Description | SEQ ID NO: |
|---|---|---|
| 2031 | melmtremegklksfpfysqdgkgddaivmkffnpyglgtwyvleaekqengdylffgyvespitpefneygyfslselenlkipikingitvsygrierdlyfervrigdiign | 42 |
| 2032 | mfgqkkefvkkmyhvgdvvelvhmddaqappsgtrgeilfvddigqihvrwengsglaliygedrfkvverkge | 43 |
| 2033 | mdllylyddltarrevydsvglsfvvkykfssrkeaqdfalkygaeliee | 44 |
| 2034 | mierrrlgmkydiftildeisrklddgelsdeqvdfllqmeilveegtitdeqaqdvmngdy | 45 |
| 2035 | mmkislkelgeeiemilaeggltfdqvdylllyletciadgsiteeqkreiicrdf | 46 |
| 2036 | mvreqerlimyleidevkcenidriefddvameivltdekvyerikrwlksneidydcredryfanlieyviritww | 47 |
| 2037 | mvtvrdvgftieerffltaqeleysevgeehesvidraialltyklrtrdfeftdeerelledafvivsdq | 48 |
| 2038 | makenvidykierqndntwsylyvtergrgnliassfgelrqkvlkrglpwndisnlftkkssdsnvrresvkniddesvladvakkssdsnvrleavrkisdnyvlidivknasdydvrreavrkindssvlediaknndenvrleavrnindesvlenisknasdskvrieaikkindetiiiklaknnndedvrieavrkindktvlidfaknasdskvrreavrkindssvlayvlkndpswivrieavr | 49 |
| 2039 | mvvkcpncfsprvskcedtnikwqcdkckckfnhgafdinaemekveqltiekiererereteqferaikeakqfereteqfererkerlerekerekiekererkerlernrikieerererikrnerirrenernriksdkrereksekrikrneirkanernsikrekrererernvmtideyyrsigygstgskvwsaiiipillviciililmfyggm | 50 |
| 2040 | mteggirqiaheylanyslvdknheffetrevigvpvesyitnepislkgldgtvneypkgtwiattritdeeemekalngeytgysittvskkfadkqiqlprrvlmkdikdpvgftislvrkpcvrgakfcsmkediengdvvseniddkleeetkgfvqsikgifnkedkdedknpededieldikaivdevtkdfvntddfetfknelekalsdkfetlgaelfkslkkslekdkaeeakksgr | 51 |
| 2041 | mgneatlnqlvneqekavfksmrtdmetgkavlnveqlgyflreatldntilrdadfklmksfkkhlnrvgingrvltngydvngetdpeipaadvdfganeldvkklkamceieddekednmtqaqfeqtllqmngerigedleywalfadsevarsddpllntndgwlkkcanhissrsiapsngmfdiedgpeamfdamikalpprfrknrrmlkfyvpfevedayrnilinrgtglgdsaqigfnalsykgipiehcstlddedgrgmlgnrvcsm | 52 |
| 2042 | mrrrclnspehngmishiivlllicfiglveailmalvdwedlaisvrksprklynvlkdelglpewnelsvlerrsmkkryavirdsfpelppweelsvidrrshkrlykliksvydgdyddspslegppaavgpqkeipleeaeyp | 53 |
| 2043 | mtwigtedvieftgvkpqtfrfekgdtsslletllekwilqaegllisycnydfndleeippavvnvclrltanmvalaqarkdtpviqvkewnvqtvssnifsndlkrdltpfvherksykgdeidffvitgdddsw | 54 |
| 2044 | mVklqidveelkpleprfkkvakrtvltanelqrnlkklspvdhgrlqgswvifqtgelertvkssakyaifvndgtglygplghkirpknqkflaftpnkgkfkglvvvpwtrgqkpqrfversmenterrvqefmirammemds | 55 |
| 2045 | mrfvntaslvpqtvkaylereiceglledvetlipsvnsdvpvdppaiwivqhpttrwsgsqpnlsnkiamsvpfefvcveysddleaeilgislasrvgsslmknfnkvkvddsmpnrffhklefetlypvgevtvvgkseripatsiifnfvyvvdwlkcnrryd | 56 |
| 2046 | mgirvvgmkeearygvaesapdfhqevskakaslnstpntkssgsrmkkaragvykptaniegevdlkrighylkafldnyhftdggsnpnvhefwggennklssftlwvtfdifektivgslldnfkmevsdeymkftadfvykteesdeienielykvklldgdwalmfydvsveidenappgivssfsfdgknninvdktiglsgrpgpqrkaaagrdisisfvstleretleliqkaeygevgtepseck | 57 |

FIG. 4B-5

| GAMOLA ORF | Amino acid sequence / Description | SEQ ID NO: |
|---|---|---|
| 2047 | mvvvkksdilkgvkkiekvkiealdgdemylrplsqaeinevdeieakamgifetnetahrgrqkpksvveskginlelqkaqhqaktkaiflsldneknvgeeawseteieqmphklfeelfnhvkrlsgieldeddvdtfh | 58 |
| 2049 | mpssnvmliivkaedmassvaqkvensfrklgntidstfttslsntkfnqeltsfgtdldkvtqrlkgvgvnggssfnqltnaerrtleklsefdpvsaqvlqhlsrigitggqtfnqlsvseqkslmmmkstaqgleevnsklrvvgigaaqaannlnqmkldpsvgsnldraklkvsemgysldstkgkilvlgtaigtslgnkwdsiktkvqttatnirtalgnaltsvkskvqnignafsglggiissaig | 59 |
| 2052 | masvtkypsnvsqttggkfvsfsnlaniknnadgahavssvlikskqspnrpstvsckgfgfslpegaeptkitvtyrhrknagsdysknkthicniggptisllgvsgfssksgsgcttmtthtkafsvhgklsraqvnsanfgvkldyptnsntyngymrisyvrvtveyitsqysvskhvsgtyededyvvslgisnknltsynptctltvpagftykgvtgaatgtvtvnnrtfswnpqlqgragsrqislafepnvtfpegtdsy | 60 |
| 2053 | mgiaivvmdneenflqfldpdlctinetieelglrtlefnykfqdyvedrdlfrignkiwisnsqsledclyvintpvensvyqenyfaceieevlaelyyaplfsqteltsangftlrttngeqtvdvdwnalnywfglyfnigvvgeclgtyanritvngtmnrlnlirsieegtgnrfvtryekdlldntihryldflnpvnsknwklnieydfiyeddgeyceaytsdgnpiseiyddieeddivdfpp | 61 |
| Lysis | | |
| 2055 | mvekitvspqevrgygnvvdekeledgsyrcdvsesseviikgveerifsvsgvpapalsianvtedtrgrcahisasfedgegdglddkaislksgddvlatittgsgenvfdvvlydsaqlyavfdgddyyppavseaitvnpakslwdvefildeeyevgdtailsgtvgtivdeivdgeivtrrqmeanvtltlvtdlgirrcstnangefvlqvpniqgnqwrvviaatsthlvfnglidvpvhdysl | 62 |
| 2058 | mvrfsrdmlqdgakrmfkwlrkgeglpnylimydmdrnkeyklvpkeyaglyesrnifwikngrepnyvtlsvarnplvmdyqntnytccptslslasqmlyhyksesecakalgtsksgstspaqlianapklgfkliipikrdskevkkylkkgfpvichwqvngsrnckgdytgnfghygliwdmtsthyvvadpakgvnrkyfscldnankgyrqnyvvcpa | 63 |
| Lysogenic conversion | | |
| 2061 | mkkhcfyflgdsfadicneamfcekhlvegnyldsiiragkaseiitvnicelegqdgliissgqkkrlemlgykgiisydiykrlnhirkirnkavhghlsdiednanilhaylylicayfykeyrdtnfsaedytgpimdiaskpketasetsednenigefisspldddylfekyddsyllnelsklkdsskeaveddnlsefkeylhidrsiqedflkalnratsfnsshlimlcgsvgdgkshlianlkknpelfnqfaihydatesfdpeknaidtlasvlepfndnnlnnsteklilainlgvlnnflessyanedytklklilieeanifesnevsdniygdkvsfvtfsdynmfelnddensnytsskyisslfnkitqkedtnpfyvaylkdkdshfinpliynyemlmdeevqktiidylikifkyrkiistrdllnfiyeiivppeflksedlnindfmdyslpnllfgyppersdlkclcneldpthrneseldkfiidlnindddtekilnryfdftrfnfleeygeylvdfrefnnsekekvtnilirfavfygksiiknnfkdkvylnylnylkylyayntgshkdykylftevkdaifnwkgsykkntlcidtldsfkvykynlklkpsvdkfekslldglflgnrfktdikiyfsvesnkkkiplnvdfslyqyimklyngfkpnqsdkddlliildefinnlldedtdddlyvisletyeeflfesndfgtfefkrg | 64 |
| 2062 | mdfsenynillkqmtcdvnkrlihqingnspllpfktntpkkanfengfdillgelsrillnktieknfkldnivsnlidnnieiedgtkeyitkllneylfdekndlkishpnlylyiplsnnksssngevalflrdfckmqnlinffesydsnhlilnlilkntpnlhhkit | 65 |

FIG. 4B-6

| GAMOLA ORF | Amino acid sequence / Description | SEQ ID NO: |
|---|---|---|
| | etkyvihfeeianlfnedinyailykkffmenignifayyyffyisqllikiskgfndnnefeklyylldwesasknrkslnsyslkh hskplyakmavidqintllgtnllekdiseyfnnldinsknnflhflkkwvsdyryvrnfddkelpdnlleltellfeslkneklgvd gavqsryalnlediakkyllkrrgsygyvlninrdmllvltalcvkdkkiklnqlfiefekrgvyfdkyskeevvnfltklnlidkksd sgdaqyvkpvl | |
| 2063 | mlnqfydylsnkllnyfddtkilsgekffisfdeddqimsfynslrsiaetnfscsefiyvhtisgkeyntysiningvkfviseslti nvdflvtlrnqvtsqegvwkdtalvicneaidsigkgmrnlqegmplnvksisknledeindsqilnysdkqiakfsiniqeeelfq ttlwdyetilsiinkgfvsdedlrelnlfkddqlnqnspqkmlkrlkenydtfnevnkfsqyqdkkeqlknmftdsgvsilskddwyka ewknvkskddfinqqnplnynenlekitenglnyweipnsftktgkrkrniivfnpnhshevslkfsfdqilsnsflntnskkftiar qkslivnftldssepifktikyhkneniseftfnivvlnfepeifnsiksrfsvnvkskqiivtndedsfdivfgtgskeiekliken geklylyddeslliseqspawndgklsfklykdnnyapflikeksktlpvnsyviwnlkrrnmenfifngvkavqdvnsfylveefke flkmereiikqdifyakrnidgslekievsfsneletaymdifnyyktfddspednlpslvylnddlkelykkfitifnkeiseieens ilsdfkykknlklqrietdnkimysplpnlayqlevskqcgnedlsvnilerlvpnnlipyicsdgkelfrpiyqeeahewliye kseevsigttnvfisnvteklnqfvkhfnylfsfnnsspikinlinikddkevvkgvfnfirsrlpdktktkvipveiniyndaeks sfdnlfdcqseiqlleefgikklksdifdpidilihmiqnnisyykhpfkkeeyeyahlsfykvkshnniandnmdkietglsnglss vtsttkhseyrtgfgtnnilnmsnpliktvininelvensknfgkntysknksvittveleedniieelydkshwvtfieptfgieyfds sdsnliiihysdqyssssskydtitvtnkstqyeelirdflgskyvkvtdeelydvikmfnsingewllrvisnsghydreklsiisaik yclsildhkdivwipvsmeeilriagnvkldknkgifdsklikgnhsddllfigvkfnednrlevifypievkiglnnastikkqksql dntyklktqlninvensefrnkffrnffiqillsneqklvtnhiwdekgldrieefkaellndeydilygleeyigkgslvsfkkes hhisiymdvdkqvielpedfayyglatpireihdeiqsdntdilaetllshvdiseiraknndicdsnedmsidddfnsefedsfie eseiseepdeeltdatsssdnesieniegespskisnvraligtqkgynhkvwefghpslanrhmliggksggqktyfiqrmlkelsi gqipsiiidytdgfkpsqlepnfkdslgdkisqyfvvkenfpinpfkrntimidkdifieednstiasrfkslinsvyglgiqqsntly qtvldcldkyddnfdlnilkeeilkdesnsaqtvlnklnelldknpfastddwsvldnkdgkvyiiqltalskdiqtiitefilwdlw nykltngsednpfivvldeahnldfsndspcskilkegrkfgwsgwfatqsvkgsmkideiaklenadekiyfhptdvstiakdlskdn edkkiyekelsqltkgycivqgsaidssgnlyqpnpvtvkieeisfden | 66 |
| 2064 | meskdrientifndkrmdayidkyfeeftlsseqeealniwidklnndqltsekgnyhnffeiiledllgykrsdvkheenigdeghpv efvlekdgkdyviielkgttykdltkrrpgqqspveqatnyasakketewatvsnydefrfnptardnyisfkfrqlkdleifkkfll vfskfslidedipkkllnetkvierelenefyqlysdtrlmiikeleyssedinrieaiklsqiilnrfilcfaedialmeettadv lltplkhrnligntmwnrlnelfifanqgnkhrripafnggfeddlsnlkirdeiedrsffenwnlkedfedkyediakligvykdt1 npifnllistydfdseldvnlghifensisdieelkndnqeqrkkdgvvytpeyitdyicrntiipylsisgkastvhellyeyes snsldvldskltnikvldpacgsgsmlnksvdilfeihealhaskyagdslrdffdslekrkeiisnniygvdlneesveitkislfl klattvgikegfqlpsldkhikcgdslvddesiagnkafnwyesfsevfesggfdiivgnppyvdikemdektakyifdnyetsfnrin lystfveksyyllknegifsfimpnsilfnstyskirelilnntsilnivrtsddvfkdakvepiilifkkgydegnktkilikkddmd eipinnysehfftgerwfennsiinifsddftfdllkkidgnnerlidycdfslgltpydykygmsediiknrkfhskildtfkell dgsditrynvkwgekeyikygdwlgapreekffknprilirqilsiapkesrkrifaayteeelynaqiafnlvlkegfddknllkyfl | 67 |

FIG. 4B-7

| GAMOLA ORF | Amino acid sequence / Description | SEQ ID NO: |
|---|---|---|
| | giinsknmtwyyeerfmdknkknfakilienaknlpvilnsnfldeivsnvdsiielnkefysvrnafqtwlkiefeieklskklenyy dlnfeeflkeikkkvvirpnqigdlselfneslgkieylqreikeadekinllvyelyglnheeieiiensfnd | |
| 2065 | mddetlilieyirnaptremvlksfegvdfirpiqisrktgihpnnvskklkdlrehelvyvinpeyhvpklyrltekgknmlqfl | 68 |
| | Phage integration site, genome integration locus | |
| 2069 | mnkkiilslllvllvaisvsavaaadadvtyindaadvddvadekvapltasadaqdiqtkldnakpgdtielenktydvdttfnvtkq vtikgqdtvikasgasqgggsgalfianeagtafegitfintdghknygeqvsgyaiqlaiengtvdnckfidwssgvygkgasfcsitn syfngsseqvtnggkkeygtkainlmgshditvtgctfeggvldaisiasnsgmnimtdntfidncyaiyfggastq | 69 |

FIG. 5

```
              (101) 101                110              120               130               140              150
    PeiP      (98)  SRYNRFKEWNG EPRVWEIY G--GGPSVEL ETFKDICKR WQ PLEENRR
    PeiW      (83)  RRYEDFVRINGA WNIILEQG--KSDHV GTFKDWLRP KDFVRINGR
MRU ORF2058   (74)  ------VA   PLVMDYQNTNYICCPT LSLAS Q LYH KSES---
  Consensus   (101)        RY  F   INGREP VIFI NG        VSL TFKDMLKRYK FL  N R
                                                                              Section 4

(151) 151                160              170              180              190              200
    PeiP      (146) EPRIVYT TPPEPPVPIEVR EMPRVL F K-T A QLYTLVSRRC YRFYYN
    PeiW      (131) EPNTISIQPQPSLKGHWT T    I KI TYH- A SLYERV KT C YRFYYN
MRU ORF2058   (110) -------BC A A L TSKG   SG TSPAQ L A AP LG FKII
  Consensus   (151)   EP   I I P            EM K LGTFK SATSLY LVAK CRYRFYYN
                                                                              Section 5

(201) 201                210              220              230              240              250
    PeiP      (195) DQTPNREALKKMVTD INCTDAC LFKPVIECLC SVRIEHVKVKCNDNK
    PeiW      (180) DQVPNHVAVMRM TS INCTDAC LFSKV EMC   KIEHVRVKCNDGK
MRU ORF2058   (141) PIKR SKEVKRYL K  PVICHW   QSRMCKG  TG  -----
  Consensus   (201)  DQ PN  AVRKMLT GINCTDAC LF    VIE LGYSVRIEHVKVKCND K
                                                                              Section 6

(251) 251                260              270              280              290              300
    PeiP      (245) WY   L RV   SEQ ID NO:70         RWTYWDYVSATKTGRPLGAPCCSRGIQH
    PeiW      (230) WY   L RV   SEQ ID NO:71         --TH DYVSATKTGRPLGVPCCTAGFQH
MRU ORF2058   (180) -- G IW I   SEQ ID NO:72         ---VAD   V RKYK  CLDN MKGY
  Consensus   (251) WYGHY LRVA  SEQ ID NO:73            TVWDYVSATKTGRPLG  PCCS  G  QH
                                                                              Section 7

(301) 301                312
    PeiP      (295) LGWGI VS RHD-
    PeiW      (273) LGWGI G VIDK
MRU ORF2058   (220) Q  V  PA---
  Consensus   (301) LGWGIV P HD
```

SEQ ID NO:70
SEQ ID NO:71
SEQ ID NO:72
SEQ ID NO:73

SEQ ID NO:70
SEQ ID NO:71
SEQ ID NO:72
SEQ ID NO:73

SEQ ID NO:70
SEQ ID NO:71
SEQ ID NO:72
SEQ ID NO:73

SEQ ID NO:70
SEQ ID NO:71
SEQ ID NO:72
SEQ ID NO:73

SEQ ID NO:70
SEQ ID NO:71
SEQ ID NO:72
SEQ ID NO:73

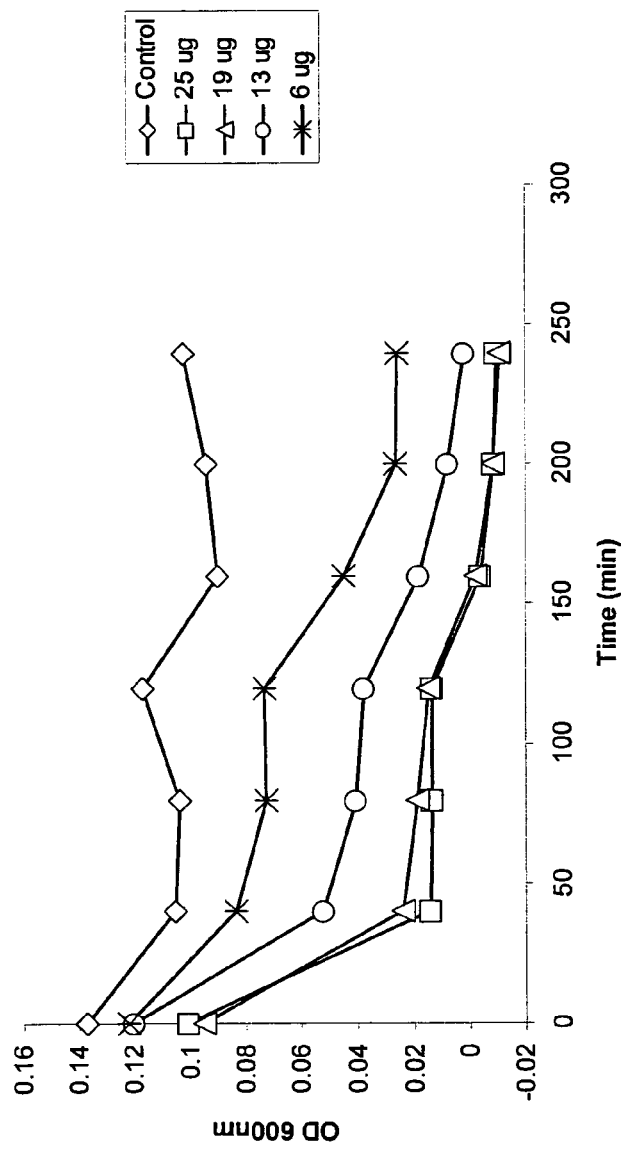

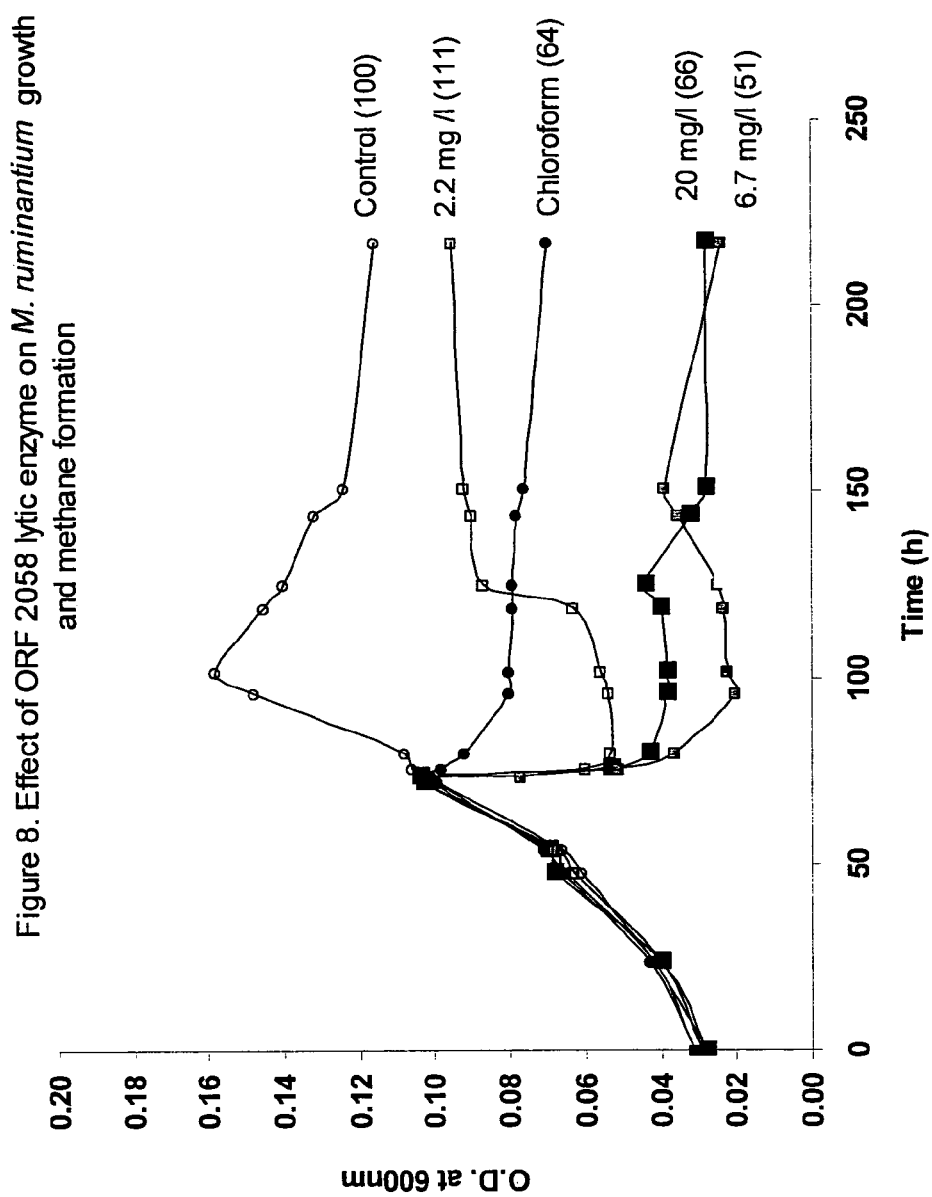
Figure 8. Effect of ORF 2058 lytic enzyme on *M. ruminantium* growth and methane formation

PHAGE φMRU POLYNUCLEOTIDES AND POLYPEPTIDES AND USES THEREOF

RELATED APPLICATIONS

This is a national phase application of PCT/NZ2008/000248, filed Sep. 25, 2008, which claims the benefit of U.S. Provisional Application No. 60/975,104, filed Sep. 25, 2007, U.S. Provisional Application No. 60/989,840, filed Nov. 22, 2007, and U.S. Provisional Application No. 60/989,841, filed Nov. 22, 2007, the contents of all of which are incorporated by reference herein in their entirety.

FIELD OF THE INVENTION

The invention relates to compositions and methods for delivering inhibitory molecules into microbial cells, in particular, methanogen cells. Specifically, the invention relates to newly identified phage φmru, including phage induction, phage particles, and the phage genome, and also phage polypeptides, as well as polynucleotides which encode these polypeptides. The invention also relates to expression vectors and host cells for producing these polypeptides. The invention further relates to methods for detecting, targeting, and inhibiting microbial cells, especially methanogen cells, using the disclosed phage, polypeptides, polynucleotides, expression vectors, and host cells.

BACKGROUND OF THE INVENTION

In New Zealand, agricultural activity accounts for the majority of greenhouse gas emissions. Therefore, reducing agricultural emissions of greenhouse gases is important for meeting New Zealand's obligations under the Kyoto Protocol. The Protocol requires reduction of greenhouse gases to 1990 levels by the end of the first commitment period (2008-2012). To this end, agricultural sector groups and the New Zealand government established the Pastoral Greenhouse Gas Research Consortium (PGGRC) to identify means for reducing New Zealand's agricultural greenhouse gas emissions.

An important part of the PGGRC's activities has been research into reducing methane emissions from New Zealand's grazing ruminants. Mitigating methane emissions from ruminants is of commercial interest for two reasons. First, failure to meet commitments under the Kyoto Protocol will force the government to purchase carbon credits. This is currently estimated to cost $350 million. Second, methane production results in the loss of 8-12% of the gross energy produced in the rumen. This energy could be used, instead, to improve ruminant productivity.

Methane is produced in the rumen by microbes called methanogens which are part of the phylum Euryarchaeota within the kingdom Archaea. Most methanogens grow on $CO_2$ and $H_2$ as their sole energy source, but some can use acetate or methyl compounds for growth. Several different genera of methanogenic archaea exist in the rumen, but species of the genus *Methanobrevibacter*, especially *M. ruminantium*, and *M. smithii* are thought to be the predominant methanogens in New Zealand ruminants. *M. ruminantium* is currently the subject of a genome sequencing project funded by the PGGRC. The project is the first genome sequencing of a rumen methanogen and it aims to build a better understanding of the biology of *Methanobrevibacter* to discover targets for inhibition of methane formation.

Reducing methane production in the rumen requires the inhibition of methanogens or the inactivation of their methanogenesis pathway. A means of inhibiting methane production is to deliver specific inhibitory molecules into methanogen cells. This may be achieved, for example, by use of agents, such as bacteriophage, which specifically target methanogens. Several phage have been characterised for non-rumen methanogens but there have been no published accounts of phage able to infect or lyse rumen methanogens. Therefore, it would be highly advantageous to identify phage that have the ability to infect methanogen cells and/or deliver inhibitors.

SUMMARY OF THE INVENTION

The invention features an isolated phage φmru, including a phage particle and/or phage genome, produced in whole or in part, as well as isolated polynucleotides and polypeptides of the phage as described in detail herein.

The invention also features an isolated polypeptide comprising at least one phage amino acid sequence selected from the group consisting of SEQ ID NO:1-69. In a particular aspect, the polypeptide comprises the amino acid sequence selected from the group consisting of SEQ ID NO:2-5 and 62-68. In a further aspect, the polypeptide comprises the amino acid sequence of SEQ ID NO:63. In another aspect, the polypeptide is a fragment, for example, comprising at least one amino acid sequence extending from residues 32-186 of SEQ ID NO:63.

The invention additionally features an isolated polynucleotide comprising a coding sequence for at least one phage polypeptide. In one aspect, the polynucleotide comprises a coding sequence for at least one amino acid sequence selected from the group consisting of SEQ ID NO:1-69. In a particular aspect, the polynucleotide comprises a coding sequence for a sequence selected from the group consisting of SEQ ID NO:2-5 and 62-68. In a further aspect, the polynucleotide comprises a coding sequence for SEQ ID NO:63. In another aspect, the polynucleotide comprises a fragment of a coding sequence, for example, least one amino acid sequence extending from residues 32-186 of SEQ ID NO:63.

In an additional aspect, the invention features an isolated polynucleotide comprising a phage nucleic acid sequence selected from the group consisting of SEQ ID NO:74-142. In a particular aspect, the polynucleotide comprises a nucleic acid sequence selected from the group consisting of SEQ ID NO:75-78 and 135-141, or is particularly, SEQ ID NO:136. In another aspect, the polynucleotide is a fragment or an oligonucleotide comprising, for example, the nucleic acid sequence extending from nucleotides 94-558 of SEQ ID NO:136. In addition, the invention encompasses an isolated polynucleotide, or fragment thereof, which hybridizes to any one of the nucleic acid sequences of SEQ ID NO:74-142. The invention further encompasses an isolated polynucleotide comprising the complement, reverse complement, reverse sequence, or fragments thereof, of any one of the nucleic acid sequences.

The invention features an expression vector comprising a polynucleotide comprising a coding sequence for at least one phage polypeptide. In one aspect, the expression vector comprises a coding sequence for at least one amino acid sequence selected from the group consisting of SEQ ID NO:1-69. In a particular aspect, the expression vector comprises a coding sequence for at least one amino acid sequence of SEQ ID NO:2-5 and 62-68. In a further aspect, the expression vector comprises a coding sequence for at least one amino acid sequence of SEQ ID NO:63. In another aspect, the expression vector comprises a coding sequence for at least one amino acid sequence extending from residues 32-186 of SEQ ID NO:63.

As a specific aspect, the invention features an expression vector which produces phage φmru, in whole or in part, as described in detail herein. In particular, the expression vector may produce phage particles, a phage genome, or modified phage, including any alterations, derivatives, variants, or fragments thereof.

The invention also features a host cell, for example, a microbial host cell, comprising at least one expression vector.

The invention specifically features an antibody raised to a polypeptide or polynucleotide as disclosed herein. In certain aspects, the antibody is directed to at least one polypeptide sequence selected from the group consisting of SEQ ID NO:1-69, or a modified sequence thereof. In alternate aspects, the antibody is raised to at least a fragment of a polynucleotide selected from the group consisting of SEQ ID NO:74-142, or a complement; or modified sequence thereof. In another aspect, the antibody includes one or more fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention additionally features modified phage polypeptides, e.g., for at least one of SEQ ID NO:1-69, including biologically active alterations, fragments, variants, and derivatives, described herein. The invention additionally features modified antibodies, e.g., directed to at least one of SEQ ID NO:1-69, including biologically active alterations, fragments, variants, and derivatives, described herein. Also featured are polynucleotides encoding these modified polypeptides, as well as alterations, fragments, variants, and derivatives of the disclosed polynucleotides, expression vectors comprising these polynucleotides, and host cells comprising these vectors. In specific aspects, the compositions and methods of the invention employ these modified polynucleotides or polypeptides, or corresponding expression vectors or host cells.

In addition, the invention features phage polypeptides, e.g., at least one of SEQ ID NO:1-69 or modified sequences thereof, which include fusions or conjugates with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein.

The invention features a composition comprising an isolated polypeptide, e.g., at least one of SEQ ID NO:1-69, or a modified sequence thereof. The invention additionally features a composition comprising an antibody, e.g., directed to at least one of SEQ ID NO:1-69, or a modified sequence thereof. Also featured is a composition comprising an isolated polynucleotide, e.g., at least one of SEQ ID NO:74-142, or a complement or modified sequence thereof. Further featured is a composition that includes an expression vector, or host cell comprising an expression vector, in accordance with the invention. The composition can include any one of the biologically active alterations, fragments, variants, and derivatives described herein. The compositions can include at least one cell inhibitor (e.g., as a fusion or conjugate), and can be formulated, for example, as pharmaceutical compositions or as food supplements, in particular, ruminant feed components.

The invention also features a composition of the invention as part of a kit for targeting and/or inhibiting microbial cells, especially methanogen cells, in accordance with the disclosed methods. The kits comprise: a) at least one composition as set out herein; and b) optionally, instructions for use, for example, in targeting cells or inhibiting cell growth or replication for methanogens or other microbes.

The invention features a method for producing a phage, the method comprising: a) culturing an expression vector or host cell comprising an expression vector, which comprises at least part of the phage genome under conditions suitable for the production of the phage; and b) recovering the phage from the culture. In particular aspects, the phage comprises at least one polypeptide selected from the group consisting of SEQ ID NO:1-69, or modified sequences thereof. In further aspects, the phage comprises at least one polynucleotide selected from the group consisting of SEQ ID NO:74-142, or modified sequences thereof.

The invention also features a method for producing a phage polypeptide, the method comprising: a) culturing an expression vector or host cell comprising an expression vector, which comprises at least part of a coding sequence for at least one phage polypeptide under conditions suitable for the expression of the polypeptide; and b) recovering the polypeptide from the culture. In particular aspects, the polypeptide comprises at least one amino acid sequence selected from the group consisting of SEQ ID NO:1-69, or modified sequences thereof.

The invention additionally features a method for producing a phage polypeptide, e.g., for at least one of SEQ ID NO:1-69, which comprises a fusion or conjugate with at least one cell inhibitor, for example, anti-methanogenesis compounds (e.g., bromoethanesulphonic acid), antibodies and antibody fragments, lytic enzymes, peptide nucleic acids, antimicrobial peptides, and other antibiotics as described in detail herein. Such method comprises: a) culturing an expression vector or host cell comprising an expression vector, which comprises a coding sequence for at least one phage polypeptide under conditions suitable for the expression of the polypeptide; b) forming the phage fusion or conjugate (e.g., by expression of the fused sequence or chemical conjugation to the cell inhibitor); and c) recovering the fusion or conjugate. In particular aspects, the polypeptide comprises at least one amino acid sequence selected from the group consisting of SEQ ID NO:1-69, or modified sequences thereof.

In addition, the invention features a method of inhibiting (e.g., inhibiting growth or replication) of a microbial cell, in particular, a methanogen cell, comprising: a) optionally, producing or isolating at least one phage polypeptide; and b) contacting the cell with the phage polypeptide. In a particular aspect, the polypeptide comprises at least one amino acid sequence selected from the group consisting of SEQ ID NO:1-69, or a modified sequence thereof.

As an added feature, the invention encompasses a method of inhibiting (e.g., inhibiting growth or replication) of a microbial cell, in particular, a methanogen cell, comprising: a) optionally, producing or isolating at least one phage polypeptide, which further comprises at least one cell inhibitor; and b) contacting the cell with the phage polypeptide. In a particular aspect, the polypeptide comprises at least one amino acid sequence selected from the group consisting of SEQ ID NO:1-69, or a modified sequence thereof.

The invention also features a method of detecting and/or measuring the levels of a phage, or a corresponding phage polypeptide or polynucleotide, comprising: 1) contacting a sample from a subject with an antibody raised to a phage polypeptide (e.g., at least one of SEQ ID NO:1-69, or a modified sequence thereof) or a corresponding polynucleotide; and 2) determining the presence or levels of the antibody complex formed with the polypeptide or polynucleotide in the sample. Such methods can also be used for detecting and/or measuring the levels of a microbial cell, in particular, a methanogen cell.

The invention features, as well, a method of detecting and/or measuring the levels of a phage, or a corresponding phage polynucleotide (e.g., a phage coding sequence), comprising: 1) contacting a sample from a subject with a complementary polynucleotide (e.g., a sequence complementary to any one of SEQ ID NO:74-142, or modified sequence thereof); and 2) determining the presence or levels of the hybridization complex formed with the phage polynucleotide in the sample. Such methods can also be used for detecting and/or measuring the levels of a microbial cell, in particular, a methanogen cell.

In particular aspects, the methods of the invention utilize in vivo or in vitro expression components. In other aspects, the methods employ polypeptides produced by recombinant, synthetic, or semi-synthetic means, or polypeptides produced by endogenous means.

Other aspects and embodiments of the invention are described herein below.

BRIEF DESCRIPTION OF THE DRAWINGS

This invention is described with reference to specific embodiments thereof and with reference to the figures.

FIG. 2. Prophage φmru open reading frame annotation and comments.

FIG. 3. Prophage φmru open reading frame annotation, predicted function, and comments.

FIGS. 4A-4B. *M. ruminantium* prophage φmru sequence information, including coding sequences of phage φmru (FIG. 4A), and amino acid sequences of phage φmru (FIG. 4B).

FIG. 5. Sequence alignment of phage φmru ORF 2058 with PeiP from *M. marburgensis* and PeiW from *M. wolfeii*.

Figure 1:
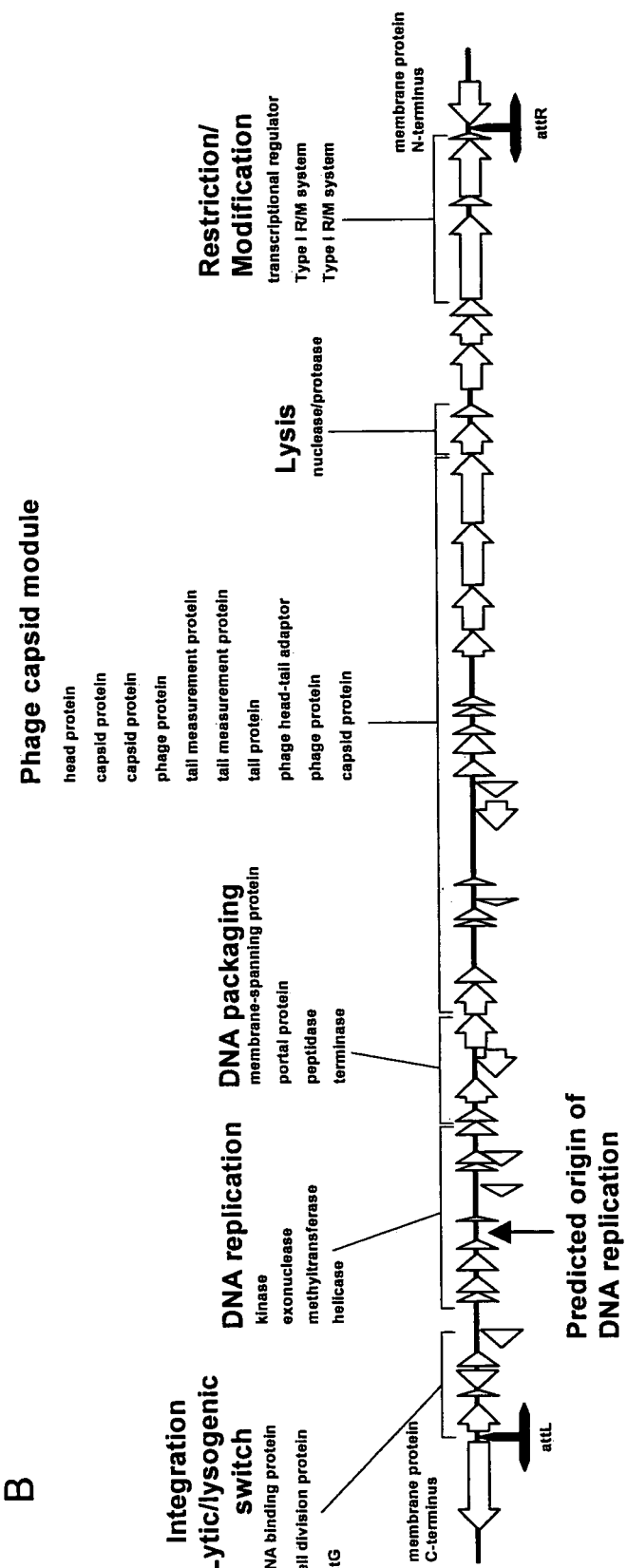
FIGS. 1A-1B. *M. ruminantium* prophage φmru showing putative integration site sequences attL and attR (FIG. 1A), and predicted phage functional modules and gene structure (FIG. 1B).
FIG. 1C: Phage induction using sterile air (oxygen stress).
FIG. 1D: Initial phage induction using MitomycinC.
FIG. 1E: Agarose gel electrophoresis of PCR amplicons of induced (oxygen challenge) and uninduced *M. ruminantium*. Lanes 2 and 4: 1 kb DNA marker ladder by Invitrogen. Lanes 1 and 3 represent PCRs using primer-pair R1F-L2R on DNA isolated from induced and uninduced *M. ruminantium* cultures, respectively.

The terms "cell inhibitor" or "inhibitor," as used herein, refer to agents that decrease or block the growth or replication of microbial cells, especially methanogen cells. A cell inhibitor can act to decrease or block, for example, cellular division. An inhibitor can decrease or block, for example, DNA synthesis, RNA synthesis, protein synthesis, or post-translational modifications. An inhibitor can also decrease or block the activity of enzymes involved in the methanogenesis pathway. An inhibitor can also target a cell for recognition by immune system components. Inhibition of a cell also includes cell killing and cell death, for example, from lysis, apoptosis, necrosis, etc. Useful inhibitors include, but are not limited to, anti-methanogenesis compounds (e.g., bromoethanesulphonic acid), antibodies and antibody fragments, lytic enzymes, peptide nucleic acids, antimicrobial peptides, and other antibiotics as described in detail herein.

The terms "complementary" or "complementarity," as used herein, refer to the natural binding of polynucleotides under permissive salt and temperature conditions by base-pairing. For the sequence A-G-T, the complementary sequence is T-C-A, the reverse complement is A-C-T and the reverse sequence is T-G-A. Complementarity between two single-stranded molecules may be partial, in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

The term "derivative", as used herein, refers to the chemical modification of a nucleic acid encoding a phage polypeptide, or a nucleic acid complementary thereto. Such modifications include, for example, replacement of hydrogen by an alkyl, acyl, or amino group. In preferred aspects, a nucleic acid derivative encodes a polypeptide which retains the biological or immunological function of the natural molecule. A derivative polypeptide is one which is modified by glycosylation, pegylation, or any similar process which retains one or more biological function (e.g., cell association, cell permeabilisation, or cell lysis) or immunological function of the sequence from which it was derived.

The term "homology", as used herein, refers to a degree of complementarity. There may be partial homology (i.e., I identity) or complete homology (i.e., 100% identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction.

The term "hybridization", as used herein, refers to any process by which a strand of nucleic acid binds with a complementary strand through base pairing.

An "insertion" or "addition", as used herein, refers to a change in an amino acid or nucleotide sequence resulting in the addition of one or more amino acid residues or nucleotides, respectively, as compared to the naturally occurring molecule.

A "methanogen," as used herein, refers to microbes that produce methane gas, which include *Methanobrevibacter, Methanothermobacter, Methanomicrobium, Methanobacterium*, and *Methanosarcina*. Specific methanogens include, but are not limited to, *Methanobrevibacter ruminantium, Methanobrevibacter smithii, Methanobrevibacter acididurans, Methanobrevibacter thaueri, Methanobacterium bryantii, Methanobacterium formicicum, Methanothermobacter marburgensis, Methanothermobacter wolfeii, Methanosphaera stadtmanae, Methanomicrobium mobile, Methanosarcina barkeri, Methanosarcina mazei, Methanococcoides burtonii*, and *Methanolobus taylorii*. The *Methanobrevibacter ruminantium* strain $M1^T$ is publicly available in depositories at the Leibniz Institute DSMZ-German Collection of Microorganisms and Cell Cultures; Braunschweig, Germany (DSM No. DSM1093) and at the American Type Culture Collection (ATCC; Manassas, Va., USA) (ATCC No. 35063). All methanogen genera and species are encompassed by this term.

"Microbial" cells as used herein, refers to naturally-occurring or genetically modified microbial cells including archaebacteria such as methanogens, halophiles, and thermoacidophiles, and eubacteria, such as cyanobacteria, spirochetes, proteobacteria, as well as gram positive and gram negative bacteria.

The term "modified" refers to altered sequences and to sequence fragments, variants, and derivatives, as described herein.

"Nucleic acid sequence" or "nucleotide sequence" as used herein, refers to a sequence of a polynucleotide, oligonucleotide, or fragments thereof, and to DNA or RNA of natural, recombinant, synthetic, or semi-synthetic origin which may be single or double stranded, and can represent the sense or antisense strand, and coding or non-coding regions. The sequences of the invention most preferably include polypeptide coding sequences that comprise at least 12, 15, 30, 45, 60, 75, 90, 105, 120, 135, 150, 300, 450, 600, 750 nucleotides, preferably at least 15 to 30, 30 to 60, 60 to 90, 90 to 120, 120 to 150, 150 to 300, 300 to 450, 450 to 600, or 600 to 750 nucleotides, or at least 1000 nucleotides, or at least 1500 nucleotides. It will be understood that each reference to a "nucleic acid sequence" or "nucleotide sequence" herein, will include the original, full-length sequence, as well as any complements, fragments, alterations, derivatives, or variants, thereof.

The term "oligonucleotide" refers to a nucleic acid sequence comprising at least 6, 8, 10, 12, 15, 18, 21, 25, 27, 30, or 36 nucleotides, or at least 12 to 36 nucleotides, or at least 15 to 30 nucleotides, which can be used, for example, in PCR amplification, sequencing, or hybridization assays. As used herein, oligonucleotide is substantially equivalent to the terms "amplimers," "primers," "oligomers," "oligos," and "probes," as commonly defined in the art.

"Polypeptide," as used herein, refers to the isolated polypeptides of the invention obtained from any species, preferably microbial, from any source whether natural, synthetic, semi-synthetic, or recombinant. Specifically, a phage polypeptide can be obtained from methanogen cells, such as *Methanobrevibacter* cells, in particular, *M. ruminantium*, or *M. smithii* cells. For recombinant production, a polypeptide of the invention can be obtained from microbial or eukaryotic cells, for example, *Escherichia, Streptomyces, Bacillus, Salmonella*, yeast, insect cells such as *Drosophila*, animal cells such as COS and CHO cells, or plant cells. It will be understood that each reference to a "polypeptide," herein, will include the original, full-length sequence, as well as any fragments, alternations, derivatives, or variants, thereof.

The term "polynucleotide," when used in the singular or plural, generally refers to any nucleic acid sequence, e.g., any polyribonucleotide or polydeoxyribonucleotide, which may be unmodified RNA or DNA or modified RNA or DNA. This includes, without limitation, single and double stranded DNA, DNA including single and double-stranded regions, single and double stranded RNA, and RNA including single and double stranded regions, hybrid molecules comprising DNA and RNA that may be single stranded or, more typically, double stranded or include single and double stranded regions. Also included are triple-stranded regions comprising RNA or DNA or both RNA and DNA. Specifically included are mRNAs, cDNAs, and genomic DNAs, and any fragments thereof. The term includes DNAs and RNAs that contain one or more modified bases, such as tritiated bases, or unusual bases, such as inosine. The polynucleotides of the invention can encompass coding or non-coding sequences, or sense or antisense sequences, or iRNAs such as siRNAs. It will be understood that each reference to a "polynucleotide" or like term, herein, will include the full length sequences as well as any complements, fragments, alterations, derivatives, or variants thereof.

"Peptide nucleic acid" or "PNA" as used herein, refers to an antisense molecule or anti-gene agent which comprises bases linked via a peptide backbone.

The term "ruminant," as used herein, refers to animals that have a rumen as a special type of digestive organ. Ruminants include, but are not limited to, cattle, sheep, goats, buffalo, moose, antelope, caribou, and deer.

The terms "stringent conditions" or "stringency," as used herein, refer to the conditions for hybridization as defined by the nucleic acid, salt, and temperature. These conditions are well known in the art and may be altered in order to identify or detect identical or related polynucleotide sequences. See, e.g., Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "subject" includes human and non-human animals. Non-human animals include, but are not limited to, birds and mammals, such as ruminants, and in particular, mice, rabbits, cats, dogs, pigs, sheep, goats, cows, and horses.

The terms "substantially purified" or "isolated" as used herein, refer to nucleic or amino acid sequences that are removed from their cellular, recombinant, or synthetic environment, and are at least 60% free, preferably 75% free, and most preferably at least 90% free or at least 99% free from other components with which they are associated in a cellular, recombinant, or synthetic environment.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of a polypeptide, as used herein, refers to an amino acid sequence that is altered by one or more amino acids. A variant polynucleotide is altered by one or more nucleotides. A variant may result in "conservative" changes, wherein a substituted amino acid has similar structural or chemical properties, e.g., replacement of leucine with isoleucine. More rarely, a variant may result in "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The invention also encompasses variants which retain at least one biological activity (e.g., cell association, cell permeabilisation, or cell lysis) or immunological activity of the polypeptide. A preferred variant is one having substantially the same or a functionally equivalent sequence, for example, at least 80%, and more preferably at least 90%, sequence identity to a disclosed sequence. A most preferred variant is one having at least 95%, at least 97%, at least 98%, at least 99%, at least 99.5%, at least 99.8%, or at least 99.9% sequence identity to a sequence disclosed herein. The percentage identity is determined by aligning the two sequences to be compared as described below, determining the number of identical residues in the aligned portion, dividing that number by the total number of residues in the inventive (queried) sequence, and multiplying the result by 100. A useful alignment program is AlignX (Vector NTI).

DESCRIPTION OF THE INVENTION

Methane is produced in the foregut of ruminants by methanogens which act as terminal reducers of carbon in the rumen system. The multi-step methanogenesis pathway is well elucidated, mainly from the study of non-rumen methanogens, but the adaptations that allow methanogens to grow and persist in the rumen are not well understood. *Methanobrevibacter ruminantium* is a prominent methanogen in New Zealand ruminants. As described herein, the genome of *M. ruminantium* has been sequenced and shown as approximately 3.0 Mb in size with a GC content of 33.68%. As an unexpected finding, the *M. ruminantium* genome was found to include a prophage sequence (designated ϕmru) with distinct functional modules encoding phage integration, DNA replication and packaging, capsid proteins, lysis, and lysogenic conversion functions.

The *M. ruminantium* phage was identified during high through-put sequencing, when a 30 to 40 kb region of the genome was found to be over-represented in the sequenced clones. This suggested that a part of the genome was present in higher copy number than normal, and could be attributed to the replication of a resident phage. The over-represented region was investigated and detailed bioinformatic analyses of the predicted open reading frames present indicated that it contained phage-like genes. A low GC region found at the distal end of the phage sequence (lysogenic conversion) has been shown to harbour a predicted DNA modification system by sulphur (dnd) which might provide additional modification of host or foreign DNA. The *M. ruminantium* prophage sequence is described in detail herein. In various aspects of the invention, the prophage polynucleotides and polypeptides can be used as a means for inhibiting methanogens and/or methanogenesis in the rumen, and to further elucidate the role of *M. ruminantium* in methane formation.

The invention therefore encompasses phage polypeptides, including those comprising at least one of SEQ ID NO:1-69, and fragments, variants, and derivatives thereof. The invention also encompasses the use of these polypeptides for targeting and inhibiting microbial cells, especially methanogen cells. The invention further encompasses the use of the polypeptides for the inhibition of growth or replication of such cells. The polypeptides of the present invention may be expressed and used in various assays to determine their biological activity. The polypeptides may be used for large-scale synthesis and isolation protocols, for example, for commercial production. Such polypeptides may be used to raise antibodies, to isolate corresponding amino acid sequences, and to quantitatively determine levels of the amino acid sequences. The polypeptides of the present invention may also be used as compositions, for example, pharmaceutical compositions, and as food supplements, e.g., ruminant feed components. The polypeptides of the present invention also have health benefits. In heath-related aspects, inhibitors of methanogens can be used to restore energy to the subject that is normally lost as methane. In particular aspects, slow-release ruminal devices can be used in conjunction with the polypeptides, and compositions (e.g., pharmaceutical compositions and food supplements) of the invention.

The polypeptides of the present invention comprise at least one sequence selected from the group consisting of: (a) polypeptides comprising at least one amino acid sequence selected from the group consisting of SEQ ID NO:1-69, or fragments, variants, or derivatives thereof; (b) polypeptides comprising a functional domain of at least one amino acid sequence selected from the group consisting of SEQ ID NO:1-69, and fragments and variants thereof; and (c) polypeptides comprising at least a specified number of contiguous residues of at least one amino acid sequence selected from the group consisting of SEQ ID NO:1-69, or variants or derivatives thereof. In one embodiment, the invention encompasses an isolated polypeptide comprising the amino acid sequence of at least one of SEQ ID NO:1-69. All of these sequences are collectively referred to herein as polypeptides of the invention.

The invention also encompasses polynucleotides that encode at least one phage polypeptide, including those of SEQ ID NO:1-69, and fragments, variants, and derivatives thereof. The invention also encompasses the use of these polynucleotides for preparing expression vectors and host cells for targeting and inhibiting microbial cells, especially methanogen cells. The invention further encompasses the use of the polynucleotides for the inhibition of growth or replication of such cells. The isolated polynucleotides of the present invention also have utility in genome mapping, in physical mapping, and in cloning of genes of more or less related phage. Probes designed using the polynucleotides of the present invention may be used to detect the presence and examine the expression patterns of genes in any organism having sufficiently homologous DNA and RNA sequences in their cells, using techniques that are well known in the art, such as slot blot techniques or microarray analysis. Primers designed using the polynucleotides of the present invention may be used for sequencing and PCR amplifications. The polynucleotides of the present invention may also be used as compositions, for example, pharmaceutical compositions, and as food supplements, e.g., ruminant feed components. The polynucleotides of the present invention also have health benefits. For such benefits, the polynucleotides can be presented as expression vectors or host cells comprising expression vectors. In particular aspects, slow-release ruminal devices can be used in conjunction with the polynucleotides, vectors, host cells, and compositions (e.g., pharmaceutical compositions and food supplements) of the invention.

The polynucleotides of the present invention comprise at least one sequence selected from the group consisting of: (a) sequences comprising a coding sequence for at least one amino acid sequence selected from the group consisting of SEQ ID NO:1-69, or fragments or variants thereof; (b) complements, reverse sequences, and reverse complements of a coding sequence for at least one amino acid sequence selected from the group consisting of SEQ ID NO:1-69, or fragments or variants thereof; (c) open reading frames contained in the coding sequence for at least one amino acid sequence selected from the group consisting of SEQ ID NO:1-69, and their fragments and variants; (d) functional domains of a coding sequence for at least one amino acid sequence selected from the group consisting of SEQ ID NO:1-69, and fragments and variants thereof; and (e) sequences comprising at least a specified number of contiguous residues of a coding sequence for at least one amino acid sequence selected from the group consisting of SEQ ID NO:1-69, or variants thereof. In one embodiment, the invention encompasses an isolated polynucleotide comprising a coding sequence for at least one amino acid sequence selected from the group consisting of SEQ ID NO:1-69.

The polynucleotides of the present invention comprise at least one sequence selected from the group consisting of: (a) sequences comprising at least one nucleic acid sequence selected from the group consisting of SEQ ID NO:74-142, or fragments or variants thereof; (b) complements, reverse sequences, and reverse complements of a coding sequence for at least one nucleic acid sequence selected from the group consisting of SEQ ID NO:74-142, or fragments or variants thereof; (c) open reading frames contained in the nucleic acid sequence selected from the group consisting of SEQ ID NO:74-142, and their fragments and variants; (d) functional domains of a coding sequence of at least one nucleic acid sequence selected from the group consisting of SEQ ID NO:74-142, and fragments and variants thereof; and (e) sequences comprising at least a specified number of contiguous residues of at least one nucleic acid sequence selected from the group consisting of SEQ ID NO:74-142, or variants thereof. Oligonucleotide probes and primers and their variants obtained from any of the disclosed sequences are also provided. All of these polynucleotides and oligonucleotides are collectively referred to herein, as polynucleotides of the invention.

It will be appreciated by those skilled in the art that as a result of the degeneracy of the genetic code, a multitude of nucleotide sequences encoding the polypeptides of the invention, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard bacterial triplet genetic code as applied to naturally occurring amino acid sequences, and all such variations are to be considered as being specifically disclosed.

Nucleotide sequences which encode the phage polypeptides, or their fragments or variants, are preferably capable of hybridizing to the nucleotide sequence of the naturally occurring sequence under appropriately selected conditions of stringency. However, it may be advantageous to produce nucleotide sequences encoding a polypeptide, or its fragment or derivative, possessing a substantially different codon usage. Codons may be selected to increase the rate at which expression of the polypeptide occurs in a particular prokaryotic or eukaryotic host in accordance with the frequency with which particular codons are utilized by the host. For example, codons can be optimized for expression in E. coli in accordance with known methods. Other reasons for substantially altering the nucleotide sequence encoding polypeptides and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode the polypeptides, or their fragments or variants, entirely by synthetic chemistry. After production, the synthetic sequence may be inserted into any of the many available expression vectors and cell systems using reagents that are well known in the art. Moreover, synthetic chemistry may be used to introduce mutations into a sequence encoding a polypeptide, or any variants or fragment thereof. Also encompassed by the invention are polynucleotide sequences that are capable of hybridizing to the claimed nucleotide sequences, and in particular, those shown in SEQ ID NO:74-149, or their complements, under various conditions of stringency as taught in Wahl, G. M. and S. L. Berger (1987; Methods Enzymol. 152:399-407) and Kimmel, A. R. (1987; Methods Enzymol. 152:507-511).

Methods for DNA sequencing which are well known and generally available in the art and may be used to practice any of the embodiments of the invention. The methods may employ such enzymes as the Klenow fragment of DNA polymerase I, SEQUENASE (U.S. Biochemical Corp, Cleveland, Ohio), Taq polymerase (Perkin Elmer), thermostable T7 polymerase Amersham Pharmacia Biotech (Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) the ABI Catalyst and 373 and 377 DNA Sequencers (Perkin Elmer), or the Genome Sequencer 20™ (Roche Diagnostics).

The nucleic acid sequences encoding the polypeptides may be extended utilizing a partial nucleotide sequence and employing various methods known in the art to detect upstream sequences such as promoters and regulatory elements, and downstream elements such as terminators and non-coding RNA structures. For example, one method which may be employed, "restriction-site" PCR, uses universal primers to retrieve unknown sequence adjacent to a known locus (Sarkar, G. (1993) PCR Methods Applic. 2:318-322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Another useful method is inverse PCR, also called IPCR (see, e.g., Ochman H, Gerber A S, Hartl D L. Genetics. 1988 November; 120(3):621-3). Inverse PCR can be employed when only one internal sequence of the target DNA is known. The inverse PCR method includes a series of digestions and self-ligations with the DNA being cut by a restriction endonuclease. This cut results in a known sequence at either end of unknown sequences. In accordance with this method, target DNA is lightly cut into smaller fragments of several kilobases by restriction endonuclease digestion. Self-ligation is then induced under low concentrations causing the phosphate backbone to reform and produce a circular DNA ligation product. Target DNA is then restriction digested with a known endonuclease. This generates a cut within the known internal sequence generating a linear product with known terminal sequences. This product can then be used for standard PCR conducted with primers complementary to the known internal sequences.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

Recently, pyrosequencing has emerged as a useful sequencing methodology. See, e.g., Ronaghi, M. et al. 1996. Real-time DNA sequencing using detection of pyrophosphate release. Anal. Biochem. 242: 84-89; Ronaghi, M. et al. 1998. A sequencing method based on real-time pyrophosphate. Science 281: 363-365; Ronaghi, M. et al. 1999. Analyses of secondary structures in DNA by pyrosequencing. Anal. Biochem. 267: 65-71; Ronaghi 2001. Genome Res. Vol. 11, Issue 1, 3-11; Nyrén The history of pyrosequencing. Methods Mol. Biol. 2007; 373:1-14. Pyrosequencing has the advantages of accuracy, flexibility, parallel processing, and can be easily automated. Furthermore, the technique dispenses with the need for labeled primers, labeled nucleotides, and gel-electrophoresis. In accordance with this method, polymerase catalyzes incorporation of nucleotides into a nucleic acid chain. As a result of the incorporation, pyrophosphate molecules are released and subsequently converted by sulfurylase to ATP. Light is produced in the luciferase reaction during which a luciferin molecule is oxidized. After each nucleotide addition, a washing step is performed to allow iterative addition. The nucleotides are continuously degraded by nucleotide-degrading enzyme allowing addition of subsequent nucleotide. Pyrosequencing has been successfully applied as a platform for large-scale sequencing, including genomic and metagenomic analysis (see, e.g., The Genome Sequencer FLX™ from 454 Life Sciences/Roche).

The SOLiD™ System has also been developed for sequencing (see, e.g., Applied Biosystems. Application Fact Sheet for the SOLiD™ System. Foster City, Calif.). This methodology is based on sequential ligation of dye-labeled oligonucleotides to clonally amplified DNA fragments linked to magnetic beads. In this method, the DNA sequence is generated by measuring serial ligation. The ligation reaction is based on probe recognition, not sequential addition, and is therefore less prone to accumulation of errors. The nature of the chemistry virtually eliminates the possibility of spurious insertions or deletions. The ligation step and phosphatase treatment of unligated probes prevents dephasing. In addition, after seven cycles of ligation, the original primer is stripped from the template and a new primer is hybridized to begin interrogating at the n−1 position. Use of this "reset" phase allows for reduction in systemic noise and allows for longer read lengths. In addition, two base encoding is used to discriminate between measurement errors as opposed to true polymorphisms. Changes at a single position are identified as random errors and can be removed by the software in data analysis. As an analytical platform, the SOLiD™ System has applications in large-scale sequencing, digital gene expression, ChIP and methylation studies, and is particularly useful for detecting genomic variation.

In another embodiment of the invention, polynucleotides or fragments thereof which encode polypeptides may be used in recombinant DNA molecules to direct expression of the polypeptides, or fragments or variants thereof, in appropriate host cells. Due to the inherent degeneracy of the genetic code, other DNA sequences which encode substantially the same or a functionally equivalent amino acid sequence may be produced, and these sequences may be used to clone and express phage polypeptides. The nucleotide sequences of the present invention can be engineered using methods generally known in the art in order to alter amino acid-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, introduce mutations, and so forth.

In another embodiment of the invention, natural, modified, or recombinant nucleic acid sequences encoding polypeptides may be ligated to a heterologous sequence to encode a fusion protein. For example, it may be useful to encode a chimeric sequence that can be recognized by a commercially available antibody. A fusion protein may also be engineered to contain a cleavage site located between the polypeptide of the invention and the heterologous protein sequence, so that the polypeptide may be cleaved and purified away from the heterologous moiety.

In another embodiment, sequences encoding polypeptides may be synthesized, in whole or in part, using chemical methods well known in the art (see Caruthers, M. H. et al. (1980) Nucl. Acids Res. Symp. Ser. 215-223, Horn, T. et al. (1980) Nucl. Acids Res. Symp. Ser. 225-232). Alternatively, the polypeptide itself may be produced using chemical methods to synthesize the amino acid sequence, or a fragment thereof. For example, polypeptide synthesis can be performed using various solid-phase techniques (Roberge, J. Y. et al. (1995) Science 269:202-204; Merrifield J. (1963) J. Am. Chem. Soc. 85:2149-2154) and automated synthesis may be achieved, for example, using the ABI 431A Peptide Synthesizer (Perkin Elmer). Various fragments of polypeptides may be chemically synthesized separately and combined using chemical methods to produce the full length molecule.

The newly synthesized polypeptide may be isolated by preparative high performance liquid chromatography (e.g., Creighton, T. (1983) Proteins Structures and Molecular Principles, WH Freeman and Co., New York, N.Y.). The composition of the synthetic polypeptides may be confirmed by amino acid analysis or sequencing (e.g., the Edman degradation procedure; Creighton, supra). Additionally, the amino acid sequence of the polypeptide, or any part thereof, may be altered during direct synthesis and/or combined using chemical methods with sequences from other proteins, or any part thereof, to produce a variant molecule.

In order to express biologically active polypeptides, the nucleotide sequences encoding the polypeptide or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding the polypeptide and appropriate transcriptional and translational control elements. These methods include in vitro recombinant DNA techniques, synthetic techniques, and in vivo genetic recombination. Such techniques are described in Sambrook, J. et al. (2001) Molecular Cloning, A Laboratory Manual, Cold Spring Harbor Press, Plainview, N.Y., and Ausubel, F. M. et al. (2007) Current Protocols in Molecular Biology, John Wiley & Sons, New York, N.Y.

A variety of expression vector/host systems may be utilized to contain and express sequences encoding the polypeptides of the invention. These include, but are not limited to, microorganisms such as bacteria transformed with recombinant phage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. For bacteria, useful plasmids include pET, pRSET, pTrcHis2, and pBAD plasmids from Invitrogen, pET and pCDF plasmids from Novagen, and Director plasmids from Sigma-Aldrich. For methanogens, useful plasmids include, but are not limited to pME2001, pMV15, and pMP1. In particular, *Escherichia coli* can be used with the expression vector pET. The invention is not limited by the expression vector or host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector.

In bacterial systems, a number of expression vectors may be selected depending upon the use intended for the polypeptide. For example, when large quantities of polypeptide are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding a polypeptide may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503-5509); and the like.

pGEX vectors (Promega, Madison, Wis.) may also be used to express the polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor Xa protease cleavage sites so that the cloned polypeptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516-544.

Specific initiation signals may also be used to achieve more efficient translation of sequences encoding the polypeptides of the invention. Such signals include the ATG initiation codon and adjacent sequences. In cases where sequences encoding a polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed polypeptide in the desired fashion. Such modifications of the sequence include, but are not limited to, acetylation, carboxylation, glycosylation, phosphorylation, lipidation, and acylation. Post-translational processing which cleaves a "prepro" form of the polypeptide may also be used to facilitate correct insertion, folding, and/or function. Different host cells which have specific cellular machinery and characteristic mechanisms for post-translational activities are available from the American Type Culture Collection (ATCC; Bethesda, Md.) and may be chosen to ensure the correct modification and processing of the sequence. Specific host cells include, but are not limited to, methanogen cells, such as *Methanobrevibacter* cells, in particular, *M. ruminantium*, or *M. smithii* cells. Host cells of interest include, for example, *Rhodotorula, Aureobasidium, Saccharomyces, Sporobolomyces, Pseudomonas, Erwinia* and *Flavobacterium*; or such other organisms as *Escherichia, Lactobacillus, Bacillus, Streptomyces*, and the like. Specific host cells include *Escherichia coli*, which is particularly suited for use with the present invention, *Saccharomyces cerevisiae, Bacillus thuringiensis, Bacillus subtilis, Streptomyces lividans*, and the like.

There are several techniques for introducing nucleic acids into eukaryotic cells cultured in vitro. These include chemical methods (Feigner et al., Proc. Natl. Acad. Sci., USA, 84:7413 7417 (1987); Bothwell et al., Methods for Cloning and Analysis of Eukaryotic Genes, Eds., Jones and Bartlett Publishers Inc., Boston, Mass. (1990), Ausubel et al., Short Protocols in Molecular Biology, John Wiley and Sons, New York, N.Y. (1992); and Farhood, Annal. NY Acad. Sci., 716:23 34 (1994)), use of protoplasts (Bothwell, supra) or electrical pulses (Vatteroni et al., Mutn. Res., 291:163 169 (1993); Sabelnikov, Prog. Biophys. Mol. Biol., 62: 119 152 (1994); Bothwell et al., supra; and Ausubel et al., supra), use of attenuated viruses (Davis et al., J. Virol. 1996, 70(6), 3781 3787; Brinster et al. J. Gen. Virol. 2002, 83(Pt 2), 369 381; Moss, Dev. Biol. Stan., 82:55 63 (1994); and Bothwell et al., supra), as well as physical methods (Fynan et al., supra; Johnston et al., Meth. Cell Biol., 43(Pt A):353 365 (1994); Bothwell et al., supra; and Ausubel et al., supra).

Successful delivery of nucleic acids to animal tissue can be achieved by cationic liposomes (Watanabe et al., Mol. Reprod. Dev., 38:268 274 (1994)), direct injection of naked DNA or RNA into animal muscle tissue (Robinson et al., Vacc., 11:957 960 (1993); Hoffman et al., Vacc. 12:1529 1533; (1994); Xiang et al., Virol., 199:132 140 (1994); Webster et al., Vacc., 12:1495 1498 (1994); Davis et al., Vacc., 12:1503.1509 (1994); Davis et al., Hum. Molec. Gen., 2:1847 1851 (1993); Dalemans et al. Ann NY Acad. Sci. 1995, 772, 255 256. Conry, et al. Cancer Res. 1995, 55(7), 1397-1400), and embryos (Naito et al., Mol. Reprod. Dev., 39:153 161 (1994); and Burdon et al., Mol. Reprod. Dev., 33:436 442 (1992)), intramuscular injection of self replicating RNA vaccines (Davis et al., J Virol 1996, 70(6), 3781 3787; Balasuriya et al. Vaccine 2002, 20(11 12), 1609 1617) or intradermal injection of DNA using "gene gun" technology (Johnston et al., supra).

A variety of protocols for detecting and measuring the expression of the polypeptides of the invention, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay can be used with monoclonal antibodies reactive to two non-interfering epitopes on the polypeptide, but a competitive binding assay can also be used. These and other assays are described, among other places, in Hampton, R. et al. (1990; Serological Methods, a laboratory Manual, APS Press, St Paul, Minn.) and Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences encoding the polypeptides, or any fragments or variants thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and US Biochemical. Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Expression vectors or host cells transformed with expression vectors may be replicated under conditions suitable for the expression and recovery of the polypeptide from culture. The culture can comprise components for in vitro or in vivo expression. In vitro expression components include those for rabbit reticulocyte lysates, *E. coli* lysates, and wheat germ extracts, for example, Expressway™ or RiPs systems from Invitrogen, Genelator™ systems from iNtRON Biotechnology, EcoPro™ or STP3™ systems from Novagen, TNT® Quick Coupled systems from Promega, and EasyXpress systems from QIAGEN. The polypeptide produced from culture may be secreted or contained intracellularly depending on the sequence and/or the vector used. In particular aspects, expression vectors which encode a phage polypeptide can be designed to contain signal sequences which direct secretion of the polypeptide through a prokaryotic or eukaryotic cell membrane.

Other constructions may include an amino acid domain which will facilitate purification of the polypeptide. Such domains include, but are not limited to, metal chelating peptides such as histidine-tryptophan (e.g., 6X-HIS (SEQ ID NO: 150)) modules that allow purification on immobilized metals, protein A domains that allow purification on immobilized immunoglobulin, and the domain utilized in the FLAG® extension/affinity purification system (Immunex Corp., Seattle, Wash.). Useful epitope tags include 3XFLAG®, HA, VSV-G, V5, HSV, GST, GFP, MBP; GAL4, and β-galactosidase. Useful plasmids include those comprising a biotin tag (e.g., PinPoint™ plasmids from Promega), calmodulin binding protein (e.g., pCAL plasmids from Stratagene), streptavidin binding peptide (e.g., InterPlay™ plasmids from Stratagene), a c-myc or FLAG® tag (e.g., Immunoprecipitation plasmids from Sigma-Aldrich), or a histidine tag (e.g., QIAExpress plasmids from QIAGEN).

To facilitate purification, expression vectors can include a cleavable linker sequences such as those specific for Factor Xa or enterokinase (Invitrogen, San Diego, Calif.). For example, the vector can include one or more linkers between the purification domain and the polypeptide. One such expression vector provides for expression of a fusion protein comprising a polypeptide of the invention and a nucleic add encoding 6 histidine residues preceding a thioredoxin or an enterokinase cleavage site. The histidine residues facilitate purification on IMAC (immobilized metal ion affinity chromatography as described in Porath, J. et al. (1992) Prot. Exp. Purif. 3: 263-281) while the enterokinase cleavage site provides a means for purifying the polypeptide from the fusion protein. A discussion of vectors which contain fusion proteins is provided in Kroll, D. J. et al. (1993; DNA Cell Biol. 12:441-453).

Antibodies of the invention may be produced using methods which are generally known in the art, for example, for use in purification or diagnostic techniques. In particular, polypeptides or polynucleotides may be used to produce antibodies in accordance with generally known protocols. Such antibodies may include, but are not limited to, polyclonal, monoclonal, chimeric, and single chain antibodies, Fab fragments, and fragments produced by a Fab expression library. Neutralizing antibodies, (i.e., those which inhibit function) are especially preferred for use with the invention.

For the production of antibodies, various hosts including goats, rabbits, rats, mice, humans, and others, may be immunized by injection with a polypeptide, polynucleotide, or any fragment thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the polypeptides or fragments used to induce antibodies have an amino acid sequence comprising at least five amino acids and more preferably at least 10 amino acids. It is also preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin and antibody produced against the chimeric, molecule.

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell. Biol. 62:109-120). Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86:3833-3837; Winter, G. et al. (1991) Nature 349:293-299).

In addition, techniques can be used for the production of "chimeric antibodies", e.g., the combining of antibody genes to obtain a molecule with appropriate antigen specificity and biological activity (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120-3).

Those of skill in the art to which the invention relates will appreciate the terms "diabodies" and "triabodies". These are molecules which comprise a heavy chain variable domain (VH) connected to a light chain variable domain (VL) by a short peptide linker that is too short to allow pairing between the two domains on the same chain. This promotes pairing with the complementary domains of one or more other chains and encourages the formation of dimeric or trimeric molecules with two or more functional antigen binding sites. The resulting antibody molecules may be monospecific or multispecific (e.g., bispecific in the case of diabodies). Such antibody molecules may be created from two or more antibodies using methodology standard in the art to which the invention relates; for example, as described by Todorovska et al. (Design and application of diabodies, triabodies and tetrabodies for cancer targeting. J. Immunol. Methods. 2001 Feb. 1; 248 (1-2):47-66).

Antibody fragments which contain specific binding sites may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse, W. D. et al. (1989) Science 254: 1275-1281).

Various immunoassays may be used for screening to identify antibodies having binding specificity. Numerous protocols for competitive binding or immunoradiometric assays using either polyclonal or monoclonal antibodies with established specificities are well known in the art. Such immunoassays typically involve the measurement of complex formation between a polypeptide or polynucleotide and its specific antibody. A two-site, monoclonal-based immunoassay utilizing monoclonal antibodies reactive to two non-interfering epitopes is preferred, but a competitive binding assay may also be employed (Maddox, supra).

The phage polypeptides described herein have the ability to target, permeabilise, and/or inhibit cells and are also useful as carrier molecules for the delivery of additional inhibitory molecules into microbial cells. The chemistry for coupling compounds to amino acids is well developed and a number of different molecule types could be linked to the polypeptides. The most common coupling methods rely on the presence of free amino (alpha-amino or Lys), sulfhydryl (Cys), or carboxylic acid groups (Asp, Glu, or alpha-carboxyl). Coupling methods can be used to link the polypeptide to the cell inhibitor via the carboxy- or amino-terminal residue. In some cases, a sequence includes multiple residues that may react with the chosen chemistry. This can be used to produce multimers, comprising more than one cell inhibitor. Alternatively, the polypeptide can be shortened or chosen so that reactive residues are localized at either the amino or the carboxyl terminus of the sequence.

For example, a reporter molecule such as fluorescein can be specifically incorporated at a lysine residue (Ono et al., 1997) using N-α-Fmoc-NE-1-(4,4-dimethyl-2,6 dioxocyclohex-1-ylidene-3-methylbutyl)-L-lysine during polypeptide synthesis. Following synthesis, 5- and 6-carboxyfluorescein succinimidyl esters can be coupled after 4,4-dimethyl-2,6 dioxocyclohex-1-ylidene is removed by treatment with hydrazine. Therefore coupling of an inhibitory molecule to the phage polypeptide can be accomplished by inclusion of a lysine residue to the polypeptide sequence, then reaction with a suitably derivatised cell inhibitor.

EDC (1-ethyl-3-(3-dimethylaminopropyl) carbodiimide hydrochloride) or the carbodiimide coupling method can also be used. Carbodiimides can activate the side chain carboxylic groups of aspartic and glutamic acid as well as the carboxyl-terminal group to make them reactive sites for coupling with primary amines. The activated polypeptides are mixed with the cell inhibitor to produce the final conjugate. If the cell inhibitor is activated first, the EDC method will couple the cell inhibitor through the N-terminal alpha amine and possibly through the amine in the side-chain of Lys, if present in the sequence.

m-Maleimidobenzoyl-N-hydroxysuccinimide ester (MBS) is a heterobifunctional reagent that can be used to link polypeptides to cell inhibitors via cysteines. The coupling takes place with the thiol group of cysteine residues. If the chosen sequence does not contain Cys it is common to place a Cys residue at the N- or C-terminus to obtain highly controlled linking of the polypeptide to the cell inhibitor. For synthesis purposes, it may be helpful for the cysteine to be placed at the N-terminus of the polypeptide. MBS is particularly suited for use with the present invention.

Glutaraldehyde can be used as a bifunctional coupling reagent that links two compounds through their amino groups. Glutaraldehyde provides a highly flexible spacer between the polypeptide and cell inhibitor for favorable presentation. Glutaraldehyde is a very reactive compound and will react with Cys, Tyr, and His to a limited extent. The glutaraldehyde coupling method is particularly useful when a polypeptide contains only a single free amino group at its amino terminus. If the polypeptide contains more than one free amino group, large multimeric complexes can be formed.

In one aspect, the polypeptides of the invention can be fused (e.g., by in-frame cloning) or linked (e.g., by chemical coupling) to cell inhibitors such as antimicrobial agents. Included among these are antimicrobial peptides, for example, bactericidal/permeability-increasing protein, cationic antimicrobial proteins, lysozymes, lactoferrins, and cathelicidins (e.g., from neutrophils; see, e.g., Hancock and Chapple, 1999, Antimicrob. Agents Chemother. 43:1317-1323; Ganz and Lehrer, 1997, Curr. Opin. Hematol. 4:53-58; Hancock et al., 1995, Adv. Microb. Physiol. 37:135-175). Antimicrobial peptides further include defensins (e.g., from epithelial cells or neutrophils) and platelet microbiocidal proteins (see, e.g., Hancock and Chapple, 1999, Antimicrob. Agents Chemother. 43:1317-1323). Additional antimicrobial peptides include, but are not limited to, gramicidin S, bacitracin, polymyxin B, tachyplesin, bactenecin (e.g., cattle bactenecin), ranalexin, cecropin A, indolicidin (e.g., cattle indolicidin), and nisin (e.g., bacterial nisin).

Also included as antimicrobial agents are ionophores, which facilitate transmission of an ion, (such as sodium), across a lipid barrier such as a cell membrane. Two ionophore compounds particularly suited to this invention are the RUMENSIN™ (Eli Lilly) and Lasalocid (Hoffman LaRoche). Other ionophores include, but are not limited to, salinomycin, avoparcin, aridcin, and actaplanin. Other antimicrobial agents include penicillin, Monensin™ and azithromycin, metronidazole, streptomycin, kanamycin, and penicillin, as well as, generally, β-lactams, aminoglycosides, macrolides, chloramphenicol, novobiocin, rifampin, and fluoroquinolones (see, e.g., Horn et al., 2003, Applied Environ. Microbiol. 69:74-83; Eckburg et al., 2003, Infection Immunity 71:591-596; Gijzen et al., 1991, Applied Environ. Microbiol. 57:1630-1634; Bonelo et al., 1984, FEMS Microbiol. Lett. 21:341-345; Huser et al., 1982, Arch. Microbiol. 132:1-9; Hilpert et al., 1981, Zentbl. Bakteriol. Mikrobiol. Hyg. 1 Abt Orig. C 2:21-31).

Particularly useful inhibitors are compounds that block or interfere with methanogenesis, including bromoethanesulphonic acid, e.g., 2-bromoethanesulphonic acid (BES) or a salt thereof, for example, a sodium salt. Sodium molybdate (Mo) is an inhibitor of sulfate reduction, and can be used with bromoethanesulphonic acid. Other anti-methanogenesis compounds include, but are not limited to, nitrate, formate, methyl fluoride, chloroform, chloral hydrate, sodium sulphite, ethylene and unsaturated hydrocarbons, acetylene, fatty acids such as linoleic and cis-oleic acid, saturated fatty acids such as behenic and stearic acid, and, also lumazine (e.g., 2,4-pteridinedione). Additional compounds include 3-bromopropanesulphonate (BPS), propynoic acid, and ethyl 2-butynoate.

Further included as antimicrobial agents are lytic enzymes, including phage lysozyme, endolysin, lysozyme, lysin, phage lysin, muralysin, muramidase, and virolysin. Useful enzymes exhibit the ability to hydrolyse specific bonds in the bacterial cell wall. Particular lytic enzymes include, but are not limited to, glucosaminidases, which hydrolyse the glycosidic bonds between the amino sugars (e.g., N-acetylmuramic acid and N-acetylglucosamine) of the peptidoglycan, amidases, which cleave the N-acetylmuramoyl-L-alanine amide linkage between the glycan strand and the cross-linking peptide, and endopeptidases, which hydrolyse the interpeptide linkage (e.g., cysteine endopeptidases) and endoisopeptidases that attack pseudomurein of methanogens from the family Methanobacteriacaea.

The polypeptides encoded by ORF 2058 or ORF 2055, described in detail herein and below, are useful as rumen methanogen-specific lytic enzymes. The native enzymes can be prepared from freshly φmru-lysed *M. ruminantium* cells. Alternatively, ORF 2058 or ORF 2055 can be cloned in an expression vector and expressed in a heterologous host such as *Escherichia coli*. This was accomplished previously with PeiP and PeiW and the recombinant proteins were shown to be active against *Methanothermobacter* cell walls under reducing conditions (Luo et al., 2002). ORF 2058 or ORF 2055 lytic enzymes or any other lytic enzyme can be used in compositions, for example, as a feed additive for ruminants or it can be incorporated into a slow release capsule or bolus device for delivery over a longer time period within the rumen. The lytic enzymes can be used either in combination or sequentially with other methanogen inhibitor(s) to avoid adaptation of the host methanogens and resistance to the enzymes. Random and/or targeted mutations in the enzymes can also be used to avoid adaptation. The lytic/lysogenic switch components (e.g., ORF 1981 and ORF 1983-ORF 1986) can be used in a similar manner as the lytic enzymes Additionally, PNAs are included as antimicrobial agents. PNAs are peptide-nucleic acid hybrids in which the phosphate backbone has been replaced by an achiral and neutral backbone made from N-(2-aminoethyl)-glycine units (see, e.g., Eurekah Bioscience Collection. PNA and Oligonucleotide Inhibitors of Human Telomerase. G. Gavory and S. Balasubramanian, Landes Bioscience, 2003). The bases A, G, T, C are attached to the amino nitrogen on the backbone via methylenecarbonyl linkages (P. E. Nielsen et al., Science 1991. 254: 1497-1500; M. Egholm et al., Nature 1993. 365: 566-568). PNAs bind complementary sequences with high specificity, and higher affinity relative to analogous DNA or RNA (M. Egholm et al., supra). PNA/DNA or PNA/RNA hybrids also exhibit higher thermal stability compared to the corresponding DNA/DNA or DNA/RNA duplexes (M. Egholm et al., supra). PNAs also possess high chemical and biological stability, due to the unnatural amide backbone that is not recognized by nucleases or proteases (V. Demidov et al., Biochem Pharmacol 1994. 48: 1310-1313). Typically, PNAs are at least 5 bases in length, and include a terminal lysine. PNAs may be pegylated to further extend their lifespan (Nielsen, P. E. et al. (1993) Anticancer Drug Des. 8:53-63).

In one particular aspect, the polypeptides of the invention can be fused (e.g., by in-frame cloning) or linked (e.g., by chemical coupling) to cell inhibitors such as antibodies or fragments thereof. The antibodies or antibody fragments can be directed to microbial cells, or particularly methanogen cells, or one or more cell components. For example, cell surface proteins, e.g., extracellular receptors, can be targeted. Included are immunoglobulin molecules and immunologically active portions of immunoglobulin (Ig) molecules, i.e., molecules that contain an antigen binding site that specifically binds (immunoreacts with) an antigen.

Figure 6:
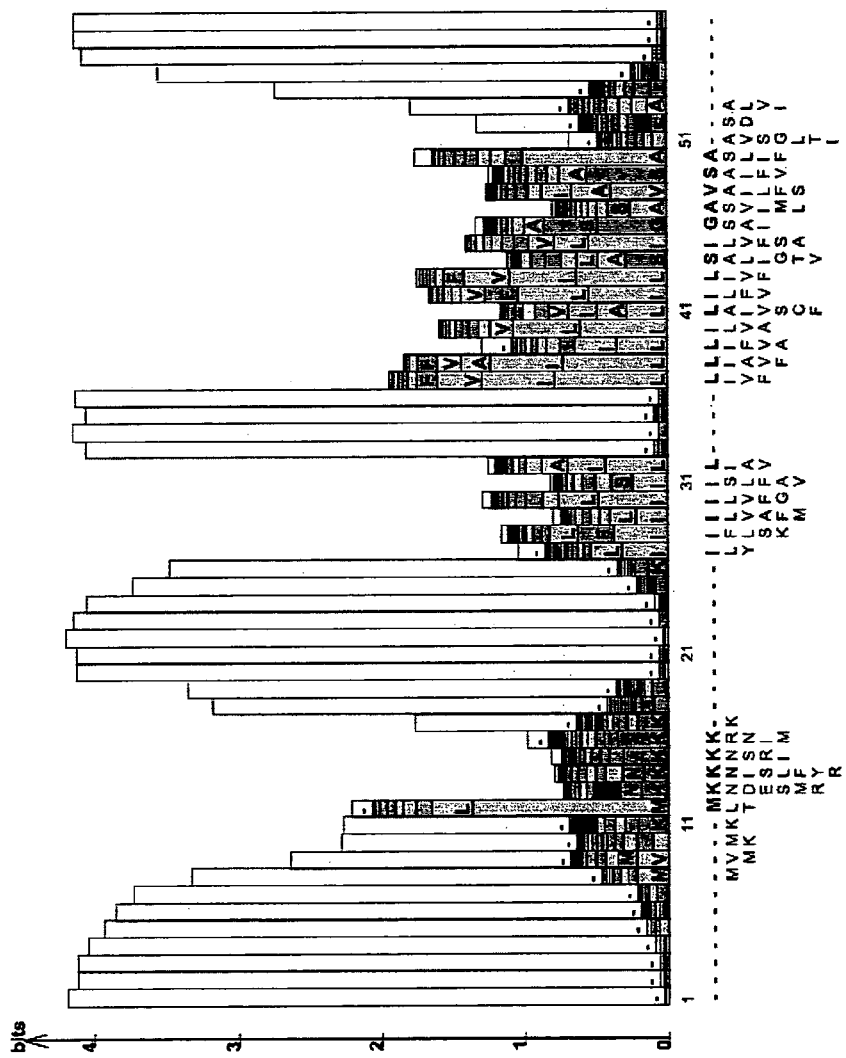
FIG. 6.

The polypeptides of the invention find particular use in targeting a microbial cell, in particular, a methanogen cell. In certain aspects, the polypeptides can be used to associate with or bind to the cell wall or membrane, permeabilise the cell, and/or inhibit growth or replication of the cell. As such, the polypeptides can be used for transient or extended attachment to the cell, or to penetrate the cell wall or membrane and/or accumulate in the intracellular environment. It is understood that the phage polypeptides, as well as the corresponding polynucleotides, expression vectors, host cells, and antibodies of the invention, can be used to target various microbes, for example, *Methanobrevibacter ruminantium*, which is the primary methanogen in ruminants, and *Methanobrevibacter smithii*, which is the primary methanogen in humans. To effect targeting, the microbial cell can be contacted with the phage polypeptide as isolated from one or more natural sources, or produced by expression vectors and/or host cells, or synthetic or semi-synthetic chemistry as described in detail herein. For enhanced permeabilisation, the polypeptide can be fused or linked to one or more signal sequences (predicted consensus sequence: [ML]KKKK[K]{0,1}X{0,9}[IL][IFL][IL][IS][LIA]X{0,4}[LIVF][LIAV][LI][ILV][LAIV][ILFV][LI VF][SAL][ILV][GSA][AS][VAI][SA]A (SEQ ID NO: 151), see FIG. 6). See also Pérez-Bercoff, A., Koch, J. and Bürglin, T. R. (2006) LogoBar: bar graph visualization of protein logos with gaps. Bioinformatics 22, 112-114. In particular aspects, the polypeptide is delivered to subjects as composition described in detail herein, for example, through use of a slow-release device for ruminants.

In certain embodiments, the polypeptide is fused or linked to a cell inhibitor, for example, an anti-methanogenesis compound (e.g., bromoethanesulphonic acid), an antibody or antibody fragment, lytic enzyme, peptide nucleic acid, antimicrobial peptide, or other antibiotic. The polypeptide-inhibitor is delivered to subjects as a composition to inhibit growth and/or replication of microbial cells, in particular, methanogen cells. The composition comprises, for example: a) an isolated phage, phage particle, phage genome, or alteration, fragment, variant, or derivative thereof; b) an isolated phage polypeptide, or an alteration, fragment, variant, or derivative thereof; c) an isolated polynucleotide, or an alteration, fragment, variant, or derivative thereof; d) an expression vector comprising this polynucleotide; or e) a host cell comprising this expression vector. The compositions of the invention can be specifically packaged as part of kits for targeting, permeabilising, and/or inhibiting microbial cells, especially methanogen cells, in accordance with the disclosed methods. The kits comprise at least one composition as set out herein and instructions for use in targeting or permeabilising cells, or inhibiting cell growth or replication, for methanogens or other microbes.

As an additional embodiment, the invention relates to a pharmaceutical composition in conjunction with a pharmaceutically acceptable carrier, for use with any of the methods discussed above. Such pharmaceutical compositions may comprise a phage polypeptide, in combination with a cell inhibitor. Alternatively, the pharmaceutical compositions may comprise an expression vector or host cell as described in detail herein. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a subject alone, or in combination with other agents, drugs (e.g., antimicrobial drugs), or hormones.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.). The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

Pharmaceutical compositions for oral administration can be formulated using pharmaceutically acceptable carriers well known, in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilising agents may be added, such as the crosslinked polyvinyl pyrrolidone, agar, alginic acid, or a salt thereof, such as sodium alginate.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, that is combined with buffer prior to use. After pharmaceutical compositions have been prepared, they can be placed in an appropriate container and labeled for treatment of an indicated condition. For administration of a composition of the invention, such labeling would include amount, frequency, and method of administration.

Pharmaceutical compositions suitable for use in the invention include compositions wherein the active ingredients are contained in an effective amount to achieve the intended purpose. For any compound, the therapeutically effective dose can be estimated initially either in cell assays, e.g., in microbial cells, or in particular, in methanogen cells, or in animal models, usually mice, rabbits, dogs, or pigs, or in ruminant species such as sheep, cattle, deer, and goats. The animal model may also be used to determine the appropriate concentration range and route of administration. Such information can then be used to determine useful doses and routes for administration. Normal dosage amounts may vary from 0.1 to 100,000 micrograms, up to a total dose of about 1 g, or more, depending upon the route of administration. Guidance as to particular dosages and methods of delivery is provided in the literature and generally available to practitioners in the art. Those skilled in the art will employ different formulations for polynucleotides than for polypeptides. Similarly, delivery of polynucleotides or polypeptides will be specific to particular cells, conditions, locations, etc.

Phage-based therapeutics are known, and methods of manufacture of such compositions are published in the art. Phage therapeutics have been described, for example, for targeting *Staphylococcus* (e.g., *S. aureus*), *Pseudomonas* (e.g., *P. aeruginosa*), *Escherichia* (e.g., *E. coli*), *Klebsiella* (e.g., *K. ozaenae, K. rhinoscleromatis scleromatis* and *K. pneumonia*), *Proteus, Salmonella, Shigella* (see, e.g., Carlton, R. M. (1999). Archivum Immunologiae et Therapiae Experimentalis, 47: 267-274; Liu, J. et al. (2004). Nat. Biotechnol. 22, 185-191; Projan, S. (2004). Nat. Biotechnol. 22, 167-168; Sulakvelidze, A., Alavidze, Z. and Morris, J. G. (2001). Antimicrobial Agents and Chemotherapy, 45 (3): 649-659; Weber-Dabrowska, Mulczyk, M. and Gorski, A. (2000). Archivum Immunologiae et Therapiae Experimentalis, 48: 547-551. Phage therapies have inherent advantages over traditional anti-microbials, in that phage are highly specific and don't affect the normal microflora of the human body; phage do not infect eukaryotic cells, and have no known serious side effects; phage can localize to the site of infection; and phage can replicate exponentially, so treatments require only a small dose and are generally low in cost (see, e.g., Sulakvelidze et al., supra). For current review, see Fischetti V A, Nelson. D, Schuch R. Reinventing phage therapy: are the parts greater than the sum? Nat. Biotechnol. 2006 December; 24(12):1508-11.

Peptide- and polypeptide-based therapeutics have also been described, for example, for denileukin, difitox, octreotide, vapreotide, lanreotide, RC-3940 series peptides, decapeptyl, lupron, zoladex, cetrorelix (see, e.g., Lu et al., 2006, AAPS J 8:E466-472), hemocidins, staphopains (see, e.g., Dubin et al., 2005, Acta Biochemica Polonica, 52:633-638), as well as indolicidin, defensins, antibiotics, microcidin B17, histatins, and maganin (see, e.g., Yeaman and Yount, 2003, Pharmacol Rev 55:27-55). General guidance for peptide and polypeptide therapeutics can also be found in Degim et al., 2007, Curr Pharm Des 13:99-117 and Shai et al., 2006, Curr Prot Pept Sci, 7:479-486. Recently approved peptide-based drugs include Hematide™ (synthetic peptide-based erythropoiesis-stimulating agent, Affymax, Inc.), Exenatide (synthetic exendin-4, Amylin/Eli Lilly), Natrecor (nesiritide, natriuretic peptide, Scios), Plenaxis (abarelix, Praecis Pharmaceuticals), and SecreFlo (secretin, Repligen).

The exact dosage will be determined by the practitioner, in light of factors related to the subject that requires treatment. Dosage and administration are adjusted to provide sufficient levels of the active agent or to maintain the desired effect. Factors which may be taken into account include the severity of the disease state, general health of the subject, age, weight, and gender of the subject, diet, time, and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Particularly useful for the compositions of the invention (e.g., pharmaceutical compositions) are slow release formulas or mechanisms. For example, intra-ruminal devices include, but are not limited to, Time Capsule™ Bolus range by Agri-Feeds Ltd., New Zealand, originally developed within AgResearch Ltd., New Zealand, as disclosed in WO 95/19763 and NZ 278977, and CAPTEC by Nufarm Health & Sciences, a division of Nufarm Ltd., Auckland, New Zealand, as disclosed in AU 35908178, PCT/AU81/100082, and Laby et al., 1984, *Can. J. Anim. Sci.* 64 (Suppl.), 337-8, all of which are incorporated by reference herein. As a particular example, the device can include a spring and plunger which force the composition against a hole in the end of a barrel.

As a further embodiment, the invention relates to a composition for a water supplement, e.g., drenching composition, or food supplement, e.g., ruminant feed component, for use with any of the methods discussed above. In particular aspects, the food supplement comprises at least one vegetable material that is edible, and a peptide or polypeptide of the invention. Alternatively, the food supplement comprises at least one vegetable material that is edible, and a polypeptide or peptide, or a polynucleotide encoding a peptide or polypeptide disclosed herein, for example, as an expression vector or host cell comprising the expression vector. In particular, the composition further includes a cell inhibitor, as fused or linked to the resultant sequence. The preferred vegetable material include any one of hay, grass, grain, or meal, for example, legume hay, grass hay, corn silage, grass silage, legume silage, corn grain, oats, barley, distillers grain, brewers grain, soy bean meal, and cotton seed meal. In particular, grass silage is useful as a food composition for ruminants. The plant material can be genetically modified to contain one or more components of the invention, e.g., one or more polypeptides or peptides, polynucleotides, or vectors.

In another embodiment, antibodies which are raised to the polypeptides or polynucleotides of the invention may be used to determine the presence of microbes, especially methanogens, or in assays to monitor levels of such microbes. The antibodies useful for diagnostic purposes may be prepared in the same manner as those described above. Diagnostic assays include methods which utilize the antibody and a label to detect a polypeptide in human body fluids or extracts of cells or tissues.

The antibodies may be used with or without modification, and may be labeled by joining them, either covalently or non-covalently, with a reporter molecule. A wide variety of reporter molecules which are known in the art may be used, several of which are described above.

A variety of protocols for measuring levels of a polypeptide or polynucleotide are known in the art (e.g., ELISA, RIA, FACS, and blots, such as Southern, Northern, Western blots), and provide a basis for determining the presence or levels of a microbe, especially a methanogen. Normal or standard levels established by combining body fluids or cell extracts taken from normal subjects, e.g., normal humans or ruminants, with the antibody under conditions suitable for complex formation. The amount of standard complex formation may be quantified by various methods, but preferably by photometric means. Quantities of polypeptide or polynucleotide expressed in subject, control, and treated samples (e.g., samples from treated subjects) are compared with the standard values. Deviation between standard and subject values establishes the parameters for determining the presence or levels of the microbe.

In a particular embodiment of the invention, the polynucleotides may be used for diagnostic purposes using particular hybridization and/or amplification techniques. The polynucleotides which may be used include oligonucleotides, complementary RNA and DNA molecules, and PNAs. The polynucleotides may be used to detect and quantitate gene expression in samples in which expression may be correlated with the presence or levels of a microbe. The diagnostic assay may be used to distinguish between the absence, presence, and alteration of microbe levels, and to monitor levels during therapeutic intervention.

In one aspect, hybridization with PCR probes may be used to identify nucleic acid sequences, especially genomic sequences, which encode the polypeptides of the invention. The specificity of the probe, whether it is made from a highly specific region, e.g., 10 unique nucleotides in the 5' regulatory region, or a less specific region, e.g., in the 3' coding region, and the stringency of the hybridization or amplification (maximal, high, intermediate, or low) will determine whether the probe identifies only naturally occurring sequences, alleles, or related sequences. Probes may also be used for the detection of related sequences, and should preferably contain at least 50% of the nucleotides from any of the coding sequences. The hybridization probes of the subject invention may be DNA or RNA and derived from the nucleotide sequence of SEQ ID NO:74-142, or complements, or modified sequences thereof, or from genomic sequences including promoter, enhancer elements, and introns of the naturally occurring sequence.

Means for producing specific hybridization probes for DNAs include the cloning of nucleic acid sequences into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as $^{32}P$ or $^{35}S$, or enzymatic labels, such as alkaline phosphatase coupled to the probe via avidin/biotin coupling systems, and the like. The polynucleotides may be used in Southern or northern analysis, dot blot, or other membrane-based technologies; in PCR technologies; or in dipstick, pin, ELISA assays, or microarrays utilizing fluids or tissues from subject biopsies to detect the presence or levels of a microbe. Such qualitative or quantitative methods are well known in the art.

In a particular aspect, the nucleic acid sequences may be useful in various assays labelled by standard methods, and added to a fluid or tissue sample from a subject under conditions suitable for hybridization and/or amplification. After a suitable incubation period, the sample is washed and the signal is quantitated and compared with a standard value. If the amount of signal in the test sample is significantly altered from that of a comparable control sample, the presence of altered levels of nucleotide sequences in the sample indicates the presence or levels of the microbe. Such assays may also be used to evaluate the efficacy of a particular treatment regimen in animal studies, in clinical trials, or in monitoring the treatment of a subject.

In order to provide a basis for the diagnosis of the presence or levels of a microbe, a normal or standard profile for expression is established. This may be accomplished by combining body fluids or cell extracts taken from normal subjects, with a polynucleotide or a fragment thereof, under conditions suitable for hybridization and/or amplification. Standard levels may be quantified by comparing the values obtained from normal subjects with those from an experiment where a known amount of a substantially purified polynucleotide is used. Standard values obtained from normal samples may be compared with values obtained from samples from subjects treated for microbial growth. Deviation between standard and subject values is used to establish the presence or levels of the microbe.

Once the microbe is identified and a treatment protocol is initiated, hybridization and/or amplification assays may be repeated on a regular basis to evaluate whether the level of expression in the subject begins to decrease relative to that which is observed in the normal subject. The results obtained from successive assays may be used to show the efficacy of treatment over a period ranging from several days to months.

Particular diagnostic uses for oligonucleotides designed from the nucleic acid sequences may involve the use of PCR. Such oligomers may be chemically synthesized, generated enzymatically, or produced in vitro. Oligomers will preferably consist of two nucleotide sequences, one with sense orientation (5'.->.3') and another with antisense orientation (3'.->.5'), employed under optimized conditions for identification of a specific nucleotide sequence or condition. The same two oligomers, nested sets of oligomers, or even a degenerate pool of oligomers may be employed under less stringent conditions for detection and/or quantitation of closely related DNA or RNA sequences.

Methods which may also be used to quantitate expression include radiolabeling or biotinylating nucleotides, coamplification of a control nucleic acid, and standard curves onto which the experimental results are interpolated (Melby, P. C. et al. (1993) J. Immunol. Methods, 159:235-244; Duplaa, C. et al. (1993) Anal. Biochem. 229-236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotides described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents. In one embodiment, the microarray is prepared and used according to methods known in the art such as those described in PCT application WO 95/11995 (Chee et al.), Lockhart, D. J. et al. (1996; Nat. Biotech. 14: 1675-1680) and Schena, M. et al. (1996; Proc. Natl. Acad. Sci. 93: 10614-10619).

In one aspect, the oligonucleotides may be synthesized on the surface of the microarray using a chemical coupling procedure and an ink jet application apparatus, such as that described in PCT application WO 95/251116 (Baldeschweiler et al.). In another aspect, a "gridded" array analogous to a dot or slot blot (HYBRIDOT apparatus, Life Technologies) may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including multichannel pipettors or robotic instruments; Brinkmann, Westbury, N.Y.) and may include, for example, 24, 48, 96, 384, 1024, 1536, or 6144 spots or wells (e.g., as a multiwell plate), or more, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs are appropriate probes. Therefore, in one aspect, mRNA is used to produce cDNA which, in turn and in the presence of fluorescent nucleotides, is used to produce fragments or antisense RNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and oligolabeling kits (Amersham Pharmacia Biotech) well known in the area of hybridization technology.

In another embodiment of the invention, the polypeptides of the invention or functional or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the polypeptide and the agent being tested, may be measured.

One technique for drug screening which may be used provides for high throughput screening of compounds having suitable binding affinity to the polypeptide of interest as described in published PCT application WO 84/03564. In this method, large numbers of different small test compounds are synthesized on a solid substrate, such as plastic pins or some other surface. The test compounds are reacted with the polypeptide, or fragments thereof, and washed. Bound polypeptide is then detected by methods well known in the art. Purified polypeptide can also be coated directly onto plates for use in the aforementioned drug screening techniques. Alternatively, non-neutralizing antibodies can be used to capture the polypeptide and immobilize it on a solid support.

In another technique, one may use competitive drug screening assays in which neutralizing antibodies capable of binding the polypeptide specifically compete with a test compound for binding to the polypeptide. In this manner, the antibodies can be used to detect the presence of a test compound which shares one or more antigen binding sites with the antibody.

EXAMPLES

The examples described herein are for purposes of illustrating embodiments of the invention. Other embodiments, methods, and types of analyses are within the scope of per-sons of ordinary skill in the molecular diagnostic arts and need not be described in detail hereon. Other embodiments within the scope of the art are considered to be part of this invention.

Example 1

Genome Size Estimation

*Methanobrevibacter ruminantium* strain M1$^T$ (DSM1093) was grown on BY+ medium (basal medium, Joblin et al., 1990) which consists of [g/l] NaCl (1), $KH_2PO_4$ (0.5), $(NH_4)_2SO_4$ (0.25), $CaCL_2.2H_2O$ (0.13), $MgSO_4.7H_2O$ (0.2), $K_2HPO_4$ (1), clarified rumen fluid (300 ml), $dH_2O$ (360 ml), $NaHCO_3$ (5), resazurin (0.2 ml), L-cysteine-HCl (0.5), yeast extract (2), and Balch's trace elements solution (10 ml) (added trace elements; Balch et al., 1979) which consists of (g/l) nitrilotriacetic acid (1.5), $MgSO_4.7H_2O$ (3), $MnSO_4.H_2O$ (0.5), NaCl (1), $FeSO_4.7H_2O$ (0.1), $CoCl_2.6H_2O$ (0.1), $CaCl_2$ (0.1), $ZnSO_4.7H_2O$ (0.1), $CuSO_4.5H_2O$ (0.01), $AlK(SO_4)_2.12H_2O$ (0.01), $H_3BO_3$ (0.01), $Na_2MoO_4.2H_2O$ (0.01), $NiSO_4.6H_2O$ (0.03), $Na_2SeO_3$ (0.02), and $Na_2Wo_4.2H_2O$ (0.02). Genomic DNA was extracted by freezing cell pellets in liquid $N_2$ and grinding using a pre-chilled, sterilised mortar and pestle. Cell homogenates were imbedded in agarose plugs and subsequent manipulations were carried out in the plugs to reduce the physical shearing of genomic DNA. Digests were performed with restriction endonucleases and DNA fragments were separated using pulsed-field gel electrophoresis (PFGE).

Example 2

DNA Cloning and Sequencing

The DNA of the *M. ruminantium* genome was sequenced by Agencourt Biosciences Corporation (Massachusetts, USA) using a random shotgun cloning approach (Fleischmann et al., 1995) and by Macrogen Corporation (Rockville, Md., USA) using pyrosequencing. Briefly, libraries of *M. ruminantium* DNA were constructed in *Escherichia coli* by random physical disruption of genomic DNA and separation of fragments by gel electrophoresis. Large fragments in the 40 Kb range were retrieved from the gel and used to generate a large insert fosmid library. DNA fragments in the 2 to 4 Kb range were recovered and used to generate a small insert plasmid library. Clones resulting from both large and small insert libraries were grown, and their fosmid or plasmid DNA was recovered and sequenced using high throughput sequencing technology. A sufficient number of clones were sequenced to give a theoretical 8 fold coverage of the *M. ruminantium* genome. Pyrosequencing was performed on randomly sheared genomic DNA fragments to give a final theoretical 10 fold coverage.

Example 3

Sequence Assembly and Prophage Annotation

DNA sequences were aligned to find sequence overlaps and assembled into contiguous (contig) sequences using Paracel Genome Assembler (Paracel Inc, CA, USA) and the Staden package (Staden et al., 1998) in combination with sequence from both standard and inverse PCRs. Contigs were analysed using the open reading frame (ORF) finder GLIMMER (gene Locator Interpolated Markov Model ER, Delcher et al., 1999) and each ORF was analysed by gapped BLASTP (Basic Local Alignment Search Tool (Altschul et al., 1997) against the National Center for Biotechnology Information (NCBI) non-redundant nucleotide and protein databases. The contigs from the 8 fold draft phase sequence were joined at random by artificial linking of sequences to generate a "pseudomolecule" and submitted to The Institute for Genomic Research (TIGR, DC, USA) for autoannotation. The contigs assembled from the 10 fold pyrosequencing were reanalysed using GLIMMER and ORFs were autoannotated using GAMOLA (Global Annotation of Multiplexed On-site Blasted DNA sequences; Altermann and Klaenhammer, 2003). ORFs were categorised by function using the clusters of orthologous proteins (COG) database (threshold 1e-02) (hypertext transfer protocol://worldwideweb.pnas.org/cgi/content/full/102/11/3906; Tatusov et al., 2001).

Protein motifs were determined by HMMER (hypertext transfer protocol://hmmer.wustl.edu) using PFAM HMM and TIGRFAM libraries, with global and local alignment (hypertext transfer protocol://pfam.wustl.edu) and standard and fragment-mode TIGRFAM HMMs models (hypertext transfer protocol://world wide web.tigr.org/TIGRFAMs) respectively (threshold 1e-02). tRNAs were identified by using TRNASCAN-SE (Lowe and Eddy, 1997) and nucleotide repeats were identified using the KODON software package (Applied Maths, Austin, Tex., USA) and REPUTER (Kurtz and Schleiermacher, 1999). Automated annotations were subsequently verified manually. Genome atlas visualizations were constructed using GENEWIZ (Jensen et al., 1999) and underlying data structures were generated by customised in-house developed algorithms. Pathway reconstructions from the predicted *M. ruminantium* ORFeome were carried out in conjunction with the KEGG (Kyoto Encyclopedia of Genes and Genomes, Kanehisa et al., 2004) on-line database using in-house developed software (PathwayVoyager; Altermann and Klaenhammer, 2005).

Example 4

Sequencing Results and Analysis

Size estimation of the *M. ruminantium* genome by restriction enzyme digestion of genomic DNA and sizing of fragments via PFGE, indicated a single chromosome of approximately 2.5-2.9 Mb. Initial sequencing of large and small insert clones (6 fold draft coverage) and assembly of the sequence into contigs indicated that a 40 Kb region of the genome was highly over-represented (>20 fold), particularly within the small insert library. This was possibly due to a high copy number plasmid (although no extrachromosomal DNAs had been identified) or a lysogenic bacteriophage that had replicated during the growth of the culture used for DNA extraction. Because of this large sequence bias, additional sequencing was carried out (2 fold theoretical genome coverage) for only small insert clones yielding a final 8 fold coverage from Sanger sequencing. The 8 fold draft phase sequence was assembled into 756 contigs which were linked via 105 scaffolds. Further pyrosequencing was carried out to an additional ~10-fold coverage and incorporation of these sequences into the assembly resulted in the contig number dropping to 27. Subsequent gap closure using inverse and long range PCR techniques reduced the contig number to 14, with one misassembly remaining.

During the high-throughput sequencing phase, a bias was observed in the sequence coverage towards a region (~50 Kb) of significantly higher G+C content immediately adjacent to a low G+C region (~12 Kb). Analysis of the genome sequence via GAMOLA and GeneWiz led to the discovery of a prominent high-GC region located immediately adjacent to a large low-GC spike. Detailed analyses of the high G+C region revealed the presence of gene-products with similarities to a phage-related integrase, the large subunit of the phage terminase, a phage portal protein, a phage capsid protein, and a predicted peptidase acting as phage lysin (FIG. 3). These gene products were used as anchor points for the overall structure of the predicted M. ruminantium prophage, designated φmru. Based on analyses of DNA secondary structures, the likely phage integration sites attL and attR were identified (FIG. 1A). Phage integration at the aft site appears to have disrupted a putative membrane protein encoded by ORFs 1980 and 2069, and this gene may harbour the original integration site for the φmru phage genome, attB.

The general structure (FIG. 1B) and DNA sequence (FIG. 4A) of φmru were determined based on commonly recognized modular structure of phage genomes combined with similarities to sequence and functional databases. See, e.g., Altermann E, Klein J R, Henrich B. Primary structure and features of the genome of the *Lactobacillus gasseri* temperate bacteriophage (phi)adh. Gene. 1999 Aug. 20; 236(2):333-46; Desiere F, Lucchini S, Canchaya C, Ventura M, Brüssow H. Antonie Van Leeuwenhoek: Comparative genomics of phages and prophages in lactic acid bacteria. 2002 August; 82(1-4):73-91. The predicted (φmru phage ORFeome was successfully classified into modules encoding phage integration, DNA replication and packaging, phage structural proteins, and a lysis cassette, and approximately 40% of the phage ORFs were functionally characterised. A terminator-like structure in a large non-coding region (244 bp), flanked by a large number of direct and indirect repeats and determined within the DNA replication module was characterised as a putative origin of DNA replication. Several genes within the phage genome sequence were predicted on the antisense strand and these coincided with low-GC regions. It is to be determined if these genes inactivate phage function or indicate misassembly within the phage genome.

The low-GC region between the predicted phage lysin and attR, was found to harbour a DNA sulphur modification system, dnd (degradation during electrophoresis), including a type II restriction m6 adenine DNA methyltransferase and a transcriptional regulator likely to be specific for the dnd system. Furthermore, non-coding RNA structures were identified both within and flanking the phage genome. Within the predicted DNA replication module, an rbcL was identified. rbcL represents a 5' UTR RNA stabilising element from *Chlamydomonas reinhardtii*. The family is thought to be involved in the stabilisation of the rbcL gene which codes for large subunit of ribulose-1,5-bisphosphate carboxylase. Mutations in this family can lead to a 50-fold acceleration in transcript degradation.

Flanking the phage genome, three group I intron structures were identified. Group I catalytic introns are large self-splicing ribozymes. They catalyse their own excision from mRNA, tRNA and rRNA precursors in a wide range of organisms. The core secondary structure consists of 9 paired regions (P1-P9). These fold to essentially two domains—the P4-P6 domain (formed from the stacking of P5, P4, P6 and P6a helices) and the P3-P9 domain (formed from the P8, P3, P7 and P9 helices). The secondary structure mark-up for this family represents only this conserved core. Group I catalytic introns often have long ORFs inserted in loop regions. These non-coding RNA structures are located in the non-coding regions between upstream of ORE 1980 (SEQ ID NO:74), downstream of ORF 2065 (SEQ ID NO:141) and attR and upstream of ORF 2069 (SEQ ID NO:142).

Example 5A

Phage Genes

The discovery of a prophage sequence within the M. ruminantium genome sequence was unexpected. There have been no previous reports of *Methanobrevibacter ruminantium* strain M1 (DSM 1093) being susceptible to either lytic or lysogenic phage, although there have been reports of phage being identified for other *Methanobrevibacter* species (Baresi and Bertani, 1984; Knox and Harris, 1986). The sequence of the ϕmru prophage is significantly higher in G+C content than the surrounding *M. ruminantium* genome suggesting that it originated from another organism. The observed levels of homology do not suggest an obvious host from which it originated, and indicates that ϕmru is unlike any other phage encountered to date.

The ϕmru DNA sequence is inserted within a predicted *M. ruminantium* membrane protein and is flanked by DNA sequences with secondary structures consistent with attL and attR sites. Despite the lack of strong homology to other known proteins, all of the functional module characteristics of a phage could be identified within the ϕmru sequence. An interesting feature of the sequence is a low G+C region at the 3' end which shows homology to proteins involved in a DNA sulphur modification system (dnd) system. These genes are located upstream of the attR attachment site of ϕmru and were therefore likely brought into the *M. ruminantium* genome during phage integration. The region encodes several dnd associated ORFs (dnd 1, 2, and 3), and a Type II methylase subunit along with a putative transcriptional regulator.

The dnd phenotype sensitises its DNA to degradation during electrophoresis. Analyses of respective dnd ORF functions suggested an incorporation of sulphur or a sulphur-containing substance into the hosts' genome. The Dnd phenotype was also discovered to exist in DNA of widespread bacterial species of variable origin and diverse habitat. Similarly organized gene clusters were found in several bacterial genomes representing different genera and in eDNA of marine organisms, suggesting such modification as a widespread phenomenon. A coincidence between the Dnd phenotype and DNA modification by sulphur was demonstrated to occur in several representative bacterial genomes by the in vivo (35) S-labelling experiments (Zhou X, He X, Liang J, Li A, Xu T, Kieser T, Helmann J D, Deng Z. A novel DNA modification by sulphur. Mol. Microbiol. 2005 September; 57(5):1428-38).

Type II R\M systems are the simplest and the most prevalent. Instead of working as a complex, the methyltransferase and endonuclease are encoded as two separate proteins and act independently. There is no specificity protein. Both proteins recognize the same recognition site, and therefore compete for activity. The methyltransferase acts as a monomer, methylating the duplex one strand at a time. The endonuclease acts as a homodimer, which facilitates the cleavage of both strands. Cleavage occurs at a defined position close to or within the recognition sequence. At this point it is unclear how the predicted functionality acts together with the dnd system. Yet, it is clear that the phage has utility as a gene delivery vehicle. In particular, the lysogenic conversion region can be used as the locus of gene replacement.

It is likely that the dnd system was transported to *M. ruminantium*: by the phage. As such, the role of the ϕmru dnd system in protecting or modifying *M. ruminantium* or foreign DNA is unknown. Another interesting feature of the ϕmru sequence is the number of ORFs encoded on the antisense strand. These ORFs correspond with low GC regions and have weak BLAST matches to proteins from a variety of organisms. This could suggest that these genes have been accumulated within the φmru genome since its integration into *M. ruminantium*. It is not clear if these ORFs represent an ongoing accumulation of insertions that may eventually lead to phage inactivation and domestication or if φmru is fully active.

One φmru gene of particular interest to methane mitigation is ORF2058 located in the lysis cassette. ORF 2058 is annotated as a peptidase and has a Protein Family (Pfam) match (Score: −13.7, E value: 0.00054) to Peptidase C39 family proteins. These proteins are cysteine peptidases and are part of the larger clan of CA peptidases as defined by the MEROPS peptidase database (Rawlings et al., 2006). The C39 peptidase family are usually associated with ABC transporters and function as maturation proteases during the export and processing of bacteriocins. The CA peptidase clan also includes the viral cysteine endopeptidases such as the C71 archaeal phage endoisopeptidases that cleave the crosslinking peptides of the archaeal cell wall. The cell walls of methanogenic archaea belonging to the Methanobacteriales family contain parallel chains of pseudomurein, a polymer of N-acetyl-L-talosaminurinic acid crosslinked by a peptide. The C71 pseudomurein endoisopeptidases are able to cleave the cell wall peptide crosslinks of archaea and lyse the cells.

Based on the location and synteny with the pseudomurein endoisopeptidase from *Methanothermobacter marburgensis* phage ψM2 (FIG. 3), ORF 2058 may have a role as a methanogen lysin gene which encodes the lytic enzyme involved in cell lysis prior to release of phage progeny. Alignment of ORF 2058 with PeiP from *M. marburgensis* and PeiW from *M. woffeii* (FIG. 5) shows low overall homology between the proteins. However there is conservation of the histidine and aspartic acid residues involved in the endoisopeptidase catalytic triad and a cysteine residue in ORF 2058 is positioned near the conserved cysteine of PeiP and PeiW which makes up the third conserved site of the catalytic triad (Makarova et al., 1999, Luo et al., 2002). Furthermore, the Gly-His-Tyr motif surrounding the catalytic His residue in PeiP and PeiW is also found in ORF 2058. These observations indicate that ORF 2058 is a φmru lysin gene which functions to lyse *M. ruminantium* cells during the phage lytic cycle. The differences observed between ORF 2058 and PeiP and PeiW may reflect different archaeal cell wall peptide crosslinks and therefore peptidase substrate specificity.

Example 5B

Phage Induction

*Methanobrevibacter ruminantium* strain M1$^T$ (DSM1093) was grown on BY+ medium (basal medium, Joblin et al., 1990) which consists of [g/l] NaCl (1), $KH_2PO_4$ (0.5), $(NH_4)_2SO_4$ (0.25), $CaCL_2.2H_2O$ (0.13), $MgSO_4.7H_2O$ (0.2), $K_2HPO_4$ (1), clarified rumen fluid (300 ml), $dH_2O$ (360 ml), $NaHCO_3$ (5), resazurin (0.2 ml), L-cysteine-HCl (0.5), yeast extract (2), and Balch's trace elements solution (10 ml) (added trace elements; Balch et al., 1979) which consists of (g/l) nitrilotriacetic acid (1.5), $MgSO_4.7H_2O$ (3), $MnSO_4.H_2O$ (0.5), NaCl (1), $FeSO_4.7H_2O$ (0.1), $CoCl_2.6H_2O$ (0.1), $CaCl_2$ (0.1), $ZnSO_4.7H_2O$ (0.1), $CuSO_4.5H_2O$ (0.01), $AlK(SO_4)_2.12H_2O$ (0.01), $H_3BO_3$ (0.01), $Na_2MoO_4.2H_2O$ (0.01), $NiSO_4.6H_2O$ (0.03), $Na_2SeO_3$ (0.02), and $Na_2Wo_4.2H_2O$ (0.02).

Figure 1C:
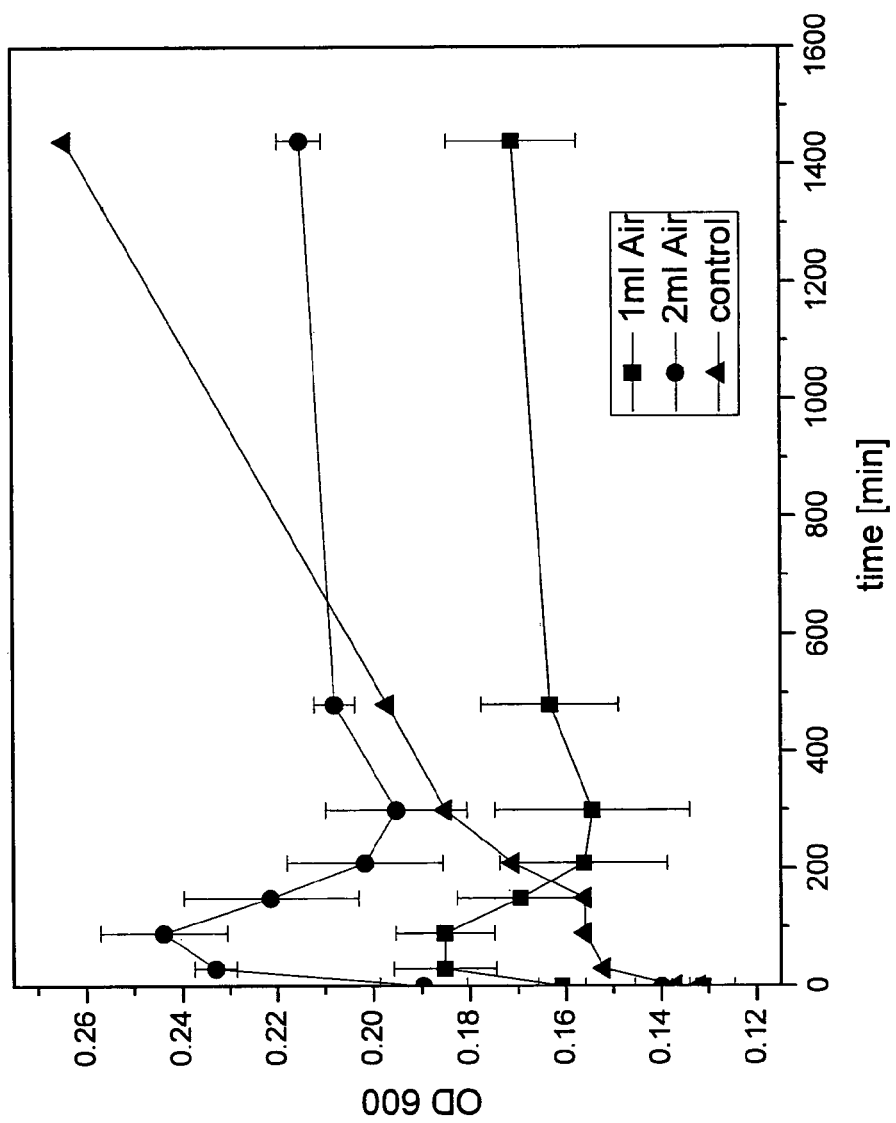

At optical densities (OD), measured at a wavelength of 600 ($OD_{600}$), between 0.10 and 0.14, *M. ruminantium* was challenged with 1 ml and 2 ml of sterile air (~160 to 320 µl oxygen), respectively (FIG. 1C) and 2 µg/ml MitomycinC (FIG. 1D). Typical lysis curves could be observed for both challenges, with latent times of ~90 min for air challenge. Initial results for MitomycinC challenge indicate a very short latent period. To verify the excision of the phage from the host genome, 2 oligonucleotides were designed, facing both phage attachment sites, respectively (R1F: caaagagagattaaagaagcagacg; SEQ ID NO:146 and L2R agtagtgttggaatcagtgaaaagg; SEQ ID NO:147). This primer pair only produces an amplicon if the phage genome recircularises upon excision.

FIG. 1E depicts the initial excision experiments when *M. ruminantium* was challenged with air. Upon induction, a clear and unambiguous amplicon of the expected size was found, indicating successful excision and recircularisation. A similar, albeit weaker band was also found in uninduced *M. ruminantium* cells, indicating that φmru has the ability to spontaneously excise during normal, unchallenged growth.

Example 5C

Lytic Enzyme Bioassays

The polypeptide encoded by ORF 2058 is useful as a rumen methanogen-specific lytic enzyme and has been sub-cloned in an *E. coli* expression vector for production of recombinant protein. ORF 2058 was amplified by PCR using the primers Mbbrum11for 22 (1122For, cac cat ggt tag att cag cag aga c; SEQ ID NO:148) and Mbbrum11rev22 (1122Rev, tca tgc agg aca gac aac ata gta g; SEQ ID NO:149) in 150 µL reaction volume containing: 121.5 ng *M. ruminantium* strain M1 genomic DNA; 0.2 µM 1122For and 1122Rev primers; 15 µL Accuprime Pfx buffer (with dNTPs, InVitrogen); 2.4 µL Accuprime Pfx (InVitrogen). PCR conditions were 95° C. for 2 min initial denaturation followed by 35 cycles of 95° C. for 15 seconds, 55° C. for 30 seconds and 68° C. for 40 seconds. No final extension was used. The PCR product was purified and quantified using a Nanodrop (Thermo Scientific, GA, USA).

ORF 2058 cloning: The PCR-amplified ORF 2058 was cloned into either pET 100 or pET 151-D Topo vectors (InVitrogen) according to the manufacturer's recommendations, and transformed into chemically competent TOP 10 cells (InVitrogen). Transformants were analysed by colony PCR, and plasmid DNA purified and sequenced. Clones with DNA sequences matching that of ORF 2058 were selected.

ORF 2058 expression: Plasmid DNA from clones containing verified ORF 2058 inserts were transformed via electroporation into electro-competent BL21* or Rosetta 2 cells. The best growth conditions for expression of soluble ORF 2058 protein was found to be in LB media, with induction being carried out between 0.48-0.6 Absorbance 600 nm using 0.5 mM IPTG and continuing growth for approximately six hours at 30° C. Cells were then harvested by centrifugation and frozen at −20° C.

Cell lysis: The cell pellet was thawed and resuspended in the following buffer (pH 7.5): 300 mM NaCl, 2 mM DTT, 10 mM imidazole, 20 mM Tris, 20% glycerol, 1% Triton-X, 5 mM $CaCl_2$, and 10 mM $MgCl_2$. Lysozyme was added to 1 mg/ml final concentration, followed by incubation on ice with gentle agitation for 30 min. DNase I and RNase I were each added to 5 µg/ml final concentration followed by incubation on ice with gentle agitation for 30 min. The cell lysate was centrifuged at 12,000 rpm for 15 min and the crude lysate was filtered through a 0.8 µm filter.

Nickel affinity chromatography: The filtered supernatant from the cell lysis procedure was applied to an 80 mL nickel affinity column and eluted using a 20 mM to 250 mM imidazole gradient in the following buffer (pH 7.5): 300 mM NaCl, 2 mM DTT, 20 mM Tris, and 20% glycerol. Fractions elided from the column containing the expressed ORF 2058 protein were concentrated using a Millipore ultra filtration cell with a 10,000 kDa molecular weight cut-off membrane. The ORF 2058 construct in pET100 expressed in *E. coli* BL21* cells was eluted from the nickel column by the following elution buffer, pH 8.2 (20 mM Tris, 250 mM imidazole, 300 mM NaCl, 10 mM b-mercaptoethanol, 10% glycerol), and the enzyme was stored in a buffer in which additional glycerol and dithiothreitol were added to achieve a final concentration of 40% glycerol, 1 mM dithiothreitol, pH 8.2)

Desalting: Desalting of the concentrated protein expressed from the pET 151 construct in Rosetta 2 cells was performed using a 250 mL BioGel P6 DG (BioRad, CA, USA) column with the following buffer (pH 7.0):20 mM MOPS, 1 mM DTT, 300 mM NaCl, and 20% glycerol. Fractions from the column were concentrated as described above and the final sample was filtered and snap-frozen in liquid nitrogen before being stored at −20° C.

Lysis of resting *M. ruminantium* cells: Five ml cultures of *M. ruminantium* M1 (DSM 1093) were grown in BY+ medium in Hungate tubes to late log phase and cells were collected by centrifugation of the Hungate tubes at 5,000×g at room temperature for 30 minutes. The tubes were moved into an anaerobic chamber (95% $CO_2$—5% $H_2$ atmosphere, Coy Laboratory Products, MI, USA) where the supernatant was discarded and the cells from 10 ml culture were resuspended in 1 ml MOPS buffer pH 6.8 (50 mM MOPS, 5 mM $CaCl_2$, 1 mM dithiothreitol). The cell suspension was adjusted to an OD (600 nm) of ~0.12 by dilution with additional MOPS buffer.

The standardised cell suspension (50 μl) was dispensed into a microtitre plate and varying concentrations of ORF 2058 lytic enzyme (prepared from the pET 100 construct) were added and the total volume of the reaction was made up to 250 ml with buffer. The cell and protein mixtures were incubated at 37° C. and OD readings were recorded. The effects of the enzyme additions (μg enzyme added per assay) on resting *M. ruminantium* cells are shown in FIG. 7. The enzyme additions decreased the OD 600 nm readings of the suspended cells in a dose-dependant manner compared to the control cells without added enzyme. This indicates that the ORF 2058 lytic enzyme is able to attack and lyse resting cells of *M. ruminantium* under anaerobic conditions.

Lysis of growing *M. ruminantium* cells: *M. ruminantium* was grown in RM02 medium. RM02 medium was composed of the following ingredients (g/L): $KH_2PO_4$ (1.4), $(NH_4)_2SO_4$ (0.6), KCl (1.5), trace element solution SL10 (1 ml), selenite/tungstate solution, (1 ml), 0.1% (w/v) resazurin solution (4 drops). The components were mixed and boiled under $O_2$-free 100% $CO_2$ and cooled in an ice bath while bubbling with 100% $CO_2$. After cooling $NaHCO_3$ (4.2 g) and L-cysteine.$HCl-H_2O$ (0.5 g) were added and 9.5 ml of the medium was dispensed into Hungate tubes while gassing the tubes with 100% $CO_2$. The tubes were autoclaved and stored in the dark for 24 h before using. Prior to inoculation, NoSubRFV (0.5 ml per tube, containing substrates, yeast extract, vitamins) was added. After inoculation tubes were gassed with 80% $CO_2$/20% $H_2$ to 25 lb/$in^2$. *M. ruminantium* was grown to mid-log (OD 600 nm ~0.1) at which point ORF 2058 lytic enzyme (prepared from the pET 151D Topo clone) was added to cultures at varying concentrations. Incubation of cultures continued and OD readings were recorded. The effect of the enzyme additions on *M. ruminantium* growth and methane formation (% methane production relative to the no-addition control after 217 hours growth are indicated in brackets) are shown in FIG. 8. The results show that the ORF 2058 lytic enzyme dramatically affected the growth of *M. ruminantium* in a dose-dependant manner, decreasing the OD 600 nm of growing cultures within 2 hours of addition. The two highest levels of enzyme addition also reduced methane formation to an extent similar to that of chloroform addition (100 μl/10 ml culture addition).

Example 6

Overview

An unexpected discovery from the sequencing of the *M. ruminantium* genome was the presence of a prophage sequence. Analysis of the genome sequence identified a region of unusually high GC content which contained a number of phage-related genes. The overall structure of the predicted prophage was identified by further bioinformatic analyses and designated as φmru. Approximately 40% of the phage genes were assigned to discrete functional groups including phage integration, DNA replication and packaging, phage structural proteins and lysis. DNA sequences flanking the phage genome were found to represent potential sites for phage integration (attL and attR).

The phage appears to have inserted itself into a *M. ruminantium* putative membrane protein which likely harbours the original methanogen integration site for the φmru phage genome, attB. Furthermore, a terminator-like structure found within the DNA replication module is thought to represent an origin of phage DNA replication. A low-GC region at the 3' end of the phage genome harbours what appears to be a DNA modification system by sulphur, including a gene that is likely to control the expression of the dnd system. These genes were probably carried into the *M. ruminantium* genome during phage integration and their role with respect to modifying phage, host or foreign DNA remains to be elucidated. The retention of the dnd system by *M. ruminantium* suggests it has imparted a benefit to the host. However the role of the φmru dnd system in modifying *M. ruminantium* or foreign DNA is still under investigation.

Another interesting feature of the φmru sequence is the number of genes encoded on the antisense strand which correspond with low GC regions and have weak matches to proteins from a variety of organisms. This suggests that these genes have accumulated within the φmru genome since its integration into *M. ruminantium* and it may be that these genes represent an ongoing build up of insertions that might eventually lead to phage inactivation and phage domestication. The high GC content of the φmru phage sequence compared to the *M. ruminantium* genome suggests that it originated from another organism. However, the previous host is not obvious as the φmru proteins appear somewhat unique by comparison to other phage encountered to date.

The φmru genes of notable interest in regard to methane mitigation are those located within the lysis cassette. One gene in particular encodes a protein with similarity to family C39 peptidases. This peptidase family includes, among others, viral cysteine endopeptidases such as the C71 archaeal phage endoisopeptidases that cleave the crosslinking peptides of pseudomurein which makes up *Methanobrevibacter* cell walls. Based on gene location within the phage genome and synteny with pseudomurein endoisopeptidases from other non-rumen methanogen phage genomes, this gene may have a role as a lysin gene encoding the lytic enzyme involved in cell lysis prior to release of phage progeny. This gene and its encoded enzyme are of obvious interest as possible control mechanism for *M. ruminantium* and other rumen methanogens with similar cell walls.

Ruminant phage and their enzymes that are involved in lysing host cells represent significant opportunities for controlling both methanogen populations and other community members (bacteria, protozoa and fungi) in the rumen. In addition, it is possible to identify key host enzyme targets that are susceptible to inhibition by phage proteins through understanding the life cycles of phage. The inventors have surveyed the composition of rumen phage in cows, sheep and deer and shown them to display temporal variation in numbers and type. New Zealand methanogen isolates that are affected by phage have also been identified. Pure cultures of methanogens have been used to evaluate phage lytic enzymes, and culture-based and PCR-based techniques have been developed to screen for novel phage. Purified phage from rumen samples have been shown to be amenable to random DNA sequence analysis which enables phage enzymes to be discovered.

There are several advantages to the use of phage or their enzymes in mitigation techniques for lowering methane emissions. Phage are natural members of the rumen microbial community and, thus, would not be viewed as antibiotic treatment (and could more easily overcome any regulatory constraints). Phage are usually specific for a narrow range of hosts potentially enabling the selected targeting of methanogens. Phage therapy is now recognised as a treatment for antibiotic resistant organisms and generally regarded as safe. Once produced, phage are usually relatively stable. Introduction of methanogens strains into the rumen that are susceptible to phage could have long-term beneficial effects, particularly if inoculation occurs at an early age (e.g., in young lambs and calves). Certain methanogens are known to either contain phage genomes, be susceptible to lytic phage, or undergo autolysis (suggestive of lytic enzymes) including *Methanobrevibacter smithii* (strain PS), *Methanobacterium bryantii* and *Methanobrevibacter* strain MF-1. One notable example of phage being used to inhibit agriculturally problematic organisms is the use of phage to target *Escherichia coli*. 0157:H7.

*Methanobrevibacter ruminantium* was chosen for genome sequencing because of its prevalence in the rumen under a variety of dietary conditions (based on cultivation and molecular detection data), the availability of cultures, its amenity to routine growth in the laboratory, and the relatively large amount of previous studies and background literature available for this organism. The present invention provides important data regarding the *M. ruminantium* genome, and constructs a detailed picture of the phage within the rumen. The ϕmru prophage sequence provides specific reagents for inhibition of *M. ruminantium* and for future genetic manipulations to assist in determining gene function. The phage can be used to block conserved functions/components among methanogens to prevent or reduce methane formation in the rumen.

REFERENCES

Altermann E, Klaenhammer T R (2005) PathwayVoyager: pathway mapping using the Kyoto Encyclopedia of Genes and Genomes (KEGG) database. *BMC Genomics* 6:60-66.

Altermann, E Klaenhammer T R (2003) GAMOLA: a new local solution for sequence annotation and analyzing draft and finished prokaryotic genomes. *OMICS: A journal of integrative biology* 7, 161-169.

Altschul S F, Madden T L, Schaffer A A, Zhang J, Zhang Z, Miller W, Lipman D J (1997) Gapped BLAST and PSI-BLAST: a new generation of protein database search programs. *Nucleic Acids Research* 25, 3389-3402.

Balch W E, Fox G E, Magrum L J, Woese C R, Wolfe R S (1979) Methanogens: reevaluation of a unique biological group. *Microbiological Reviews* 43, 260-296.

Baresi, L. and Bertani, G. 1984. Isolation of a bacteriophage for a methanogenic bacterium. In *Abstracts of the Annual Meeting of the American Society for Microbiology*. Washington D.C.: American Society for Microbiology, p. 133.

Bickle, T. A. and D. H. Kruger. 1993. Biology of DNA restriction. Microbiol. Rev. 57:434-450.

Bult C J, et al. (1996) Complete genome sequence of the methanogenic archaeon, *Methanococcus jannaschii*. *Science* 273, 1058-1073.

Coutinho P M, Henrissat B (1999) Carbohydrate-active enzymes: an integrated database approach. In 'Recent Advances in Carbohydrate Bioengineering' (Eds H J Gilbert, G Davies, B Henrissat and B Svensson) pp. 3-12 (The Royal Society of Chemistry, Cambridge) (Carbohydrate Active Enzymes database, http://www.cazy.org/).

Delcher A L, Harmon D, Kasif S, White O, Salzberg S L (1999) Improved microbial gene identification with GLIMMER. *Nucleic Acids Research* 27, 4636-4641.

Fleischmann, R D, et al. (1995) Whole-genome random sequencing and assembly of *Haemophilus influenzae* Rd. *Science* 269, 496-512.

Fricke W F, Seedorf H, Henne A, Kruer M, Liesegang H, Hedderich R, Gottschalk G, Thauer R K (2006) The genome sequence of *Methanosphaera stadtmanae* reveals why this human intestinal archaeon is restricted to methanol and $H_2$ for methane formation and ATP synthesis. *Journal of Bacteriology* 188, 642-658.

Godde J S, Bickerton A (2006) The repetitive DNAe called CRISPRs and their associated genes: evidence of horizontal transfer among prokaryotes. *Journal of Molecular Evolution* 62, 718-729.

Haft D H, Selengut J, Mongodin E F, Nelson K E (2005) A guild of 45 CRISPR-associated (Cas) protein families and multiple CRISPR/Cas subtypes exist in prokaryotic genomes. *PLoS Computational Biology* 1:474-483

Jansen R, Embden J D, Gaastra W, Schouls L M (2002) Identification of genes that are associated with DNA repeats in prokaryotes. *Molecular Microbiology* 43, 1565-1575.

Jansen R, van Embden J D, Gaastra W, Schouls L M (2002) Identification of a novel family of sequence repeats among prokaryotes. *OMICS: A journal of integrative biology* 6, 23-33.

Jensen L J, Friis C, Ussery D W (1999) Three views of microbial genomes. *Research in Microbiology* 150, 773-777.

Joblin K N, Naylor G E, Williams A G (1990) Effect of *Methanobrevibacter smithii* on xylanolytic activity of anaerobic ruminal fungi. *Applied and Environmental Microbiology* 56, 2287-2295.

Kanehisa M, Goto S, Kawashima S, Okuno Y, Hattori M (2004) The KEGG resource for deciphering the genome. *Nucleic Acids Research* 32, D277-D280.

Kiener, A., Konig, H., Winter, J. and Leisinger, T. 1987. Purification and use of *Methanobacterium wolfeii* pseudomurein endopeptidase for lysis of *Methanobacterium thermoautotrophicum*. J. Bacteriol. 169, 1010-1016.

Knox, M. R. and Harris, J. E. 1986. Isolation and characterisation of a bacteriophage of *Methanobrevibacter smithii*.

In *Abstracts of the XIV International Congress on Microbiology*. Manchester. International Union of Microbiological Societies.

Kurtz S, Schleiermacher C (1999) REPuter fast computation of maximal repeats in complete genomes. *Bioinformatics* 15, 426-427.

Lowe T M, Eddy S R (1997) tRNAscan-SE: a program for improved detection of transfer RNA genes in genomic sequence. *Nucleic Acids Research* 25, 955-964.

Loenen, W. and N. Murray. 1986. Modification enhancement by restriction alleviation protein (Ra1) of bacteriophage lambda. J. Mol. Biol. 190:11-22.

Lucchini, S., F. Desiere, and H. Brussow. 1999. Comparative genomics of *Streptococcus thermophilus* phage species supports a modular evolution theory. J. Virol. 73:8647-8656.

Luo, Y. N., Pfister, P., Leisinger, T. and Wasserfallen, A. 2002. Pseudomurein endoisopeptidases PeiW and PeiP, two moderately related members of a novel family of proteases produced in *Methanothermobacter* strains. FEMS Microbiol. Lett. 208, 47-51

Makarova, K. S., Aravind, L. and Koonin, E. V. 1999. A superfamily of archaeal, bacterial, and eukaryotic proteins homologous to animal transglutaminases. Protein Sci. 8, 1714-1719.

Makarova K S, Grishin N V, Shabalina, S A, Wolf Y I, Koonin E V (2006) A putative RNA-interference-based immune system in prokaryotes: computational analysis of the predicted enzymatic machinery, functional analogies with eukaryotic RNAi, and hypothetical mechanisms of action. *Biology Direct* 1:7-32.

New Zealand Statistics 2005 (www.stats.govt.nz)

New Zealand's Greenhouse Gas Inventory 1990-2004. The National Inventory Report and Common Reporting Format. (2006) Ministry for the Environment. http://www.mfe.govt.nz/publications/climate/nir-apr06/nir-apr06.pdf.

Reeve J N, Nolling J Morgan R M, Smith D R (1997) Methanogenesis: genes, genomes and who's on first? *Journal of Bacteriology* 179, 5975-5986.

Rawlings, N. D., Morton, F. R. and Barrett, A. J. 2006. MEROPS: the peptidase database. Nucleic Acids Res. 34, D270-D272.

Samuel B S, Hansen E E, Manchester J K, Coutinho P M, Henrissat B, Fulton R, Latreille P, Kim K, Wilson R K, Gordon J I (2007) Genomic adaptations of *Methanobrevibacter smithii* to the human gut. *Proceedings of the National Academy of Sciences USA* 104, 10643-10648.

Smith D R, et al. (1997) Complete genome sequence of *Methanobacterium thermoautotrophicum* ΔH: Functional analysis and comparative genomics. *Journal of Bacteriology* 179, 7135-7155.

Smith P H, Hungate R E (1958) Isolation and characterization of *Methanobacterium ruminantium* n. sp. *Journal of Bacteriology* 75, 713-718.

Staden R, Beal K F, Bonfield J K (1998) The Staden Package. *Methods in Molecular Biology: Bioinformatics Methods and Protocols* 132, 115-130.

Tatusov R L, Natale D A, Garkavtsev I V, Tatusova T A, Shankavaram U T, Rao B S, Kiryutin B, Galperin M Y, Fedorova N D, Koonin E V (2001) The COG database: new developments in phylogenetic classification of proteins from complete genomes *Nucleic Acids Research* 29, 22-28.

All publications and patents mentioned in the above specification are herein incorporated by reference.

Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the spirit and scope of the invention.

---

What we claim is:

1. An isolated polypeptide a) which comprises amino acid sequence SEQ ID NO: 63; b) which shares at least 90% identity with SEQ ID NO: 63; c) which shares at least 80% identity with SEQ ID NO: 63; or d) which comprises residues 74-228 of SEQ ID NO:63.

2. A conjugate molecule or fusion molecule, comprising the isolated polypeptide of claim 1.

3. A method of inhibiting a methanogen cell, comprising contacting the cell with the isolated polypeptide of claim 1.

4. The method of claim 3, wherein the cell is *Methanobrevibacter ruminantium*.

5. The method of claim 4, wherein the cell is *Methanobrevibacter ruminantium* strain $M1^T$ (DSM1093).

6. The conjugate molecule or fusion molecule of claim 2, which further comprises an anti-methanogenesis compound, a signal sequence, an antibody or antibody fragment, a peptide nucleic acid, an antimicrobial peptide, or an antibiotic.

7. A method of inhibiting a methanogen cell, comprising contacting the cell with the conjugate molecule or fusion molecule of claim 2 or claim 6.

8. The method of claim 7, wherein the cell is *Methanobrevibacter ruminantium*.

9. The method of claim 8, wherein the cell is *Methanobrevibacter ruminantium* strain $M1^T$ (DSM1093).

10. A pharmaceutical composition comprising the isolated polypeptide of claim 1.

11. The method of claim 3, wherein the methanogen cell is in or from a ruminant.

12. The method of claim 7, wherein the methanogen cell is in or from a ruminant.

13. The method of claim 3, further comprising the initial step of producing or isolating the polypeptide of claim 1.

14. The method of claim 7, further comprising the initial step of producing or isolating the conjugate molecule or fusion molecule of claim 2 or claim 6.

* * * * *

SEQUENCE LISTING

```
<160> NUMBER OF SEQ ID NOS: 151

<210> SEQ ID NO 1
<211> LENGTH: 258
<212> TYPE: PRT
<213> ORGANISM: Methanobrevibacter ruminantium

<400> SEQUENCE: 1

Val Arg Asn Met Lys Asn Lys Ser Leu Ile Leu Ile Ser Leu Leu Leu
1               5                   10                  15

Leu Ile Thr Ile Ile Ser Ile Gly Ser Val Val Ala Thr Asp Asn Glu
            20                  25                  30

Glu Ile Asn Met Asp Asn Ile Asn Asn Ile Asp Asn Asn Glu Asp Ile
        35                  40                  45

Ala Asn Ile Asp Asn Val Asp Asn Val Asp Asn Ser Asn Ile Asn Asn
    50                  55                  60

Pro Thr Asp Ile Arg Ile Asp Asn Ser Asn Leu Asn Arg Glu Thr Glu
65                  70                  75                  80

Leu Asp Ser Asn Leu Asn Lys Ser Asn Gln Ile Arg Glu Asp Glu Leu
                85                  90                  95

Glu Gln Ser Asn Ala Lys Ser Asn Leu Lys Ser Ser Lys Leu Ser Ser
            100                 105                 110
```

```
Thr Ile Thr Val Asp Gly Ser Asp Glu Asn Gln Met Ser Asn Pro Thr
            115                 120                 125
Ile Gln Ser Ala Ile Asp Ser Ala Asn Ala Gly Asp Thr Ile Ile Ile
    130                 135                 140
Thr Gly Lys Ser Tyr Val His Cys His Phe Ile Val Asn Lys Pro Leu
145                 150                 155                 160
Thr Ile Ile Ser Glu Ile Gly Thr Ser Met Ser Pro Cys Pro Ser Asn
            165                 170                 175
Thr Lys Gly Ser Gly Ala His Gly Ile Phe Tyr Ile Ser Pro Glu Ala
            180                 185                 190
Ser Gly Thr Val Leu Lys Gly Phe Asn Leu Thr Asn Thr Tyr Gly Asp
            195                 200                 205
Tyr Asp Asp Tyr Gly Ile Leu Ile Arg Gly Ala Glu Asn Val Glu Ile
    210                 215                 220
Ile Asn Cys Thr Ile Asn Thr Val Ser Asp Gly Asp Gly Ile Arg Ile
225                 230                 235                 240
Glu Asn Ala Thr Asn Thr Lys Ile Ala Asp Cys Leu Ile Lys Asp Ser
            245                 250                 255
Asn Ile

<210> SEQ ID NO 2
<211> LENGTH: 255
<212> TYPE: PRT
<213> ORGANISM: Methanobrevibacter ruminantium

<400> SEQUENCE: 2

Met Lys Thr Phe Arg Gln Gln Leu Leu Glu Asp Pro Glu Phe Gln Asn
1               5                   10                  15
Tyr Leu Leu Gln Arg Pro Asn Leu Thr Glu Ser Ser Leu Gln Ser Tyr
            20                  25                  30
Leu Asn Ala Ala Thr Asn Phe Val Arg Phe Thr Gly Glu Pro Phe Tyr
        35                  40                  45
Lys Thr Val His Glu Leu Arg Ser Gln Gln Asn Asp Arg Ile Glu Asn
    50                  55                  60
Asn Ile Ile Ile Arg Phe Asn Pro Asn Gln Ser Arg Ile Asn Ile Met
65                  70                  75                  80
Gln Phe Glu Phe Ile Glu Tyr Leu Lys Gly Arg Gly Cys Thr Glu Val
                85                  90                  95
Ser Ile Asp Ser Tyr Val Arg Tyr Met Arg Thr Ile Leu Ser Thr Leu
            100                 105                 110
Gly Ile Ile Leu Pro Lys Ser Pro Lys Leu Asp Asp Thr Pro Gln Asp
        115                 120                 125
Trp Tyr Leu Leu Thr Lys Asp Asp Ile Lys Tyr Val Leu Asp Thr Ala
    130                 135                 140
Asn Leu Gln Tyr Lys Ala Val Ile Asn Phe Ala Ala Val Thr Gly Leu
145                 150                 155                 160
Arg Val Arg Asp Met Arg Ser Leu Thr Ile Lys Asp Phe Met Thr Ala
                165                 170                 175
Thr Glu Glu Tyr His Gly Cys Thr Glu Val Glu Asp Phe Leu Asp Ser
            180                 185                 190
Ala Pro Asp Gly Met Ile Gly Phe Trp Glu Leu Phe Pro Gln Lys Thr
        195                 200                 205
Arg Lys Phe Arg Leu Pro Cys Lys Val Cys Asn Thr Pro Glu Ser Ser
    210                 215                 220
Asp Leu Leu Leu Phe Ser Leu Asn Glu Arg Val Lys Tyr Phe Glu Trp
```

```
                225                 230                 235                 240
Lys Asn Glu Lys Asp Gly Thr Asp Leu Lys Ile Thr Lys Asn Asp
                    245                 250                 255

<210> SEQ ID NO 3
<211> LENGTH: 98
<212> TYPE: PRT
<213> ORGANISM: Methanobrevibacter ruminantium

<400> SEQUENCE: 3

Met Asn Thr Leu Lys Ile Glu Cys Ser Lys Asp Asp Tyr Ile Ile Lys
1               5                   10                  15

Thr Ala Lys Ala Asn Ser Glu Asn Glu Leu Lys Val Glu Val Pro Glu
                20                  25                  30

Asn Trp Asn Cys Asp Tyr Val Asn Ala Val Leu Trp Glu Glu Asp Ile
            35                  40                  45

Cys Glu Val Leu Glu Lys Gly Asp Glu Arg Met Leu Leu Ile Pro Met
50                  55                  60

Cys Gly Glu Leu Leu Glu Gly Val Gln Glu Asp Glu Tyr Ile Lys
65                  70                  75                  80

Tyr Ile Cys Leu Pro Val Lys Tyr Gln Asp Gln Met Val Leu Ile Ala
                85                  90                  95

Lys Ile

<210> SEQ ID NO 4
<211> LENGTH: 255
<212> TYPE: PRT
<213> ORGANISM: Methanobrevibacter ruminantium

<400> SEQUENCE: 4

Met Gly Met Lys Lys Val Lys Ile Glu Ser Lys Ala Lys Asn Asn Met
1               5                   10                  15

Thr Arg Asn Glu Lys Leu Phe Tyr Lys Leu Tyr Asp Asp Leu Tyr Asn
                20                  25                  30

Glu Asp Arg Leu Ile Leu Phe Ser Thr Tyr Phe Asn Ile Tyr Asp Lys
            35                  40                  45

Phe Ile Phe Lys Lys Asp Ile Ile His Tyr Val Leu Met Asn Tyr Ser
50                  55                  60

Glu Asn Glu Ile Ile Glu Ala Met Lys Lys Ile Asp Glu Ile Gln Ser
65                  70                  75                  80

Glu Gly Ile Asp Ile Lys Thr Phe Ile Pro Lys Tyr Cys Pro Lys
                85                  90                  95

Cys Lys Lys Val Met Asp Ser Tyr Gly Lys Ile Cys Pro Asp Cys Gly
                100                 105                 110

Thr Ile Leu Ile Glu Asp Glu Lys Lys Ile Gln Glu Leu Gln Ala Lys
            115                 120                 125

Asp Lys Ala Tyr Glu Glu Tyr Leu Glu Lys Glu Tyr Asn Ile Tyr Leu
            130                 135                 140

Gln Asn Ser Tyr His Asn Met Ile Gln Gly Ser Tyr Thr Ile Lys Ile
145                 150                 155                 160

Arg Thr Arg Lys Pro Lys Thr Glu Thr Glu Ile Val Arg Ile Pro Ala
                165                 170                 175

Gln Thr Val Thr Ser Arg Gly Lys Phe Asn Ser Ile Ser Gln His Tyr
            180                 185                 190

Pro Ser Glu Thr Tyr Thr Arg Gln Lys Val Thr Arg Ala Lys Tyr Lys
            195                 200                 205
```

```
Glu Cys Arg Val Leu Phe Asp Lys Glu Lys Met Ile Leu Asn Ile Asp
            210                 215                 220

Gly Thr Ala Thr Lys Leu Tyr Tyr Asp Glu Val Cys Glu Leu Glu Tyr
225                 230                 235                 240

Pro Glu Gln Glu Val Asn Glu Leu Val Thr Leu Thr Leu His Asn
                245                 250                 255

<210> SEQ ID NO 5
<211> LENGTH: 228
<212> TYPE: PRT
<213> ORGANISM: Methanobrevibacter ruminantium

<400> SEQUENCE: 5

Met Lys Thr Gln Asp Leu Ile Asn Ile Ile Asn Asp Glu Glu Ser Pro
1               5                   10                  15

Val Phe Leu Asn Arg Glu Val Phe Glu Met Asp Tyr Val Pro Asp Ile
                20                  25                  30

Tyr Lys Tyr Arg Asp Glu Gln Leu Ala Lys Met Ala Met Tyr Cys Asn
            35                  40                  45

Ser Ile Pro Asp Asn Ile Ala Pro Lys Asn Leu Gln Leu Cys Gly Gly
        50                  55                  60

Asn Ala Thr Gly Lys Thr Thr Thr Leu Lys Gln Phe Phe Lys Met Leu
65                  70                  75                  80

Asn Glu Ala Phe Pro Asn Ile Val Thr Val Tyr Ile Asn Cys Gln Leu
                85                  90                  95

Phe Asn Thr Glu Asn Thr Val Tyr Gly Lys Ile Tyr Asn Lys Leu Tyr
                100                 105                 110

Gly Val Lys Gly Ser Ile Asn Gly Lys Ser Asn Thr Met Leu Phe Asp
            115                 120                 125

Lys Ile Val Ala Arg Leu Lys Lys Glu Asn Lys Ile Leu Ile Ile Gly
        130                 135                 140

Leu Asp Asp Phe Asp Ser Phe Lys Ser Arg Asp Gly Leu Asn Lys Met
145                 150                 155                 160

Leu Tyr Asn Phe Leu Arg Ile His Glu Ala Glu Glu Gly Ile Gln Ile
                165                 170                 175

Cys Ile Phe Thr Val Ser Asn Lys Gly Glu Ser Glu Ser Leu Leu Leu
                180                 185                 190

Pro Ser Arg Gln Ser Ser Thr Gly Phe Arg Tyr Ser Leu Thr Ser Thr
            195                 200                 205

Pro Trp Ser Arg Cys Thr Thr Tyr Trp Thr Thr Gly Ala Pro Ser Val
        210                 215                 220

Ser Ile Leu Ala
225

<210> SEQ ID NO 6
<211> LENGTH: 255
<212> TYPE: PRT
<213> ORGANISM: Methanobrevibacter ruminantium

<400> SEQUENCE: 6

Met Phe Leu Glu Lys Cys Asp Gly Lys Asp Thr Ile Ser Met Ser Leu
1               5                   10                  15

Gln Glu Lys Met Asn Leu Ile Leu Glu Thr Met Glu Ser Lys Gly Ser
                20                  25                  30

Pro Phe Ile Ser Cys Ile His Cys Asn Ile Pro Ile Asn Glu Ala Glu
            35                  40                  45

Glu Trp Tyr Lys Asn Gly Glu Ile Gly Asp Gln Asp Phe Ile Asn Phe
```

```
                    50                  55                  60
Tyr Asp Asp Val Asn Leu Ile Glu Glu Ser Phe Gly Phe Glu Ile Tyr
 65                  70                  75                  80

Lys Lys Ser Glu Tyr Pro Thr Leu His Thr Gln Ser Ile Asn Gln Ile
                 85                  90                  95

Ala Ser Thr Tyr Pro Met Asn Arg Thr Gln Asn Glu Lys Thr Pro Leu
            100                 105                 110

Phe Leu Arg Arg Glu Arg Lys Leu Tyr Glu Ile Thr Asn Ile Phe Lys
        115                 120                 125

Ser His Ser Thr Asn Glu Ile Phe Ile Ser Met Asp Ser Lys Ser Lys
130                 135                 140

Leu Lys His Glu Ile Lys Tyr Asp Phe Thr Leu Lys Glu Leu Asn Glu
145                 150                 155                 160

Ile Phe Lys Asn Tyr Leu Glu Glu Asp Cys Ser Ile Tyr Ile Leu Asn
                165                 170                 175

Asp Asn Arg Ala Phe Val Met Thr Leu Gly His Phe Gln Phe Glu Phe
            180                 185                 190

Asp Val Phe Gly Ser Ala Lys Glu Ser Tyr Val Phe Asp Val Glu Ile
        195                 200                 205

Asp Asp Glu Lys Tyr Asp Lys Ile Phe Ile Arg Ser Ser Tyr Tyr Phe
210                 215                 220

Asn Ile Pro Val Asp Glu Leu Asp Gly Leu Ala Lys Ile Leu Lys Gln
225                 230                 235                 240

Lys Arg Ile Ile Glu Glu Gly Phe Phe Glu Gly Gln Phe Leu Tyr
                245                 250                 255

<210> SEQ ID NO 7
<211> LENGTH: 68
<212> TYPE: PRT
<213> ORGANISM: Methanobrevibacter ruminantium

<400> SEQUENCE: 7

Met Ile Ile Phe Leu Lys Leu Lys Phe Gly Arg Val Ile Met Glu Lys
 1               5                  10                  15

Leu Ile Glu Ile Asp Gly Val Gln Tyr Thr Glu Ala Gln Ile Arg Arg
             20                  25                  30

Ala Leu Ala Ile Glu Arg Asp Val Arg Ser Pro Asn Phe Val Asp Met
         35                  40                  45

Leu Leu Gly Lys Ile Lys Pro Ser Glu Leu Ala Ser Arg Val Ser Glu
     50                  55                  60

Lys Gly Asp Ala
 65

<210> SEQ ID NO 8
<211> LENGTH: 51
<212> TYPE: PRT
<213> ORGANISM: Methanobrevibacter ruminantium

<400> SEQUENCE: 8

Met Cys Tyr Val Gly Asn Thr Arg Thr Leu Val Tyr His Thr Glu Asp
 1               5                  10                  15

Cys Phe Cys Asn His Trp Leu Leu Asn Glu Asn Lys Thr Ile Leu Glu
             20                  25                  30

Glu Lys Pro Val Asp Met Lys Pro Cys Ser Phe Cys Lys Pro Gln Phe
         35                  40                  45

Asp Thr Glu
     50
```

<210> SEQ ID NO 9
<211> LENGTH: 77
<212> TYPE: PRT
<213> ORGANISM: Methanobrevibacter ruminantium

<400> SEQUENCE: 9

Met Leu Asp Met Val Ala Glu Met Val Glu Asn Ile Arg Lys Gly Glu
1               5                   10                  15

Gly Asp Gly Tyr Ser Ile Tyr Pro Pro Phe Ser Cys Ile Val Phe Leu
            20                  25                  30

Gln Gly Lys Lys Tyr Ser Glu Cys Cys Cys Lys Ala Glu Ala Arg Asp
        35                  40                  45

Gln Lys Phe Ala Leu Val Asn Leu Val Gly Phe Arg Arg Glu Asp Val
    50                  55                  60

Lys Val Ile Asp Pro Arg Thr Asn Glu Glu Leu Phe Val
65                  70                  75

<210> SEQ ID NO 10
<211> LENGTH: 53
<212> TYPE: PRT
<213> ORGANISM: Methanobrevibacter ruminantium

<400> SEQUENCE: 10

Met Ser Met Leu Ala Asp Phe Glu Pro Ala Arg Leu His Lys Arg Thr
1               5                   10                  15

Trp Ala Glu Arg His Asp Val Glu Ile Leu Ala Val Ile Cys Leu Ala
            20                  25                  30

Ile Ser Ile Ala Met Leu Leu Leu Phe Phe Ala Leu Ala Glu Pro Thr
        35                  40                  45

Val Ala Gly Val Ile
    50

<210> SEQ ID NO 11
<211> LENGTH: 150
<212> TYPE: PRT
<213> ORGANISM: Methanobrevibacter ruminantium

<400> SEQUENCE: 11

Met Thr Lys Glu Phe Glu Asp Phe Met Arg Arg Asn Thr Gly Leu Leu
1               5                   10                  15

Val Phe Leu Arg Trp Asp Thr Val Ala Tyr Leu Lys Tyr Leu Glu Ser
            20                  25                  30

His Tyr Asp Glu Arg Lys Tyr Glu Cys Ala Tyr Arg Leu Leu Glu Ala
        35                  40                  45

Ile Asp Asn Leu Phe Asp Phe Tyr Gln Ile Thr Phe Ser Lys Lys Thr
    50                  55                  60

Glu Arg Glu Ile Pro Asp Gln Leu Phe Glu Lys Asp Lys Ile Asn Lys
65                  70                  75                  80

Gly Phe Leu Ser His Ile Gly Lys Ala Cys Lys Lys Gln Ser Asp Phe
                85                  90                  95

Tyr Gly Gln Arg Trp Lys Ser Thr Arg Gly Ile Arg Asp Ala Tyr Gly
            100                 105                 110

His Tyr Ser Ala Gly Asn Phe Leu Phe Ala Asp Ile Tyr Gly Cys Leu
        115                 120                 125

His Arg Ile Ser Asp Asp Cys Tyr Arg Ile Leu Asn Phe Ser Glu Tyr
    130                 135                 140

Glu Ile Glu Glu Lys Ala

```
<210> SEQ ID NO 12
<211> LENGTH: 251
<212> TYPE: PRT
<213> ORGANISM: Methanobrevibacter ruminantium

<400> SEQUENCE: 12

Met Asn Glu Ile Val Thr Thr Thr Asn Glu Asn Asn Val Pro Val Asp
1               5                   10                  15

Val Asp Tyr Ala Ile Glu Glu Trp Lys Ala Tyr Gln Arg Leu Thr Arg
            20                  25                  30

Glu Leu Leu Asp Glu Thr Asp Tyr Gln Thr His Arg Gly Arg Lys Tyr
        35                  40                  45

Lys Thr Lys Ser Ala Trp Gln Lys Tyr Ala Arg Ala Phe Asn Ile Asn
    50                  55                  60

Thr Gln Ile Ile Asp Lys Glu Ile Val Lys Asn Asp Lys Gly Ile Val
65                  70                  75                  80

Ile Glu Ala Glu Tyr Thr Val Arg Ala Thr Leu Pro Asn Gly Arg Phe
                85                  90                  95

Val Glu Ser Asp Gly Ser Cys Asp Arg Arg Ser Gly Lys Arg Glu
            100                 105                 110

Met Ser Asn His Ser Ile Lys Ala Thr Ala Lys Thr Arg Ala Thr Asn
        115                 120                 125

Arg Ala Ile Ser Glu Leu Ile Gly Ala Gly Asp Val Ser Ala Asp Glu
    130                 135                 140

Leu Asp Pro Ala Phe Asp Lys Val Gln His Ser Lys Thr Asn His Val
145                 150                 155                 160

Ile Glu Ala Glu Val Ala Glu Ile Ile Glu Ser Pro Tyr Asp Lys Asn
                165                 170                 175

Ala Gly Phe Glu Thr Ala Asp Lys Ile Glu Pro Val Asp Glu Asp Pro
            180                 185                 190

Val Cys Lys Asn Trp Val Lys Thr Ile Cys Lys Thr Ile Lys Ala Glu
        195                 200                 205

Gly Lys Pro Cys Leu Lys Gly Val Leu Ile Gln Lys Ala Arg Thr Ile
    210                 215                 220

Gly Thr Met Thr Asp Glu Glu Arg Asn Arg Leu Ile Glu Tyr Ile Lys
225                 230                 235                 240

Thr Leu Pro Lys Gly Glu Val Asn Leu Asp Asp
                245                 250

<210> SEQ ID NO 13
<211> LENGTH: 76
<212> TYPE: PRT
<213> ORGANISM: Methanobrevibacter ruminantium

<400> SEQUENCE: 13

Met Ile Glu Cys Ile Gln Glu Glu Gly Asp Phe Thr Asp Trp Glu Val
1               5                   10                  15

Pro Ser Ser Ser Asp Ile Lys Tyr Ile Val Ser Val Asp Asp Glu
            20                  25                  30

Gly Asn Leu Phe Cys Ser Cys Pro Asp Phe Tyr Tyr Arg Lys Ser Arg
        35                  40                  45

Met Asn Pro His Ile Ser Asn Pro Glu Ser Tyr Cys Lys His Ile Arg
    50                  55                  60

Gln Val Leu Glu Glu Asp Asn Arg Leu Gln Met Leu
65                  70                  75
```

<210> SEQ ID NO 14
<211> LENGTH: 255
<212> TYPE: PRT
<213> ORGANISM: Methanobrevibacter ruminantium

<400> SEQUENCE: 14

```
Met Asp Asn Ile Asn Lys Thr Lys Thr Ser Leu Ala Lys Phe Glu Glu
1               5                   10                  15

Phe Phe Ser Thr Val Tyr Lys Asp Glu Val Met Glu Val Leu Glu Lys
            20                  25                  30

Tyr Pro Glu Glu Arg Thr Leu Val Val Asp Tyr Glu Asn Leu Glu Met
        35                  40                  45

Phe Asp Pro Asp Leu Ala Asp Leu Leu Ile Glu Lys Pro Asp Glu Val
50                  55                  60

Ile Ala Ala Ser Gln Lys Ala Ile Lys Asn Ile Asp Pro Leu Met Lys
65                  70                  75                  80

Asp Pro Lys Leu Asp Ile Lys Phe Lys Asn Val Ser Asn Cys Ile Asp
                85                  90                  95

Phe Val Asn Ala Asp Ser Lys Tyr Ile Gly Lys Leu Ile Ser Phe Glu
            100                 105                 110

Ala Lys Val Met Glu Ala Lys Glu Pro Lys Pro Ile Leu Asp Ile Ala
        115                 120                 125

Val Tyr Glu Cys Arg Gly Cys Met Ser Leu Arg Glu Ile Pro Gln Thr
130                 135                 140

Ile Asn Ser Ser Leu Glu Pro Ser Leu Cys Pro Glu Cys Gly Gly Arg
145                 150                 155                 160

Ser Phe Arg Leu Leu Gln Asp Glu Ser Glu Phe Leu Glu Ser Gln Leu
                165                 170                 175

Leu Ile Val Ser Ser Asp Asp Thr Ser Lys Ser Leu Lys Val Leu Leu
            180                 185                 190

Leu Arg Asp Glu Cys Ser Phe Asp Leu Tyr Ser Met Gly Gln Glu Val
        195                 200                 205

Arg Ile Thr Gly Ile Leu Lys Ser Phe Ser Ser Asn Tyr Gly Tyr Glu
210                 215                 220

Tyr Phe Leu Glu Cys Asn Leu Ile Glu Ile Leu Asn Asp Ser Glu Asp
225                 230                 235                 240

Ser Glu Tyr Asp Glu Tyr Gly Asn Arg Asn Ser Pro Glu Tyr Arg
                245                 250                 255
```

<210> SEQ ID NO 15
<211> LENGTH: 143
<212> TYPE: PRT
<213> ORGANISM: Methanobrevibacter ruminantium

<400> SEQUENCE: 15

```
Met Ala Asn Lys Ile Arg Val Asn Leu Thr Val Asp Pro Asn Leu Trp
1               5                   10                  15

Gln Leu Ala Lys Asp Lys Leu Pro Cys Ser Arg Ser Glu Phe Phe Glu
            20                  25                  30

Asn Gln Leu Lys Met Phe Leu Gly Ile Glu Asp Asp Glu Ser Glu Ile
        35                  40                  45

Ile Lys Asp Ile Gln Thr Lys Glu Asn Glu Ile Asn Ala Leu Arg Asp
50                  55                  60

Lys Leu Cys His Val Arg Lys Ser Lys Gln Leu Lys Leu Glu Ser Asn
65                  70                  75                  80
```

```
Lys Ser Met Glu Lys Ala Met Ala Ser Leu Asn Arg Met His Lys Lys
                85                  90                  95

Tyr Gly Lys Ile Gly Glu Asn Gln Ile Arg Asn Leu Ala His Val His
            100                 105                 110

Lys Val Asp Phe Asp Asp Leu Lys Lys Glu Cys Gln Asp Asn Cys Met
        115                 120                 125

Asn Ile Phe Glu Phe Ala Glu Val Pro Lys His Asp Ser Val Met
    130                 135                 140

<210> SEQ ID NO 16
<211> LENGTH: 134
<212> TYPE: PRT
<213> ORGANISM: Methanobrevibacter ruminantium

<400> SEQUENCE: 16

Met Thr Ile Gly Ser Leu Asp Asn Phe Gly Lys Ser Asp Gly Glu Asn
1               5                   10                  15

Met Asn Pro Glu Asp Phe Asp Cys Ser Val Phe Glu Met Tyr Lys
                20                  25                  30

Ala Leu Phe Glu Ile Leu Asp Val Glu Val Gly Ser Phe Ala Glu Leu
            35                  40                  45

Leu Asp Val Tyr Lys Asn Val Glu Met Asp Tyr Thr Leu Lys Arg His
    50                  55                  60

Ala Leu Lys Gln Lys Glu Ile Leu Tyr Trp Phe Asn Thr Asp Trp Lys
65                  70                  75                  80

Glu Glu Leu Gly Lys Gly Lys Pro Thr Glu Lys Asp Lys Glu Lys Trp
                85                  90                  95

Ile Arg Gln Lys Ile Gly Tyr Asp Ser Phe Val Val Glu Gln Leu Glu
            100                 105                 110

Val Lys Leu Lys His Ile Arg Arg Met Tyr Glu Thr Ala Leu Lys His
        115                 120                 125

Ser Phe Glu Ala Ile Lys
    130

<210> SEQ ID NO 17
<211> LENGTH: 91
<212> TYPE: PRT
<213> ORGANISM: Methanobrevibacter ruminantium

<400> SEQUENCE: 17

Met Asn Val Lys Thr Val Met Asn Asp Leu Ile Gly Leu Ser Lys Glu
1               5                   10                  15

Phe Glu Gly Val Glu Tyr Glu Ile Glu Ser Lys Asn Ser Ile Tyr Phe
                20                  25                  30

Tyr Ser Phe Pro Lys Tyr Met Lys Glu Gly Ile Val Ile Leu Lys Tyr
            35                  40                  45

Ser Ala Ile Tyr Asp Leu His Thr Ile Leu Lys Gly Met Asp Gly Ile
    50                  55                  60

Ile Val Asp Ile Leu Glu Val Glu Asp Asn Pro Gly Asp Glu Lys Lys
65                  70                  75                  80

Asp Leu Leu Tyr Val Gln Ile Glu Val Lys Glu
                85                  90

<210> SEQ ID NO 18
<211> LENGTH: 77
<212> TYPE: PRT
<213> ORGANISM: Methanobrevibacter ruminantium

<400> SEQUENCE: 18
```

```
Met Ile Ser Asp Glu Trp Glu Glu Tyr Tyr Val Lys Val Asn Glu
1               5                   10                  15

Glu Leu Glu Gln Val Glu Val Arg Phe Phe Ser Lys Val Asp Arg Leu
            20                  25                  30

Val Phe Ala Gln Ser Tyr Ser Ser Ser Ser Phe Ser Phe Glu Glu
            35                  40                  45

Ala Glu Ile Leu Cys Asp Arg Ile Cys Asp Ile Leu Thr Asn Asp Leu
    50                  55                  60

Gly Asn Ala Lys Tyr Tyr Leu Gly Gly Lys Asp Glu Leu
65              70                  75

<210> SEQ ID NO 19
<211> LENGTH: 49
<212> TYPE: PRT
<213> ORGANISM: Methanobrevibacter ruminantium

<400> SEQUENCE: 19

Met Asn Tyr Arg Glu Trp Val Ala Ser Gln Phe Glu Leu Arg Met Thr
1               5                   10                  15

Glu Asp Gly Arg Val Cys Phe Lys Thr Pro Cys Ser Tyr Tyr Thr Phe
            20                  25                  30

Ser Lys Glu Asp Phe Glu Ile Ile Arg Glu Met Phe Leu Asn Phe Glu
        35                  40                  45

Ser

<210> SEQ ID NO 20
<211> LENGTH: 57
<212> TYPE: PRT
<213> ORGANISM: Methanobrevibacter ruminantium

<400> SEQUENCE: 20

Met Asp Arg Ile Lys Glu Leu Asn Val Cys Gly Thr Cys Lys His Ser
1               5                   10                  15

His Leu Ile Pro Asp Ile Asn Gly Glu Ile Ala Val Asn Ile Cys Arg
            20                  25                  30

Ile Gly Ser Glu Ala Val Asn Lys Asp Gly Gly Leu Thr Tyr Cys Val
        35                  40                  45

Asp Trp Thr Pro Arg Arg Lys Leu Ser
    50                  55

<210> SEQ ID NO 21
<211> LENGTH: 111
<212> TYPE: PRT
<213> ORGANISM: Methanobrevibacter ruminantium

<400> SEQUENCE: 21

Met Leu Ser Lys Lys Glu Ala Ile Gln Met Thr Leu Asp Asn Glu Lys
1               5                   10                  15

His Tyr Pro Val Lys Cys Lys Tyr Cys Gly Lys Pro Phe Thr Lys Ser
            20                  25                  30

His Asn Arg Gln Met Tyr Cys Ser Asp Ser Cys Arg Arg Asn Ala Leu
        35                  40                  45

Arg Glu Gln Lys Ala Arg Tyr Gln Ala Lys Arg Leu Lys Ile Lys
    50                  55                  60

Gln Lys Val Leu Ile Val Asp Glu Tyr Lys Leu Tyr Gly Leu Gly Ser
65              70                  75                  80

Tyr Gly Thr Ser Ala Asn Gly His Arg Lys Asn Phe Ser His Glu
            85                  90                  95
```

```
Tyr Met Ala Ile Gln Lys Glu Met Lys Arg Ile Gly Leu Lys Arg
                100                 105                 110

<210> SEQ ID NO 22
<211> LENGTH: 183
<212> TYPE: PRT
<213> ORGANISM: Methanobrevibacter ruminantium

<400> SEQUENCE: 22

Met Tyr Leu Ala Lys Phe Cys Pro Asn Cys Gly Asn Lys Val Glu Glu
1               5                   10                  15

Asn Asp Lys Phe Cys Ile Tyr Cys Gly Asn Lys Leu Arg Val Ile Ile
                20                  25                  30

Pro Glu Lys Lys Val Lys Arg Ser Ser Asn Ser Ile Asn Asp Glu Lys
            35                  40                  45

Thr Ser Lys Tyr Val Glu Val Ile Asp Gly Leu Met Arg Tyr Lys Val
    50                  55                  60

Phe Pro Ser Ser Leu Pro Val Lys Tyr Ile Ile Tyr Lys Val Asn Tyr
65                  70                  75                  80

Gly Thr Thr Ser Asp Glu Ile Lys Asn Ile Leu Glu Asn Gly Asn Tyr
                85                  90                  95

Asn Tyr Lys Ile Asn Ile His Tyr Phe Leu Gln Asn Lys Lys Leu Tyr
                100                 105                 110

Phe Arg Ser Pro Lys Asn Pro Asn Met Phe Phe Lys Phe His Asn Asp
            115                 120                 125

Arg Phe Asn Glu Glu Met Arg Lys Asp Asn Lys Glu Ile Ile His Ile
130                 135                 140

Ser Ser Tyr Ala Arg Val His Arg Pro Ser Leu Thr Lys Ile Phe Asn
145                 150                 155                 160

Phe Asn Gln Glu Lys Thr Phe Ile Leu Ala Asn Lys His Phe Glu Glu
                165                 170                 175

Asn Ile Arg Lys Thr Arg Leu
            180

<210> SEQ ID NO 23
<211> LENGTH: 77
<212> TYPE: PRT
<213> ORGANISM: Methanobrevibacter ruminantium

<400> SEQUENCE: 23

Met Ile Tyr Asp Lys Ala Thr Val Thr Ser Leu Ile Val Ala Ile Leu
1               5                   10                  15

Leu Pro Leu Met Ser Met Leu Gly Ile Gly Glu Leu Thr Gln Asn Tyr
                20                  25                  30

Ile Leu Ala Ile Val Ser Gly Met Ile Ala Leu Val Val Trp Tyr Tyr
            35                  40                  45

Asn Glu Lys His Asn Ser Asp Leu Val Ser Gly Thr Thr Lys Cys Asp
        50                  55                  60

Cys Glu Leu Cys Tyr Gly Gly Asp Asp Glu Ala Leu Ile
65                  70                  75

<210> SEQ ID NO 24
<211> LENGTH: 112
<212> TYPE: PRT
<213> ORGANISM: Methanobrevibacter ruminantium

<400> SEQUENCE: 24

Met Lys His Leu Tyr Glu Ile Ile Pro Tyr Arg Arg Thr Val Trp Ile
```

-continued

```
                1               5              10              15
Thr Gly Phe Leu Lys Thr Thr Val Ser Ser Ala Met Ile Thr Thr Gly
                    20                  25                  30

Val Val Ile Leu Phe Asn Ser Ile Thr Glu His Pro Tyr Phe Met Glu
                    35                  40                  45

Trp Asp Glu Ile Gly Ile Val Leu Gly Ile Val Ser Ile Thr Ile Ala
                    50                  55                  60

Cys Ile Tyr Ile Ala Met Ile Asp Arg Trp Lys Glu Arg Lys Lys
65                      70                  75                  80

Glu Glu Leu Asp Thr Ile Glu Asp Tyr Ile Asn Arg Lys Ala Glu Glu
                    85                  90                  95

Ile Ala Asn Met Lys Val Leu Arg Lys Leu Glu Glu Leu Glu Glu Glu
                    100                 105                 110
```

<210> SEQ ID NO 25
<211> LENGTH: 204
<212> TYPE: PRT
<213> ORGANISM: Methanobrevibacter ruminantium

<400> SEQUENCE: 25

```
Met Ile Glu Ile Ser Thr Ile Lys Ile Thr Asp Ile Lys Pro Ala Glu
1               5                   10                  15

Tyr Asn Pro Arg Ile Met Ser Gln Leu Glu His Thr Lys Leu Arg Asn
                    20                  25                  30

Ser Met Glu Thr Phe Gly Val Val Asp Pro Ile Ile Ile Asn Leu Lys
                    35                  40                  45

Asn Asn His Ile Ile Gly Gly His Gln Arg Tyr Glu Val Leu Leu Asp
                    50                  55                  60

Lys Ser Met Glu Asp Asn Glu Phe Ile Lys Glu Leu His Leu Ile Arg
65                      70                  75                  80

Leu Gly Asp Val Gly Trp Ala Phe Pro Glu Ser Asp Leu Glu Val Glu
                    85                  90                  95

Asp Asp Asp His Glu Lys Ala Leu Asn Leu Ala Leu Asn Asn Ile Glu
                    100                 105                 110

Gly Glu Trp Asp Leu Pro Lys Leu Glu Pro Ile Leu Thr Asp Leu Lys
                    115                 120                 125

Asp Val Gly Phe Asp Ile Glu Leu Thr Gly Phe Ser Asp Ile Glu Leu
                    130                 135                 140

Thr Glu Leu Asn Leu Glu Asn Asn Leu Val Phe Ala Glu Glu Phe Glu
145                     150                 155                 160

Pro Asp Glu Ser Glu Glu Asp Val Asp Leu Glu Asp Ile Tyr Asp Glu
                    165                 170                 175

Pro Val Lys Glu Met Leu Gln Cys Pro Ala Cys Asp His Val Asp Val
                    180                 185                 190

Val Lys Arg Phe Lys Arg Val Asp Ser Gln Gly Asp
                    195                 200
```

<210> SEQ ID NO 26
<211> LENGTH: 152
<212> TYPE: PRT
<213> ORGANISM: Methanobrevibacter ruminantium

<400> SEQUENCE: 26

```
Met Asp Val Asp Asn Leu Leu Gly Tyr Asp Lys Val Leu Glu Leu Arg
1               5                   10                  15

Ser Leu Leu Glu Glu Val Thr Asp Lys Val Ile Pro Val Trp His Lys
                    20                  25                  30
```

```
Asn Arg Gly Ile Lys Asp Phe Lys Gln Met Cys Gln Asp Tyr Asn Phe
         35                  40                  45

Val Ser Ile Ser Gly Trp Arg Asn Glu Asp Val Lys Asp Asp Gln Phe
 50                  55                  60

Ile His Phe Val Arg His Ala His Arg Asn Gly Cys Arg Ile His Gly
 65                  70                  75                  80

Leu Gly Leu Thr Arg Arg Lys Val Leu Asp Arg Val Pro Phe Asp Ser
                 85                  90                  95

Val Asp Ser Ser Ser Trp Leu Gln Thr Ile Leu Tyr Ala Arg Leu Gly
                100                 105                 110

Gln Lys Gln Leu Asp Ser Lys Phe Ala Thr Glu Arg Gly Asp Leu
                115                 120                 125

Ala Val Leu Ser Tyr Ile Lys Trp Met Lys Thr Gln Glu Glu Tyr Tyr
                130                 135                 140

Lys Lys Trp Arg His Tyr His Asp
145                 150

<210> SEQ ID NO 27
<211> LENGTH: 218
<212> TYPE: PRT
<213> ORGANISM: Methanobrevibacter ruminantium

<400> SEQUENCE: 27

Met Ile Asn Glu Arg Ile Arg Pro Tyr Leu Asn Phe Ser Phe Asn Asp
 1               5                  10                  15

Lys Lys Val Ile Phe Val Thr Leu Phe Val Ser Asn Leu Ile Ser
                 20                  25                  30

Asn Leu Leu Ala Ile Lys Val Phe Asn Leu Gly Phe Trp Gly Leu Thr
         35                  40                  45

Thr Asp Cys Gly Asn Leu Leu Phe Pro Leu Gly Tyr Leu Met Ala Asp
 50                  55                  60

Val Ile Thr Glu Val Tyr Gly Glu Arg Thr Ala Arg Arg Val Ile Leu
 65                  70                  75                  80

Leu Gly Leu Phe Ala Asn Ile Leu Leu Ile Val Ala Thr Thr Leu Thr
                 85                  90                  95

Val Tyr Met Pro Tyr Pro Ser Tyr Trp Thr Gly Gln Gly Ala Tyr Ala
                100                 105                 110

Tyr Met Phe Gly Phe Thr Pro Arg Ile Val Leu Ala Gly Phe Ile Ala
                115                 120                 125

Tyr Leu Val Gly Gln Phe Val Asn Ala Arg Leu Met Val Leu Ile Lys
                130                 135                 140

Lys Trp Thr Asn Ser Lys Tyr Leu Phe Met Arg Thr Ile Gly Ser Thr
145                 150                 155                 160

Leu Gly Gly Glu Leu Cys Asp Ser Cys Ile Cys Ser Ser Ile Ala Tyr
                165                 170                 175

Tyr Gly Ile Val Pro Asn Ser Gly Ile Leu Leu Phe Ile Leu Met Gln
                180                 185                 190

Tyr Val Val Lys Val Thr Trp Glu Val Val Met Gln Pro Leu Thr Tyr
                195                 200                 205

Lys Ser Ile Ala Trp Ala Arg Lys Asp Gly
    210                 215

<210> SEQ ID NO 28
<211> LENGTH: 194
<212> TYPE: PRT
<213> ORGANISM: Methanobrevibacter ruminantium
```

<400> SEQUENCE: 28

Met Pro Glu Pro Trp Glu Arg Gln Arg Asp Glu Asn Gly Lys Leu Glu
1               5                   10                  15

Pro Ile Lys Ala Phe Glu Tyr Phe Thr Glu Tyr Leu Thr Met Asp Lys
            20                  25                  30

Pro Arg Ser Met Arg Val Leu Cys Glu Arg Leu Gly Lys Lys Asp Gly
        35                  40                  45

Tyr Ile Arg Gln Leu His Ala Tyr Ser Ser Thr Trp Asn Trp Val Glu
50                  55                  60

Arg Ala Glu Ala Tyr Asp Glu His Ile Ile Leu Lys Lys Arg Leu Arg
65                  70                  75                  80

Lys Glu Lys Phe Tyr Asp Glu Leu Val Glu Ser Glu Leu Pro Asn Leu
                85                  90                  95

Arg Lys Arg Leu Glu Tyr Tyr Asn Lys Asn Met Asn Asp Ile Glu Thr
            100                 105                 110

Asp Met Thr Thr Lys Pro Thr Ser Lys Ala His Ala Tyr Asp Lys Asn
        115                 120                 125

Ser Lys Ala His Ser Thr Thr Leu Asn Glu Ile Leu Leu Met Ile Gly
130                 135                 140

Lys Pro Thr Glu Ile Lys Glu Thr Ser Leu Glu Ala Asp Ile Glu Ser
145                 150                 155                 160

Asp Asn Lys Ile Asp Leu Glu Asn Arg Val Glu Val Asp Ile Thr Ser
                165                 170                 175

Asp Glu Phe Met Glu Ser Glu Leu Glu Tyr Met Arg Lys Met Ile Glu
            180                 185                 190

Glu Lys

<210> SEQ ID NO 29
<211> LENGTH: 255
<212> TYPE: PRT
<213> ORGANISM: Methanobrevibacter ruminantium

<400> SEQUENCE: 29

Met Lys Asp Ile Val Asn His Tyr Gly Tyr Leu Ser Pro Tyr Lys Pro
1               5                   10                  15

Thr Ile Arg Ser Asp Ser Lys Ala Lys Asn Lys Phe Lys Leu Asn Glu
            20                  25                  30

Pro Tyr Arg Gly Gln Met Leu Ser Ala Gly Ala Gly Ser Ile Met
        35                  40                  45

Gly Tyr Gly Ala Gly Leu Leu Ile Val Asp Asp Pro Ile Lys Asn Val
50                  55                  60

Ala Glu Ala Glu Ser Lys Val Arg Gln Ala Lys Leu Lys Asp Trp Trp
65                  70                  75                  80

Gly Gly Thr Ile Lys Ser Arg Val Gln Arg Ser Asn Gly Leu Pro
                85                  90                  95

Pro Ile Lys Ile Val Ile Ala Gln Arg Leu His Leu Lys Asp Leu His
            100                 105                 110

Gly Ile Ile Lys Glu Thr Glu Pro Thr Ile Pro Ala Asn Asp Ala Phe
        115                 120                 125

Arg Ile Leu Arg Asn Gly Gly Ser Ile Asp Pro Asn Thr Trp Val Asp
130                 135                 140

Phe Asn Leu Pro Ala Ile Cys Asp Ser Glu Asp Asp Ile Leu Gly Arg
145                 150                 155                 160

Lys Ile Gly Glu Val Leu Trp Glu Glu Gln Arg Asp Tyr Glu Trp Leu

```
                    165                 170                 175
Met Ala Glu Lys Arg Ser Met Gly Ser Tyr Leu Phe Asn Ser Ile Tyr
            180                 185                 190

Gln Gly Gln Pro Val Glu Arg Asp Gly Glu Ile Phe Lys Arg Glu Trp
        195                 200                 205

Phe Gln Asp Glu Val Asn His Lys Leu Thr Cys Leu Ile Asp Pro Lys
    210                 215                 220

Asp Ile Pro Lys Asp Leu Pro Gln Leu Arg Tyr Trp Asp Phe Gly Ala
225                 230                 235                 240

Ser Gly Asp Ala Gly Asp Gly Thr Ser Ala Ile Leu Thr Ser Tyr
                245                 250                 255

<210> SEQ ID NO 30
<211> LENGTH: 261
<212> TYPE: PRT
<213> ORGANISM: Methanobrevibacter ruminantium

<400> SEQUENCE: 30

Met Ser Lys Lys Gln Glu Met Met Arg Ile Glu Arg Leu Lys His Tyr
1               5                   10                  15

Ala Tyr Gln Thr Gly Leu Ile Ile Pro Ile Phe Lys Asn His Asp Leu
            20                  25                  30

Ile Lys Lys Ile Glu Asn Gly Lys Ile Thr Asn Thr Asp Glu Ile Lys
        35                  40                  45

Ile Tyr Ile Glu Glu Asn Glu Lys Gln Ile Lys Arg Arg Arg Glu Phe
    50                  55                  60

Ile Ser Ile Ile Tyr Asp Asn Cys Lys Tyr Phe Lys Tyr Asp Ser Ile
65                  70                  75                  80

Cys Tyr Lys Leu Ile Ser Lys Val Asn Asn Phe Glu Ile Lys Ser Leu
                85                  90                  95

Glu Glu Leu Met Asn Glu Ile Glu Ser Glu Lys Lys Lys Asn Gly Phe
            100                 105                 110

Arg Lys Asn Ile Glu Glu Lys Glu Leu Ile Lys Glu Asn Glu Asn Lys
        115                 120                 125

Gly Arg Leu Lys Glu Tyr Val Arg Ile Val Arg Arg Glu Tyr Gly Leu
    130                 135                 140

Asp Phe Thr Ser Val Lys Lys Leu Lys Leu Lys Ile Asp Asn Asn Lys
145                 150                 155                 160

Ile Arg Ser Lys Glu Glu Leu Asn Glu Ile Ile Glu Glu Lys Lys
                165                 170                 175

Lys Thr Glu Leu Arg Arg Ile Val Tyr Asp Ser Asp Leu Asn Trp Asp
            180                 185                 190

Leu Lys Trp Glu Leu Glu Ser Lys Ile Arg His Asn Gly Ile Thr Thr
        195                 200                 205

Lys Glu Glu Leu Ile Lys Glu Ile Arg Arg Ile Glu Phe Ile Asn Ile
    210                 215                 220

Ile Tyr Asp Asn Asn Arg Asp Phe Lys Leu Asp Tyr Val Thr Ile Gln
225                 230                 235                 240

Lys Leu Val Ser Lys Ile Gly Ser Asn Glu Ile Thr Thr Lys Glu Glu
                245                 250                 255

Leu Ile Lys Glu Met
            260

<210> SEQ ID NO 31
<211> LENGTH: 255
<212> TYPE: PRT
```

<213> ORGANISM: Methanobrevibacter ruminantium

<400> SEQUENCE: 31

| | | | | | | | | | | | | | | | |
|---|---|---|---|---|---|---|---|---|---|---|---|---|---|---|---|
|Met|Ser|Lys|Asn|Ala|Lys|Ala|Asp|Ala|Phe|Val|Val|Thr|Thr|Glu|Asp|
|1| | |  |5| | | | |10| | | | |15| |

Gly Ser Tyr Asp Ile Val Asp Ala Asp Val Leu Glu Arg Tyr Ala Ile
            20                  25                  30

Lys Ser Glu Ser Asp Glu Thr Gly Ser Lys Gln Leu Lys Thr Asp Gly
        35                  40                  45

Trp Glu Tyr Asp Asp Thr Leu Leu Glu Pro Leu Tyr Asp Pro Leu Gln
 50                  55                  60

Leu Cys Glu Leu Leu Glu Ile Asn Thr Tyr His Glu Asn Cys Val Asp
 65                  70                  75                  80

Val Val Ala Arg Asp Ser Ala Gly Ile Gly Tyr Asp Ile Val Pro Val
                 85                  90                  95

Thr Gly Glu Lys Glu Lys Glu Leu Asn Lys Pro Lys Leu Thr Asn Phe
            100                 105                 110

Leu Glu Asn Ile Glu Pro Asn Ile Asn Glu Leu Leu Tyr Gln Met Asn
        115                 120                 125

Tyr Asp Arg Arg Ala Thr Gly Tyr Gly Ala Leu Glu Leu Ile Arg Lys
130                 135                 140

Asp Lys Ser Lys Ser Glu Pro Val Asn Leu Ser His Ile Ser Ser Tyr
145                 150                 155                 160

Thr Leu Arg Arg Thr Ser Asp Gly Lys Arg Val Lys Gln Arg Val Gly
                165                 170                 175

Thr Lys Thr Val Trp Phe Val Ile Tyr Gly Lys Asn Tyr Asp Lys Glu
            180                 185                 190

Gly Asn Leu Cys Asp Val His Ser Glu Thr Gly Glu Phe His Pro Tyr
        195                 200                 205

Asn Ser Leu Ser Lys Glu Glu Arg Ala Asn Glu Leu Leu Trp Thr Met
210                 215                 220

Glu Tyr Thr Thr Lys Ser Lys Tyr Tyr Gly Leu Pro Lys Ile Val Gly
225                 230                 235                 240

Ala Ile Pro Ala Ile Tyr Ser Asp Ile Ser Arg Ser Lys Tyr Asn
                245                 250                 255

<210> SEQ ID NO 32
<211> LENGTH: 254
<212> TYPE: PRT
<213> ORGANISM: Methanobrevibacter ruminantium

<400> SEQUENCE: 32

Met Met Ala Leu Lys Val Arg His Ser Lys Arg Gln Ile Gln Asn Ile
1               5                   10                  15

Lys Arg Glu Tyr Arg Arg Leu Ile Leu Glu Glu Gln Cys Ser Arg
            20                  25                  30

Glu Ile Ala Asp Phe Phe Arg Arg Leu Glu Arg Lys Ile His Lys Val
        35                  40                  45

Met Asp Glu His Trp Glu Ser Glu Leu Gly Leu Phe His Leu Asn Lys
 50                  55                  60

Val Ser Asp Ile Ile Gln Asp Ser Arg Gln Glu Tyr Tyr Asp Ile Leu
 65                  70                  75                  80

Phe Lys Tyr Cys Lys Asp Ser Tyr Met Lys Gly Arg Glu Ala Thr Glu
                 85                  90                  95

Arg Arg Phe Asn Arg Lys Leu Glu Asn Ile Ser Met Lys Ala Asp Val
            100                 105                 110

```
Asn Ile Thr Arg Leu Glu Asp Leu Phe Lys Pro Asp Pro Thr Ile Arg
            115                 120                 125

Tyr Asn Leu Asn Asn Lys Val Phe Gln Ala Ser Ala His Thr Met Asp
        130                 135                 140

Arg Val Asp Asn Arg Ile Met Glu Asn Ile Thr Gln Ser Tyr Asp Asp
145                 150                 155                 160

Gly Leu Gly Ile Asp Glu Ala Lys Asp Arg Leu Thr Val Glu Tyr Asn
                165                 170                 175

Gly Leu Lys Ser Trp Glu Ala Gln Arg Ile Ala Arg Thr Glu Ile Asn
            180                 185                 190

Ser Ala Gln Asn Asp Gly Ala Phe Asp Val Tyr Gly Glu Leu Gly Val
        195                 200                 205

Glu Tyr His Gln Trp Trp Thr Ala Gln Asp Arg Val Arg Glu Thr
210                 215                 220

Pro Gln Ala Asp His Arg Glu Leu His Gly Lys Ile Val Lys Val Gly
225                 230                 235                 240

Asn Ser Phe Ser Asn Gly Leu Gln Tyr Pro Gly Asp Arg Thr
                245                 250

<210> SEQ ID NO 33
<211> LENGTH: 87
<212> TYPE: PRT
<213> ORGANISM: Methanobrevibacter ruminantium

<400> SEQUENCE: 33

Met Ile Ile Glu Ile Pro Gly Asn Asp Arg Thr Glu Glu Ile Asn Leu
1               5                   10                  15

Pro Asn Gly Gln Phe Val Leu Ile Thr Tyr Leu Gln Glu Asn Asp Met
            20                  25                  30

Met Ser Leu Pro Asp Gly Lys Tyr Val Cys Pro Phe Arg Met Ile Gln
        35                  40                  45

Leu Phe Thr Glu Glu Gly Gly Glu Leu Ile Gly Glu Cys Ile Glu Glu
    50                  55                  60

Asn Pro His Tyr Asn Thr Arg Phe Tyr Asn Thr Val Phe Glu His Leu
65                  70                  75                  80

Asp Glu Gly Ile Glu Tyr Arg
                85

<210> SEQ ID NO 34
<211> LENGTH: 179
<212> TYPE: PRT
<213> ORGANISM: Methanobrevibacter ruminantium

<400> SEQUENCE: 34

Met Leu Arg Val Val Glu Arg Thr Tyr Tyr Gln Gln Glu Glu Ile Lys
1               5                   10                  15

Thr Leu Asp Cys Arg Ile Arg Glu Ala Gly Val Asn Thr Tyr Ser Leu
            20                  25                  30

Ala Arg Gln Gly Ala Val Asp Tyr Pro Thr Tyr Glu Ser Tyr Asn Glu
        35                  40                  45

Val Arg Glu Glu Arg Ile Lys Glu Ala Lys Glu Lys Tyr Gly Glu Ser
    50                  55                  60

Tyr Tyr Tyr His Trp Arg Asp Val Glu Thr Tyr Phe Tyr Leu Gly
65                  70                  75                  80

Arg Phe Phe Ser Asp Leu Glu Glu Ile Glu Lys Tyr Leu Glu Arg Thr
                85                  90                  95
```

```
Val Thr Tyr Lys Pro His Arg Glu Glu Leu Lys Glu Ala Met Glu Arg
                100                 105                 110

Leu Asp Lys Arg Phe Glu Val Ile Asn Glu Phe Trp Tyr Ser Leu
            115                 120                 125

Glu Glu Tyr Glu Asp Ile Thr Glu Asp Val Leu Glu Gln Leu Lys Glu
        130                 135                 140

Gly Asp Cys Thr Val His Cys Glu Phe Leu Ile Lys Glu Phe Lys Lys
145                 150                 155                 160

Phe Val Asn Val Ile Cys Arg Ile Ile Lys Gln Asn Glu Ile Asn His
                165                 170                 175

Lys Glu Phe

<210> SEQ ID NO 35
<211> LENGTH: 96
<212> TYPE: PRT
<213> ORGANISM: Methanobrevibacter ruminantium

<400> SEQUENCE: 35

Met Asp Ala Ile Asn Val Ile Asn Gln Asn Lys Ile Leu Val Asp Val
1               5                   10                  15

Leu Tyr Arg Gly Thr Val Asn Leu Ile Asp Ile Val Ile Gly Asp Ala
            20                  25                  30

Leu Val Tyr Asp Asn Pro Thr Val Val Lys Cys Tyr Thr Thr Asp
            35                  40                  45

Leu Ala Phe Ala Thr Thr Glu Ile Asp Glu Ile Val Leu Glu Asn Glu
        50                  55                  60

Glu Phe Glu Leu Leu Ile Thr Tyr Glu Asp Gly Glu Phe Ser Ile Leu
65                  70                  75                  80

Leu Lys Ser His Asn Leu Gly Glu Leu Gly Tyr Ile Glu Trp Val Ile
                85                  90                  95

<210> SEQ ID NO 36
<211> LENGTH: 101
<212> TYPE: PRT
<213> ORGANISM: Methanobrevibacter ruminantium

<400> SEQUENCE: 36

Met Val Phe Val Asp Leu Cys Glu Asn Glu Ile Ala Asp Met Val Glu
1               5                   10                  15

Ser Phe Tyr Arg Asn Gly Asp Gly Ser Ser Arg Ile Leu Thr Asn Arg
            20                  25                  30

Ala Val Gly Glu Ile Val Glu His Tyr Cys Ser Phe Val Asp Gly
            35                  40                  45

Arg Ile Thr Thr Asn Leu Arg Asp Phe Leu Leu Tyr Ser Val Val Leu
        50                  55                  60

Tyr Asp Thr Ile Gly Glu Ala Val Asp Asp Gly Val Asn Leu Glu Glu
65                  70                  75                  80

Val Phe Ile Ile Glu Asp Arg Asn Cys Tyr Thr Gly Lys Ser Gln Val
                85                  90                  95

Ile Leu Ile Gly Gly
            100

<210> SEQ ID NO 37
<211> LENGTH: 185
<212> TYPE: PRT
<213> ORGANISM: Methanobrevibacter ruminantium

<400> SEQUENCE: 37
```

Met Val Asn Trp Leu Lys Ala Ile Gly Asp Asn Phe Ser Val Asp Tyr
1               5                   10                  15

Leu Leu Leu Ala Leu Phe Ser Ser Gly Asp Leu Ile Leu Val Ala Ile
            20                  25                  30

Val Leu Asn Ser Tyr Gly Val Ile Ser Pro Glu Asn Val Arg Glu Leu
        35                  40                  45

Val Ile Asp Tyr Ile Ser Tyr Arg Lys Val Asp Ile Phe Trp Arg His
    50                  55                  60

Leu Arg Arg Pro Arg Met Ser Phe Glu Asp Tyr Val Leu Asp Asn Phe
65                  70                  75                  80

Glu Glu Met Glu Thr Gly Glu Leu Thr Arg Gly Gln Val Glu Phe
                85                  90                  95

Val Ser Arg Gln Glu Arg Lys Gly Leu Thr Phe Cys Asn Glu Ile Phe
            100                 105                 110

Ile Ala Val Pro Leu Lys Lys Gly Ser Lys Asp Asp Ile Val Glu Ile
        115                 120                 125

Leu Trp Asn Glu Tyr Phe Val Glu Asp Tyr Lys Glu Asn Trp Leu Glu
    130                 135                 140

Gln His Glu Asn Leu Gly Trp Asn Asp Trp Lys Lys Leu Leu Lys Lys
145                 150                 155                 160

Glu Ile Val Glu Asn Gly Gly Asp Asp Phe Gln Ile Phe Arg Asn His
                165                 170                 175

Leu Ile Asp Cys Val Leu Met Glu Tyr
            180                 185

<210> SEQ ID NO 38
<211> LENGTH: 63
<212> TYPE: PRT
<213> ORGANISM: Methanobrevibacter ruminantium

<400> SEQUENCE: 38

Met Thr Met Lys Val Thr Phe Glu Asp Glu Asn Gly Glu Arg Thr Val
1               5                   10                  15

Glu Phe Gly Asp Asp Val Asp Phe Val Leu Ile Glu Ser Asp Asp Asp
            20                  25                  30

Gly Asn Ile Glu Ile Arg Glu Gly Asp Trp Glu Leu Asp Gly Asp Ser
        35                  40                  45

Asp Asp Asp Trp Glu Glu Tyr Asp Asp Trp Asp Glu Glu Glu Phe
    50                  55                  60

<210> SEQ ID NO 39
<211> LENGTH: 93
<212> TYPE: PRT
<213> ORGANISM: Methanobrevibacter ruminantium

<400> SEQUENCE: 39

Met Asp Glu Phe Val Glu Thr Leu Phe Asp Thr Tyr Trp Lys Val Asn
1               5                   10                  15

Glu Asn Gly Glu Tyr Met Ser Leu Thr Asp Cys Gly Asp Phe Tyr Ile
            20                  25                  30

Ala Lys Val Ala Pro Cys Val Arg Asn Trp Ser Ile Val Ile Glu Cys
        35                  40                  45

Asn Cys Phe Cys Phe His Cys Lys Glu Phe Val Tyr His Glu Asn Gly
    50                  55                  60

Ala Ile Leu Glu Ile Gly Met Glu Ile Ser Ser Leu Tyr Leu Ser Gln
65                  70                  75                  80

Met Glu Ile Lys Asp Leu Lys Ile Tyr Met Ile Asp Cys
            85                  90

<210> SEQ ID NO 40
<211> LENGTH: 119
<212> TYPE: PRT
<213> ORGANISM: Methanobrevibacter ruminantium

<400> SEQUENCE: 40

```
Met Phe Leu Glu Gly Ile Phe Glu Gln Asp Gly Glu Asn Val Arg Glu
1               5                   10                  15

Gln Val Ile Tyr Trp Arg Lys Ser Asn Gln Val His Asn Trp Phe Val
            20                  25                  30

Val Asn Ala Gln Asp Gly Glu Asp Asn Cys Gln Pro His Ser Val Ser
        35                  40                  45

Arg Glu Gln Leu Glu Leu Arg Asp Leu Cys Arg Ala Val Leu Ala
    50                  55                  60

Asp Asn Asp Lys Ala Glu Glu Leu Leu Pro Thr Arg Pro Gly Phe Phe
65                  70                  75                  80

Phe Gly Ala Ile Asp Tyr Asp Glu Trp Tyr Tyr Tyr Asp Leu Gln Tyr
                85                  90                  95

Thr Val Glu Lys Ile Asp Glu Val Leu Lys Asp Asp Arg Tyr Leu Tyr
            100                 105                 110

Phe Glu Tyr Cys Ser Trp Trp
        115
```

<210> SEQ ID NO 41
<211> LENGTH: 57
<212> TYPE: PRT
<213> ORGANISM: Methanobrevibacter ruminantium
<220> FEATURE:
<221> NAME/KEY: MOD_RES
<222> LOCATION: (42)..(42)
<223> OTHER INFORMATION: Any amino acid

<400> SEQUENCE: 41

```
Met Gln Leu Val Val Glu Gly Glu Asn Met Glu Cys Pro Cys Asp Asn
1               5                   10                  15

Cys Glu Met Leu Arg Glu Asn Glu Pro Ile Lys Val Ile Asp Trp Lys
            20                  25                  30

Ser Asn Ser Pro Phe Gly Asn Gly Ile Xaa Ile His Phe Trp Arg Glu
        35                  40                  45

Arg Leu Gln Asp Val Gly Tyr Asn Gly
    50                  55
```

<210> SEQ ID NO 42
<211> LENGTH: 116
<212> TYPE: PRT
<213> ORGANISM: Methanobrevibacter ruminantium

<400> SEQUENCE: 42

```
Met Glu Leu Met Thr Arg Glu Met Glu Gly Lys Leu Lys Ser Phe Pro
1               5                   10                  15

Phe Tyr Ser Gln Asp Gly Lys Gly Asp Asp Ala Ile Val Val Met Lys
            20                  25                  30

Phe Phe Asn Pro Tyr Gly Leu Gly Thr Trp Tyr Val Leu Glu Ala Glu
        35                  40                  45

Lys Gln Glu Asn Gly Asp Tyr Leu Phe Phe Gly Tyr Val Glu Ser Pro
    50                  55                  60

Ile Thr Pro Glu Phe Asn Glu Tyr Gly Tyr Phe Ser Leu Ser Glu Leu
65                  70                  75                  80
```

```
Glu Asn Leu Lys Ile Pro Ile Lys Ile Asn Gly Ile Thr Val Ser Tyr
                85                  90                  95
Gly Arg Ile Glu Arg Asp Leu Tyr Phe Glu Arg Val Arg Ile Gly Asp
            100                 105                 110
Ile Ile Gly Asn
        115

<210> SEQ ID NO 43
<211> LENGTH: 74
<212> TYPE: PRT
<213> ORGANISM: Methanobrevibacter ruminantium

<400> SEQUENCE: 43

Met Phe Gly Gln Lys Lys Glu Phe Val Lys Met Tyr His Val Gly
1               5                   10                  15
Asp Val Val Glu Leu Val His Met Asp Asp Ala Gln Ala Pro Pro Ser
            20                  25                  30
Gly Thr Arg Gly Glu Ile Leu Phe Val Asp Asp Ile Gly Gln Ile His
        35                  40                  45
Val Arg Trp Glu Asn Gly Ser Gly Leu Ala Leu Ile Tyr Gly Glu Asp
    50                  55                  60
Arg Phe Lys Val Val Glu Arg Lys Gly Glu
65                  70

<210> SEQ ID NO 44
<211> LENGTH: 50
<212> TYPE: PRT
<213> ORGANISM: Methanobrevibacter ruminantium

<400> SEQUENCE: 44

Met Asp Leu Leu Tyr Leu Tyr Asp Asp Leu Thr Ala Arg Arg Glu Val
1               5                   10                  15
Tyr Asp Ser Val Gly Leu Ser Phe Val Val Lys Tyr Lys Phe Ser Ser
            20                  25                  30
Arg Lys Glu Ala Gln Asp Phe Ala Leu Lys Tyr Gly Ala Glu Leu Ile
        35                  40                  45
Glu Glu
    50

<210> SEQ ID NO 45
<211> LENGTH: 62
<212> TYPE: PRT
<213> ORGANISM: Methanobrevibacter ruminantium

<400> SEQUENCE: 45

Met Ile Glu Arg Arg Arg Leu Gly Met Lys Tyr Asp Ile Phe Thr Ile
1               5                   10                  15
Leu Asp Glu Ile Ser Arg Lys Leu Asp Asp Gly Glu Leu Ser Asp Glu
            20                  25                  30
Gln Val Asp Phe Leu Leu Gln Met Glu Ile Leu Val Glu Glu Gly Thr
        35                  40                  45
Ile Thr Asp Glu Gln Ala Gln Asp Val Met Asn Gly Asp Tyr
    50                  55                  60

<210> SEQ ID NO 46
<211> LENGTH: 55
<212> TYPE: PRT
<213> ORGANISM: Methanobrevibacter ruminantium

<400> SEQUENCE: 46
```

Met Met Lys Leu Ser Leu Lys Glu Leu Gly Glu Ile Glu Met Ile
1               5                   10                  15

Leu Ala Glu Gly Gly Leu Thr Phe Asp Gln Val Asp Tyr Leu Leu Tyr
            20                  25                  30

Leu Glu Thr Cys Ile Ala Asp Gly Ser Ile Thr Glu Gln Lys Arg
            35                  40                  45

Glu Ile Ile Cys Arg Asp Phe
    50              55

<210> SEQ ID NO 47
<211> LENGTH: 77
<212> TYPE: PRT
<213> ORGANISM: Methanobrevibacter ruminantium

<400> SEQUENCE: 47

Met Val Arg Glu Gln Glu Arg Leu Ile Met Tyr Leu Glu Ile Asp Glu
1               5                   10                  15

Val Lys Cys Glu Asn Ile Asp Arg Ile Glu Phe Asp Asp Val Ala Met
            20                  25                  30

Glu Ile Val Leu Thr Asp Glu Lys Val Tyr Glu Arg Ile Lys Arg Trp
            35                  40                  45

Leu Lys Ser Asn Glu Ile Asp Tyr Asp Cys Arg Glu Asp Arg Tyr Phe
        50                  55                  60

Ala Asn Leu Ile Glu Tyr Val Ile Arg Ile Thr Trp Trp
65                  70                  75

<210> SEQ ID NO 48
<211> LENGTH: 71
<212> TYPE: PRT
<213> ORGANISM: Methanobrevibacter ruminantium

<400> SEQUENCE: 48

Met Val Thr Val Arg Asp Val Gly Phe Thr Ile Glu Glu Arg Phe Phe
1               5                   10                  15

Leu Thr Ala Gln Glu Leu Glu Tyr Ser Glu Val Gly Glu Glu His Glu
            20                  25                  30

Ser Val Ile Asp Arg Ala Ile Ala Leu Leu Tyr Thr Lys Leu Arg Thr
            35                  40                  45

Arg Asp Phe Glu Phe Thr Asp Glu Glu Arg Glu Leu Leu Glu Asp Ala
        50                  55                  60

Phe Val Ile Val Ser Asp Gln
65                  70

<210> SEQ ID NO 49
<211> LENGTH: 255
<212> TYPE: PRT
<213> ORGANISM: Methanobrevibacter ruminantium

<400> SEQUENCE: 49

Met Ala Lys Glu Asn Val Ile Asp Tyr Lys Ile Glu Arg Gln Asn Asp
1               5                   10                  15

Asn Thr Trp Ser Tyr Leu Tyr Val Thr Glu Arg Gly Arg Gly Asn Ile
            20                  25                  30

Ile Ala Ser Ser Phe Gly Glu Leu Arg Gln Lys Val Leu Lys Arg Gly
            35                  40                  45

Leu Pro Trp Asn Asp Ile Ser Asn Leu Phe Thr Lys Lys Ser Ser Asp
        50                  55                  60

Ser Asn Val Arg Arg Glu Ser Val Lys Asn Ile Asp Asp Glu Ser Val

```
                65                  70                  75                  80
Leu Ala Asp Val Ala Lys Lys Ser Ser Asp Ser Asn Val Arg Leu Glu
                    85                  90                  95

Ala Val Arg Lys Ile Ser Asp Asn Tyr Val Leu Ile Asp Ile Val Lys
                100                 105                 110

Asn Ala Ser Asp Tyr Asp Val Arg Arg Glu Ala Val Arg Lys Ile Asn
                115                 120                 125

Asp Ser Ser Val Leu Glu Asp Ile Ala Lys Asn Asn Asp Glu Asn
                130                 135                 140

Val Arg Leu Glu Ala Val Arg Asn Ile Asn Asp Glu Ser Val Leu Glu
145                 150                 155                 160

Asn Ile Ser Lys Asn Ala Ser Asp Ser Lys Val Arg Ile Glu Ala Ile
                165                 170                 175

Lys Lys Ile Asn Asp Glu Thr Ile Ile Lys Leu Ala Lys Asn Asn
                180                 185                 190

Asn Asp Glu Asp Val Arg Ile Glu Ala Val Arg Lys Ile Asn Asp Lys
                195                 200                 205

Thr Val Ile Ile Asp Phe Ala Lys Asn Ala Ser Asp Ser Lys Val Arg
210                 215                 220

Arg Glu Ala Val Arg Lys Ile Asn Asp Ser Ser Val Leu Ala Tyr Val
225                 230                 235                 240

Leu Lys Asn Asp Pro Ser Trp Ile Val Arg Ile Glu Ala Val Arg
                245                 250                 255

<210> SEQ ID NO 50
<211> LENGTH: 231
<212> TYPE: PRT
<213> ORGANISM: Methanobrevibacter ruminantium

<400> SEQUENCE: 50

Met Val Val Lys Cys Pro Asn Cys Phe Ser Pro Arg Val Ser Lys Cys
1               5                   10                  15

Glu Asp Thr Asn Ile Lys Trp Gln Cys Asp Lys Cys Lys Cys Lys Phe
                20                  25                  30

Asn His Gly Ala Phe Asp Ile Asn Ala Glu Met Glu Lys Val Glu Gln
                35                  40                  45

Leu Thr Ile Glu Lys Ile Glu Arg Glu Arg Glu Arg Thr Glu Gln Phe
50                  55                  60

Glu Arg Ala Ile Lys Glu Ala Lys Glu Gln Phe Glu Arg Glu Arg Thr
65                  70                  75                  80

Glu Gln Phe Glu Arg Glu Arg Lys Glu Arg Leu Glu Arg Glu Lys Arg
                85                  90                  95

Glu Lys Glu Arg Glu Lys Ile Glu Lys Glu Arg Glu Lys Glu Arg
                100                 105                 110

Leu Glu Arg Asn Arg Ile Lys Ile Glu Glu Arg Glu Arg Glu Arg Ile
                115                 120                 125

Lys Arg Asn Glu Arg Ile Arg Arg Glu Asn Glu Arg Asn Arg Ile Lys
                130                 135                 140

Ser Asp Lys Arg Glu Arg Glu Lys Ser Glu Glu Lys Arg Ile Lys Arg
145                 150                 155                 160

Asn Glu Arg Ile Arg Lys Ala Asn Glu Arg Asn Ser Ile Lys Arg Glu
                165                 170                 175

Lys Arg Glu Arg Glu Arg Glu Arg Asn Val Met Thr Ile Asp Glu Tyr
                180                 185                 190

Tyr Arg Ser Ile Gly Tyr Gly Ser Thr Gly Lys Ser Lys Val Trp Ser
```

```
                195                 200                 205
Ala Ile Ile Ile Pro Ile Leu Leu Val Ile Cys Ile Ile Leu Ile Leu
210                 215                 220

Met Phe Tyr Gly Gly Gly Met
225                 230

<210> SEQ ID NO 51
<211> LENGTH: 248
<212> TYPE: PRT
<213> ORGANISM: Methanobrevibacter ruminantium

<400> SEQUENCE: 51

Met Thr Glu Gly Gln Ile Arg Gln Ile Ala His Glu Tyr Leu Ala Asn
1               5                   10                  15

Tyr Ser Leu Val Asp Lys Asn His Glu Phe Phe Glu Thr Arg Glu Val
                20                  25                  30

Ile Gly Val Pro Val Glu Ser Tyr Ile Thr Asn Glu Pro Ile Ser Leu
            35                  40                  45

Lys Gly Leu Asp Gly Thr Val Asn Glu Tyr Pro Lys Gly Thr Trp Ile
        50                  55                  60

Ala Thr Thr Arg Ile Thr Asp Glu Glu Met Glu Lys Ala Leu Asn
65                  70                  75                  80

Gly Glu Tyr Thr Gly Tyr Ser Ile Thr Thr Val Ser Lys Lys Phe Ala
                85                  90                  95

Asp Lys Gln Ile Gln Leu Pro Arg Arg Val Leu Met Lys Asp Ile Lys
                100                 105                 110

Asp Pro Val Gly Phe Thr Ile Ser Leu Val Arg Lys Pro Cys Val Arg
            115                 120                 125

Gly Ala Lys Phe Cys Ser Met Lys Glu Asp Ile Glu Asn Gly Asp Val
        130                 135                 140

Val Ser Glu Asn Ile Asp Asp Lys Leu Glu Glu Thr Lys Gly Phe
145                 150                 155                 160

Val Gln Ser Ile Lys Gly Ile Phe Asn Lys Glu Asp Lys Asp Glu Asp
                165                 170                 175

Lys Asn Pro Glu Asp Glu Asp Ile Glu Leu Asp Ile Lys Ala Ile Val
                180                 185                 190

Asp Glu Val Thr Lys Asp Phe Val Asn Thr Asp Phe Glu Thr Phe
            195                 200                 205

Lys Asn Glu Leu Glu Lys Ala Leu Ser Asp Lys Phe Glu Thr Leu Gly
        210                 215                 220

Ala Glu Leu Phe Lys Ser Leu Lys Lys Ser Leu Glu Lys Asp Lys Ala
225                 230                 235                 240

Glu Glu Ala Lys Lys Ser Gly Arg
                245

<210> SEQ ID NO 52
<211> LENGTH: 280
<212> TYPE: PRT
<213> ORGANISM: Methanobrevibacter ruminantium

<400> SEQUENCE: 52

Met Gly Asn Glu Ala Thr Leu Asn Gln Leu Val Asn Glu Gln Glu Lys
1               5                   10                  15

Ala Val Phe Lys Ser Met Arg Thr Asp Met Glu Thr Gly Lys Ala Val
                20                  25                  30

Leu Asn Val Glu Gln Leu Gly Tyr Phe Leu Arg Glu Ala Thr Leu Asp
            35                  40                  45
```

```
Asn Thr Ile Leu Arg Asp Ala Asp Phe Lys Leu Met Lys Ser Phe Lys
         50                  55                  60

Lys His Leu Asn Arg Val Gly Ile Asn Gly Arg Val Leu Thr Asn Gly
 65                  70                  75                  80

Tyr Asp Val Asn Gly Glu Thr Asp Pro Glu Ile Pro Ala Ala Asp Val
                 85                  90                  95

Asp Phe Gly Ala Asn Glu Leu Asp Val Lys Lys Leu Lys Ala Met Cys
                100                 105                 110

Glu Ile Glu Asp Asp Glu Lys Glu Asp Asn Met Thr Gln Ala Gln Phe
            115                 120                 125

Glu Gln Thr Leu Leu Gln Met Met Gly Glu Arg Ile Gly Glu Asp Leu
130                 135                 140

Glu Tyr Trp Ala Leu Phe Ala Asp Ser Glu Val Ala Arg Ser Asp Asp
145                 150                 155                 160

Pro Leu Leu Asn Thr Asn Asp Gly Trp Leu Lys Lys Cys Ala Asn His
                165                 170                 175

Ile Ser Ser Arg Ser Ile Ala Pro Ser Asn Gly Met Phe Asp Ile Glu
            180                 185                 190

Asp Gly Pro Glu Ala Met Phe Asp Ala Met Ile Lys Ala Leu Pro Pro
            195                 200                 205

Arg Phe Arg Lys Asn Arg Arg Met Leu Lys Phe Tyr Val Pro Phe Glu
210                 215                 220

Val Glu Asp Ala Tyr Arg Asn Ile Leu Ile Asn Arg Gly Thr Gly Leu
225                 230                 235                 240

Gly Asp Ser Ala Gln Ile Gly Phe Asn Ala Leu Ser Tyr Lys Gly Ile
                245                 250                 255

Pro Ile Glu His Cys Ser Thr Leu Asp Asp Asp Gly Arg Gly Met
            260                 265                 270

Leu Gly Asn Arg Val Cys Ser Met
            275                 280

<210> SEQ ID NO 53
<211> LENGTH: 147
<212> TYPE: PRT
<213> ORGANISM: Methanobrevibacter ruminantium

<400> SEQUENCE: 53

Met Arg Arg Arg Cys Leu Asn Ser Pro Glu His Asn Gly Met Ile Ser
 1               5                  10                  15

His Ile Ile Val Leu Leu Ile Cys Phe Ile Gly Leu Val Glu Ala Ile
                20                  25                  30

Leu Met Ala Leu Val Asp Trp Glu Asp Leu Ala Ile Ser Val Arg Lys
             35                  40                  45

Ser Pro Arg Lys Leu Tyr Asn Val Leu Lys Asp Glu Leu Gly Leu Pro
         50                  55                  60

Glu Trp Asn Glu Leu Ser Val Ile Glu Arg Arg Ser Met Lys Lys Arg
 65                  70                  75                  80

Tyr Ala Val Ile Arg Asp Ser Phe Pro Glu Leu Pro Pro Trp Glu Glu
                 85                  90                  95

Leu Ser Val Ile Asp Arg Arg Ser His Lys Arg Leu Tyr Lys Leu Ile
                100                 105                 110

Lys Ser Val Tyr Asp Gly Asp Tyr Asp Asp Ser Pro Ser Leu Glu Gly
            115                 120                 125

Pro Pro Ala Ala Val Gly Pro Gln Lys Glu Ile Pro Leu Glu Glu Ala
130                 135                 140
```

Glu Tyr Pro
145

<210> SEQ ID NO 54
<211> LENGTH: 137
<212> TYPE: PRT
<213> ORGANISM: Methanobrevibacter ruminantium

<400> SEQUENCE: 54

Met Thr Trp Ile Gly Thr Glu Asp Val Ile Glu Phe Thr Gly Val Lys
1               5                   10                  15

Pro Gln Thr Phe Arg Phe Glu Lys Gly Asp Thr Ser Ser Leu Glu Thr
            20                  25                  30

Leu Leu Glu Lys Trp Ile Leu Gln Ala Glu Gly Leu Ile Ile Ser Tyr
        35                  40                  45

Cys Asn Tyr Asp Phe Asn Asp Leu Glu Glu Ile Pro Pro Ala Val Val
    50                  55                  60

Asn Val Cys Leu Arg Leu Thr Ala Asn Met Val Ala Leu Ala Gln Ala
65                  70                  75                  80

Arg Lys Asp Thr Pro Val Ile Gln Val Lys Glu Trp Asn Val Gln Thr
                85                  90                  95

Val Ser Ser Asn Ile Phe Ser Asn Asp Leu Lys Arg Asp Leu Thr Pro
            100                 105                 110

Phe Val His Glu Arg Lys Ser Tyr Lys Gly Asp Glu Ile Asp Phe Phe
        115                 120                 125

Val Ile Thr Gly Asp Asp Asp Ser Trp
    130                 135

<210> SEQ ID NO 55
<211> LENGTH: 148
<212> TYPE: PRT
<213> ORGANISM: Methanobrevibacter ruminantium

<400> SEQUENCE: 55

Met Val Lys Leu Gln Ile Asp Val Glu Glu Leu Lys Pro Leu Glu Pro
1               5                   10                  15

Arg Phe Lys Lys Val Ala Lys Arg Thr Val Val Leu Thr Ala Asn Glu
            20                  25                  30

Leu Gln Arg Asn Leu Lys Lys Leu Ser Pro Val Asp His Gly Arg Leu
        35                  40                  45

Gln Gly Ser Trp Val Ile Phe Gln Thr Gly Leu Glu Arg Thr Val
    50                  55                  60

Lys Ser Ser Ala Lys Tyr Ala Ile Phe Val Asn Asp Gly Thr Gly Leu
65                  70                  75                  80

Tyr Gly Pro Leu Gly His Lys Ile Arg Pro Lys Asn Gly Lys Phe Leu
                85                  90                  95

Ala Phe Thr Pro Asn Lys Gly Lys Phe Lys Gly Lys Leu Val Val Val
            100                 105                 110

Pro Trp Thr Arg Gly Gln Lys Pro Gln Arg Phe Val Glu Arg Ser Met
        115                 120                 125

Glu Met Thr Glu Arg Arg Val Gln Glu Phe Met Ile Arg Ala Met Met
    130                 135                 140

Glu Met Asp Ser
145

<210> SEQ ID NO 56
<211> LENGTH: 169

```
<212> TYPE: PRT
<213> ORGANISM: Methanobrevibacter ruminantium

<400> SEQUENCE: 56

Met Arg Phe Val Asn Thr Ala Ser Leu Val Pro Gln Thr Val Lys Ala
1               5                   10                  15

Tyr Leu Glu Arg Glu Ile Cys Glu Gly Gly Leu Leu Glu Asp Val Glu
            20                  25                  30

Thr Leu Ile Pro Ser Val Asn Ser Asp Val Pro Val Asp Pro Pro Ala
        35                  40                  45

Ile Trp Ile Val Gln His Pro Thr Thr Arg Trp Ser Gly Ser Gln Pro
    50                  55                  60

Asn Leu Ser Asn Lys Ile Ala Met Ser Val Pro Phe Glu Phe Val Cys
65                  70                  75                  80

Val Glu Tyr Ser Asp Asp Leu Glu Glu Ala Glu Ile Leu Gly Ile Ser
                85                  90                  95

Leu Ala Ser Arg Val Gly Ser Ser Leu Met Lys Asn Phe Asn Lys Val
            100                 105                 110

Lys Val Asp Asp Ser Met Pro Asn Arg Phe Phe His Lys Leu Glu Phe
        115                 120                 125

Glu Thr Leu Tyr Pro Val Gly Glu Val Thr Val Gly Lys Ser Glu
130                 135                 140

Arg Ile Pro Ala Thr Ser Ile Ile Phe Asn Phe Val Tyr Val Val Asp
145                 150                 155                 160

Trp Leu Lys Cys Asn Arg Arg Tyr Asp
                165

<210> SEQ ID NO 57
<211> LENGTH: 255
<212> TYPE: PRT
<213> ORGANISM: Methanobrevibacter ruminantium

<400> SEQUENCE: 57

Met Gly Ile Arg Val Val Gly Met Lys Glu Glu Ala Arg Tyr Gly Val
1               5                   10                  15

Ala Glu Ser Ala Pro Asp Phe His Gln Glu Val Ser Lys Ala Lys Ala
            20                  25                  30

Ser Leu Asn Ser Thr Pro Asn Thr Lys Ser Ser Gly Ser Arg Met Lys
        35                  40                  45

Lys Lys Ala Arg Ala Gly Val Tyr Lys Pro Thr Ala Asn Ile Glu Gly
    50                  55                  60

Glu Val Asp Leu Lys Arg Ile Gly His Tyr Leu Lys Ala Phe Leu Asp
65                  70                  75                  80

Asn Tyr His Phe Thr Asp Gly Gly Ser Asn Pro Asn Val His Glu Phe
                85                  90                  95

Trp Gly Gly Glu Asn Asn Lys Leu Ser Ser Phe Thr Leu Trp Val Thr
            100                 105                 110

Phe Asp Ile Phe Glu Lys Thr Ile Val Gly Ser Leu Leu Asp Asn Phe
        115                 120                 125

Lys Met Glu Val Ser Asp Glu Tyr Met Lys Phe Thr Ala Asp Phe Val
    130                 135                 140

Tyr Lys Thr Glu Glu Ser Asp Glu Ile Glu Asn Ile Glu Leu Tyr Lys
145                 150                 155                 160

Val Lys Leu Leu Asp Gly Asp Trp Ala Leu Met Phe Tyr Asp Val Ser
                165                 170                 175

Val Glu Ile Asp Glu Asn Ala Pro Pro Gly Ile Val Ser Ser Phe Ser
```

```
                    180                 185                 190
Phe Asp Gly Lys Asn Asn Ile Asn Val Asp Lys Thr Ile Gly Leu Gly
                195                 200                 205

Ser Arg Gly Pro Gln Arg Lys Ala Ala Ala Gln Gly Arg Asp Ile Ser
            210                 215                 220

Ile Ser Phe Val Ser Thr Leu Glu Arg Glu Thr Leu Glu Leu Ile Gln
225                 230                 235                 240

Lys Ala Glu Tyr Gly Glu Val Gly Thr Glu Pro Ser Glu Cys Lys
                245                 250                 255

<210> SEQ ID NO 58
<211> LENGTH: 146
<212> TYPE: PRT
<213> ORGANISM: Methanobrevibacter ruminantium

<400> SEQUENCE: 58

Met Val Val Lys Lys Ser Asp Ile Leu Lys Gly Val Lys Lys Ile
1               5                   10                  15

Glu Lys Val Lys Ile Glu Ala Leu Asp Gly Asp Glu Met Tyr Leu Arg
            20                  25                  30

Pro Leu Ser Gln Ala Glu Ile Asn Glu Val Asp Glu Ile Glu Ala Lys
        35                  40                  45

Ala Met Gly Ile Phe Glu Thr Asn Glu Thr Ala His Arg Gly Arg Arg
    50                  55                  60

Gln Lys Pro Lys Ser Val Val Glu Ser Lys Gly Lys Ile Asn Leu Glu
65                  70                  75                  80

Leu Gln Gln Lys Ala Gln His Gln Ala Lys Thr Lys Ala Ile Phe Leu
                85                  90                  95

Ser Leu Asp Asn Glu Lys Asn Val Gly Glu Glu Ala Trp Ser Glu Thr
            100                 105                 110

Glu Ile Glu Gln Met Pro His Lys Leu Phe Glu Glu Leu Phe Asn His
        115                 120                 125

Val Lys Arg Leu Ser Gly Ile Glu Leu Asp Glu Asp Val Asp Thr
    130                 135                 140

Phe His
145

<210> SEQ ID NO 59
<211> LENGTH: 255
<212> TYPE: PRT
<213> ORGANISM: Methanobrevibacter ruminantium

<400> SEQUENCE: 59

Met Pro Ser Ser Asn Val Met Asn Ile Ile Val Lys Ala Glu Asp Met
1               5                   10                  15

Ala Ser Ser Val Ala Gln Lys Val Glu Asn Ser Phe Arg Lys Leu Gly
            20                  25                  30

Asn Thr Ile Asp Ser Thr Phe Thr Thr Ser Leu Ser Asn Thr Lys Phe
        35                  40                  45

Asn Gln Glu Leu Thr Ser Phe Gly Thr Asp Leu Asp Lys Val Thr Gln
    50                  55                  60

Arg Leu Lys Gln Val Gly Val Asn Gly Gln Ser Ser Phe Asn Gln Leu
65                  70                  75                  80

Thr Asn Ala Glu Arg Arg Thr Leu Glu Lys Leu Ser Glu Phe Asp Pro
                85                  90                  95

Val Ser Ala Gln Val Leu Gln His Leu Ser Arg Ile Gly Ile Thr Gly
            100                 105                 110
```

```
Gln Gln Thr Phe Asn Gln Leu Ser Val Ser Glu Gln Lys Ser Leu Met
            115                 120                 125

Asn Met Lys Ser Thr Ala Gln Gln Leu Glu Glu Val Asn Ser Lys Leu
130                 135                 140

Arg Val Val Gly Ile Gly Ala Ala Gln Ala Ala Asn Met Leu Asn Gln
145                 150                 155                 160

Met Lys Leu Asp Pro Ser Val Gly Ser Asn Leu Asp Arg Ala Lys Leu
            165                 170                 175

Lys Val Ser Glu Met Gly Tyr Ser Leu Asp Ser Thr Lys Gly Lys Ile
            180                 185                 190

Leu Val Leu Gly Thr Ala Ile Gln Thr Ser Leu Gly Asn Lys Trp Asp
            195                 200                 205

Ser Ile Lys Thr Lys Val Gln Thr Thr Ala Thr Asn Ile Arg Thr Ala
            210                 215                 220

Leu Gly Asn Ala Leu Thr Ser Val Lys Ser Lys Val Gln Asn Leu Gly
225                 230                 235                 240

Asn Ala Phe Ser Gly Leu Gly Gly Ile Ile Ser Ser Ala Ile Gly
            245                 250                 255

<210> SEQ ID NO 60
<211> LENGTH: 274
<212> TYPE: PRT
<213> ORGANISM: Methanobrevibacter ruminantium

<400> SEQUENCE: 60

Met Ala Ser Val Thr Lys Tyr Pro Ser Asn Val Ser Gln Thr Thr Gly
1               5                   10                  15

Gly Lys Phe Val Ser Phe Ser Asn Leu Ala Asn Ile Lys Asn Asn Ala
            20                  25                  30

Asp Gly Ala His Ala Val Ser Ser Val Leu Ile Lys Ser Lys Lys Gln
            35                  40                  45

Ser Pro Asn Arg Pro Ser Thr Val Ser Cys Lys Gly Phe Gly Phe Ser
50                  55                  60

Leu Pro Glu Gly Ala Glu Pro Thr Lys Ile Thr Val Thr Tyr Arg His
65                  70                  75                  80

Arg Lys Asn Ala Gly Ser Asp Tyr Ser Ser Lys Asn Lys Thr His Ile
            85                  90                  95

Cys Asn Ile Gly Gly Pro Thr Ile Ser Leu Leu Gly Val Ser Gly Phe
            100                 105                 110

Ser Ser Lys Gly Ser Gly Cys Thr Thr Thr Met Thr Thr His Thr Lys
            115                 120                 125

Ala Phe Ser Val His Gly Lys Leu Ser Arg Ala Gln Val Asn Ser Ala
130                 135                 140

Asn Phe Gly Val Lys Leu Asp Tyr Pro Thr Asn Ser Asn Thr Tyr Asn
145                 150                 155                 160

Gly Tyr Met Arg Ile Ser Tyr Val Arg Val Thr Val Glu Tyr Ile Thr
            165                 170                 175

Ser Gln Tyr Ser Val Ser Val Lys His Val Ser Gly Tyr Thr Glu Asp
            180                 185                 190

Glu Asp Tyr Val Val Ser Leu Gly Ile Ser Asn Lys Asn Leu Thr Ser
            195                 200                 205

Tyr Asn Pro Thr Cys Thr Leu Thr Val Pro Ala Gly Phe Thr Tyr Lys
            210                 215                 220

Gly Val Thr Gly Ala Ala Thr Gly Thr Val Thr Lys Val Asn Asn Arg
225                 230                 235                 240
```

```
Thr Phe Ser Trp Asn Pro Gln Leu Gln Gly Arg Ala Gly Ser Arg Gln
                245                 250                 255

Ile Ser Leu Ala Phe Glu Pro Asn Val Thr Phe Pro Glu Gly Thr Asp
                260                 265                 270

Ser Tyr

<210> SEQ ID NO 61
<211> LENGTH: 255
<212> TYPE: PRT
<213> ORGANISM: Methanobrevibacter ruminantium

<400> SEQUENCE: 61

Met Gly Ile Ala Ile Val Val Met Asp Asn Glu Glu Asn Phe Leu Gln
1               5                   10                  15

Phe Leu Asp Pro Asp Leu Cys Thr Ile Asn Glu Thr Ile Glu Glu Leu
                20                  25                  30

Gly Leu Arg Thr Leu Glu Phe Asn Tyr Lys Phe Gln Asp Tyr Val Glu
            35                  40                  45

Asp Arg Asp Leu Phe Arg Ile Gly Asn Lys Ile Trp Ile Ser Asn Ser
        50                  55                  60

Gln Ser Leu Glu Asp Cys Leu Tyr Val Ile Asn Thr Pro Val Glu Asn
65                  70                  75                  80

Ser Val Tyr Gln Glu Asn Tyr Phe Ala Cys Ile Glu Glu Val Leu
                85                  90                  95

Ala Glu Leu Tyr Tyr Ala Pro Leu Phe Ser Gln Thr Glu Leu Thr Ser
                100                 105                 110

Ala Asn Gly Phe Thr Leu Arg Thr Thr Asn Gly Glu Gln Thr Val Asp
            115                 120                 125

Val Asp Trp Asn Ala Leu Asn Tyr Trp Phe Gly Leu Tyr Phe Asn Ile
        130                 135                 140

Gly Val Val Gln Glu Cys Leu Gly Thr Tyr Ala Asn Arg Ile Thr Val
145                 150                 155                 160

Asn Gly Thr Met Asn Arg Leu Asn Leu Leu Arg Ser Ile Glu Glu Gln
                165                 170                 175

Thr Gly Asn Arg Phe Val Thr Arg Tyr Glu Lys Asp Leu Leu Asp Asn
                180                 185                 190

Thr Ile His Arg Tyr Leu Asp Phe Leu Asn Pro Val Asn Val Ser Lys
            195                 200                 205

Asn Trp Lys Leu Asn Ile Glu Tyr Asp Phe Ile Tyr Glu Asp Asp Gly
        210                 215                 220

Glu Tyr Cys Glu Ala Tyr Thr Ser Asp Gly Asn Pro Ile Ser Glu Ile
225                 230                 235                 240

Tyr Asp Asp Ile Glu Glu Asp Asp Ile Val Asp Phe Pro Pro
                245                 250                 255

<210> SEQ ID NO 62
<211> LENGTH: 255
<212> TYPE: PRT
<213> ORGANISM: Methanobrevibacter ruminantium

<400> SEQUENCE: 62

Met Val Glu Lys Ile Thr Val Ser Pro Gln Val Arg Gly Tyr Gly
1               5                   10                  15

Asn Val Val Asp Glu Lys Glu Leu Glu Asp Tyr Gly Ser Tyr Arg Cys
                20                  25                  30

Asp Val Ser Glu Ser Ser Glu Val Ile Lys Gly Val Glu Glu Arg Ile
```

```
            35                  40                  45
Phe Ser Val Ser Gly Val Pro Ala Pro Ala Leu Ser Ile Ala Asn Val
 50                  55                  60

Thr Glu Asp Thr Arg Arg Gly Arg Cys Ala His Ile Ser Ala Ser Phe
65                  70                  75                  80

Glu Asp Gly Glu Gly Asp Gly Leu Asp Asp Lys Ala Ile Ser Leu Lys
                85                  90                  95

Ser Gly Asp Asp Val Leu Ala Thr Ile Thr Thr Gly Ser Gly Glu Asn
            100                 105                 110

Val Phe Asp Val Val Leu Tyr Asp Ser Ala Gln Leu Tyr Ala Val Phe
            115                 120                 125

Asp Gly Asp Asp Tyr Tyr Pro Pro Ala Val Ser Glu Ala Ile Thr Val
            130                 135                 140

Asn Pro Ala Lys Ser Leu Trp Asp Val Glu Phe Ile Leu Asp Glu Glu
145                 150                 155                 160

Glu Tyr Glu Val Gly Asp Thr Ala Ile Leu Ser Gly Thr Val Gly Thr
                165                 170                 175

Ile Val Asp Glu Ile Val Asp Gly Glu Ile Val Thr Arg Arg Gln Met
            180                 185                 190

Glu Ala Asn Val Thr Leu Thr Leu Val Thr Asp Leu Gly Ile Arg Arg
            195                 200                 205

Cys Ser Thr Asn Ala Asn Gly Glu Phe Val Leu Gln Val Pro Asn Ile
            210                 215                 220

Gln Gln Asn Gln Trp Arg Val Val Ile Ala Ala Thr Ser Thr His Leu
225                 230                 235                 240

Val Phe Asn Gly Leu Ile Asp Val Pro Val His Asp Tyr Ser Leu
                245                 250                 255

<210> SEQ ID NO 63
<211> LENGTH: 228
<212> TYPE: PRT
<213> ORGANISM: Methanobrevibacter ruminantium

<400> SEQUENCE: 63

Met Val Arg Phe Ser Arg Asp Met Leu Gln Asp Gly Ala Lys Arg Met
1               5                   10                  15

Phe Lys Trp Leu Arg Lys Gly Glu Gly Leu Pro Asn Tyr Leu Ile Met
                20                  25                  30

Tyr Asp Met Asp Arg Asn Lys Glu Tyr Lys Leu Val Pro Lys Glu Tyr
            35                  40                  45

Ala Gly Leu Tyr Glu Ser Arg Asn Ile Phe Trp Ile Lys Asn Gly Arg
 50                 55                  60

Glu Pro Asn Tyr Val Thr Leu Thr Ser Val Ala Arg Asn Pro Leu Val
65                  70                  75                  80

Met Asp Tyr Gln Asn Thr Asn Tyr Thr Cys Cys Pro Thr Ser Leu Ser
                85                  90                  95

Leu Ala Ser Gln Met Leu Tyr His Tyr Lys Ser Glu Ser Glu Cys Ala
            100                 105                 110

Lys Ala Leu Gly Thr Ser Lys Gly Ser Gly Thr Ser Pro Ala Gln Leu
            115                 120                 125

Ile Ala Asn Ala Pro Lys Leu Gly Phe Lys Ile Pro Ile Lys Arg
            130                 135                 140

Asp Ser Lys Glu Val Lys Lys Tyr Leu Lys Lys Gly Phe Pro Val Ile
145                 150                 155                 160

Cys His Trp Gln Val Asn Gln Ser Arg Asn Cys Lys Gly Asp Tyr Thr
```

```
                        165                 170                 175
Gly Asn Phe Gly His Tyr Gly Leu Ile Trp Asp Met Thr Ser Thr His
                180                 185                 190

Tyr Val Ala Asp Pro Ala Lys Gly Val Asn Arg Lys Tyr Lys Phe
            195                 200                 205

Ser Cys Leu Asp Asn Ala Asn Lys Gly Tyr Arg Gln Asn Tyr Tyr Val
210                 215                 220

Val Cys Pro Ala
225

<210> SEQ ID NO 64
<211> LENGTH: 749
<212> TYPE: PRT
<213> ORGANISM: Methanobrevibacter ruminantium

<400> SEQUENCE: 64

Met Lys Lys His Cys Phe Tyr Phe Leu Gly Asp Ser Phe Ala Asp Ile
1               5                   10                  15

Cys Asn Glu Ala Met Phe Cys Glu Lys His Leu Val Glu Gly Asn Tyr
            20                  25                  30

Leu Asp Ser Ile Ile Arg Ala Gly Lys Ala Ser Glu Ile Ile Thr Val
        35                  40                  45

Asn Ile Cys Glu Leu Glu Gly Gln Asp Gly Leu Ile Ser Ser Gly Gln
50                  55                  60

Lys Lys Arg Leu Glu Met Leu Gly Tyr Lys Gly Ile Ile Ser Tyr Asp
65                  70                  75                  80

Ile Tyr Lys Arg Leu Asn His Ile Arg Lys Ile Arg Asn Lys Ala Val
                85                  90                  95

His Gly His Leu Ser Asp Ile Glu Asp Asn Ala Asn Ile Leu His Ala
            100                 105                 110

Tyr Leu Tyr Leu Ile Cys Ala Tyr Phe Tyr Lys Glu Tyr Arg Asp Thr
        115                 120                 125

Asn Phe Ser Ala Glu Asp Tyr Thr Gly Pro Ile Met Asp Ile Ala Ser
130                 135                 140

Lys Pro Lys Glu Thr Ala Ser Glu Thr Ser Glu Asp Asn Glu Asn Ile
145                 150                 155                 160

Gly Glu Phe Ile Ser Ser Pro Leu Asp Asp Tyr Leu Phe Glu Lys Tyr
                165                 170                 175

Asp Asp Ser Tyr Leu Leu Asn Glu Leu Ser Lys Leu Lys Asp Ser Ser
            180                 185                 190

Lys Glu Ala Val Glu Asp Asp Asn Leu Ser Glu Phe Lys Glu Tyr Leu
        195                 200                 205

His Ile Asp Arg Ser Ile Gln Glu Asp Phe Leu Lys Ala Leu Asn Arg
210                 215                 220

Ala Thr Ser Phe Asn Ser Ser His Leu Ile Met Leu Cys Gly Ser Val
225                 230                 235                 240

Gly Asp Gly Lys Ser His Leu Ile Ala Asn Leu Lys Lys Lys Asn Pro
                245                 250                 255

Glu Leu Phe Asn Gln Phe Ala Ile His Tyr Asp Ala Thr Glu Ser Phe
            260                 265                 270

Asp Pro Glu Lys Asn Ala Ile Asp Thr Leu Ala Ser Val Leu Glu Pro
        275                 280                 285

Phe Asn Asp Asn Asn Leu Asn Asn Ser Thr Glu Lys Leu Ile Leu Ala
290                 295                 300

Ile Asn Leu Gly Val Leu Asn Asn Phe Leu Glu Ser Ser Tyr Ala Asn
```

```
          305                 310                 315                 320
Glu Asp Tyr Thr Lys Leu Lys Leu Ile Ile Glu Glu Ala Asn Ile Phe
                    325                 330                 335

Glu Ser Asn Glu Val Ser Asp Asn Ile Tyr Gly Asp Lys Val Ser Phe
                    340                 345                 350

Val Thr Phe Ser Asp Tyr Asn Met Phe Glu Leu Asn Asp Asp Glu Asn
                    355                 360                 365

Ser Asn Tyr Thr Ser Ser Lys Tyr Ile Ser Ser Leu Phe Asn Lys Ile
            370                 375                 380

Thr Gln Lys Glu Asp Thr Asn Pro Phe Val Ala Tyr Leu Lys Asp
385                 390                 395                 400

Lys Asp Ser His Phe Ile Asn Pro Ile Ile Tyr Asn Tyr Glu Met Leu
                    405                 410                 415

Met Asp Glu Glu Val Gln Lys Thr Ile Ile Asp Tyr Leu Ile Lys Ile
                    420                 425                 430

Phe Ile Lys Tyr Arg Lys Ile Ile Ser Thr Arg Asp Leu Leu Asn Phe
                    435                 440                 445

Ile Tyr Glu Ile Ile Val Pro Pro Glu Phe Leu Lys Ser Glu Asp Leu
            450                 455                 460

Asp Asn Ile Asn Asp Phe Met Asp Tyr Ser Leu Pro Asn Leu Leu Phe
465                 470                 475                 480

Gly Tyr Pro Glu Arg Ser Asp Leu Leu Lys Leu Cys Asn Glu Leu Asp
                    485                 490                 495

Pro Thr Leu His Arg Asn Glu Ser Leu Asp Lys Phe Ile Ile Asp Leu
                    500                 505                 510

Asn Ile Asn Asp Asp Thr Glu Lys Ile Leu Asn Arg Tyr Phe Asp Phe
            515                 520                 525

Thr Arg Phe Asn Phe Leu Glu Glu Tyr Gly Glu Tyr Leu Val Asp Phe
            530                 535                 540

Arg Glu Phe Asn Asn Ser Glu Lys Glu Lys Val Thr Asn Ile Leu Ile
545                 550                 555                 560

Arg Phe Ala Val Phe Tyr Gly Lys Ser Ile Ile Lys Asn Asn Phe Lys
                    565                 570                 575

Asp Lys Val Tyr Leu Asn Tyr Leu Lys Tyr Leu Tyr Ala Tyr Asn Thr
                    580                 585                 590

Gln Ser His Lys Asp Tyr Lys Tyr Leu Phe Thr Glu Val Lys Asp Ala
                    595                 600                 605

Ile Phe Asn Trp Lys Gly Ser Tyr Lys Lys Asn Thr Ile Cys Ile Asp
            610                 615                 620

Thr Leu Asp Ser Phe Lys Val Tyr Lys Asn Leu Lys Leu Lys Pro Ser
625                 630                 635                 640

Val Asp Lys Phe Glu Lys Ser Leu Leu Asp Gly Leu Phe Leu Gly Asn
                    645                 650                 655

Arg Phe Lys Thr Asp Ile Lys Ile Tyr Phe Ser Val Glu Ser Asn Lys
                    660                 665                 670

Lys Lys Ile Pro Leu Asn Val Asp Phe Ser Leu Tyr Gln Tyr Ile Met
            675                 680                 685

Lys Leu Tyr Asn Gly Phe Lys Pro Asn Gln Ser Asp Lys Asp Leu
            690                 695                 700

Ile Ile Leu Asp Glu Phe Ile Asn Asn Leu Leu Asp Glu Asp Thr Asp
705                 710                 715                 720

Asp Asp Leu Tyr Val Ile Ser Leu Glu Thr Tyr Glu Glu Phe Leu Phe
                    725                 730                 735
```

Glu Ser Asn Asp Phe Gly Thr Phe Glu Phe Lys Arg Gly
                740                 745

<210> SEQ ID NO 65
<211> LENGTH: 456
<212> TYPE: PRT
<213> ORGANISM: Methanobrevibacter ruminantium

<400> SEQUENCE: 65

Met Asp Phe Ser Glu Asn Tyr Asn Ile Leu Leu Lys Gln Met Thr Cys
1               5                   10                  15

Asp Val Asn Lys Arg Lys Leu Ile His Gln Ile Asn Gln Asn Ser Pro
            20                  25                  30

Leu Leu Pro Phe Lys Thr Asn Thr Pro Lys Lys Ala Asn Phe Glu Asn
            35                  40                  45

Gly Phe Asp Ile Ile Leu Gly Glu Leu Ser Arg Ile Leu Leu Asn Lys
        50                  55                  60

Thr Ile Glu Lys Asn Phe Lys Leu Asp Asn Ile Val Ser Asn Leu Ile
65                  70                  75                  80

Asp Asn Asn Ile Glu Ile Glu Asp Gly Thr Lys Glu Tyr Ile Thr Lys
                85                  90                  95

Leu Leu Asn Glu Tyr Leu Phe Asp Glu Lys Asn Asp Leu Lys Ile Ser
            100                 105                 110

His Pro Asn Leu Tyr Leu Tyr Ile Pro Leu Ser Asn Asn Lys Ser Ser
        115                 120                 125

Asn Gly Glu Gln Glu Val Ala Leu Phe Leu Arg Asp Ile Phe Cys Lys
    130                 135                 140

Asn Asn Gln Asn Leu Ile Asn Phe Phe Glu Ser Tyr Asp Ser Asn His
145                 150                 155                 160

Ile Ile Leu Asn Leu Ile Leu Lys Asn Thr Pro Asn Leu His His Lys
                165                 170                 175

Ile Thr Glu Thr Lys Tyr Val Ile His Phe Glu Glu Ile Ala Asn Leu
            180                 185                 190

Phe Asn Glu Asp Ile Asn Tyr Ala Ile Leu Tyr Lys Lys Phe Phe Met
        195                 200                 205

Glu Asn Ile Gly Asn Ile Phe Ala Tyr Tyr Tyr Phe Phe Tyr Ile Ser
    210                 215                 220

Gln Leu Ile Leu Lys Ile Ser Lys Gly Phe Asn Asp Asn Asn Glu Phe
225                 230                 235                 240

Glu Lys Leu Tyr Tyr Leu Leu Asp Trp Glu Ser Ala Ser Lys Asn Arg
                245                 250                 255

Lys Ser Leu Asn Ser Tyr Ser Leu Leu Lys His His Ser Lys Pro Leu
            260                 265                 270

Tyr Ala Lys Met Ala Val Ile Asp Gln Ile Asn Thr Leu Leu Gly Thr
        275                 280                 285

Asn Asn Leu Leu Glu Lys Asp Ile Ser Glu Tyr Phe Asn Asn Leu Asp
    290                 295                 300

Ile Asn Ser Lys Asn Asn Phe Leu His Phe Leu Lys Lys Trp Val Ser
305                 310                 315                 320

Asp Tyr Arg Tyr Val Arg Asn Phe Asp Lys Glu Leu Pro Asp Asn
                325                 330                 335

Leu Leu Glu Leu Thr Glu Ile Leu Phe Glu Ser Leu Lys Asn Glu Lys
            340                 345                 350

Leu Gly Val Asp Gly Ala Val Gln Ser Arg Tyr Ala Leu Asn Leu Glu
        355                 360                 365

```
Asp Ile Ala Lys Lys Tyr Leu Leu Lys Arg Arg Gly Ser Tyr Gly Tyr
    370                 375                 380

Val Leu Asn Ile Asn Arg Asp Met Leu Leu Val Leu Thr Ala Leu Cys
385                 390                 395                 400

Val Lys Asp Lys Lys Ile Lys Leu Asn Gln Leu Phe Ile Glu Phe Glu
                405                 410                 415

Lys Arg Gly Val Tyr Phe Asp Lys Tyr Ser Lys Glu Glu Val Val Asn
            420                 425                 430

Phe Leu Thr Lys Leu Asn Leu Ile Asp Lys Lys Ser Asp Ser Gly Asp
        435                 440                 445

Ala Gln Tyr Val Lys Pro Val Leu
    450                 455

<210> SEQ ID NO 66
<211> LENGTH: 1740
<212> TYPE: PRT
<213> ORGANISM: Methanobrevibacter ruminantium

<400> SEQUENCE: 66

Met Leu Asn Gln Phe Tyr Asp Tyr Leu Ser Asn Lys Leu Leu Asn Tyr
1               5                   10                  15

Phe Asp Asp Thr Lys Ile Leu Ser Gly Glu Lys Phe Phe Ile Ser Phe
                20                  25                  30

Asp Glu Asp Gln Ile Met Ser Phe Tyr Asn Ser Leu Arg Ser Ile
            35                  40                  45

Ala Glu Thr Asn Phe Ser Cys Ser Glu Phe Ile Tyr Val His Thr Ile
    50                  55                  60

Ser Gly Lys Glu Tyr Asn Thr Tyr Ser Ile Asn Ile Asn Gly Val Lys
65                  70                  75                  80

Phe Val Ile Ser Glu Ser Leu Thr Ile Asn Val Asp Phe Leu Val Thr
                85                  90                  95

Leu Arg Asn Gln Val Thr Ser Gln Glu Gly Val Trp Lys Asp Thr Ala
                100                 105                 110

Leu Leu Val Ile Cys Asn Glu Ala Ile Asp Ser Ile Gly Lys Gly Met
            115                 120                 125

Arg Asn Leu Gln Lys Glu Gly Met Pro Leu Asn Val Lys Ser Ile Ser
130                 135                 140

Lys Asn Leu Glu Asp Glu Ile Asn Asp Ser Gln Ile Leu Asn Tyr Ser
145                 150                 155                 160

Asp Lys Gln Ile Ala Lys Phe Ser Leu Asn Ile Gln Glu Glu Leu
                165                 170                 175

Phe Gln Thr Thr Leu Trp Asp Tyr Glu Thr Ile Leu Ser Ile Ile Asn
            180                 185                 190

Lys Gly Phe Val Ser Asp Glu Asp Leu Arg Glu Leu Asn Leu Phe Lys
        195                 200                 205

Asp Asp Gln Leu Asn Gln Asn Ser Pro Gln Lys Met Leu Lys Arg Leu
    210                 215                 220

Lys Glu Asn Tyr Asp Thr Phe Asn Glu Val Asn Lys Phe Ser Gln Tyr
225                 230                 235                 240

Gly Asp Lys Lys Glu Gln Leu Lys Asn Met Phe Thr Asp Ser Gly Val
                245                 250                 255

Ser Ile Leu Ser Lys Asp Asp Trp Tyr Lys Ala Glu Trp Lys Met Val
                260                 265                 270

Lys Lys Ser Lys Asp Asp Phe Ile Asn Gln Gln Asn Pro Leu Asn Tyr
            275                 280                 285
```

-continued

```
Asn Glu Asn Leu Glu Lys Ile Thr Glu Asn Gly Leu Asn Tyr Trp Glu
            290                 295                 300
Ile Pro Asn Ser Phe Thr Lys Thr Gly Lys Arg Lys Arg Asn Ile Ile
305                 310                 315                 320
Val Phe Asn Pro Asn His Ser His Glu Val Ser Leu Lys Phe Ser Phe
                    325                 330                 335
Asp Gln Ile Leu Ser Asn Ser Phe Leu Asn Thr Asn Ser Lys Lys Phe
            340                 345                 350
Thr Ile Ala Arg Gly Lys Ser Leu Ile Val Asn Phe Thr Leu Asp Ser
            355                 360                 365
Ser Glu Pro Ile Phe Lys Thr Ile Lys Tyr Lys His Lys Asn Glu Asn
            370                 375                 380
Ile Ser Glu Phe Thr Phe Asn Ile Val Val Leu Asn Phe Glu Pro Glu
385                 390                 395                 400
Ile Phe Asn Ser Ile Lys Ser Arg Phe Ser Val Asn Val Lys Ser Lys
                    405                 410                 415
Gln Ile Ile Val Thr Asn Asp Glu Asp Ser Phe Asp Ile Val Phe Gly
            420                 425                 430
Thr Gly Ser Lys Glu Ile Glu Lys Leu Ile Lys Glu Asn Gly Glu Lys
            435                 440                 445
Leu Tyr Leu Tyr Asp Asp Glu Ser Leu Ile Ile Ser Glu Gln Ser Pro
450                 455                 460
Ala Trp Asn Asp Gly Lys Leu Ser Phe Lys Leu Tyr Lys Asp Asn Asn
465                 470                 475                 480
Tyr Ala Pro Phe Leu Ile Lys Glu Lys Ser Lys Lys Thr Leu Pro Val
                    485                 490                 495
Asn Ser Tyr Val Ile Trp Asn Leu Lys Arg Arg Asn Met Glu Asn Phe
            500                 505                 510
Ile Phe Asn Gly Val Lys Ala Val Gln Asp Val Asn Ser Phe Tyr Leu
            515                 520                 525
Val Glu Glu Phe Lys Glu Phe Leu Lys Met Glu Arg Glu Ile Ile Lys
            530                 535                 540
Gln Asp Ile Phe Tyr Ala Lys Arg Asn Ile Asp Gly Ser Leu Glu Lys
545                 550                 555                 560
Ile Glu Val Ser Phe Ser Asn Glu Leu Glu Thr Ala Tyr Met Asp Ile
                    565                 570                 575
Phe Asn Tyr Tyr Lys Thr Phe Asp Asp Ser Pro Glu Asp Asn Leu Pro
            580                 585                 590
Ser Leu Val Tyr Leu Asn Asp Asp Leu Lys Glu Leu Tyr Lys Lys Phe
            595                 600                 605
Ile Thr Ile Phe Asn Lys Glu Ile Ser Glu Ile Glu Glu Asn Ser Ile
            610                 615                 620
Leu Ser Asp Phe Lys Tyr Lys Asn Leu Leu Lys Leu Gly Arg Ile
625                 630                 635                 640
Glu Thr Asp Asn Lys Ile Met Tyr Ser Pro Leu Ser Pro Leu Asn Ile
                    645                 650                 655
Ala Tyr Gln Leu Glu Val Ser Lys Gln Cys Gly Asn Glu Asp Leu Ser
            660                 665                 670
Val Asn Ile Leu Glu Arg Leu Val Pro Asn Asn Leu Ile Pro Tyr Ile
            675                 680                 685
Cys Ser Asp Asp Gly Lys Glu Leu Phe Arg Pro Ile Tyr Gln Glu Glu
            690                 695                 700
Ala His Glu Trp Leu Ile Tyr Glu Lys Ser Glu Glu Val Ser Ile Gly
705                 710                 715                 720
```

```
Thr Thr Asn Val Phe Ile Ser Asn Val Val Thr Glu Lys Leu Asn Gln
            725                 730                 735

Phe Val Lys His Phe Asn Tyr Leu Phe Ser Phe Asn Asn Ser Ser Pro
            740                 745                 750

Ile Lys Ile Asn Leu Ile Asn Ile Lys Asp Asp Lys Glu Val Val Lys
            755                 760                 765

Gly Val Phe Asn Phe Ile Arg Ser Arg Leu Pro Asp Lys Thr Lys Thr
770                 775                 780

Lys Lys Val Ile Pro Val Glu Ile Asn Ile Tyr Asn Asp Ala Glu Lys
785                 790                 795                 800

Ser Ser Phe Asp Asn Leu Phe Asp Cys Gln Ser Glu Ile Gln Leu Leu
                805                 810                 815

Glu Glu Phe Gly Ile Lys Lys Leu Lys Ser Asp Ile Phe Asp Pro Ile
            820                 825                 830

Asp Ile Ile His Met Ile Gln Asn Asn Ile Ser Tyr Tyr Lys His Pro
            835                 840                 845

Phe Lys Lys Glu Glu Tyr Glu Tyr Ala His Leu Ser Phe Tyr Lys Val
            850                 855                 860

Lys Ser His Asn Asn Ile Ala Asn Asp Asn Met Asp Lys Ile Glu Thr
865                 870                 875                 880

Gly Leu Ser Leu Asn Gly Leu Leu Ser Ser Val Thr Ser Thr Thr Lys
                885                 890                 895

His Ser Glu Tyr Arg Thr Gly Phe Gly Thr Asn Asn Ile Leu Asn Met
            900                 905                 910

Ser Asn Pro Leu Ile Lys Thr Val Ile Asn Leu Asn Glu Leu Val Glu
            915                 920                 925

Asn Ser Lys Asn Phe Gly Lys Asn Thr Tyr Ser Lys Asn Lys Ser Val
            930                 935                 940

Ile Thr Thr Val Glu Leu Glu Glu Asp Asn Ile Glu Glu Leu Tyr Asp
945                 950                 955                 960

Lys Ser His Trp Val Thr Phe Ile Glu Pro Thr Phe Gly Ile Glu Tyr
                965                 970                 975

Phe Asp Ser Ser Asp Ser Asn Leu Ile Ile Ile His Tyr Ser Asp Gln
            980                 985                 990

Tyr Ser Ser Ser Lys Tyr Asp Thr Ile Thr Val Thr Asn Lys Ser
            995                1000                1005

Thr Gln Tyr Glu Glu Ile Ile Arg Asp Phe Leu Gln Ser Lys Tyr
    1010                1015                1020

Val Lys Val Thr Asp Glu Glu Leu Tyr Asp Val Ile Lys Met Phe
1025                1030                1035

Asn Ser Ile Asn Gly Glu Trp Leu Leu Arg Val Ile Ser Asn Ser
    1040                1045                1050

Gly His Tyr Asp Arg Glu Lys Leu Ser Ile Ile Ser Ala Ile Lys
    1055                1060                1065

Tyr Cys Leu Ser Ile Leu Asp His Lys Asp Ile Val Trp Ile Pro
    1070                1075                1080

Val Ser Met Glu Glu Ile Leu Arg Ile Ala Gly Asn Val Lys Leu
    1085                1090                1095

Asp Lys Asn Lys Gly Ile Phe Asp Ser Lys Leu Ile Lys Gly Asn
    1100                1105                1110

His Ser Asp Asp Leu Leu Phe Ile Gly Val Lys Phe Asn Glu Asp
    1115                1120                1125

Asn Arg Ile Glu Val Ile Phe Tyr Pro Ile Glu Val Lys Ile Gly
```

|  |
| --- |
| 1130        1135        1140 |
| Leu Asn Asn Ala Ser Thr Ile Lys Lys Gly Lys Ser Gln Leu Asp<br>1145            1150            1155 |
| Asn Thr Tyr Lys Leu Leu Lys Thr Gln Leu Gln Asn Ile Asn Val<br>1160            1165            1170 |
| Glu Asn Ser Glu Phe Arg Asn Lys Phe Arg Asn Phe Phe Ile<br>1175            1180            1185 |
| Gln Ile Leu Leu Ser Asn Glu Gln Lys Leu Val Thr Asn His Ile<br>1190            1195            1200 |
| Trp Asp Glu Lys Gly Leu Asp Arg Ile Glu Glu Phe Lys Ala Glu<br>1205            1210            1215 |
| Leu Leu Asn Asp Glu Tyr Asp Ile Leu Tyr Gly Leu Glu Glu Tyr<br>1220            1225            1230 |
| Ile Gly Lys Gly Ser Leu Val Ser Phe Lys Lys Glu Ser His His<br>1235            1240            1245 |
| Ile Ser Ile Tyr Met Asp Val Asp Lys Gln Val Ile Glu Leu Pro<br>1250            1255            1260 |
| Glu Asp Phe Ala Tyr Tyr Gly Leu Ala Thr Pro Ile Arg Glu Ile<br>1265            1270            1275 |
| His Asp Glu Ile Gln Ser Asp Asn Thr Asp Ile Leu Ala Glu Thr<br>1280            1285            1290 |
| Leu Leu Ser His Val Asp Ile Ser Glu Ile Arg Ala Lys Asn Asn<br>1295            1300            1305 |
| Asp Ile Cys Asp Ser Asn Glu Asp Met Ser Ile Asp Asp Asp Phe<br>1310            1315            1320 |
| Asp Asn Leu Ser Glu Phe Glu Asp Ser Phe Ile Glu Glu Glu Ser<br>1325            1330            1335 |
| Glu Ile Ser Glu Glu Pro Asp Glu Glu Leu Thr Asp Ala Thr Ser<br>1340            1345            1350 |
| Ser Ser Asp Asn Glu Ser Ile Glu Asn Ile Gly Glu Ser Pro Ser<br>1355            1360            1365 |
| Lys Ile Ser Asn Val Arg Ala Leu Ile Gly Thr Gln Lys Gly Tyr<br>1370            1375            1380 |
| Asn His Lys Val Tyr Trp Glu Phe Gly His Pro Ser Leu Ala Asn<br>1385            1390            1395 |
| Arg His Met Leu Ile Gln Gly Lys Ser Gly Gln Gly Lys Thr Tyr<br>1400            1405            1410 |
| Phe Ile Gln Arg Met Leu Lys Glu Leu Ser Ile Gln Gly Ile Pro<br>1415            1420            1425 |
| Ser Ile Ile Ile Asp Tyr Thr Asp Gly Phe Lys Pro Ser Gln Leu<br>1430            1435            1440 |
| Glu Pro Asn Phe Lys Asp Ser Leu Gly Asp Lys Ile Ser Gln Tyr<br>1445            1450            1455 |
| Phe Val Val Lys Glu Asn Phe Pro Ile Asn Pro Phe Lys Arg Asn<br>1460            1465            1470 |
| Thr Ile Met Ile Asp Lys Asp Ile Phe Ile Glu Glu Asp Asn Ser<br>1475            1480            1485 |
| Thr Ile Ala Ser Arg Phe Lys Ser Ile Ile Asn Ser Val Tyr Gly<br>1490            1495            1500 |
| Leu Gly Ile Gln Gln Ser Asn Thr Leu Tyr Gln Thr Val Leu Asp<br>1505            1510            1515 |
| Cys Leu Asp Lys Tyr Asp Asp Asn Phe Asp Leu Asn Ile Leu Lys<br>1520            1525            1530 |

-continued

```
Glu Glu Ile Leu Lys Asp Glu Ser Asn Ser Ala Gln Thr Val Leu
    1535                1540                1545

Asn Lys Leu Asn Glu Leu Leu Asp Lys Asn Pro Phe Ala Ser Thr
1550                1555                1560

Asp Phe Asp Trp Ser Val Leu Asp Asn Lys Asp Gly Lys Val Tyr
    1565                1570                1575

Ile Ile Gln Leu Thr Ala Leu Ser Lys Asp Ile Gln Thr Ile Ile
1580                1585                1590

Thr Glu Phe Ile Leu Trp Asp Leu Trp Asn Tyr Lys Leu Thr Asn
    1595                1600                1605

Gly Ser Glu Asp Asn Pro Phe Ile Val Val Leu Asp Glu Ala His
1610                1615                1620

Asn Leu Asp Phe Ser Asn Asp Ser Pro Cys Ser Lys Ile Leu Lys
    1625                1630                1635

Glu Gly Arg Lys Phe Gly Trp Ser Gly Trp Phe Ala Thr Gln Ser
1640                1645                1650

Val Lys Gly Ser Met Lys Ile Asp Glu Ile Ala Lys Leu Glu Asn
    1655                1660                1665

Ala Asp Glu Lys Ile Tyr Phe His Pro Thr Asp Val Ser Thr Ile
1670                1675                1680

Ala Lys Asp Leu Ser Lys Asp Asn Glu Asp Lys Lys Ile Tyr Glu
    1685                1690                1695

Lys Glu Leu Ser Gln Leu Thr Lys Gly Tyr Cys Ile Val Gln Gly
1700                1705                1710

Ser Ala Ile Asp Ser Ser Gly Asn Leu Tyr Gln Pro Asn Pro Val
    1715                1720                1725

Thr Val Lys Ile Glu Glu Ile Ser Phe Asp Glu Asn
1730                1735                1740

<210> SEQ ID NO 67
<211> LENGTH: 1054
<212> TYPE: PRT
<213> ORGANISM: Methanobrevibacter ruminantium

<400> SEQUENCE: 67

Met Glu Ser Lys Asp Arg Ile Glu Asn Thr Ile Phe Asn Asp Lys Arg
1               5                   10                  15

Met Asp Ala Tyr Ile Asp Lys Tyr Phe Glu Glu Phe Thr Leu Ser Ser
            20                  25                  30

Glu Gln Glu Glu Ala Leu Asn Ile Trp Ile Asp Lys Leu Asn Asn Asp
        35                  40                  45

Gln Leu Thr Ser Glu Lys Gly Asn Tyr His Asn Phe Phe Glu Ile Ile
    50                  55                  60

Leu Glu Asp Leu Leu Gly Tyr Lys Arg Ser Asp Val Lys His Glu Glu
65                  70                  75                  80

Asn Ile Gly Asp Glu Gly His Pro Val Glu Phe Val Leu Glu Lys Asp
                85                  90                  95

Gly Lys Asp Tyr Val Ile Ile Glu Leu Lys Gly Thr Thr Tyr Lys Asp
            100                 105                 110

Leu Thr Lys Arg Arg Pro Gly Gln Gln Ser Pro Val Glu Gln Ala Thr
        115                 120                 125

Asn Tyr Ala Ser Ala Lys Lys Glu Thr Glu Trp Ala Thr Val Ser Asn
    130                 135                 140

Tyr Asp Glu Phe Arg Phe Phe Asn Pro Thr Ala Arg Asp Asn Tyr Ile
145                 150                 155                 160
```

```
Ser Phe Lys Phe Arg Gln Leu Lys Asp Leu Glu Ile Phe Lys Lys Phe
            165                 170                 175

Leu Leu Val Phe Ser Lys Phe Ser Leu Ile Asp Glu Asp Ile Pro Lys
        180                 185                 190

Lys Leu Leu Asn Glu Thr Lys Val Ile Glu Arg Glu Leu Glu Asn Glu
            195                 200                 205

Phe Tyr Gln Leu Tyr Ser Asp Thr Arg Leu Met Ile Ile Lys Glu Leu
        210                 215                 220

Glu Tyr Ser Ser Glu Asp Ile Asn Arg Ile Glu Ala Ile Lys Leu Ser
225                 230                 235                 240

Gln Ile Ile Leu Asn Arg Phe Ile Phe Leu Cys Phe Ala Glu Asp Leu
                245                 250                 255

Ala Leu Met Glu Glu Thr Thr Ala Asp Val Leu Leu Thr Pro Leu
            260                 265                 270

Lys His Arg Asn Leu Ile Gly Asn Thr Met Trp Asn Arg Leu Asn Glu
            275                 280                 285

Leu Phe Ile Phe Ala Asn Gln Gly Asn Lys His Arg Arg Ile Pro Ala
        290                 295                 300

Phe Asn Gly Gly Leu Phe Glu Asp Asp Leu Ser Asn Leu Lys Ile Arg
305                 310                 315                 320

Asp Glu Ile Glu Asp Arg Ser Phe Phe Glu Asn Trp Asn Leu Lys Glu
                325                 330                 335

Asp Phe Glu Asp Lys Tyr Glu Asp Ile Ala Lys Leu Ile Gly Val Tyr
            340                 345                 350

Lys Asp Thr Leu Asn Pro Ile Phe Ile Asn Leu Leu Ile Ile Ser Thr
        355                 360                 365

Tyr Asp Phe Asp Ser Glu Leu Asp Val Asn Ile Leu Gly His Ile Phe
        370                 375                 380

Glu Asn Ser Ile Ser Asp Ile Glu Glu Leu Lys Asn Asp Asn Gln Glu
385                 390                 395                 400

Gln Arg Lys Lys Asp Gly Val Tyr Tyr Thr Pro Glu Tyr Ile Thr Asp
            405                 410                 415

Tyr Ile Cys Arg Asn Thr Ile Ile Pro Tyr Leu Ser Ile Ser Gly Lys
        420                 425                 430

Ala Ser Thr Val His Glu Leu Leu Tyr Glu Tyr Glu Ser Ser Asn Ser
            435                 440                 445

Leu Asp Val Leu Asp Ser Lys Leu Thr Asn Ile Lys Val Leu Asp Pro
        450                 455                 460

Ala Cys Gly Ser Gly Ser Met Leu Asn Lys Ser Val Asp Ile Leu Phe
465                 470                 475                 480

Glu Ile His Glu Ala Leu His Ala Ser Lys Tyr Ala Gly Asp Ser Ser
                485                 490                 495

Leu Asp Arg Phe Phe Asp Ser Leu Glu Lys Arg Lys Glu Ile Ile Ser
        500                 505                 510

Asn Asn Ile Tyr Gly Val Asp Leu Asn Glu Glu Ser Val Glu Ile Thr
            515                 520                 525

Lys Leu Ser Leu Phe Leu Lys Leu Ala Thr Thr Val Gly Leu Lys Glu
        530                 535                 540

Gly Phe Gln Leu Pro Ser Leu Asp Lys His Ile Lys Cys Gly Asp Ser
545                 550                 555                 560

Leu Val Asp Asp Glu Ser Ile Ala Gly Asn Lys Ala Phe Asn Trp Tyr
                565                 570                 575

Glu Ser Phe Ser Glu Val Phe Glu Ser Gly Gly Phe Asp Ile Ile Val
            580                 585                 590
```

Gly Asn Pro Pro Tyr Val Asp Ile Lys Glu Met Asp Glu Lys Thr Ala
            595                 600                 605

Lys Tyr Ile Phe Asp Asn Tyr Glu Thr Ser Phe Asn Arg Ile Asn Leu
    610                 615                 620

Tyr Ser Thr Phe Val Glu Lys Ser Tyr Tyr Leu Leu Lys Asn Glu Gly
625                 630                 635                 640

Ile Phe Ser Phe Ile Met Pro Asn Ser Ile Leu Phe Asn Ser Thr Tyr
                645                 650                 655

Ser Lys Ile Arg Glu Leu Ile Leu Asn Asn Thr Ser Ile Leu Asn Ile
            660                 665                 670

Val Arg Thr Ser Asp Asp Val Phe Lys Asp Ala Lys Val Glu Pro Ile
            675                 680                 685

Ile Leu Ile Phe Lys Lys Gly Tyr Asp Glu Gly Asn Lys Thr Lys Ile
    690                 695                 700

Leu Ile Lys Lys Asp Asp Met Asp Glu Ile Pro Ile Asn Asn Tyr Ser
705                 710                 715                 720

Glu His Phe Phe Thr Gln Glu Arg Trp Phe Glu Asn Asn Ser Ile Ile
                725                 730                 735

Asn Ile Phe Ser Asp Asp Phe Thr Phe Asp Leu Leu Lys Lys Ile Asp
            740                 745                 750

Gly Asn Asn Glu Arg Leu Ile Asp Tyr Cys Asp Phe Ser Leu Gly Leu
            755                 760                 765

Thr Pro Tyr Asp Lys Tyr Lys Gly Met Ser Glu Asp Ile Ile Lys Asn
    770                 775                 780

Arg Lys Phe His Ser Lys Ile Lys Leu Asp Asp Thr Phe Lys Glu Leu
785                 790                 795                 800

Leu Asp Gly Ser Asp Ile Thr Arg Tyr Asn Val Lys Trp Gly Glu Lys
                805                 810                 815

Glu Tyr Ile Lys Tyr Gly Asp Trp Leu Gly Ala Pro Arg Glu Glu Lys
            820                 825                 830

Phe Phe Lys Asn Pro Arg Ile Leu Ile Arg Gln Ile Leu Ser Ile Ala
            835                 840                 845

Pro Lys Glu Ser Arg Lys Arg Ile Phe Ala Ala Tyr Thr Glu Glu Glu
    850                 855                 860

Leu Tyr Asn Ala Gln Ile Ala Phe Asn Leu Val Leu Lys Glu Gly Phe
865                 870                 875                 880

Asp Asp Lys Asn Leu Leu Lys Tyr Phe Leu Gly Ile Ile Asn Ser Lys
                885                 890                 895

Met Met Thr Trp Tyr Tyr Glu Glu Arg Phe Met Asp Lys Asn Lys Lys
            900                 905                 910

Asn Phe Ala Lys Ile Leu Ile Glu Asn Ala Lys Asn Leu Pro Val Ile
            915                 920                 925

Ile Asn Ser Asn Phe Leu Asp Glu Ile Val Ser Asn Val Asp Ser Ile
    930                 935                 940

Ile Glu Leu Asn Lys Glu Phe Tyr Ser Val Arg Asn Ala Phe Gln Thr
945                 950                 955                 960

Trp Leu Lys Ile Glu Phe Glu Ile Glu Lys Leu Ser Lys Lys Leu Glu
                965                 970                 975

Asn Tyr Tyr Asp Leu Asn Phe Glu Glu Phe Leu Lys Ile Lys Lys
            980                 985                 990

Lys Lys Val Val Ile Arg Pro Asn Gln Ile Gln Asp Leu Ser Glu Leu
    995                 1000                1005

Phe Asn Glu Ser Leu Gly Lys Ile Glu Tyr Leu Gln Arg Glu Ile

```
                1010                1015                1020

Lys Glu  Ala Asp Glu Lys Ile  Asn Leu Leu Val Tyr  Glu Leu Tyr
    1025                1030                1035

Gly Leu  Asn His Glu Glu Ile  Glu Ile Ile Glu Asn  Ser Phe Asn
    1040                1045                1050

Asp

<210> SEQ ID NO 68
<211> LENGTH: 86
<212> TYPE: PRT
<213> ORGANISM: Methanobrevibacter ruminantium

<400> SEQUENCE: 68

Met Asp Asp Glu Thr Leu Ile Leu Ile Glu Tyr Ile Arg Asn Ala Pro
1               5                   10                  15

Thr Arg Glu Met Val Leu Lys Ser Phe Glu Gly Val Asp Phe Ile Arg
                20                  25                  30

Pro Ile Gln Ile Ser Arg Lys Thr Gly Ile His Pro Asn Asn Val Ser
            35                  40                  45

Lys Lys Leu Lys Asp Leu Arg Glu His Glu Leu Val Tyr Val Ile Asn
    50                  55                  60

Pro Glu Tyr His Val Pro Lys Leu Tyr Arg Leu Thr Glu Lys Gly Lys
65                  70                  75                  80

Asn Met Leu Gln Phe Leu
                85

<210> SEQ ID NO 69
<211> LENGTH: 255
<212> TYPE: PRT
<213> ORGANISM: Methanobrevibacter ruminantium

<400> SEQUENCE: 69

Met Asn Lys Lys Ile Ile Leu Ser Leu Leu Val Leu Leu Val Ala
1               5                   10                  15

Ile Ser Val Ser Ala Val Ala Ala Asp Ala Asp Val Thr Tyr Ile
                20                  25                  30

Asn Asp Ala Ala Asp Val Asp Asp Val Ala Asp Glu Lys Val Ala Pro
            35                  40                  45

Leu Thr Ala Ser Ala Asp Ala Gln Asp Ile Gln Thr Lys Leu Asp Asn
    50                  55                  60

Ala Lys Pro Gly Asp Thr Ile Glu Leu Glu Asn Lys Thr Tyr Asp Val
65                  70                  75                  80

Asp Thr Thr Phe Asn Val Thr Lys Gln Val Thr Ile Lys Gly Gln Asp
                85                  90                  95

Thr Val Ile Lys Ala Ser Gly Ala Ser Gln Gly Gly Ser Gly Ala Leu
            100                 105                 110

Phe Ile Ala Asn Glu Ala Gly Thr Ala Phe Gly Ile Thr Phe Ile
            115                 120                 125

Asn Thr Asp Gly His Lys Asn Tyr Gly Glu Gln Val Ser Gly Tyr Ala
            130                 135                 140

Ile Gln Leu Ala Ile Glu Asn Gly Thr Val Asp Asn Cys Lys Phe Ile
145                 150                 155                 160

Asp Trp Ser Ser Gly Val Tyr Gly Lys Gly Ala Ser Phe Cys Ser Ile
                165                 170                 175

Thr Asn Ser Tyr Phe Asn Gly Ser Ser Glu Gln Val Thr Asn Gly Gly
                180                 185                 190
```

```
Lys Lys Glu Tyr Gly Thr Lys Ala Ile Asn Leu Met Gly Ser His Asp
        195                 200                 205

Ile Thr Val Thr Gly Cys Thr Phe Glu Gly Gln Val Leu Asp Ala Ile
        210                 215                 220

Ser Ile Ala Ser Asn Ser Gly Asn Asn Ile Met Thr Asp Asn Thr Phe
225                 230                 235                 240

Ile Asp Asn Cys Tyr Ala Ile Tyr Phe Gly Gly Ala Ser Thr Gln
        245                 250                 255

<210> SEQ ID NO 70
<211> LENGTH: 208
<212> TYPE: PRT
<213> ORGANISM: Methanobrevibacter marburgensis

<400> SEQUENCE: 70

Ser Arg Tyr Asn Arg Phe Lys Glu Val Asn Gly Arg Glu Pro Arg Val
1               5                   10                  15

Val Phe Ile Tyr Ser Gly Gly Pro Ser Val Ser Leu Glu Thr Phe
            20                  25                  30

Lys Asp Met Cys Lys Arg Tyr Asn Gln Phe Leu Glu Glu Asn Arg Arg
        35                  40                  45

Glu Pro Arg Ile Val Tyr Val Thr Pro Pro Glu Pro Val Pro Glu
50                  55                  60

Glu Val Arg Glu Met Arg Val Leu Gly Glu Phe Lys Thr Ala Thr
65                  70                  75                  80

Gln Leu Tyr Thr Leu Val Ser Arg Arg Cys Lys Tyr Lys Phe Tyr Tyr
                85                  90                  95

Asn Asp Gln Thr Pro Asn Arg Glu Ala Leu Lys Lys Met Val Thr Asp
                100                 105                 110

Gly Ile Asn Cys Thr Asp Ala Cys Gln Leu Phe Lys Pro Val Ile Glu
        115                 120                 125

Gly Leu Gly Tyr Ser Val Arg Ile Glu His Val Lys Val Arg Cys Asn
        130                 135                 140

Asp Asn Lys Trp Tyr Gly His Tyr Phe Leu Arg Val Ala Gly Lys Glu
145                 150                 155                 160

Leu Ala Ser Val Ser Leu Pro Ser Glu Arg Trp Thr Val Trp Asp Tyr
                165                 170                 175

Val Ser Ala Thr Lys Thr Gly Arg Pro Leu Gly Ala Pro Cys Cys Ser
            180                 185                 190

Arg Gly Ile Gln His Leu Gly Trp Gly Ile Val Ser Pro Lys His Asp
        195                 200                 205

<210> SEQ ID NO 71
<211> LENGTH: 202
<212> TYPE: PRT
<213> ORGANISM: Methanobrevibacter wolfeii

<400> SEQUENCE: 71

Arg Arg Tyr Glu Asp Phe Val Arg Ile Asn Gly Arg Glu Pro Asn Ile
1               5                   10                  15

Ile Tyr Leu Glu Gln Gly Lys Ser Asp His Val Ser Leu Gly Thr Phe
            20                  25                  30

Lys Asp Met Leu Arg Arg Tyr Lys Asp Phe Val Arg Ile Asn Gly Arg
        35                  40                  45

Glu Pro Asn Tyr Ile Ser Ile Gln Pro Gln Pro Ser Leu Lys Gly His
50                  55                  60

Trp Thr Thr Lys Val Ile Glu Lys Ile Gly Thr Phe His Asp Ala Thr
```

```
                65                  70                  75                  80
Ser Leu Tyr Glu Arg Val Lys Lys Thr Cys Lys Tyr Lys Tyr Tyr Tyr
                    85                  90                  95

Asn Asp Gln Val Pro Asn His Val Ala Val Met Arg Met Thr Thr Ser
                100                 105                 110

Gly Ile Asn Cys Thr Asp Ala Cys Gln Leu Phe Ser Lys Val Leu Glu
                115                 120                 125

Glu Met Gly Tyr Glu Val Lys Ile Glu His Val Arg Val Lys Cys Asn
            130                 135                 140

Asp Gly Lys Trp Tyr Gly His Tyr Leu Leu Arg Val Gly Gly Phe Glu
145                 150                 155                 160

Leu Lys Asp Gly Thr Ile Trp Asp Tyr Val Ser Ala Thr Lys Thr Gly
                165                 170                 175

Arg Pro Leu Gly Val Pro Cys Cys Thr Ala Gly Phe Gln His Leu Gly
                180                 185                 190

Trp Gly Ile Val Gly Pro Val Tyr Asp Lys
            195                 200

<210> SEQ ID NO 72
<211> LENGTH: 155
<212> TYPE: PRT
<213> ORGANISM: Methanobrevibacter ruminantium

<400> SEQUENCE: 72

Val Ala Arg Asn Pro Leu Val Met Asp Tyr Gln Asn Thr Asn Tyr Thr
1               5                   10                  15

Cys Cys Pro Thr Ser Leu Ser Leu Ala Ser Gln Met Leu Tyr His Tyr
                20                  25                  30

Lys Ser Glu Ser Glu Cys Ala Lys Ala Leu Gly Thr Ser Lys Gly Ser
            35                  40                  45

Gly Thr Ser Pro Ala Gln Leu Ile Ala Asn Ala Pro Lys Leu Gly Phe
        50                  55                  60

Lys Ile Ile Pro Ile Lys Arg Asp Ser Lys Glu Val Lys Lys Tyr Leu
65                  70                  75                  80

Lys Lys Gly Phe Pro Val Ile Cys His Trp Gln Val Asn Gln Ser Arg
                85                  90                  95

Asn Cys Lys Gly Asp Tyr Thr Gly Asn Phe Gly His Tyr Gly Leu Ile
                100                 105                 110

Trp Asp Met Thr Ser Thr His Tyr Val Val Ala Asp Pro Ala Lys Gly
            115                 120                 125

Val Asn Arg Lys Tyr Lys Phe Ser Cys Leu Asp Asn Ala Asn Lys Gly
        130                 135                 140

Tyr Arg Gln Asn Tyr Tyr Val Val Cys Pro Ala
145                 150                 155

<210> SEQ ID NO 73
<211> LENGTH: 212
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (4)..(5)
<223> OTHER INFORMATION: Any amino acid
```

```
<220> FEATURE:
<221> NAME/KEY: MOD_RES
<222> LOCATION: (7)..(8)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (23)..(28)
<223> OTHER INFORMATION: Any amino acid
<220> FEATURE:
<221> NAME/KEY: MOD_RES
<222> LOCATION: (32)..(32)
<223> OTHER INFORMATION: Any amino acid
<220> FEATURE:
<221> NAME/KEY: MOD_RES
<222> LOCATION: (43)..(43)
<223> OTHER INFORMATION: Any amino acid
<220> FEATURE:
<221> NAME/KEY: MOD_RES
<222> LOCATION: (46)..(47)
<223> OTHER INFORMATION: Any amino acid
<220> FEATURE:
<221> NAME/KEY: MOD_RES
<222> LOCATION: (49)..(49)
<223> OTHER INFORMATION: Any amino acid
<220> FEATURE:
<221> NAME/KEY: MOD_RES
<222> LOCATION: (53)..(54)
<223> OTHER INFORMATION: Any amino acid
<220> FEATURE:
<221> NAME/KEY: MOD_RES
<222> LOCATION: (56)..(56)
<223> OTHER INFORMATION: Any amino acid
<220> FEATURE:
<221> NAME/KEY: MOD_RES
<222> LOCATION: (58)..(58)
<223> OTHER INFORMATION: Any amino acid
<220> FEATURE:
<221> NAME/KEY: MOD_RES
<222> LOCATION: (60)..(69)
<223> OTHER INFORMATION: Any amino acid
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (80)..(80)
<223> OTHER INFORMATION: Any amino acid
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (92)..(92)
<223> OTHER INFORMATION: Any amino acid
<220> FEATURE:
<221> NAME/KEY: MOD_RES
<222> LOCATION: (103)..(103)
<223> OTHER INFORMATION: Any amino acid
<220> FEATURE:
<221> NAME/KEY: MOD_RES
<222> LOCATION: (106)..(107)
<223> OTHER INFORMATION: Any amino acid
<220> FEATURE:
<221> NAME/KEY: MOD_RES
<222> LOCATION: (115)..(115)
<223> OTHER INFORMATION: Any amino acid
```

```
<220> FEATURE:
<221> NAME/KEY: MOD_RES
<222> LOCATION: (127)..(128)
<223> OTHER INFORMATION: Any amino acid
<220> FEATURE:
<221> NAME/KEY: MOD_RES
<222> LOCATION: (132)..(132)
<223> OTHER INFORMATION: Any amino acid
<220> FEATURE:
<221> NAME/KEY: MOD_RES
<222> LOCATION: (149)..(149)
<223> OTHER INFORMATION: Any amino acid
<220> FEATURE:
<221> NAME/KEY: MOD_RES
<222> LOCATION: (156)..(156)
<223> OTHER INFORMATION: Any amino acid
<220> FEATURE:
<221> NAME/KEY: MOD_RES
<222> LOCATION: (162)..(162)
<223> OTHER INFORMATION: Any amino acid
<220> FEATURE:
<221> NAME/KEY: MOD_RES
<222> LOCATION: (165)..(166)
<223> OTHER INFORMATION: Any amino acid
<220> FEATURE:
<221> NAME/KEY: MOD_RES
<222> LOCATION: (168)..(174)
<223> OTHER INFORMATION: Any amino acid
<220> FEATURE:
<221> NAME/KEY: MOD_RES
<222> LOCATION: (191)..(191)
<223> OTHER INFORMATION: Any amino acid
<220> FEATURE:
<221> NAME/KEY: MOD_RES
<222> LOCATION: (196)..(196)
<223> OTHER INFORMATION: Any amino acid
<220> FEATURE:
<221> NAME/KEY: MOD_RES
<222> LOCATION: (198)..(198)
<223> OTHER INFORMATION: Any amino acid
<220> FEATURE:
<221> NAME/KEY: MOD_RES
<222> LOCATION: (207)..(207)
<223> OTHER INFORMATION: Any amino acid
<220> FEATURE:
<221> NAME/KEY: MOD_RES
<222> LOCATION: (209)..(209)
<223> OTHER INFORMATION: Any amino acid
<220> FEATURE:
<221> NAME/KEY: MOD_RES
<222> LOCATION: (212)..(212)
<223> OTHER INFORMATION: Any amino acid

<400> SEQUENCE: 73

Xaa Arg Tyr Xaa Xaa Phe Xaa Xaa Ile Asn Gly Arg Glu Pro Xaa Val
 1               5                  10                  15

Ile Phe Ile Xaa Asn Gly Xaa Xaa Xaa Xaa Xaa Val Ser Leu Xaa
             20                  25                  30

Thr Phe Lys Asp Met Leu Lys Arg Tyr Lys Xaa Phe Leu Xaa Xaa Asn
         35                  40                  45

Xaa Arg Glu Pro Xaa Xaa Ile Xaa Ile Xaa Pro Xaa Xaa Xaa Xaa Xaa
 50                  55                  60

Xaa Xaa Xaa Xaa Xaa Glu Met Xaa Lys Xaa Leu Gly Thr Phe Lys Xaa
 65                  70                  75                  80

Ser Ala Thr Ser Leu Tyr Xaa Leu Val Ala Lys Xaa Cys Lys Tyr Lys
                 85                  90                  95

Phe Tyr Tyr Asn Asp Gln Xaa Pro Asn Xaa Xaa Ala Val Lys Lys Met
             100                 105                 110

Leu Thr Xaa Gly Ile Asn Cys Thr Asp Ala Cys Gln Leu Phe Xaa Xaa
         115                 120                 125

Val Ile Glu Xaa Leu Gly Tyr Ser Val Lys Ile Glu His Val Lys Val
```

```
              130                 135                 140
Lys Cys Asn Asp Xaa Lys Trp Tyr Gly His Tyr Xaa Leu Arg Val Ala
145                 150                 155                 160

Gly Xaa Glu Leu Xaa Xaa Val Xaa Xaa Xaa Xaa Xaa Xaa Xaa Thr Val
                165                 170                 175

Trp Asp Tyr Val Ser Ala Thr Lys Thr Gly Arg Pro Leu Gly Xaa Pro
            180                 185                 190

Cys Cys Ser Xaa Gly Xaa Gln His Leu Gly Trp Gly Ile Val Xaa Pro
        195                 200                 205

Xaa His Asp Xaa
    210

<210> SEQ ID NO 74
<211> LENGTH: 264
<212> TYPE: DNA
<213> ORGANISM: Methanobrevibacter ruminantium

<400> SEQUENCE: 74
gtgagaaata tgaagaataa gagtttaata ttaatttctt tattattact gattacaata      60
ataagcatag gatctgttgt tgcaacggat aatgaagaaa ttaatatgga taatataaat     120
aatattgata taatgaggga tatcgctaat attgataatg tcgataatgt cgataactcc     180
aatataaaca atccaactga cataagaata gacaattcaa acctaaatag agaaacagaa     240
ctagattcaa atttaaataa atct                                            264

<210> SEQ ID NO 75
<211> LENGTH: 255
<212> TYPE: DNA
<213> ORGANISM: Methanobrevibacter ruminantium

<400> SEQUENCE: 75
atgaagactt ttagacaaca gctattggaa gaccctgaat ccagaactac cctgttgcag      60
agaccgaacc tgacggagag cagcctgcag tcatacctca atgccgccac caacttcgtg     120
aggttcacag gggagccgtt ctacaagacc gtgcatgagc tcagaagcca gcagaacgat     180
aggattgaga acaacatcat cataaggttc aacccgaacc agtcaaggat aaacatcatg     240
cagtttgagt tcata                                                      255

<210> SEQ ID NO 76
<211> LENGTH: 255
<212> TYPE: DNA
<213> ORGANISM: Methanobrevibacter ruminantium

<400> SEQUENCE: 76
atgaatacat taaaaataga atgttcaaaa gatgattata tcataaagac tgcaaaggca      60
aattctgaaa atgagttgaa agttgaagtt cctgagaact ggaactgcga ctatgtgaat     120
gctgtcctgt gggaagagga catctgcgaa gtgcttgaaa agggtgatga agaatgcgtt     180
ttgattccta tgtgcggtga actgcttctt gaaggagtgc aggaagatga atacataaag     240
tacatttgcc ttcct                                                      255

<210> SEQ ID NO 77
<211> LENGTH: 255
<212> TYPE: DNA
<213> ORGANISM: Methanobrevibacter ruminantium

<400> SEQUENCE: 77
atgggaatga aaaagttaa gatcgaaagt aaagcaaaaa ataatatgac aagaaacgaa      60
```

```
aaactcttct ataaattata tgacgattta tataatgaag atagattaat tttattctcc    120
acatatttta acatatatga taaatttatt tttaaaaaag atataatcca ttatgtttta    180
atgaactact ctgaaaatga aattattgaa gcaatgaaaa aaattgatga aattcagtca    240
gaaggcattg atatt                                                    255

<210> SEQ ID NO 78
<211> LENGTH: 255
<212> TYPE: DNA
<213> ORGANISM: Methanobrevibacter ruminantium

<400> SEQUENCE: 78
atgaaaacac aagatctaat taatataata aatgatgagg aatctcctgt attcctcaac    60
agggaagtct ttgagatgga ctatgtgccg gacatctaca aatacaggga cgagcagctg    120
gcgaaaatgg cgatgtactg caattcaata cctgacaaca tagctcccaa gaacctgcaa    180
ttgtgcggag gcaatgcgac aggaaagacc acaacattaa agcagttctt caagatgttg    240
aacgaggctt ttcca                                                    255

<210> SEQ ID NO 79
<211> LENGTH: 255
<212> TYPE: DNA
<213> ORGANISM: Methanobrevibacter ruminantium

<400> SEQUENCE: 79
atgtttttgg aaaaatgcga tgaaaagat acaatcagca tgtctcttca agaaaagatg      60
aatcttatat tggaaactat ggaaagcaaa ggaagcccct tcatatcctg tattcattgt    120 aacatacccta taaatgaagc agaagaatgg tacaaaaatg gagaaatagg agatcaggac    180
tttataaatt tctatgatga tgtaaacttg attgaagaaa gttttgggtt tgaaatttat    240
aaaaaatcag aatat                                                    255

<210> SEQ ID NO 80
<211> LENGTH: 207
<212> TYPE: DNA
<213> ORGANISM: Methanobrevibacter ruminantium

<400> SEQUENCE: 80
ttgataattt tccttaaact aaaatttgga cgtgtaatca tggaaaaatt aatcgaaatt     60
gacggagttc aatacacaga agcccaaatc agaagggctt tagccattga acgagacgtg    120
cgctctccta atttcgttga tatgttattg ggaaagatca aacctagcga acttgcaagc    180
agagtttctg aaaaaggtga tgcctaa                                        207

<210> SEQ ID NO 81
<211> LENGTH: 156
<212> TYPE: DNA
<213> ORGANISM: Methanobrevibacter ruminantium

<400> SEQUENCE: 81
atgtgctatg tgggaaacac caggacattg gtctatcaca cagaggactg cttctgcaac     60
cactggctgt tgaacgagaa caagaccatt ctagaggaaa agcctgtaga catgaaacct    120
tgcagcttct gcaaaccaca gtttgacact gaatag                              156

<210> SEQ ID NO 82
<211> LENGTH: 234
<212> TYPE: DNA
<213> ORGANISM: Methanobrevibacter ruminantium
```

<400> SEQUENCE: 82

```
gtgttggata tggttgcaga gatggttgaa aacatcagga aaggagaagg agatggatat      60
tccatctacc ctccttttc ctgcattgtt ttcctacaag gcaaaaagta ttccgaatgc      120
tgctgcaagg ctgaggcaag ggatcagaag tttgcacttg tgaaccttgt aggcttcaga     180
agagaggatg tcaaggtcat agacccaagg accaacgagg agctgttcgt atga           234
```

<210> SEQ ID NO 83
<211> LENGTH: 162
<212> TYPE: DNA
<213> ORGANISM: Methanobrevibacter ruminantium

<400> SEQUENCE: 83

```
atgagcatgc ttgcagactt cgagcctgca aggctccaca agaggacatg gctgaaagg      60 catgatgtcg aaatccttgc tgtcatatgc cttgccataa gcattgcaat gctacttctt    120
ttctttgcgc ttgcagagcc gactgttgca ggagtgattt ag                        162
```

<210> SEQ ID NO 84
<211> LENGTH: 255
<212> TYPE: DNA
<213> ORGANISM: Methanobrevibacter ruminantium

<400> SEQUENCE: 84

```
atgactaagg aatttgagga cttcatgaga aggaacacag gactgcttgt tttcttgaga     60
tgggacacag tggcatatct gaaataccttt gagtcccatt atgacgaaag gaagtacgaa   120
tgcgcttaca gattgttgga ggcaatcgac aatctctttg acttctacca gataaccttc    180
agcaaaaaga ctgaaaggga aattcctgac cagcttttg aaaaggacaa gataaacaaa     240
ggcttccttt cacac                                                       255
```

<210> SEQ ID NO 85
<211> LENGTH: 255
<212> TYPE: DNA
<213> ORGANISM: Methanobrevibacter ruminantium

<400> SEQUENCE: 85

```
atgaatgaga tagttactac aactaacgag aataatgtac ctgtcgacgt tgactatgcc     60
atcgaggaat ggaaggcata ccagcgattg accagagagc tattggacga aacagattat   120
cagacacaca gaggcaggaa gtacaagacc aagagcgctt ggcagaagta cgcacgtgcc    180
ttcaacataa acacacagat aatcgacaag gaaatcgtca agaatgacaa gggaatcgtc    240
attgaggctg agtat                                                       255
```

<210> SEQ ID NO 86
<211> LENGTH: 231
<212> TYPE: DNA
<213> ORGANISM: Methanobrevibacter ruminantium

<400> SEQUENCE: 86

```
atgattgagt gcatacagga agagggagac ttcacggatt gggaggttcc ttcctcctct     60
tccgacatca agtacatagt ttcagtggat gatgagggaa acctgttctg cagctgtcct   120
gacttctatt acaggaagtc caggatgaac cctcacatct caaaccctga atcctattgc    180
aaacacatca gacaagtctt ggaggaggac aatagattgc aaatgctcta g              231
```

<210> SEQ ID NO 87
<211> LENGTH: 255

```
<212> TYPE: DNA
<213> ORGANISM: Methanobrevibacter ruminantium

<400> SEQUENCE: 87
atggataata taaataagac aaaaacaagt ttagctaagt ttgaagagtt tttcagcact      60
gtatacaagg acgaagtcat ggaagttttg gaaaagtatc ctgaggaaag gacattggtt     120
gtggactatg agaatttgga atgtttgat cctgatttgg cagacttgtt gattgaaaag     180
cctgacgaag taatcgcagc ttcacagaaa gcaatcaaga acattgaccc attgatgaaa    240
gatccaaagt tggac                                                     255

<210> SEQ ID NO 88
<211> LENGTH: 255
<212> TYPE: DNA
<213> ORGANISM: Methanobrevibacter ruminantium

<400> SEQUENCE: 88
atggctaaca agattagagt taatctcacg gttgaccccta atttgtggca attagcaaaa      60
gacaagttac cttgcagcag aagcgaattc tttgagaatc agttgaagat gttcttaggg     120
attgaagatg acgagtcgga aatcattaag gacatccaaa ccaaagaaaa tgagattaac     180
gcactaagag acaagttatg tcatgttcgc aaatcaaagc agttgaaatt ggaatcaaac     240
aaatctatgg agaag                                                     255

<210> SEQ ID NO 89
<211> LENGTH: 255
<212> TYPE: DNA
<213> ORGANISM: Methanobrevibacter ruminantium

<400> SEQUENCE: 89
atgacaattg gaagtttgga caattttgga aagtcagatg gagaaaacat gaaccctgaa      60
gatttcgact gttctgtttt cttttgaaatg tacaaggcac tttttgagat attggatgtt     120
gaagttggca gcttcgctga actcttggat gtgtacaaga atgtcgagat ggattacacc     180
ttgaagagac atgccctcaa gcagaaggaa atcctttact ggttcaatac cgactggaag     240
gaggaacttg gaaag                                                     255

<210> SEQ ID NO 90
<211> LENGTH: 255
<212> TYPE: DNA
<213> ORGANISM: Methanobrevibacter ruminantium

<400> SEQUENCE: 90
atgaatgtga aaacagtcat gaatgacctt ataggattgt caaaggagtt cgagggagtg      60
gaatatgaga ttgaatccaa aaattcaatc tacttctatt cctttccaaa gtacatgaag     120
gaaggcattg tgattctgaa atattccgca atctatgacc tgcacaccat attgaaaggc     180
atggatggaa tcatagtgga cattctggag gttgaggaca atcctggtga tgagaagaag     240
gatttgctat atgtg                                                     255

<210> SEQ ID NO 91
<211> LENGTH: 234
<212> TYPE: DNA
<213> ORGANISM: Methanobrevibacter ruminantium

<400> SEQUENCE: 91
atgattagcg acgaatggga agaggaatac tatgtcaagg tcaacgagga actggagcag      60
gtggaagtca ggtttttcag caaggtcgac aggctcgtct ttgctcaatc ctactcttct     120
```

```
tcatcttcct tttcctttga ggaggctgaa atcctgtgcg acaggatatg cgacatactg      180
acaaacgatt tgggaaatgc caagtattat ctaggaggaa aagatgaatt atag           234
```

<210> SEQ ID NO 92
<211> LENGTH: 150
<212> TYPE: DNA
<213> ORGANISM: Methanobrevibacter ruminantium

<400> SEQUENCE: 92

```
atgaattata gggaatgggt tgcaagccag ttcgagctga ggatgactga ggacggaagg      60
gtttgcttca agacaccatg cagctactac acattttcaa aggaggactt tgagataata     120
agggagatgt tccttaattt cgagtcctga                                      150
```

<210> SEQ ID NO 93
<211> LENGTH: 174
<212> TYPE: DNA
<213> ORGANISM: Methanobrevibacter ruminantium

<400> SEQUENCE: 93

```
atggatagaa taaaggaatt gaatgtatgc ggaacctgca agcacagcca tttgattcca      60
gacatcaacg gagagatagc agtgaacatt tgcaggatag gttcagaggc tgtcaacaag     120
gacggaggac ttacatattg cgtagactgg acaccaagga ggaagctgtc atga           174
```

<210> SEQ ID NO 94
<211> LENGTH: 336
<212> TYPE: DNA
<213> ORGANISM: Methanobrevibacter ruminantium

<400> SEQUENCE: 94

```
atgttaagta aaaagaaagc catacagatg acgctggaca atgagaagca ctatcctgtt      60
aagtgcaagt actgcggaaa gccgttcacc aagtctcaca acaggcagat gtactgttca     120
gacagttgca gacggaatgc cttgagggaa cagaaggcaa gataccaggc taaaaggagg     180
ctaaaaataa agcagaaagt gctgattgta gatgaataca agaaatacgg tttgggtagc     240
tatggaacaa gtgcgaacgg acacagaaag aacaattttt cacatgagta catggctatt     300
caaaaggaga tgaaaagaat aggattgaag agataa                               336
```

<210> SEQ ID NO 95
<211> LENGTH: 261
<212> TYPE: DNA
<213> ORGANISM: Methanobrevibacter ruminantium

<400> SEQUENCE: 95

```
atgtatttgg ctaaattttg tcctaactgt ggaaataaag tagaagaaaa tgataaattc      60
tgcatttatt gtggaaataa actaagagtt ataattcctg aaaaaaaagt gaaaagaagc     120
tcaaatagta ttaatgatga aaaaactagc aaatatgttg aagtcattga tgggctaatg     180
agatataaag ttttttccatc aagtttacct gtgaaatata ttatttataa agtgaattat     240
ggaacaacat ctgatgaaat a                                               261
```

<210> SEQ ID NO 96
<211> LENGTH: 234
<212> TYPE: DNA
<213> ORGANISM: Methanobrevibacter ruminantium

<400> SEQUENCE: 96

```
atgatttatg ataaagcgac agttacaagc ctcatagtgg ctatcctatt gccattgatg      60
```

```
agcatgttag gaatcggaga attgactcag aactacatat tggcaatagt gagcggtatg      120
atagcccttg tggtttggta ctacaacgag aagcacaaca gcgatttggt gagcggaacc      180
accaagtgcg actgcgagct ttgctatggg ggagacgatg aagcacttat atga            234

<210> SEQ ID NO 97
<211> LENGTH: 255
<212> TYPE: DNA
<213> ORGANISM: Methanobrevibacter ruminantium

<400> SEQUENCE: 97
atgaagcact tatatgagat aatcccttac aggaggactg tttggattac agggttcctg      60
aagacaacag tctcctcggc aatgataacc actggcgtag tgatattgtt caacagcata     120
accgagcacc cttacttcat ggagtgggac gagataggaa tcgttcttgg aatcgttttcc    180 atcaccatcg cctgcattta catagcgatg atagacagat ggaaggaacg caggaagaag     240
gaggagcttg acacg                                                      255

<210> SEQ ID NO 98
<211> LENGTH: 255
<212> TYPE: DNA
<213> ORGANISM: Methanobrevibacter ruminantium

<400> SEQUENCE: 98
atgatagaaa tcagcaccat aaagatcacc gacataaagc ctgccgaata caatccgagg      60
ataatgagcc agcttgaaca cacaaagctc aggaactcca tggagacatt cggagtggtt     120
gacccaataa taatcaacct gaagaacaac cacatcatag gagggcacca aaggtacgag     180
gtccttctgg acaagtccat ggaggacaac gagttcataa aggagctcca cctcatcagg     240
cttggagatg taggc                                                      255

<210> SEQ ID NO 99
<211> LENGTH: 330
<212> TYPE: DNA
<213> ORGANISM: Methanobrevibacter ruminantium

<400> SEQUENCE: 99
atggacgtcg acaacctgct gggatatgac aaggtactgg aattgaggtc tttattggag      60
gaggtcacgg acaaggtgat acccgtatgg cacaagaacc gcggaatcaa ggacttcaag     120
cagatgtgcc aggactacaa tttcgtcagc ataagcggct ggagaaacga ggacgtcaag     180
gatgaccagt tcatccattt cgtcaggcat gcacacagga acggctgcag gattcacgga     240
ttgggattga cacggagaaa ggttctcgac agggttccct tcgacagcgt cgacagcagc     300
agctggctcc agaccatatt gtatgcaagg                                      330

<210> SEQ ID NO 100
<211> LENGTH: 255
<212> TYPE: DNA
<213> ORGANISM: Methanobrevibacter ruminantium

<400> SEQUENCE: 100
atgattaatg aaaggataag accttatttg aattttagct tcaatgacaa gaaagtcatt      60
ttcgtcacat tgttcgttgt gagcaatctg ataagcaacc tgttagccat caaggttttc     120
aacttgggat tttggggatt gacaaccgat tgcggaaatc tcctgttccc gttaggatac     180 cttatgcag acgtgattac agaagtctat ggagagagga cagctcgaag ggtcatattg      240
cttgggctct ttgca                                                      255
```

<210> SEQ ID NO 101
<211> LENGTH: 255
<212> TYPE: DNA
<213> ORGANISM: Methanobrevibacter ruminantium

<400> SEQUENCE: 101
atgcccgaac cttgggaaag gcaaagggac gagaacggaa agcttgagcc aataaaggca      60
ttcgagtact tcaccgagta cctgacaatg gacaagccac gaagcatgag ggttctgtgc     120
gagaggctcg gcaagaaaga tgggtatatt aggcaacttc atgcctactc atccacatgg     180
aactgggtcg aaagggcaga ggcatacgat gaacacataa tattgaagaa acggttaagg     240
aaagagaagt tttac                                                      255

<210> SEQ ID NO 102
<211> LENGTH: 255
<212> TYPE: DNA
<213> ORGANISM: Methanobrevibacter ruminantium

<400> SEQUENCE: 102
gtgaaggaca ttgtcaatca ttacggctac ctttcaccgt acaagccgac catcaggtct      60
gatagtaagg ctaaaaacaa gttcaagctc aatgagcctt atcgtggaca gatgttgagt     120
gcaggtgctg gcggttcaat catgggatac ggtgcaggtc tccttattgt cgatgaccct     180
atcaagaacg tcgctgaagc cgaatccaag gtacgtcagg caaagctcaa ggactggtgg     240
ggaggaacca tcaag                                                      255

<210> SEQ ID NO 103
<211> LENGTH: 273
<212> TYPE: DNA
<213> ORGANISM: Methanobrevibacter ruminantium

<400> SEQUENCE: 103
atgagtaaga aacaagaaat gatgagaatt gaaaggttaa acactatgc atatcaaaca       60 ggactaataa tccctatttt taaaaatcat gatttaatta aaaaaataga aaatggaaaa    120
ataactaata ctgacgaaat aaagatatat attgaggaaa atgaaaagca gataaaaaga    180
agaagagaat ttataagtat tatttatgat aattgcaaat attttaaata cgacagcata    240
tgttataaat taatatccaa agtaaataat ttt                                  273

<210> SEQ ID NO 104
<211> LENGTH: 255
<212> TYPE: DNA
<213> ORGANISM: Methanobrevibacter ruminantium

<400> SEQUENCE: 104
ttgagtaaga atgctaaagc agacgccttt gttgtgacca ctgaagacgg atcctatgac      60
attgtcgatg cagatgtctt ggagaggtat gcaataaaga gcgaatctga cgagacagga    120
agcaagcagt tgaagactga tggttgggaa tatgatgata cattgcttga gccgttgtat    180
gacccattgc agttgtgtga gctattggag ataaacacat atcatgagaa ctgtgtcgat    240
gttgttgcaa gggac                                                      255

<210> SEQ ID NO 105
<211> LENGTH: 252
<212> TYPE: DNA
<213> ORGANISM: Methanobrevibacter ruminantium

<400> SEQUENCE: 105

```
atgatggcgc tcaaggtgcg tcattcaaag aggcagattc agaatatcaa gagagaatac    60
agaaggcgtt tgatactcga agagcagtgc agtagggaga ttgcggactt cttcagaagg   120
cttgagagga aaatccacaa ggtcatggat gagcactggg aaagcgaatt gggtcttttc   180
catctgaaca aggtttcaga catcatacag gacagcaggc aggagtacta tgacatcctg   240
ttcaagtact gc                                                       252
```

```
<210> SEQ ID NO 106
<211> LENGTH: 255
<212> TYPE: DNA
<213> ORGANISM: Methanobrevibacter ruminantium

<400> SEQUENCE: 106
atgataattg aaattcctgg aaatgacagg acagaagaaa taaatttgcc gaacggacag    60
tttgtactga taacctactt gcaggaaaat gacatgatgt cattgcctga cggaagtat   120 gtctgcccat tcagaatgat tcagcttttc actgaagagg cggtgaact gattggagag   180 tgcattgagg aaaatcctca ctacaacact cgcttctaca atactgtctt tgagcatttg   240
gatgaaggaa ttgag                                                    255
```

```
<210> SEQ ID NO 107
<211> LENGTH: 255
<212> TYPE: DNA
<213> ORGANISM: Methanobrevibacter ruminantium

<400> SEQUENCE: 107
atgttaagag tcgtagagag aacctattat caacaagaag aaatcaagac actagactgt    60
cgaattagag aggcaggagt caacacttac tcccttgctc gtcaaggagc agttgactat   120
cctacctacg aatcctacaa cgaggtgaga gaggaaagga taaaagaggc taaggaaaaa   180
tacggtgaat cctactacta tcactggaga gacgttgaga cctacttcta ttacttagga   240
agattcttta gtgat                                                    255
```

```
<210> SEQ ID NO 108
<211> LENGTH: 255
<212> TYPE: DNA
<213> ORGANISM: Methanobrevibacter ruminantium

<400> SEQUENCE: 108
atggacgcga taaacgttat caaccaaaac aagatattag tagatgtttt gtaccgtggg    60
actgtaaacc tgattgacat cgtcatcggt gatgcattgg tctatgacaa tccgacagtt   120
gtagtcaagt gctacaccac agatttggct tttgcaacca cagagattga tgagattgta   180
ttagagaacg aagaatttga gttattaata acttacgagg acggagagtt ctcaattttg   240
ttgaagtccc acaat                                                    255
```

```
<210> SEQ ID NO 109
<211> LENGTH: 255
<212> TYPE: DNA
<213> ORGANISM: Methanobrevibacter ruminantium

<400> SEQUENCE: 109
atggtttttg tcgatttgtg cgagaacgaa atagcagaca tggtcgagag cttctatcgc    60
aatggagacg gtagcagcag gatattgacc aacagagcag ttggagagat agtggagcac   120
tactgttcct ttgaagtaga cggtagaatc accactaatc tccgagattt cctattatat   180
agtgttgtct tatatgacac cattggagag gctgtcgatg acggagtcaa ccttgaggaa   240
```

```
gtgttcatca tagaa                                                   255

<210> SEQ ID NO 110
<211> LENGTH: 255
<212> TYPE: DNA
<213> ORGANISM: Methanobrevibacter ruminantium

<400> SEQUENCE: 110
gtggtgaatt ggttgaaggc tattggagat aacttctcag tggattatct ccttttagca   60
ttattctcta gtggagattt gatattggtt gccatcgttc tcaattctta tggtgtcatc  120
tcacctgaga atgtaaggga actggtgatt gactatataa gttacaggaa agttgatatt  180
ttttggagac atctaaggag acctagaatg agttttgaag attatgtctt agacaatttt  240
gaagagatgg aaact                                                   255

<210> SEQ ID NO 111
<211> LENGTH: 192
<212> TYPE: DNA
<213> ORGANISM: Methanobrevibacter ruminantium

<400> SEQUENCE: 111
atgacaatga aagttacttt tgaagatgag aacggtgaga gaacagtcga gttcggcgat   60
gacgtcgatt tcgttttaat cgaaagcgat gatgacggaa acattgagat cgcgaaggga  120
gactgggaat tggacggaga ttccgacgat gattgggaag agtacgatga ctgggacgag  180
gaggagttct ga                                                      192

<210> SEQ ID NO 112
<211> LENGTH: 279
<212> TYPE: DNA
<213> ORGANISM: Methanobrevibacter ruminantium

<400> SEQUENCE: 112
gtggacgaat tcgttgagac cctgttcgac acctactgga aggtgaatga gaacggagag   60
tacatgagcc ttaccgattg cggtgatttc tacatcgcaa aggttgctcc ctgtgttcgc  120
aactggagca tagtgataga atgcaattgc ttctgttttc attgcaagga atttgtctac  180
catgagaacg gagcaatact tgagataggt atggagatta gctctctttta cctaagccaa  240 atggagataa aagatttgaa gatatacatg atagattgt                         279

<210> SEQ ID NO 113
<211> LENGTH: 255
<212> TYPE: DNA
<213> ORGANISM: Methanobrevibacter ruminantium

<400> SEQUENCE: 113 atgttttttgg aaggaatatt tgaacaagac ggagagaatg taagagaaca ggtgatttac   60
tggagaaagt ccaatcaggt acacaactgg ttcgtagtca acgctcagga cggagaggac  120
aactgccaac cacactcagt aagcagagaa cagttagagg aactaagaga cctatgcaga  180
gcagtgctcg cagacaatga caaggcagag gaacttctcc caacaagacc tggtttcttc  240
tttggtgcga tagac                                                   255

<210> SEQ ID NO 114
<211> LENGTH: 174
<212> TYPE: DNA
<213> ORGANISM: Methanobrevibacter ruminantium

<400> SEQUENCE: 114
```

```
ttgcagttgg tggtagaagg tgagaatatg gaatgccctt gcgataattg tgagatgtta        60
agagagaacg aaccaatcaa ggtgattgac tggaagtcca attctccatt tggaaatggg       120
atttktattc acttttggag ggaacggctt caggatgttg gctataatgg gtga            174

<210> SEQ ID NO 115
<211> LENGTH: 255
<212> TYPE: DNA
<213> ORGANISM: Methanobrevibacter ruminantium

<400> SEQUENCE: 115
atggaactga tgactaggga atggaaggg aaactcaaat ccttcccttt ctattcccaa         60
gacggaaaag gagatgacgc gatagtggtg atgaagttct tcaaccctta cggattggga      120
acttggtatg tattggaggc agagaaacag gagaatggtg attaccttt cttcggatat       180 gttgaatcac cgataacacc tgaattcaac gagtacggtt acttctcatt gtctgagttg      240 gagaaccttaa agata                                                      255

<210> SEQ ID NO 116
<211> LENGTH: 225
<212> TYPE: DNA
<213> ORGANISM: Methanobrevibacter ruminantium

<400> SEQUENCE: 116
atgttcggac agaagaaaga atttgtcaaa aagatgtatc atgtcggaga cgttgtcgaa        60
ctggttcata tggacgatgc acaggctcca cctagtggaa ccagaggaga aatactcttc      120
gtagacgata ttggtcaaat ccatgtgaga tgggagaacg gctcaggtct ggcactaata      180
tatggtgagg acaggttcaa agttgtagag aggaaaggag aatag                      225

<210> SEQ ID NO 117
<211> LENGTH: 153
<212> TYPE: DNA
<213> ORGANISM: Methanobrevibacter ruminantium

<400> SEQUENCE: 117
atggatttgt tgtatctttaa tgatgacctg actgcaagga gagaagtcta cgattcagtc       60
ggattgagtt ttgtggtcaa gtataaattc tcatctcgta aggaagcaca ggatttcgca      120
ttgaagtacg gtgcagaact gattgaggaa tga                                   153

<210> SEQ ID NO 118
<211> LENGTH: 189
<212> TYPE: DNA
<213> ORGANISM: Methanobrevibacter ruminantium

<400> SEQUENCE: 118
atgattgaac ggaggagatt aggaatgaag tacgatattt ttactatctt ggatgaaatt        60
tcaaggaagt tagatgacgg tgaattatcc gatgagcagg ttgatttcct gttgcagatg      120
gagattctag tagaggaagg cactatcaca gacgagcagg cacaagatgt catgaatgga      180
gattattaa                                                              189

<210> SEQ ID NO 119
<211> LENGTH: 168
<212> TYPE: DNA
<213> ORGANISM: Methanobrevibacter ruminantium

<400> SEQUENCE: 119
atgatgaaat taagtttgaa ggaactcggt gaggaaattg agatgatact tgcagaaggt        60
```

```
ggattaacct tgatcaagt cgattatctg ttgtacttgg agacctgcat tgcagacgga      120
agcataacag aggagcagaa gagagaaatt atctgtaggg acttctaa                  168

<210> SEQ ID NO 120
<211> LENGTH: 234
<212> TYPE: DNA
<213> ORGANISM: Methanobrevibacter ruminantium

<400> SEQUENCE: 120
ttggtgagag aacaggagag attgattatg tatttggaaa ttgacgaggt caagtgcgaa      60
aacattgaca gaattgagtt tgacgatgtc gcaatggaaa tcgtcctgac agacgaaaag    120
gtgtacgaga gaataaagag atggctcaag tccaatgaga ttgactacga ttgcagggaa    180
gaccggtatt tcgccaatct catagaatat gtcattagga taacttggtg gtaa          234

<210> SEQ ID NO 121
<211> LENGTH: 216
<212> TYPE: DNA
<213> ORGANISM: Methanobrevibacter ruminantium

<400> SEQUENCE: 121
gtggtaaccg tgagagatgt cggattcacc attgaggaac ggttcttcct tactgctcag     60
gaattggagt attccgaagt gggagaggaa cacgagagcg tcattgacag agccatcgca    120 tgctgtaca cgaagctcag aaccagagac ttcgagttca ccgacgaaga acgggaactc    180
ttggaggatg cttttgtcat tgtcagcgac caatag                              216

<210> SEQ ID NO 122
<211> LENGTH: 255
<212> TYPE: DNA
<213> ORGANISM: Methanobrevibacter ruminantium

<400> SEQUENCE: 122
atggctaaag aaaatgttat agattataag attgagcgac aaaatgataa cacttggagt     60
tatttatatg taactgaaag agggagagga aatatcattg cttcatcttt tggagaattg    120
aggcagaaag ttttaaaaag aggtttgcct tggaatgata tatctaacct attcactaaa    180
aagagttctg attctaatgt tcgtcgcgaa tctgtaaaga atattgatga tgaatctgtt    240
ttggctgatg tcgct                                                      255

<210> SEQ ID NO 123
<211> LENGTH: 255
<212> TYPE: DNA
<213> ORGANISM: Methanobrevibacter ruminantium

<400> SEQUENCE: 123
atggtagtca aatgtcctaa ttgttttagt ccacgtgttt caaaatgtga agatactaat     60
attaaatggc aatgtgataa atgcaaatgc aaatttaacc atggtgcttt cgatattaat    120
gctgaaatgg agaaagtaga acaattaaca atagaaaaaa ttgaaagaga acgagaaaga    180
actgaacaat tgaaagagc tattaaagaa gcaaaggaac aatttgaaag agaaagaact    240
gaacaatttg aaaga                                                      255

<210> SEQ ID NO 124
<211> LENGTH: 255
<212> TYPE: DNA
<213> ORGANISM: Methanobrevibacter ruminantium

<400> SEQUENCE: 124
```

```
ttgaccgagg gtcagataag gcagattgca catgagtatc tggcaaatta cagccttgtc    60
gacaagaacc atgagttctt cgagaccaga gaagttatag gagttcctgt ggagtcatat   120
ataacaaacg agcctataag cctcaagggc ttggacggaa cagtcaatga gtatccaaaa   180
ggaacctgga tagccaccac aaggataact gatgaagagg agatggaaaa ggcactcaat   240
ggagagtaca ctgga                                                    255
```

<210> SEQ ID NO 125
<211> LENGTH: 330
<212> TYPE: DNA
<213> ORGANISM: Methanobrevibacter ruminantium

<400> SEQUENCE: 125

```
atgggaaacg aagctacttt aaaccaattg gtaaacgagc aggaaaaggc agtcttcaag    60
tccatgagga ctgacatgga gacaggaaag gctgtattga acgtcgagca gctaggttac   120
ttccttagag aagcaacatt agacaataca attttaagag atgcggactt caagctgatg   180
aaatcattca gaagcatct caacagggta ggaataaacg aagggtcct cacaaacgga   240
```
(reproduced as printed)

```
aaatcattca gaagcatct caacagggta ggaataaacg aagggtcct cacaaacgga   240 tatgacgtga acggcgagac cgaccctgag attcctgcgg ctgacgtcga cttcggagca   300
aacgagttgg acgtcaagaa gctcaaggca                                    330
```

<210> SEQ ID NO 126
<211> LENGTH: 255
<212> TYPE: DNA
<213> ORGANISM: Methanobrevibacter ruminantium

<400> SEQUENCE: 126

```
atgcggaggc gttgcctgaa ctctccagag cataatggta tgatttcgca tatcattgtg    60
cttctcattt gctttatagg attggttgag gcgatactga tggcattggt tgattgggag   120
gacttggcaa tatccgttcg caagtctcct agaaagcttt ataatgtttt gaaggatgag   180
ttaggtcttc ctgaatggaa cgaactgtct gtgattgaaa ggagaagcat gaagaaaagg   240
tatgctgtca taaga                                                    255
```

<210> SEQ ID NO 127
<211> LENGTH: 255
<212> TYPE: DNA
<213> ORGANISM: Methanobrevibacter ruminantium

<400> SEQUENCE: 127

```
atgacttgga ttggtacgga agatgtcatc gagttcacag gagtcaagcc tcagacattc    60
aggttcgaga agggagacac ctccagcctg gaaacattgc ttgagaagtg gattctgcag   120
gcagaaggac ttataatatc ctactgcaac tacgatttca atgacttgga ggagatacct   180
ccagcagttg ttaatgtctg ccttaggctc actgcaaaca tggtcgcatt ggcacaggca   240
aggaaggaca ctcct                                                    255
```

<210> SEQ ID NO 128
<211> LENGTH: 258
<212> TYPE: DNA
<213> ORGANISM: Methanobrevibacter ruminantium

<400> SEQUENCE: 128

```
ttggtgaaat tgcagattga cgttgaggaa ctcaagccat ggagccaag gttcaaaaag    60 gttgccaaaa ggacagttgt gttgactgca atgaattgc agaaaacct caagaagttg   120 agtcctgtgg atcatggaag gcttcagggc tcttgggtaa tcttccagac aggagaattg   180
```

```
gaaaggactg tgaaaagcag tgcaaagtat gccattttcg tgaatgacgg aacaggactg      240
tacggtcctt tgggtcat                                                    258

<210> SEQ ID NO 129
<211> LENGTH: 333
<212> TYPE: DNA
<213> ORGANISM: Methanobrevibacter ruminantium

<400> SEQUENCE: 129
atgagattcg taaatactgc ttcgcttgtt cctcagactg tcaaggcata tcttgaaagg       60
gaaatctgcg aaggagggtt gcttgaggat gtagagacac tcattccgtc cgtgaacagc      120
gacgttcctg ttgacccacc tgcgatatgg atagtccagc accccactac cagatggtct      180
ggcagtcagc caaatctctc aaacaagata gctatgtcag tcccttttcga gttcgtatgc     240 gtggaataca gcgatgactt ggaagaggct gagatattgg aataagcct agccagcagg       300 gttggctcaa gcctgatgaa gaacttcaac aag                                   333

<210> SEQ ID NO 130
<211> LENGTH: 255
<212> TYPE: DNA
<213> ORGANISM: Methanobrevibacter ruminantium

<400> SEQUENCE: 130
atgggaattc gtgttgtagg aatgaaggaa gaggcaaggt atggagttgc ggagtcagcg       60
ccggacttcc atcaggaagt tagcaaggca aaggcttcct tgaactccac tccgaacaca     120
aagtcaagcg gctcaaggat gaagaagaag gcacgtgcag gcgtgtacaa gcctactgcc    180
aacatcgaag gtgaagttga cttgaagagg ataggacatt atctcaaggc tttcctggac    240
aattaccatt ttact                                                       255

<210> SEQ ID NO 131
<211> LENGTH: 255
<212> TYPE: DNA
<213> ORGANISM: Methanobrevibacter ruminantium

<400> SEQUENCE: 131
atggttgtag ttaagaaatc cgatatttta aagggcgtaa aaaagattga aaaggtgaag       60
attgaggctt tggacggaga cgagatgtac ttgagaccgt tgtcccaagc cgagatcaac     120
gaggtcgacg agattgaggc aaaggctatg ggaatcttcg agaccaacga gaccgcacac     180
aggggaagaa ggcagaagcc taagagtgtg gttgagagca aggaaagat aaatctcgaa      240 ttgcagcaga aggca                                                       255

<210> SEQ ID NO 132
<211> LENGTH: 255
<212> TYPE: DNA
<213> ORGANISM: Methanobrevibacter ruminantium

<400> SEQUENCE: 132
ttgccgtcaa gcaatgtaat gaacataata gtcaaggcag aggacatggc atcatctgtc       60
gcccaaaagg ttgaaaacag cttcaggaaa ttgggaaaca aatagacag caccttcacc      120 acatctcttt caaacaccaa gttcaatcag gaactcactc ttttggaac agacttggac       180 aaggtaaccc aaaggctgaa gcaggtaggc gtgaacggtc agtccagctt caaccagctt     240
acaaatgctg aaagg                                                       255
```

```
<210> SEQ ID NO 133
<211> LENGTH: 312
<212> TYPE: DNA
<213> ORGANISM: Methanobrevibacter ruminantium

<400> SEQUENCE: 133
atggcaagtg ttacaaaata tccgagcaac gtttcacaga ccactggagg aaagttcgtg      60
tccttcagca atctggcaaa cataaagaac aatgctgacg gagcgcatgc cgtgagcagt     120
gttcttatca aaagcaagaa gcagtctcca acagaccgt ccacagtctc atgcaaaggc     180
ttcggattca gccttcctga aggtgctgaa cctactaaaa tcacagtaac ttataggcat     240
aggaagaatg ctggaagcga ctacagctca aagaacaaga ctcacatatg caacatcgga     300
ggacctacaa tc                                                         312

<210> SEQ ID NO 134
<211> LENGTH: 255
<212> TYPE: DNA
<213> ORGANISM: Methanobrevibacter ruminantium

<400> SEQUENCE: 134
atgggcatag ctattgttgt tatggacaat gaggagaact tcctgcaatt ccttgaccct      60
gatttatgca ccatcaatga gaccatagag gaattgggct tgaggacttt ggagttcaac     120
tacaagtttc aggactatgt tgaggacagg gatcttttca ggataggtaa caagatctgg     180
attagcaatt cccagagctt ggaggactgc ctttatgtga taaacactcc tgtggagaac     240
agcgtctatc aggag                                                      255

<210> SEQ ID NO 135
<211> LENGTH: 255
<212> TYPE: DNA
<213> ORGANISM: Methanobrevibacter ruminantium

<400> SEQUENCE: 135
atggtcgaga agattacagt gagtcctcag gaagtcagag gatacggaaa tgttgttgat      60
gagaaggaat tggaagatta cggaagctac aggtgtgatg tgagcgagag ctcggaggtg     120
atcaagggag ttgaggaaag gatattcagc gtttctggtg ttcctgctcc tgctctgagc     180
attgccaatg ttactgagga cactcgcagg ggcaggtgcg cccacatctc cgcctcattt     240
gaggatgggg aaggc                                                      255

<210> SEQ ID NO 136
<211> LENGTH: 381
<212> TYPE: DNA
<213> ORGANISM: Methanobrevibacter ruminantium

<400> SEQUENCE: 136
atggttagat tcagcagaga catgctccag gacggagcga agagaatgtt caagtggcta      60
agaaagggcg aagggttgcc taactacttg ataatgtatg acatggacag gaataaggag     120
tataagttgg ttccaaagga atatgcagga ctgtatgagt ccagaaacat attctggatt     180
aagaacggaa gggagcctaa ctatgttaca ctgacttccg ttgcaaggaa tcctcttgtg     240
atggactacc agaacaccaa ttacacctgt tgcccaacca gtttgtccct tgcctcacaa     300
atgctatatc actataagtc agaaagtgaa tgcgctaagg ctttgggaac tagcaagggc     360
agtggaacaa gccctgcaca g                                               381

<210> SEQ ID NO 137
<211> LENGTH: 2250
```

<212> TYPE: DNA
<213> ORGANISM: Methanobrevibacter ruminantium

<400> SEQUENCE: 137

```
atgaaaaaac attgctttta ttttttaggg gacagttttg ccgatatatg caatgaagcc        60
atgttttgtg aaaaacattt agtagaagga aactatttgg attcaattat ccgtgcagga       120
aaggcttcag agataataac tgtaaacatt tgtgaacttg aaggtcaaga tggcttaata       180
agctctggtc agaagaaaag attggaaatg cttggatata agggtatcat ttcttatgat       240
atttataaaa gattaaacca tattcgtaaa attagaaata aggctgtcca tgggcattta       300
agtgatattg aagacaatgc aaatattctg catgcctatc tgtatctaat ttgcgcatat       360
ttctataagg aatatagaga cactaatttt tcagcggaag attatacggg ccctattatg       420
gacattgcct ctaagcctaa agagactgct tcagagactt cagaggataa tgaaaatatt       480
ggagagttta tttcaagtcc attggatgat tatcttttg aaaagtatga tgacagttac        540
ctgttaaatg aactgtctaa acttaaggac tcttcaaagg aagctgttga agacgataac       600
ttaagcgaat ttaaggaata tcttcatatt gacagatcta ttcaagaaga ttttttaaag       660
gcattgaaca gagccactag tttaattca tctcatctga ttatgctttg cggtagtgtt        720
ggagatggga aatcacactt gattgcaaat ttaaaaaaga aaaccctga actctttaat        780
caatttgcta tccattatga tgctacagag agttttgatc ctgaaaagaa tgcaatagac       840
actttagcct cagtattgga acctttcaat gacaataatc ttaacaattc gacagaaaaa       900
cttatttag ccattaactt gggtgtattg aacaatttcc tggaatcatc ttatgctaat        960
gaagattaca ctaaactcaa gttaattata gaagaagcga acatatttga atctaatgag      1020
gtttcagata cactttatgg agataaggtt agttttgtca ctttcagtga ttacaacatg      1080
tttgaattga atgatgatga aaattcaaac tacacatcat caaagtacat ctcttcccta      1140
tttaataaga taacccaaaa ggaggataca aacccttttt atgttgcata tctcaaggat      1200
aaggactctc acttatcaa tcctataatc tataattatg agatgctgat ggatgaggag       1260
gtccagaaga caatcattga ttatttaatc aagattttca taaaatacag aaaaatcatt      1320
tcaactagag acttattgaa cttcatttat gagataatag ttcctccgga attcctgaaa      1380
agtgaggatt tggacaatat caatgatttc atggactatt cattgcctaa tttactcttc      1440
ggatatccag aaaggtcaga tttattgaag ctatgcaatg aattggatcc gacattgcat      1500
cgtaatgaat ctttagataa gttcataata gacttgaaca ttaatgacga tactgaaaag      1560
atattaaatc gttattttga tttcactcgt tttaatttcc ttgaagagta tggagagtat      1620
ctggttgatt ttagggagtt taacaattct gaaaaagaga aggtcaccaa tattctaatt      1680
aggtttgcag tattctatgg aaagagcatt atcaagaata atttcaagga taaggtttat      1740
ttaaattatt taaatatctc gtatgcctat aatacacagt ctcataagga ttacaaatat      1800
ctgttcactg aagttaagga cgctatttt aattggaaag gttcctataa gaagaatact       1860
atatgtattg acactttgga ttcatttaaa gtgtataaaa atttaaaatt aaaaccatct      1920
gttgataaat ttgaaaaaag tttattagat ggtctctttt taggaaatag atttaaaaca      1980
gatataaaaa tttattttc agttgaatct aacaaaaaga aaataccttt aaatgttgat       2040
ttttcattat atcaatacat aatgaaatta tataatggtt ttaagcctaa tcaatcagat      2100
aaagacgatt taataatttt agatgaattt attaataatt tattagatga agatacagat      2160
gatgatttat atgtaattag tttagaaact tatgaagaat ttttatttga gtcaaatgat      2220
tttggcactt ttgaatttaa gaggggttaa                                       2250
```

-continued

<210> SEQ ID NO 138
<211> LENGTH: 1372
<212> TYPE: DNA
<213> ORGANISM: Methanobrevibacter ruminantium

<400> SEQUENCE: 138

```
atggattttt cagaaaatta taatatatta ttaaaacaaa tgacttgtga tgtaaataaa      60
aggaaattaa tacatcagat taatcaaaat tctccattgt tacctttaa  aactaatact     120
cctaaaaaag ctaattttga aaatggtttt gatataatat tgggtgaatt atccagaatc     180
ttattaaata aaactattga aaaaatttt  aaattagata atattgtttc aaatttaatt     240
gataataata ttgaaattga agatggaact aaggagtata taacaaaatt gctaaatgaa     300
tatttattcg atgaaaaaaa tgatttaaaa atatctcatc cgaatttgta tttatatatt     360
cctctttcaa ataataaaag ttctaatgga gaacaggaag tagcattgtt tttaagagat     420
attttttgta agaataatca aaatcttatt aactttttg  aatcatatga ttcaaatcac     480
attatcttaa atttaatttt aaaaaatact cctaatttac atcataaaat aactgaaact     540
aagtatgtaa ttcattttga ggaaattgca aattatttta tgaagatat  caattatgca     600
atactttata agaaattttt tatggaaaac attggtaata ttttgctta  ttactatttc     660
ttttatatct ctcaattaat tctaaaaatt tctaaaggct ttaatgataa taatgaattt     720
gaaaaattgt actatttatt ggactgggaa tctgcaagta aaaatcgtaa atcattaaat     780
agttatagtt tactaaaaca tcattctaaa ccattatatg caaaaatggc agtcatagat     840
caaataaata cactattagg tacaaataat ttattggaaa agatatttc  agaatatttt     900
aataatttgg acatcaattc taaaaataat ttttacatt  tcttaaaaa  atgggtttca     960
gattataggt atgtaaggaa ttttgatgat aaagaattac cagataattt attagaatta    1020
actgaaattc ttttttgaaag tttaaaaaat gaaaaactgg gtgtggatgg agctgtacaa    1080
tctaggtacg ctttaaatct tgaagatata gctaaaaaat atttgttaaa gcgtagaggt    1140
tcgtatggtt atgtattaaa tattaataga gatatgttgc ttgttttaac tgcattatgt    1200
gttaaagata agaaaattaa gttaaatcaa ctatttattg aatttgagaa aagaggagtt    1260
tattttgaca atattccaaa agaagaagta gtaaatttt  taactaaatt aaatttaatt    1320
gacaagaaaa gtgatagtgg agatgctcaa tatgttaaac cagttttatg at            1372
```

<210> SEQ ID NO 139
<211> LENGTH: 5223
<212> TYPE: DNA
<213> ORGANISM: Methanobrevibacter ruminantium

<400> SEQUENCE: 139

```
atgttaaacc agttttatga ttatctatct aataaattac taaattattt tgatgatact      60
aagattttaa gtggtgaaaa attttttcatt agttttgatg aagatgacca aataatgtct     120
ttttataata gtttaagaag tattgcagaa actaattttt cttgttctga attcatatat     180
gtccatacta tttcaggaaa ggaatataat acttattcca taaacattaa tggagtcaaa     240
tttgtcattt ctgaaagttt aacaattaac gtagatttct tagttacttt aagaaatcaa     300
gttacttctc aagagggtgt ttggaaggat actgcattat tagttatctg taatgaagca     360
atagatagta ttggaaaagg tatgagaaat ttacagaaag aaggaatgcc attaaatgta     420
aaatctattt caaaaaattt agaggatgaa attaacgatt ctcaaattct taactattcc     480
gataagcaaa tcgctaagtt ttctttgaat attcaagaag aagaattgtt tcaaacaaca     540
```

```
ttatgggatt atgaaactat cttatcaata atcaacaagg gttttgttag tgatgaagat    600
ttaagagagt tgaatctttt taaagatgac caactaaatc aaaattctcc tcaaaagatg    660
ttaaaaagat taaaagaaaa ttatgacaca tttaatgaag taaataaatt ttcacaatat    720
ggagataaaa aagaacagct taaaaatatg tttactgatt ctggagtttc tattttaagt    780
aaagatgact ggtataaagc agaatggaaa atggttaaaa aatcaaagga tgactttatt    840
aatcaacaaa atcctttaaa ttacaatgaa atcttgaaa aaatcacaga aaatggctta     900
aattattggg aaattcctaa ctcatttact aaaactggaa aaagaaaacg aaatatcatt    960
gttttaatc caaatcattc tcatgaagtt agtttaaagt tcagttttga tcagattctt    1020
agtaattcat tccttaatac aaattcaaaa aaattcacta ttgcaagagg caaatcatta    1080
atagtcaatt ttactctgga ttctagtgaa ccaattttca aaactataaa atataaacat    1140
aaaaatgaaa atatctctga atttactttt aatattgttg ttttgaattt tgagcctgaa    1200
atttttaatt ctattaaatc tcgttttagt gtcaatgtca aatctaaaca gattattgta    1260
acaaatgatg aggatagttt tgatattgtt tttggtactg gttcaaaaga aatagagaaa    1320
ttaattaaag aaaatggtga aaagttatat ctttatgatg atgaatcttt aataatttct    1380
gaacaatctc ctgcttggaa tgatggaaaa ttaagttta aattatataa agacaataat    1440
tatgccccat ttttgattaa agaaaaatct aagaaaacac tgccagtaaa ttcctatgta    1500
atttggaatt tgaaaagaag aaatatggaa aactttattt ttaatggagt aaaagctgtt    1560
caagatgtaa acagtttcta tctcgtagaa gaatttaaag aatttctaaa aatggaacga    1620
gaaatcatta aacaggacat atttatgct aaaaggaata ttgatggttc tttagaaaaa    1680
attgaagttt cattcagtaa cgagttagaa actgcttaca tggacatatt taattattat    1740
aagacttttg atgattctcc agaagacaat cttccaagtt tagtttattt aaatgatgat    1800
ttaaaagagt tatataagaa atttataact atcttcaata aggaaatatc agaaattgaa    1860
gagaattcta ttttgtctga tttttaaatat aaaaagaatt tgcttaagtt aggtcgtatt    1920
gaaactgata acaaaataat gtattctcca ttatctccac taaatatcgc ttatcaatta    1980
gaagtttcta acaatgcgg aaatgaggat ttatccgtaa atatattaga acggttagtt    2040
ccaaataact taattcctta tatttgttca gatgatggaa aagaattgtt tagacctatt    2100
tatcaagaag aagctcatga atggttgatt tatgagaaaa gtgaagaagt atcaattgga    2160
acaacaaatg tatttatttc taatgttgtt actgaaaaac ttaatcaatt tgtcaaacat    2220
tttaattact tatttagttt taacaactcc tcaccaatta aaattaactt aatcaatata    2280
aaagatgata aagaagttgt gaaaggagta tttaatttta ttagatctag attgcctgat    2340
aaaactaaaa caaaaaaagt tattcctgtt gaaatcaata tttacaacga cgctgaaaag    2400
agttcttttg acaatttatt tgattgtcag tctgaaattc agttactgga agaatttgga    2460
attaaaaaat taaaatcaga tatttttgat cctatagata ttatccatat gattcaaaat    2520
aatatttcat attataaaca tccatttaaa aaagaagaat atgaatatgc tcatctttct    2580
ttctataaag tcaaatcaca taacaatatt gcaaatgaca atatggataa aattgaaact    2640
ggattatctt taaacggttt attatcttca gttacatcaa ctactaaaca ttcagaatat    2700
agaacggtt tcggtacaaa caatatttta aatatgagta atcctcttat taaacagtg    2760
attaacttga acgaacttgt tgagaatagc aagaactttg gaaaaaatac ttattcaaaa    2820
aataaatcag ttatcactac tgttgaatta gaagaagaca atattgaaga attgtacgac    2880
aaatctcatt gggtaacatt tattgaacct acatttggta tcgaatactt tgacagttct    2940
```

```
gatagtaatt tgatcattat tcattacagc gatcaatata gttcctctag caagtatgat      3000
actattactg taactaataa atcaacacaa tatgaggaaa ttataagaga tttcctccaa      3060
tctaaatatg taaaagttac agatgaagaa ttgtatgatg taataaagat gtttaattca      3120
attaatggtg aatggttact tagagtaatt tctaattccg gccattatga tagggaaaaa      3180
ttaagtatta tttctgctat taaatattgc ttatccattt tggaccataa agatattgtt      3240
tggattccag tttctatgga agaaatctta agaattgcag gaaatgttaa attagataaa      3300
aataaaggaa tttttgactc taagttaata aaaggaaatc atagtgatga tctgctattc      3360
attggtgtaa aattcaatga agataataga atcgaagtta tattctaccc aatcgaagtt      3420
aaaataggtt tgaataatgc ttcaactatt aaaaaggta aaagtcaatt agataatact      3480
tataaacttc ttaaaactca actacaaaat attaatgtag agaattctga atttagaaat      3540
aaattcttta gaaatttctt catccaaata ttattgtcca atgagcaaaa attagtaact      3600
aatcatattt gggatgaaaa aggattggat agaattgaag aattcaaagc agaactatta      3660
aatgatgaat atgatatttt atatggttta gaagagtaca ttggtaaagg ttctttggtt      3720
tcatttaaaa aagaatctca tcacatctct atctatatgg atgttgataa gcaagtaatt      3780
gagttaccag aagattttgc ttattacggt ttagccactc ctataagaga aatccatgat      3840
gagattcagt cagacaatac agatattctt gcagaaacat tgttatcaca tgtagatata      3900
agtgaaatta gagcaaagaa taatgatata tgcgattcaa atgaggatat gtcaatagat      3960
gatgattttg ataatttaag tgaatttgag gatagtttta ttgaagaaga atcagaaatt      4020
tctgaagagc ctgatgaaga attaactgat gcaacttcaa gcagtgataa tgaatcaatt      4080
gagaatattg gagaatctcc ttctaaaatt tctaatgtca gagcattaat tggaactcag      4140
aagggttata atcataaagt ttattgggaa tttggacatc cttctttagc aaataggcat      4200
atgttaattc aaggaaaatc tggacaaggt aaaacatatt tcattcaacg aatgttaaaa      4260
gagttgtcta ttcaaggcat tcctagcata attattgatt tatactgatgg attcaagcct      4320 tctcaattag aacctaattt taaagactct ttaggagata aaataagcca atattttgtt      4380
gtaaaagaaa atttcccaat aaatccattt aaacgaaaca ctatcatgat tgataaggac      4440
atatttattg aagaagacaa cagcactatt gcgagccgat ttaaatctat cattaattct      4500
gtttatgggc taggtattca acagtccaat actttatatc aaacagtttt agattgcttg      4560
gataagtatg atgataattt tgatttgaat atcctaaaag aagaaattct aaaagacgaa      4620
tcaaatagtg cacaaacagt cttgaataaa ttaaatgagt tattggataa aaatccgttc      4680
gcatccactg atttcgactg gtctgtctta gataataaag acggtaaagt ttacattatc      4740
caattaactg cactttctaa ggatatacag acaattataa ctgaattcat cctttgggat      4800
ttatggaatt acaaattaac aaatggtagt gaagataatc cttttcattgt tgttttagat      4860 gaagctcata atcttgattt ttccaatgac tctccatgta gtaaaattct taagaaggc      4920 aggaaatttg gatggtctgg gtggtttgca acacaatctg ttaaaggatc tatgaaaatt      4980
gatgaaatag ctaaattaga gaatgcagat gagaagatat atttccatcc aacggatgtt      5040
tcaacaatag ctaagatttt gtcaaaagac aatgaagata aaaaaatata tgaaaaagag      5100
ttatctcaat tgacaaaagg atattgtatt gttcaagggt ctgcaataga ttcaagtggc      5160
aatttgtatc agccaaatcc tgtaactgta aaaattgagg agataagttt tgatgaaaat      5220
taa                                                                   5223
```

```
<210> SEQ ID NO 140
<211> LENGTH: 3165
<212> TYPE: DNA
<213> ORGANISM: Methanobrevibacter ruminantium

<400> SEQUENCE: 140
atggaaagta aagacagaat agagaatact attttcaatg ataaaagaat ggatgcttat      60
atagacaaat attttgaaga gtttactctg agttctgaac aagaagaggc actgaatatt     120
tggatagata aattaaataa cgatcaatta acaagtgaaa aagggaatta tcataatttt     180
tttgaaatta ttcttgaaga tttacttggt tataaacgtt ctgatgttaa acatgaagag     240
aatattggtg atgaaggcca tcctgtagag tttgtattag aaaaagatgg aaaagattat     300
gtgattatag aactaaaagg aacaacttat aaagacctca ctaaaagaag acctggacag     360
caatcaccag tagagcaagc tacaaattat gctagtgcta aaaaagaaac tgaatgggct     420
acagtttcaa attatgatga atttagattt tttaatccaa cagcaagaga taattatatt     480
tcattcaagt ttaggcaatt gaaagatttg gaaatcttta aaaaattttt attagtattc     540
agtaaatttt cacttatcga tgaagacata cctaaaaaat tacttaatga acaaaagtc     600 attgaaagag aattagaaaa tgaattttat caattgtata gtgacactag attaatgatt     660
attaaggaat tggaatattc ttcagaagat attaatagga ttgaagcaat aaaattatct     720
caaataatat aaatagatt tattttcctt tgttttgcag aagatttagc gcttatggag     780
gaagagacaa ctgctgatgt attattaaca cctttaaagc atagaaattt aatcggaaat     840
acaatgtgga ataggttaaa tgaattattt attttttgcaa atcaaggaaa taaacatagg     900
agaatacctg catttaatgg aggattattt gaggatgatt tatctaattt gaaaataagg     960
gatgaaattg aagataggtc tttctttgaa aattggaatt aaaagaaga ttttgaagac    1020 aaatatgagg atattgctaa actaattgga gtttataaag atactcttaa tccaattttc    1080 attaattta taataattc tacatatgac tttgattcag aacttgatgt aaatatctta    1140
ggacatattt ttgaaaacag tattagcgat attgaagagt taaaaaatga taatcaagag    1200
caaagaaaaa aagatgggagt gtattacact ccagaatata ttacagatta tatttgtaga    1260
aatacaatta ttccatattt aagtatttct ggtaaagcca gcacagttca tgaattatta    1320
tacgaatatg aatcatctaa ttcattggat gttttagatt caaaattaac taacatcaaa    1380
gttctagatc ctgcctgtgg tagtgggagc atgttaaata aatcagtaga tatattattt    1440
gaaattcatg aagcattaca tgcaagtaaa tatgctggag attcatcttt agatagattt    1500
tttgatagtt tagaaaaacg aaaggaaatt ataagtaata atatttatgg ggttgatttg    1560
aacgaggagt ccgttgaaat tactaaatta tccttattcc taaaattagc aactactgtt    1620
ggacttaaag aagggtttca acttcctagt ttagataaac atattaaatg tggggattca    1680
ttagtggatg atgagtcaat tgccggaaat aaagcattta ctggtatga atcattttca    1740 gaagttttg aaagtggcgg atttgatatt attgtaggaa atcctccgta tgtggatatt    1800
aaagaaatgg atgaaaaaac agcaaaatac atatttgata attatgaaac ttctttaac    1860 aggataaatt tatattctac atttgtggaa aaagttatt atttgctaaa aatgaaggg    1920 attttttcat ttatcatgcc taattccatt ttatttaatt ctacttactc taaaatcaga    1980
gaactaattc ttaataatac atccatatta aatattgtaa gaacttctga tgatgttttt    2040
aaagatgcta aagtggaacc tattatttta atcttcaaaa aaggatatga tgaaggaaat    2100
aagactaaga tacttataaa aaaagatgat atggatgaaa ttccaataaa taattattca    2160
gaacatttct ttacacaaga aagatggttt gaaaataatt caataattaa tatttttca    2220
```

```
gatgatttta cttttgattt attaaagaaa attgatggaa ataatgaaag attaattgat    2280
tattgtgatt ttagtttagg tttaactcct tatgataaat ataaggtat gagtgaggat    2340 attattaaaa atagaaaatt ccattcaaaa ataaaacttg acgatacttt taaagaatta    2400
ttggatgggt ccgatattac aagatataat gtaaatggg gcgaaaaaga atatattaaa    2460
tatggggact ggttaggagc acctcgggaa gaaaaattct ttaaaaatcc tagaattta    2520 ataagacaga ttttatctat agctcctaag gaatctcgaa aaggattttt tgccgcttac    2580
acagaagaag aattatataa cgctcaaatt gctttttaatt tagtattgaa agaaggcttt    2640
gatgataaaa atttattgaa atatttttta ggaataatta attctaaaat gatgacttgg    2700
tattatgaag aaagatttat ggataaaaat aaaaagaatt ttgcaaaaat tttgattgaa    2760
aatgctaaaa atcttccagt cattattaat tcaatttttt tagatgagat agtatctaat    2820
gtggattcaa aatagagtt aaataaagag ttttatagtg taagaaatgc atttcaaaca    2880
tggcttaaaa tagaatttga aattgaaaaa ctctctaaga aactagaaaa ctattatgat    2940
ttaaactttg aagaattctt aaaagagata aaaagaaaa aagtagtcat tagaccaaat    3000
caaatacagg acttgtccga attatttaat gaaagtttag gaaaaataga atatctgcaa    3060
agagagatta aagaagcaga cgaaaaaatt aacctactgg tctatgaatt atatggttta    3120
aatcatgaag aaatagaaat tatagaaaat agctttaatg attaa                    3165
```

<210> SEQ ID NO 141
<211> LENGTH: 261
<212> TYPE: PRT
<213> ORGANISM: Methanobrevibacter ruminantium

<400> SEQUENCE: 141

```
Ala Thr Gly Gly Ala Cys Gly Ala Thr Gly Ala Ala Cys Ala Thr
1               5                  10                  15

Thr Ala Ala Thr Cys Cys Thr Ala Ala Thr Thr Gly Ala Ala Thr Ala
            20                  25                  30

Cys Ala Thr Cys Ala Gly Ala Ala Ala Cys Gly Cys Gly Cys Ala
        35                  40                  45

Ala Cys Ala Ala Gly Ala Gly Ala Ala Ala Thr Gly Gly Thr Gly Cys
    50                  55                  60

Thr Thr Ala Ala Gly Thr Cys Ala Thr Thr Thr Gly Ala Ala Gly Gly
65                  70                  75                  80

Ala Gly Thr Gly Gly Ala Cys Thr Thr Thr Ala Thr Ala Ala Gly Ala
                85                  90                  95

Cys Cys Ala Ala Thr Cys Cys Ala Ala Ala Thr Thr Cys Thr Ala
            100                 105                 110

Gly Gly Ala Ala Ala Ala Cys Ala Gly Gly Cys Ala Thr Thr Cys Ala
        115                 120                 125

Cys Cys Cys Ala Ala Ala Cys Ala Ala Thr Gly Thr Cys Ala Gly Cys
    130                 135                 140

Ala Ala Gly Ala Ala Ala Thr Thr Ala Ala Gly Gly Ala Thr Cys
145                 150                 155                 160

Thr Thr Cys Gly Cys Gly Ala Ala Cys Ala Thr Gly Ala Ala Cys Thr
                165                 170                 175

Gly Gly Thr Cys Thr Ala Thr Gly Thr Cys Ala Thr Ala Ala Ala Thr
            180                 185                 190

Cys Cys Thr Gly Ala Gly Thr Ala Cys Cys Ala Thr Gly Thr Thr Cys
        195                 200                 205
```

Cys Thr Ala Ala Ala Cys Thr Thr Ala Cys Ala Gly Gly Cys Thr
            210                 215                 220

Thr Ala Cys Thr Gly Ala Ala Ala Gly Gly Thr Ala Ala Ala
225                 230                 235                 240

Ala Ala Thr Ala Thr Gly Cys Thr Cys Ala Ala Thr Thr Cys Thr
            245                 250                 255

Thr Gly Thr Ala Gly
            260

<210> SEQ ID NO 142
<211> LENGTH: 255
<212> TYPE: DNA
<213> ORGANISM: Methanobrevibacter ruminantium

<400> SEQUENCE: 142
atgaataaaa aaattatctt atccctcctt ttagtattat tagtagctat ttctgtctct      60
gcagttgcag cagcagatgc tgatgtcaca tatataaacg atgctgcaga tgtagacgat    120
gttgcagacg aaaaagttgc tcctcttaca gctagtgctg atgcacaaga catccaaact    180
aagcttgata tgctaaacc tggagacaca attgaattag aaaacaagac atatgacgtt    240
gatacaacat ttaat                                                     255

<210> SEQ ID NO 143
<211> LENGTH: 40
<212> TYPE: DNA
<213> ORGANISM: Methanobrevibacter ruminantium

<400> SEQUENCE: 143
tttttaattg attgtaataa ttaattattc tgggtctgac                            40

<210> SEQ ID NO 144
<211> LENGTH: 80
<212> TYPE: DNA
<213> ORGANISM: Methanobrevibacter ruminantium

<400> SEQUENCE: 144
aaacctttat ggaagtcgag taagtattgg tacgtattat aagtataaat acgtatccta      60
tacttacttt attaaaattt                                                  80

<210> SEQ ID NO 145
<211> LENGTH: 42
<212> TYPE: DNA
<213> ORGANISM: Methanobrevibacter ruminantium

<400> SEQUENCE: 145
cagaataagg ataataatta attatattgt ttttattttt tt                         42

<210> SEQ ID NO 146
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
caaagagaga ttaaagaagc agacg                                            25

<210> SEQ ID NO 147
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
agtagtgttg gaatcagtga aaagg                                               25

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
caccatggtt agattcagca gagac                                               25

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
tcatgcagga cagacaacat agtag                                               25

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 150

His His His His His His
1               5

<210> SEQ ID NO 151
<211> LENGTH: 39
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Met or Leu
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (7)..(15)
<223> OTHER INFORMATION: Any amino acid; This region may encompass 0-9
      residues
<220> FEATURE:
<221> NAME/KEY: MOD_RES
<222> LOCATION: (16)..(16)
<223> OTHER INFORMATION: Ile or Leu
<220> FEATURE:
<221> NAME/KEY: MOD_RES
<222> LOCATION: (17)..(17)
<223> OTHER INFORMATION: Ile, Phe or Leu

```
<220> FEATURE:
<221> NAME/KEY: MOD_RES
<222> LOCATION: (18)..(19)
<223> OTHER INFORMATION: Ile or Leu
<220> FEATURE:
<221> NAME/KEY: MOD_RES
<222> LOCATION: (20)..(20)
<223> OTHER INFORMATION: Ile or Ser
<220> FEATURE:
<221> NAME/KEY: MOD_RES
<222> LOCATION: (21)..(21)
<223> OTHER INFORMATION: Leu, Ile or Ala
<220> FEATURE:
<221> NAME/KEY: MOD_RES
<222> LOCATION: (22)..(25)
<223> OTHER INFORMATION: Any amino acid; This region may encompass 0-4
      residues
<220> FEATURE:
<221> NAME/KEY: MOD_RES
<222> LOCATION: (26)..(26)
<223> OTHER INFORMATION: Leu, Ile, Val or Phe
<220> FEATURE:
<221> NAME/KEY: MOD_RES
<222> LOCATION: (27)..(27)
<223> OTHER INFORMATION: Leu, Ile, Ala or Val
<220> FEATURE:
<221> NAME/KEY: MOD_RES
<222> LOCATION: (28)..(28)
<223> OTHER INFORMATION: Leu or Ile
<220> FEATURE:
<221> NAME/KEY: MOD_RES
<222> LOCATION: (29)..(29)
<223> OTHER INFORMATION: Ile, Leu or Val
<220> FEATURE:
<221> NAME/KEY: MOD_RES
<222> LOCATION: (30)..(30)
<223> OTHER INFORMATION: Leu, Ala, Ile or Val
<220> FEATURE:
<221> NAME/KEY: MOD_RES
<222> LOCATION: (31)..(32)
<223> OTHER INFORMATION: Ile, Leu, Phe or Val
<220> FEATURE:
<221> NAME/KEY: MOD_RES
<222> LOCATION: (33)..(33)
<223> OTHER INFORMATION: Ser, Ala or Leu
<220> FEATURE:
<221> NAME/KEY: MOD_RES
<222> LOCATION: (34)..(34)
<223> OTHER INFORMATION: Ile, Leu or Val
<220> FEATURE:
<221> NAME/KEY: MOD_RES
<222> LOCATION: (35)..(35)
<223> OTHER INFORMATION: Gly, Ser or Ala
<220> FEATURE:
<221> NAME/KEY: MOD_RES
<222> LOCATION: (36)..(36)
<223> OTHER INFORMATION: Ala or Ser
<220> FEATURE:
<221> NAME/KEY: MOD_RES
<222> LOCATION: (37)..(37)
<223> OTHER INFORMATION: Val, Ala or Ile
<220> FEATURE:
<221> NAME/KEY: MOD_RES
<222> LOCATION: (38)..(38)
<223> OTHER INFORMATION: Ser or Ala

<400> SEQUENCE: 151

Xaa Lys Lys Lys Lys Lys Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Ala
        35
```